US011717549B2

(12) United States Patent
Gaspard et al.

(10) Patent No.: US 11,717,549 B2
(45) Date of Patent: Aug. 8, 2023

(54) STEVIOL GLYCOSIDE SOLUBILITY ENHANCERS

(71) Applicant: CARGILL, INCORPORATED, Wayzata, MN (US)

(72) Inventors: Dan S. Gaspard, Victoria, MN (US); Adam T. Zarth, St. Louis Park, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 16/373,206

(22) Filed: Apr. 2, 2019

(65) Prior Publication Data

US 2019/0223481 A1    Jul. 25, 2019

Related U.S. Application Data

(63) Continuation of application No. PCT/US2018/054691, filed on Oct. 5, 2018.

(60) Provisional application No. 62/569,279, filed on Oct. 6, 2017, provisional application No. 62/676,722, filed on May 25, 2018.

(51) Int. Cl.
| A23L 2/60 | (2006.01) |
| A23L 27/30 | (2016.01) |
| A61K 36/28 | (2006.01) |
| A23L 2/56 | (2006.01) |
| C07H 15/256 | (2006.01) |
| C07K 1/18 | (2006.01) |
| C07K 1/16 | (2006.01) |
| A23L 2/68 | (2006.01) |
| A23L 27/00 | (2016.01) |
| A23L 5/40 | (2016.01) |
| A23F 3/34 | (2006.01) |
| A61K 31/192 | (2006.01) |
| A61K 31/235 | (2006.01) |
| B01D 15/36 | (2006.01) |

(52) U.S. Cl.
CPC .............. *A61K 36/28* (2013.01); *A23F 3/34* (2013.01); *A23L 2/56* (2013.01); *A23L 2/60* (2013.01); *A23L 2/68* (2013.01); *A23L 5/40* (2016.08); *A23L 27/30* (2016.08); *A23L 27/36* (2016.08); *A23L 27/39* (2016.08); *A23L 27/88* (2016.08); *A61K 31/192* (2013.01); *A61K 31/235* (2013.01); *B01D 15/361* (2013.01); *C07H 15/256* (2013.01); *C07K 1/16* (2013.01); *C07K 1/18* (2013.01); *A23V 2002/00* (2013.01); *A23V 2200/15* (2013.01); *A23V 2250/258* (2013.01); *A61K 2236/31* (2013.01); *A61K 2236/39* (2013.01)

(58) Field of Classification Search
CPC ......... A61K 36/28; A23L 27/36; A23L 27/30; A23L 2/60; A23V 2002/00

USPC ........................................................ 426/658
See application file for complete search history.

(56) References Cited

U.S. PATENT DOCUMENTS

| 3,916,028 A | 10/1975 | Lee |
| 3,924,017 A | 12/1975 | Lee |
| 4,082,858 A | 4/1978 | Morita |
| 4,312,856 A | 1/1982 | Korduner |
| 4,495,170 A | 1/1985 | Beyts |
| 4,710,583 A | 12/1987 | Chmurny |
| 4,853,237 A | 8/1989 | Prinkkila |
| 4,906,480 A | 3/1990 | Kashket |
| 5,336,513 A | 8/1994 | Riemer |
| 5,681,569 A | 10/1997 | Kuznicki |
| 5,788,971 A | 8/1998 | Togasaki |
| 5,888,549 A | 3/1999 | Buchholz |
| 6,022,576 A | 2/2000 | Cirigliano |
| 6,337,095 B1 | 1/2002 | Jain |
| 6,426,112 B1 | 7/2002 | Boatright |
| 6,475,544 B1 | 11/2002 | Hiramoto |
| 6,589,588 B1 | 7/2003 | Wester |
| 6,635,774 B2 | 10/2003 | Roden |
| 6,900,240 B2 | 5/2005 | Empie |
| 6,989,171 B2 | 1/2006 | Portman |
| 7,279,184 B2 | 10/2007 | Gow |
| 7,291,352 B2 | 11/2007 | Gow |
| 7,294,353 B2 | 11/2007 | Gow |
| 7,651,717 B2 | 1/2010 | Shioya |
| 7,727,565 B2 | 6/2010 | Jani |
| 7,750,053 B2 | 7/2010 | Suzuki |
| 7,767,238 B2 | 8/2010 | Roy |
| 7,838,044 B2 | 11/2010 | Abelyan |
| 7,879,376 B2 | 2/2011 | Boghani |

(Continued)

FOREIGN PATENT DOCUMENTS

| CN | 1085073 A | 4/1994 |
| CN | 1100894 A | 4/1995 |

(Continued)

OTHER PUBLICATIONS

Naimi, et al., "Rosemary Extract as a Potential Anti-Hyperglycemic Agent: Current Evidence and Future Perspectives", Sep. 1, 2017, Nutrients; vol. 9, Issue 9, pp. 1-19.

(Continued)

*Primary Examiner* — Jyoti Chawla

(57) ABSTRACT

A solubilized steviol glycoside composition including one or more steviol glycosides and one or more steviol glycoside solubility enhancers can be used as a sweetener composition to sweeten other compositions (sweetenable compositions) such as foods, beverages, medicines, oral hygiene compositions, pharmaceuticals, nutraceuticals, and the like.

16 Claims, 17 Drawing Sheets

(56) References Cited

U.S. PATENT DOCUMENTS

| | | |
|---|---|---|
| 7,939,563 B2 | 5/2011 | Suzuki |
| 8,017,168 B2 | 9/2011 | Prakash |
| 8,076,491 B2 | 12/2011 | Karanewsky |
| 8,088,428 B2 | 1/2012 | Yamane |
| 8,092,795 B2 | 1/2012 | Tsuchiya |
| 8,178,148 B2 | 5/2012 | Fujii |
| 8,197,875 B2 | 6/2012 | Chien |
| 8,241,680 B2 | 8/2012 | Williams |
| 8,337,929 B2 | 12/2012 | Ogura |
| 8,367,137 B2 | 2/2013 | Prakash |
| 8,512,789 B2 | 8/2013 | Prakash |
| 8,524,304 B2 | 9/2013 | Prakash |
| 8,530,527 B2 | 9/2013 | Markosyan |
| 8,703,228 B2 | 4/2014 | Boghani |
| 8,940,350 B2 | 1/2015 | Prakash |
| 8,940,351 B2 | 1/2015 | Prakash |
| 8,956,678 B2 | 2/2015 | Prakash |
| 9,011,956 B2 | 4/2015 | Prakash |
| 9,060,537 B2 | 6/2015 | Mutilangi |
| 9,101,160 B2 | 8/2015 | Prakash |
| 9,101,161 B2 | 8/2015 | Prakash |
| 9,131,719 B2 | 9/2015 | Backes |
| 9,133,229 B2 | 9/2015 | Lee |
| 9,144,251 B2 | 9/2015 | Prakash |
| 9,149,051 B2 | 10/2015 | Prakash |
| 9,358,264 B2 | 6/2016 | Ibarra |
| 9,457,009 B2 | 10/2016 | Guthrie |
| 9,492,379 B2 | 11/2016 | Park |
| 9,510,611 B2 | 12/2016 | Purkayastha |
| 9,629,795 B2 | 4/2017 | Krammer |
| 9,636,373 B1 | 5/2017 | Akao |
| 9,775,822 B2 | 10/2017 | Prasad |
| 9,844,576 B2 | 12/2017 | Brownell |
| 9,848,624 B2 | 12/2017 | Ley |
| 9,889,107 B2 | 2/2018 | Guthrie |
| 9,962,356 B2 | 5/2018 | Prasad |
| 10,188,125 B2 | 1/2019 | Ozato |
| 10,376,521 B2 | 8/2019 | Zaworotko |
| 10,420,744 B2 | 9/2019 | Prasad |
| 10,602,758 B2 | 3/2020 | Dubois |
| 10,624,372 B2 | 4/2020 | Reichelt |
| 10,772,340 B2 | 9/2020 | Hotta |
| 10,780,170 B2 | 9/2020 | Purkayastha |
| 10,798,961 B2 | 10/2020 | Marcq |
| 10,849,339 B2 | 12/2020 | Prakash |
| 10,874,130 B2 | 12/2020 | Kim |
| 10,952,458 B2 | 3/2021 | Purkayastha |
| 10,973,794 B2 | 4/2021 | Forbes |
| 11,000,497 B2 | 5/2021 | Prasad |
| 2001/0051195 A1 | 12/2001 | Miljkovic |
| 2002/0068123 A1 | 6/2002 | Verhagen |
| 2002/0187239 A1 | 12/2002 | Miljkovic |
| 2002/0197386 A1 | 12/2002 | Hiramoto |
| 2003/0003212 A1 | 1/2003 | Chien |
| 2003/0008943 A1 | 1/2003 | Slone |
| 2003/0045473 A1 | 3/2003 | Sarama |
| 2003/0138537 A1 | 7/2003 | Bailey |
| 2003/0172392 A1 | 9/2003 | Mendu |
| 2004/0086619 A1 | 5/2004 | Zhong |
| 2004/0213881 A1* | 10/2004 | Chien ............... A23C 11/103 426/534 |
| 2005/0079232 A1 | 4/2005 | Offord-Cavin |
| 2005/0106215 A1 | 5/2005 | Offord-Cavin |
| 2005/0220868 A1 | 10/2005 | Lahl |
| 2006/0083838 A1 | 4/2006 | Jackson |
| 2006/0263475 A1 | 11/2006 | Jani |
| 2006/0280835 A1 | 12/2006 | Jani |
| 2006/0286202 A1 | 12/2006 | Boghani |
| 2007/0029258 A1 | 2/2007 | Takeda |
| 2007/0054023 A1 | 3/2007 | Bingley |
| 2007/0082106 A1 | 4/2007 | Lee |
| 2007/0116800 A1 | 5/2007 | Prakash |
| 2007/0116823 A1 | 5/2007 | Prakash |
| 2007/0116828 A1 | 5/2007 | Prakash |
| 2007/0116829 A1 | 5/2007 | Prakash |
| 2007/0116838 A1 | 5/2007 | Prakash |
| 2007/0116839 A1 | 5/2007 | Prakash |
| 2007/0128311 A1 | 6/2007 | Prakash |
| 2007/0292582 A1 | 12/2007 | Prakash |
| 2008/0014331 A1 | 1/2008 | Badalov |
| 2008/0063748 A1 | 3/2008 | Massey |
| 2008/0107787 A1 | 5/2008 | Prakash |
| 2008/0226788 A1 | 9/2008 | Chang |
| 2008/0226790 A1 | 9/2008 | Johnson |
| 2008/0261916 A1 | 10/2008 | Jaszberenyi |
| 2008/0292764 A1 | 11/2008 | Prakash |
| 2008/0292765 A1 | 11/2008 | Prakash |
| 2008/0292775 A1 | 11/2008 | Prakash |
| 2009/0004360 A1 | 1/2009 | Bingley |
| 2009/0053378 A1 | 2/2009 | Prakash |
| 2010/0028325 A1 | 2/2010 | Rocabayera Bonvila |
| 2010/0099857 A1 | 4/2010 | Evans |
| 2010/0160224 A1 | 6/2010 | Thomas |
| 2010/0297327 A1 | 11/2010 | Stangle |
| 2010/0330244 A1 | 12/2010 | Nonaka |
| 2011/0033525 A1 | 2/2011 | Liu |
| 2011/0091394 A1 | 4/2011 | Abelyan |
| 2011/0104353 A1 | 5/2011 | Lee |
| 2011/0160311 A1 | 6/2011 | Prakash |
| 2011/0189360 A1 | 8/2011 | Yoo |
| 2011/0195161 A1 | 8/2011 | Upreti |
| 2011/0195170 A1 | 8/2011 | Shigemura |
| 2011/0293538 A1 | 12/2011 | Ley |
| 2012/0041078 A1 | 2/2012 | Tachdjian |
| 2012/0058236 A1 | 3/2012 | Fosdick |
| 2012/0064221 A1 | 3/2012 | Given |
| 2012/0076899 A1 | 3/2012 | Evans |
| 2012/0156351 A1 | 6/2012 | Miyazawa |
| 2012/0177602 A1 | 7/2012 | New |
| 2012/0196019 A1 | 8/2012 | Shi |
| 2012/0201935 A1 | 8/2012 | Krohn |
| 2013/0039932 A1 | 2/2013 | Park |
| 2013/0040036 A1 | 2/2013 | Zeller |
| 2013/0209658 A1 | 8/2013 | Spelman |
| 2013/0251881 A1 | 9/2013 | Mutilangi |
| 2013/0274351 A1 | 10/2013 | Markosyan |
| 2013/0316066 A1 | 11/2013 | Brown |
| 2014/0004215 A1* | 1/2014 | Brownell ............ A61K 36/752 424/745 |
| 2014/0094453 A1 | 4/2014 | Tachdjian |
| 2014/0155359 A1 | 6/2014 | Broze |
| 2014/0171519 A1 | 6/2014 | Prakash |
| 2014/0206634 A1 | 7/2014 | Liu |
| 2014/0295049 A1 | 10/2014 | Ragot |
| 2014/0302180 A1 | 10/2014 | Chapal |
| 2014/0309294 A1 | 10/2014 | Erfurt |
| 2014/0342078 A1 | 11/2014 | Hayes |
| 2015/0017284 A1* | 1/2015 | Prakash ............... A23L 27/36 426/61 |
| 2015/0050410 A1 | 2/2015 | Luo |
| 2015/0125587 A1 | 5/2015 | Asano |
| 2015/0189904 A1 | 7/2015 | Prakash |
| 2015/0223510 A1 | 8/2015 | Lee |
| 2015/0289548 A1 | 10/2015 | Given |
| 2015/0320101 A1 | 11/2015 | Walton |
| 2015/0328179 A1 | 11/2015 | Nakashima |
| 2015/0366253 A1 | 12/2015 | Shi |
| 2016/0100689 A1 | 4/2016 | Wang |
| 2016/0113316 A1 | 4/2016 | Nachbagauer |
| 2016/0165941 A1 | 6/2016 | Hofmekler |
| 2016/0183574 A1 | 6/2016 | Chen |
| 2016/0213039 A1 | 7/2016 | Kumar |
| 2016/0242452 A1 | 8/2016 | Mutilangi |
| 2016/0309761 A1 | 10/2016 | Brower, III |
| 2016/0316797 A1 | 11/2016 | Piorkowski |
| 2017/0006901 A1 | 1/2017 | Carlson |
| 2017/0055548 A1 | 3/2017 | Chakraborty |
| 2017/0095443 A1 | 4/2017 | Luo |
| 2017/0105432 A1 | 4/2017 | Karanewsky |
| 2017/0119032 A1 | 5/2017 | Patron |
| 2017/0119033 A1 | 5/2017 | Liu |
| 2017/0143012 A1 | 5/2017 | San Miguel |
| 2017/0156374 A1 | 6/2017 | Ackilli |
| 2017/0172191 A1 | 6/2017 | Prakash |

(56) References Cited

U.S. PATENT DOCUMENTS

| | | |
|---|---|---|
| 2017/0183326 A1 | 6/2017 | Kimoto |
| 2017/0273338 A1 | 9/2017 | Lee |
| 2017/0303574 A1 | 10/2017 | Luo |
| 2017/0354175 A1 | 12/2017 | Karanewsky |
| 2017/0362268 A1 | 12/2017 | Carlson |
| 2018/0000133 A1 | 1/2018 | Izumi |
| 2018/0002306 A1 | 1/2018 | Jiang |
| 2018/0086751 A1 | 3/2018 | Karanewsky |
| 2018/0092381 A1 | 4/2018 | Brijwani |
| 2018/0103670 A1 | 4/2018 | Recenti |
| 2018/0168212 A1 | 6/2018 | Markosyan |
| 2018/0177216 A1 | 6/2018 | Markosyan |
| 2018/0263269 A1 | 9/2018 | Prakash |
| 2018/0289042 A1 | 10/2018 | Bell |
| 2018/0296678 A1 | 10/2018 | Prakash |
| 2019/0116835 A1 | 4/2019 | Prakash |
| 2019/0142043 A1 | 5/2019 | Prakash |
| 2019/0175499 A1 | 6/2019 | Zhang |
| 2019/0274985 A1 | 9/2019 | Hotta |
| 2019/0313669 A1 | 10/2019 | Dubois |
| 2020/0009208 A1 | 1/2020 | Hwang |
| 2020/0023021 A1 | 1/2020 | Lewis |
| 2020/0054058 A1 | 2/2020 | Prakash |
| 2020/0085778 A1 | 3/2020 | Yamamoto |
| 2020/0138056 A1 | 5/2020 | Graz |
| 2020/0138765 A1 | 5/2020 | Prasad |
| 2020/0154737 A1 | 5/2020 | Dubois |
| 2020/0196649 A1 | 6/2020 | Mitchell |
| 2020/0197342 A1 | 6/2020 | Russo |
| 2020/0237845 A1 | 7/2020 | Suzuki |
| 2020/0275682 A1 | 9/2020 | Chakraborty |
| 2020/0305483 A1 | 10/2020 | Gan |
| 2020/0345049 A1 | 11/2020 | Galano |
| 2021/0037851 A1 | 2/2021 | Fraser |
| 2021/0051976 A1 | 2/2021 | Fraser |
| 2021/0084949 A1 | 3/2021 | Banavara |
| 2021/0092986 A1 | 4/2021 | Dubois |
| 2021/0128600 A1 | 5/2021 | Rauch |
| 2021/0153536 A1 | 5/2021 | Ozato |
| 2021/0236450 A1 | 8/2021 | Guthrie |
| 2021/0260013 A1 | 8/2021 | Lee |
| 2021/0267243 A1 | 9/2021 | Peterson |

FOREIGN PATENT DOCUMENTS

| | | |
|---|---|---|
| CN | 1336333 A | 2/2002 |
| CN | 1651398 A | 8/2005 |
| CN | 1253099 | 4/2006 |
| CN | 100341500 C | 10/2007 |
| CN | 102381974 A | 3/2012 |
| CN | 102771751 A | 11/2012 |
| CN | 102860438 A | 1/2013 |
| CN | 104397785 A | 3/2015 |
| CN | 102924544 B | 4/2015 |
| CN | 103656627 B | 9/2015 |
| CN | 103874411 A | 6/2016 |
| CN | 106138298 A | 11/2016 |
| CN | 107184482 A | 9/2017 |
| CN | 107455718 A | 12/2017 |
| DE | 29603759 U1 | 5/1996 |
| DE | 29808384 U1 | 8/1998 |
| EP | 0730830 A | 9/1996 |
| EP | 1186297 A2 | 3/2002 |
| EP | 1903890 B1 | 4/2008 |
| EP | 1716757 B1 | 7/2009 |
| EP | 1925208 B1 | 12/2011 |
| EP | 2340719 B1 | 2/2014 |
| EP | 2896301 B1 | 6/2016 |
| EP | 2643007 B1 | 8/2016 |
| EP | 3052074 A1 | 8/2016 |
| EP | 2625962 B1 | 6/2017 |
| EP | 3188604 A1 | 7/2017 |
| EP | 3257507 A1 | 12/2017 |
| EP | 3264919 A1 | 1/2018 |
| EP | 3097790 B1 | 5/2018 |
| EP | 2409696 B1 | 6/2018 |
| EP | 2753188 B1 | 1/2019 |
| EP | 2856883 B1 | 3/2019 |
| EP | 2692243 B1 | 6/2019 |
| EP | 3397072 B1 | 7/2019 |
| EP | 3513663 A1 | 7/2019 |
| EP | 3169166 B1 | 8/2019 |
| EP | 3524062 A2 | 8/2019 |
| EP | 2934181 B1 | 9/2019 |
| EP | 2124647 B2 | 12/2019 |
| EP | 3228195 B1 | 1/2020 |
| EP | 3544445 B1 | 5/2020 |
| FR | 2138067 B1 | 6/1976 |
| GB | 2348104 A | 5/1999 |
| JP | 54147976 A | 11/1979 |
| JP | 63173531 A | 7/1988 |
| JP | 0195739 A | 4/1989 |
| JP | 0427374 A | 1/1992 |
| JP | 04145048 A | 5/1992 |
| JP | 0638723 A | 2/1994 |
| JP | 07123921 A | 5/1995 |
| JP | 07135938 A | 5/1995 |
| JP | 0823939 A | 1/1996 |
| JP | 0994080 A | 4/1997 |
| JP | 09221667 A | 8/1997 |
| JP | 09266767 A | 10/1997 |
| JP | 10179079 A | 7/1998 |
| JP | 10183164 A | 7/1998 |
| JP | 10248501 A | 9/1998 |
| JP | 119189 A | 1/1999 |
| JP | 11299473 A | 11/1999 |
| JP | 2000063827 A | 2/2000 |
| JP | 2000308477 A | 11/2000 |
| JP | 2002021938 A1 | 1/2002 |
| JP | 2004528050 A | 9/2004 |
| JP | 2006006318 A | 1/2006 |
| JP | 2009517022 A | 4/2009 |
| JP | 2009523407 A | 6/2009 |
| JP | 2010521166 A | 6/2010 |
| JP | 2011168543 A | 9/2011 |
| JP | 2012005483 A | 1/2012 |
| JP | 2012240949 A | 12/2012 |
| JP | 2011071179 A | 4/2013 |
| JP | 2015506718 A | 3/2015 |
| JP | 2015511498 A | 4/2015 |
| JP | 2016084887 A | 9/2017 |
| JP | 2018085964 A | 6/2018 |
| JP | 6710115 B2 | 6/2020 |
| JP | 2019230013 A | 6/2020 |
| KR | 101500485 B1 | 3/2015 |
| PH | 12011000255 A | 7/2011 |
| WO | 1998042209 A1 | 10/1998 |
| WO | 1999030576 W | 6/1999 |
| WO | 2000030464 A1 | 6/2000 |
| WO | 2000062628 A1 | 10/2000 |
| WO | 2000069282 A1 | 11/2000 |
| WO | 2001097624 A1 | 12/2001 |
| WO | 2002041700 A1 | 5/2002 |
| WO | 02100192 W | 12/2002 |
| WO | 2002096852 A1 | 12/2002 |
| WO | 2007013616 A1 | 2/2007 |
| WO | 2007061753 A2 | 5/2007 |
| WO | 2007061795 A1 | 5/2007 |
| WO | 2007149672 A2 | 12/2007 |
| WO | 2008057965 A2 | 5/2008 |
| WO | 2008093892 A1 | 8/2008 |
| WO | 2008147723 A1 | 12/2008 |
| WO | 2008147725 A1 | 12/2008 |
| WO | 2009012051 A1 | 1/2009 |
| WO | 2010038911 A1 | 4/2010 |
| WO | 11094423 W | 8/2011 |
| WO | 2011094423 A1 | 8/2011 |
| WO | 2011105561 A1 | 9/2011 |
| WO | 2011106114 A1 | 9/2011 |
| WO | 2011112892 A1 | 9/2011 |
| WO | 2012083251 A1 | 6/2012 |
| WO | 2012107205 A1 | 8/2012 |
| WO | 2012109506 A1 | 8/2012 |
| WO | 2012166164 A1 | 12/2012 |

(56) References Cited

FOREIGN PATENT DOCUMENTS

| | | | |
|---|---|---|---|
| WO | 2013096420 A1 | 6/2013 | |
| WO | 2013148177 A1 | 10/2013 | |
| WO | 2014104408 A1 | 7/2014 | |
| WO | 2014146135 A2 | 9/2014 | |
| WO | 2014153000 A1 | 9/2014 | |
| WO | 2015023928 A1 | 2/2015 | |
| WO | 2015024218 A1 | 2/2015 | |
| WO | 2015117011 A1 | 8/2015 | |
| WO | 2016036578 A1 | 3/2016 | |
| WO | 2016049236 A1 | 3/2016 | |
| WO | 2016073251 A1 | 5/2016 | |
| WO | 16085919 W | 6/2016 | |
| WO | 16085924 W | 6/2016 | |
| WO | 16086233 W | 6/2016 | |
| WO | WO-2016100689 A1 * | 6/2016 | ............ A23L 27/36 |
| WO | 17053980 W | 3/2017 | |
| WO | 2017095932 A1 | 6/2017 | |
| WO | 17120480 W | 7/2017 | |
| WO | 17189994 W | 11/2017 | |
| WO | 2017196933 A1 | 11/2017 | |
| WO | 2018013739 A2 | 1/2018 | |
| WO | 2018102447 A2 | 6/2018 | |
| WO | 19177634 W | 9/2019 | |
| WO | 2019177634 A1 | 9/2019 | |
| WO | 19222601 W | 11/2019 | |
| WO | 2020172276 W | 8/2020 | |
| WO | 2020202193 W | 10/2020 | |
| WO | 2020237060 A1 | 11/2020 | |
| WO | 2021038830 W | 3/2021 | |
| WO | 2021038832 W | 3/2021 | |
| WO | 2021049864 W | 3/2021 | |
| WO | 2021081417 A1 | 4/2021 | |
| WO | 2021090989 A1 | 5/2021 | |
| WO | 2021091322 A1 | 5/2021 | |
| WO | 2021091327 A1 | 5/2021 | |
| WO | 2021125070 A1 | 6/2021 | |
| WO | 2021132439 W | 7/2021 | |

OTHER PUBLICATIONS

Nalte, YK, et al., Solubility Enhancement of Nevirapine by Cocrystallisation Technique. Journal of Pharmacy Research. Aug. 21, 2015, vol. 9, No. 8; pp. 556-561. ISSN:0974-6943.

Nguyen et al., "Facile preparation of water soluble curcuminoids extracted from turmeric (Curcuma longa L.) power by using steviol glucosides," Food Chemistry, 2017, 214, 366-373.

Nicoud, et al., "Estimation of the solubility of metastable polymorphs: A critical review," Cryst. Growth Des., 2018.

Notice of Opposition in EP2934181.

Ohta et al., "Characterization of Novel Steviol Glycosides from Leaves of Stevia rebaudiana Morita," 2010, J. Appl. Glycosci., 57, 199-209.

Prakash Indra et al: "Synthesis and Sensory Evaluation of ent-Kaurane Diterpene Glycosides", Molecules, [Online] vol. 17, No. 8, Jan. 1, 2012 (Jan. 1, 2012), pp. 8908-8916, XP055839039, DOI: 10.3390/molecules17088908 Retrieved from the Internet: URL:https://www.ncbi.nlm.nih.gov/pmc/artic les/PMC6268950/pdf/molecules-17-08908.pdf> [retrieved on Aug. 5, 2021].

Prakash, "Characterization and sensory evaluation of a hexa B-D-glucopyranosyl diterpene from Stevia rebaudiana," Natural Products Communications, 2013, 8:1523-1526.

Prakash, et al., "Development of novel functional confectionery using low reduced sugar," Indian Journal of Drugs, 2016, 4(4), 141-148.

Rogers et al., "Changes to the content of sugars, sugar alcohols, myo-inositol, carboxylic acids and inorganic anions in developing grains from different varieties of Robusta (Coffea canephora) and Arabica (C. arabica) coffees," Plant Science, 1999, 149, 115-123.

Roy, G., "Bitterness: reduction and inhibition," Trends Food Sci Tech, 1992, 3, 85-91.

Schwarz et al., "Investigation of plant extracts for the protection of processed foods against lipid oxidation." Eur Food Res Technol, 2001, 212:319-328.

Shibata et al., "Glucosylation of steviol and steviol-glucosides in extracts from Stevia rebaudiana Bertoni," Plant Physiol., 1991, 95, 152-156.

Shiraishi et al., "Taste-Masking Effect of Chlorogenic Acid (CGA) on Bitter Drugs Evaluated by Taste Sensor and Surface Plasmon Resonance on the Basis of CGA-Drug Interactions," 2017, 65(2):127-133, Chem Pharm Bull (Tokyo).

Standard Method Performance Requirements (SMPRs) for Determination of Phenolic Compounds in Dietary Supplements and Dietary Ingredients Containing Echinacea, Sep. 22, 2017, AOAC International.

Stukelj, et al., "Direct measurement of amorphous solubility," Analytical Chemistry, 2019.

Suarez-Quiroz et al., "Isolation of green coffee chlorogenic acids using activated carbon," Journal of Food Composition and Analysis, 2014, 33:55-58.

SUNUP® Commercially available stevia sweetened green coffee bean beverage, purchased Jun. 2018.

Sweet Drops™ Liquid Stevia Product, 2012.

Tanaka, O., "Improvement of taste of natural sweeteners," Pure & Appl. Chem., 69(4):975-683, 1997.

Trugo et al., Chlorogenic Acid Composition of Instant Coffees, Analyst, Mar. 1984, vol. 109, pp. 263-266.

Tyrer, D., "The theory of solubility," The Journal of Physical Chemistry, 1912.

Upreti, Mani et al., "Solubility Enhancement of Steviol Glycosides and Characterization of Their Inclusion Complexes with Gamma-Cyclodextrin", Int. J. Mol. Sci. 2011, 12, 7529-7553.

Weidel et al., "A Rapid Method for Quantifying Chlorogenic Acid Levels in Potato Samples," Journal of AOAC International, vol. 97, No. 3, Nov. 3, 2014.

Whole Foods 365 Stevia Extract Liquid, 2012.

Wildermuth et al., "Chlorogenic acid oxidation and its reaction with sunflower proteins to form green-colored complexes," Comprehensive Reviews in Food Science and Food Safety, 2016, vol. 15, 829-843.

Written Opinion of WO 2012/082587, dated Jun. 13, 2013.

Ana Covarrubias-Cárdenas et al, "Antioxidant Capacity and UPLC-PDA ESI-MS Phenolic Profile of Stevia rebaudiana Dry Powder Extracts Obtained by Ultrasound Assisted Extraction", Agronomy,vol. 8, No. 9, Aug. 31, 2018 (Aug. 31, 2018), p. 170.

Analysis of the chemical constituents of Stevia rebausiana and its sweetness Reb M structure, Mar. 20, 2012, Journal of Beijing University of Chemical Technology (Natural Science).

Anonymous, "Sparkling Organic Grapefruit Ginger Soda", GNPD 2012, retrieved from www.gnpd.comDatabase accession No. 1790955.

Anonymous, "Stevia production process | Cargill no-calories sweeteners | Cargill", Nov. 4, 2020 (Nov. 4, 2020), Retrieved from the Internet: URL:https://www.cargill.com/food-beverage/emea/stevia-based-sweeteners-production-process.

Anonymous, "Steviol Glycosides Based Table Sweetener", GNPD-Dec. 14, 2018 (Dec. 14, 2018), Database accession No. 6205393.

Aranda Gonzalez, et al., "Effect of different drying methods on the composition of steviol glycosides in Stevia rebaudiana Bertoni leaves," Int. Agrophys., 2017, 31, 139-144.

Arthur, R., "'The stevia story has changed!' PureCircle on the evolution of the natural sweetener," Mar. 11, 2019, Beveragedaily.com.

Augustijns and Brewster, "Solvent systems and their selection in pharmaceutics and biopharmaceutics," Springer, 2009.

Bartoshuk et al., "Sweet Taste of Water Induced by Artichoke," Dec. 1, 1972, Science, 178 (4064), 988-990.

Berte et al. (2011) J. Agric. Food Chem. 59: 5523-5527. (Year: 2011).

Brent, Rhea, "Investigating differences in solubility between crystalline and amorphous forms of pharmaceuticals," AstraZeneca, Mat 2006.

Brittain, Harry, "Thermodynamic vs. kinetic solubility: knowing which is which," American Pharmaceutical Review, 2014.

(56) References Cited

OTHER PUBLICATIONS

Chang, et al., "Stability studies of stevioside and Rebaudioside A in carbonated beverages," J. Agric. Food Chem., 1983, 31, 409-412.
Chiou, et al., "A comparison of crystallisation approaches in spray drying," Jounral of Food Engineering, 2008.
Cilliers, et al., "Total polyphenols in apples and ciders; correlation with chlorogenic acid," Journal of Food Science, vol. 55, No. 5, 1990, pp. 1458-1459.
Clifford, "Chlorogenic acids and other cinnamates—nature, occurance, and dietary burden," Journal of the Science of Food and Agriculture, 79:362-372 (1999).
Coquerel, Gerard, "Crystallization of molecular systems from solution: phase diagrams, supersturation, and other basic concepts," Chem Soc Rev, 2014.
Craig et al., "Performance review of a fast HPLC-UV method for the quantification of chorogenic acids in green coffee bean extracts," Talanta, 154 (2016) 481-485.
Crammer and R I Kan B: II Properties and syntheses of sweetening agents, Chemical Society Reviews, Royal Society of Chemistry, UK, vol. 6, Jan. 1, 1977 (Jan. 1, 1977), pp. 431-465, XP009150156, ISSN 0306-0012 p. 437, paragraph 2—p. 438, paragraph 1.
Cros et al., "Solvent Extraction of Oil and Chlorogenic Acid from Green Cofffee Part I: Equilibrium Data," Journal of Food Engineering 10 (1989) 1-11.
Deladino L., et al., "Major phenolics in Yerba mate extracts(*Ilex paraguariensis*) and their contribution to the total antioxidant capacity," Food and Nutritional Science, 4, 2013.
Douglass, et al., "Kinetics of dissolution of an amorphous solid," J. Phys. Chem. B, 2018.
DuBois, G. E., et al., "Concentration-Response relationship of sweeteners," ACS Syposium Series, 1991.
Edgar Naegele, "Determination of Chlorogenic Acid in Coffee Products According to DIN 10767," Sep. 1, 2016, Agilent Technology, INC.
Fu et al., "Production of chlorogenic acid and its derivatives in hairy root cultures of Stevia rebaudiana," Jan. 14, 2015, Journal of Agriculatural and Food Chemistry, 63(1):262-268.
Gawel-Beben et al., "Stevia rebuadiana Bert. Leaf extracts as a multifunctional source of natural antioxidants," Molecules, Mar. 27, 2015.
Giordani, Antonio, "The amorphous form in drug development," Crystal Forms, 2012.
Hancock, B. C., et al. "What is the true solubility advantage for amorphous pharmaceuticals?," Pharm Res, 17:397-404, 2000.
Hernandez T et al., "Variations in the phenolic composition of fruit juices with different treatments," European Food Research and Technology, vol. 204, No. 2, 1997, p. 151-155.
Hildebrand, Joel, "Theory of solubility," Physical Review, 1923.
Islam, et al., "Particle crystallization during spray drying in humid air," Journal of Food Engineering, 2010.
Jeon et al., "Contents of chlorogenic acids and caffeine in various coffee-related products," Journal of Advanced Research, 17 (2019), 85-94.
Julia Y.Q. Low et al, "Psychophysical Evaluation of Sweetness Functions Across Multiple Sweeteners", Chemical Senses.,vol. 42, No. 2, Oct. 20, 2016 (Oct. 20, 2016), p. 111-120.
Kellie P Burris et al, "Composition and Bioactive Properties of Yerba Mate (*Ilex paraguariensis* A. St.-Hil.): A Review", Chillán Jun. 2012 (Jun. 2012), p. 268-275.
Kremr et al., "Unremitting Problems with Chlorogenic Acid Nomenclature: A Review," Quim. Nova, vol. 39, No. 4, 530-533, 2016.
Kren, V., et al., "Glycosides in Medicine: The Role of Glycosidic Residue in Biological Activity", Current Medicinal Chemistry, 2001, 8, 1313-1338.
Kroyer, G., "Stevioside and Stevia-sweetener in food: application, stability and interaction with food ingredients," J. Verbr. Lebensm., 2010, 5:225-229.
Ky et al., "Camparison of Five Purification Methods for Chlorogenic Acids in Green Coffee Beans (*Coffea* sp.)," J. Agric. Food Chem. 1997, 45, 786-790, obtained from https://horizon.documentation.ird.fr/exl-doc/pleins_textes/pleins_textes_6/b_fdi_47-48/010010457.pdf.
Lee et al., "Chicoric acid: chemistry distribution, and production," Frontiers in Chemistry, 2013, 1(40).
Liquid Stevia and Liquid Stevia (flavored) from Stevita Co., 2012.
Maietta et al., "Artichoke (*Cynara cardunculus* L. var. *scolymus*) waste as a natural source of carbonyl trapping and antiglycative agents," Food Research International, 100 (2017) 780-790.
Masuda, et al., "Powder Technology Handbook," Taylor & Francis, 2006.
Meilgaard MC, Civille GV, and Carr BT (2007). Sensory Evaluations Techniques, CRC Press, Boca Raton, FL.
Meinhart et al., "Analysis of chlorogenic acids isomers and caffeic acid in 89 herbal infusions (tea)," Journal of Food Composition and Analysis, 73 (2018) 76-82.
Meinhart et al., "Chlorogenic acid isomer contents in 100 plants commercialized in Brazil," Food Research International, 99 (2017) 522-530.
Meireles et al., "Stevia (*Stevia rebaudiana* Bertoni):—Futuristic view of the sweeter side of life," Floriculture, Ornamental and Plant Biotechnology Volumn IV, 2006, Global Science Books.
Miura et al., "Molecularly imprinted polymer for chlorogenic acid by modified precipitation polymerization and its application to extraction of chlorogenic acid from Eucommia ulmodies leaves," Journal of Pharmaceutical and Biomedical Analysis, 114 (2015) 139-144.
Murdande, et al., "Aqueous solubility of crytalline and amorphous drugs: challenges in measurement," Pharmaceutical Development and Technology, 2011.
Murdande, et al., "Solubility Advantage of amorphous pharmaceuticals: I. A thremodynamic analysis," Wiley InterScience, 2009.
Murshedkav, Tooba, "Effect of crystalline to amorphous coversion on solubility of cefuroxime axetil," Univeristy of Rhode Island, 2002.
Abeywardena M. Y., et al. (2010) Acute administration of chlorogenic acid reduces blood pressure in the rat. Hypertension 55, 1493 [abstract 002]. DOI:10.1161/HYP.0b013e3181df4279.
Albas C. S., et al (2014) Avaliação da genotoxicidade da *Ilex paraguariensis* (erva mate) pelo teste do micronúcleo /[Evaluation of the genotoxicity of *Ilex paraguariensis* (yerba mate) by micronucleus test]. Rev. Bras. Plantas Med. 16, 2, Suppl 1, 345-349 [Portuguese, English abstract], DOI:10.1590/1983-084X/12_058.
Alkhatib A. and Atcheson, R. (2017) Yerba maté (*Ilex paraguariensis*) metabolic, satiety, and mood state effects at rest and during prolonged exercise. Nutrients 9, 882 [15pp] DOI:10.3390/nu9080882.
Balsan G., et al. (2019) Effect of yerba mate and green tea on paraoxonase and leptin levels in patients affected by overweight or obesity and dyslipidemia: a randomized clinical trial. Nutr. J. 18, 5 [10pp]. DOI:10.1186/s12937-018-0426-y.
Bariana D. S., et al. (1965) Chlorogenic acid: further evidence for its antigenic and allergenic activity. Nature 207, 1155-1157 DOI:10.1038/2071155a0.
Bidau C. J., et al. (2004) Evaluation of the genotoxicity of aqueous extracts of Ilex paraguariensis St. Hil. (Aquifoliaceae) using the Allium test. Cytologia 69, 109-117. DOI:10.1508/cytologia.69.109.
Boaventura B. C., et al. (2012) Association of mate tea (*Ilex paraguariensis*) intake and dietary intervention and effects on oxidative stress biomarkers of dyslipidemic subjects. Nutrition 28, 657-664. DOI:10.1016/j.nut.2011.10.017.
Boaventura B. C., et al. (2013) Antioxidant potential of mate tea (*Ilex paraguariensis*) in type 2 diabetic mellitus and pre-diabetic individuals. J. Funct. Foods 5, 1057-1064. DOI:10.1016/j.jff.2013.03.001.
Boaventura B. C., et al. (2015) Effect of yerba mate (*Ilex paraguariensis* A. St. Hil.) infusion obtained by freeze concentration technology on antioxidant status of healthy individuals. LWT Food Sci. Technol. 62, 948-954. DOI:10.1016/j.lwt.2015.02.028.
Boaventura, B. C. B., et al (2013). Enhancement of bioactive compounds content and antioxidant activity of aqueous extract of mate (*Ilex paraguariensis* A. St. Hil.) through freeze concentration technology. Food Research International, 53, 686e692.

(56) References Cited

OTHER PUBLICATIONS

Borges M. C., et al. (2013) The effect of mate tea (*Ilex paraguariensis*) on metabolic and inflammatory parameters in high-fat diet-fed Wistar rats. Int. J. Food Sci. Nutr. 64, 561-569. DOI:10.3109/09637486.2012.759188.

Bortoluzzi M.-C., et al (2014) Frequency of micronucleus in oral epithelial cells after exposure to mate-tea in healthy humans. Med. Oral Patol. Oral Cir. Bucal. 19, e345-e349 DOI:10.4317/medoral.19570.

Carvalho Ribeiro M., et al (2017) The effects of roasted yerba mate (*Ilex paraguariensis* A. St. Hil.) consumption on glycemia and total serum creatine phosphokinase in patients with traumatic brain injury. J. Funct. Foods 28, 240-245. DOI:10.1016/j.jff.2016.11.

Chaube S. and Swinyard C. A. (1976) Teratological and toxicological studies of alkaloidal and phenolic compounds from *Solanum tuberosum* L. Toxicol. Appl. Pharmacol. 36, 227-237. DOI:10.1016/0041-008X(76)90002-8.

Chen J., et al. (2018) Dietary chlorogenic acid improves growth performance of weaned pigs through maintaining antioxidant capacity and intestinal digestion and absorption function. J. Anim. Sci. 96, 1108-1118. DOI:10.1093/jas/skx078.

Cuesta A., et al (2018) Efecto agudo del consumo de yerba mate (*Ilex paraguariensis*) sobre el ritmo cardíaco en pacientes derivados para estudio Holter [Acute effect of yerba mate (*Ilex paraguariensis*) consumption on heart rhythm in patients referred for Holter study] [epub ahead of print]. Arch. Cardiol. Mex. xxx, Jun. 2, 2018 [1-6] [Spanish, English abstract]. DOI:10.1016/j.acmx.2018.05.004.

de Andrade F., Coehlo de Albuquerque C. A., Maraschin M. and da Silva E. L. (2012) Safety assessment of yerba mate (*Ilex paraguariensis*) dried extract: results of acute and 90 days subchronic toxicity studies in rats and rabbits. Food Chem. Toxicol. 50, 328-334. DOI:10.1016/j.fct.2011.08.028.

De Meneses Fujii et al. (2014) Yerba Mate (*Ilex paraguariensis*) modulates NF-kappaB pathway and AKT expression in the liver of rats fed on a high-fat diet. Int. J. Food Sci. Nutr. 65, 967-976. DOI:10.3109/09637486.2014.945153.

de Morais E. C., et al (2009) Consumption of yerba mate (*Ilex paraguariensis*) improves serum lipid parameters in healthy dyslipidemic subjects and provides an additional LDL-cholesterol reduction in individuals on statin therapy. J. Agric. Food Chem. 57, 8316-8324. DOI:10.1021/jf901660g.

Eklund A. (1975) Effect of chlorogenic acid in a casein diet for rats. Nutritional and pathological observations. Nutr. Metab. 18, 258-264. DOI:10.1159/000175603.

Enokuchi Y., et al. (2020) Effects of chlorogenic acids on menopausal symptoms in healthy women: a randomized, placebo-controlled, double-blind, parallel-group trial. Nutrients 12, 3757 [12pp]. DOI:10.3390/nu12123757.

Erk T., et al. (2012) Dose-dependent absorption of chlorogenic acids in the small intestine assessed by coffee consumption in ileostomists. Mol. Nutr. Food Res. 56, 1488-1500. DOI:10.1002/mnfr.201200222.

Folwarczna J., et al. (2012) Effects of caffeic and chlorogenic acids on bone mechanical properties in female rats. Bone 50, Suppl. 1, S158 [abstract PP306]. DOI:10.1016/j.bone.2012.02.495.

Fonseca C. A., et al (2000) Nontoxic, mutagenic, and clastogenic activities of mate-chimarrao (*Ilex paraguariensis*). J. Environ. Pathol. Toxicol. Oncol. 19, 333-346.

Frank J., et al. (2003) The dietary hydroxycinnamate caffeic acid and its conjugate chlorogenic acid increase vitamin E and cholesterol concentralions in Sprague-Dawley rats. J. Agric. Food Chem. 51, 2526-2531. DOI:10.1021/jf026127k.

Freedman S. O., et al. (1961) Chlorogenic acid: an allergen in green coffee bean. Nature 192, 241-243. DOI:10.1038/192241a0.

Freedman S. O., et al. (1964) Antigenic and allergenic properties of chlorogenic acid man, rabbit, guinea pig. Can. Med. Assoc. J. 90, 473-474.

Gebara K. S., et al. (2020) A randomized crossover intervention study on the effect a standardized maté extract (*Ilex paraguariensis* A. St.-Hil.) in Men predisposed to cardiovascular risk. Nutrients, 13, 14 [14pp], DOI:10.3390/nu13010014.

Gómez-Juaristi M., Martínez-López S., Sarria B., Bravo L. and Mateos R. (2018) Absorption and metabolism of yerba mate phenolic compounds in humans. Food Chem. 240, 1028-1038. DOI:10.1016/j.foodchem.2017.08.003.

Gonthier M.-P., et al. (2006) Microbial metabolism of caffeic acid and its esters chlorogenic and caftaric acids by human faecal microbiota in vitro. Biomed. Pharmacother. 60, 536-540 DOI:10.1016/j.biopha.2006.07.084.

Grzesiuk J. D., et al (2012) Evaluation of mutagenicity and antimutagenicity of Ilex paraguariensi} A. St.-Hil.: Aquifoliaceae infusion on Allium cepa assay. Arq. Cienc. Saude UNIPAR 16, 73-78. DOI:10.25110/arqsaude.v16i2.2012.4840.

Gu R., et al. (2007) Simultaneous determination of 1,5-dicaffeoylquinic acid and its active metabolites in human plasma by liquid chromatography-tandem mass spectrometry for pharmacokinetic studies. J. Chromatogr. B. 852, 85-91. DOI:10.1016/j.jchromb.2006.12.055.

Hernandes L. C., et al. (2016) Cytotoxicity and genotoxicity of chlorogenic acid alone or associated with the demethylating drug 5-azacytidine in Jurkat cells. Toxicol. Lett. 258, Suppl. S, S56 [abstract OSC01-007]. DOI:10.1016/i.toxlet.2016.06.1295.

IARC (1991) Mate. In Coffee, Tea, Mate, Methylxanthines and Methylglyoxal. IARC Working Group, Feb. 27-Mar. 6, 1990, Lyon. IARC Monographs on the Evaluation of Carcinogenic Risks to Humans, vol. 51, pp. 273-287. World Health Organization (WHO), International Agency for Research on Cancer (IARC).

IARC (2018) Drinking mate and very hot beverages. In Drinking Coffee, Mate, and Very Hot Beverages. Expert Opinions of IARC Working Group on the Evaluation of Carcinogenic Risks to Humans, May 24-31, 2016, Lyon, France. IARC Monographs on the Evaluation of Carcinogenic Risks to Humans, vol. 116, pp. 427-496. Lyon, France: International Agency for Research on Cancer (IARC), Lyon, France.

Jin S., et al. (2015) Chlorogenic acid improves late diabetes through adiponectin receptor signaling pathways in db/db mice. PLoS ONE 10, e0120842 [15pp]. DOI:10.1371/journal.pone.0120842.

Kato M., et al. (2018) Effect of chlorogenic acid intake on cognitive function in the elderly: a pilot study. Evid. Based. Complement. Alternat. Med. 2018, Article ID 8608497 [8pp]. DOI:10.1155/2018/8608497.

Kim H. J., et al. (2012) Effect of green mate in overweight volunteers: a randomised placebo-controlled human study. J. Funct. Foods 4, 287-293. DOI:10.1016/j.jff.2011.12.005.

Kim S.-Y., et al. (2015) Anti-obesity effects of Yerba Mate (*Ilex paraguariensis*): a randomized, double-blind, placebo-controlled clinical trial. BMC Complement. Altern. Med. 15, 338 [8pp]. DOI:10.1186/s12906-015-0859-1.

Klein G. A., et al (2011) Mate tea (*Ilex paraguariensis*) improves glycemic and lipid profiles of type 2 diabetes and pre-diabetes individuals: a pilot study. J. Am. Coll. Nutr. 30, 320-332.

Kujawska M (2018) Yerba mate (*Ilex paraguariensis*) beverage: nutraceutical ingredient or conveyor for the intake of medicinal plants? Evidence from Paraguayan folk medicine. Evid. Based. Complement. Alternat. Med. 2018, Article ID 6849317 [17pp]. DOI:10.1155/2018/6849317.

Laird Layton L., et al. (1964) Pure chlorogenic acid is not allergenic in atopy to green coffee: A specific protein probably is involved. Nature 203, 188-189. DOI:10.1038/203188a0.

Leitão A. C. and Braga R. S. (1994) Mutagenic and genotoxic effects of mate (*Ilex paraguariensis*) in prokaryotic organisms. Braz. J. Med. Biol. Res. 27, 1517-1525.

Lin M., et al. (2013) Evaluation of the potential sensitization of chlorogenic Acid: a meta-analysis. Evid. Based. Complement. Alternat. Med. 2013, Article ID 208467 DOI:10.1155/2013/208467.

Liu B., et al. (2017) Preparation, phytochemical investigation, and safety evaluation of chlorogenic acid products from Eupatorium adenophorum. Molecules 22, 67 [12pp]. DOI:10.3390/molecules22010067.

(56) References Cited

OTHER PUBLICATIONS

Liu Z., et al. (2010) Evaluation of the immunosensitizing potential of chlorogenic acid using a popliteal lymph node assay in BALB/c mice. Food Chem. Toxicol. 48, 1059-1065. DOI:10.1016/j.fct.2010.01.024.

Lowell F. C. (1965) Allergenicity of chlorogenic acid. J. Allergy 36, 308. DOI:10.1016/0021-8707(65)90091-2.

Marques V. X. and Farah A. (2010) Urinary excretion of chlorogenic acids and metabolites in humans after green mate (*I. paraguariensis*) consumption. FASEB J. 24, 1, Suppl., [abstract 922.1] DOI:10.1096/fasebj.24.1_supplement.922.1.

Matsumoto R. L. T., et al. (2009) Effects of maté tea (*Ilex paraguariensis*) ingestion on mRNA expression of antioxidant enzymes, lipid peroxidation, and total antioxidant status in healthy young women. J. Agric. Food Chem. 57, 1775-1780. DOI:10.1021/jf803096g.

Mello F. W., et al. (2018) Maté consumption association with upper aerodigestive tract cancers: a systematic review and meta-analysis. Oral Oncol. 82, 37-47 [plus supplementary data]. DOI:10.1016/j.oraloncology.2018.04.023.

Messina D., et al. (2017) Maté tea and lipid profile in overweight women under caloric restriction. Ann Nutr. Metab. 71, 384 [abstract 144-1131]. DOI:10.1159/000480486.

Mikulasova M., et al. (2005) Genotoxic effects of the hydroxycinnamic acid derivatives—caffeic, chlorogenic and cichoric acids. Biologia (Bratisl.) 60, 275-279.

Minuzzi Becker A., et al. (2019) Spray-dried yerba mate extract capsules: clinical evaluation and antioxidant potential in healthy individuals. Plant oods Hum. Nutr. 74, 495-500 [plus supplementary tables], DOI:10.1007/s11130-019-00764-4.

Miranda D. D. C., et al. (2008) Protective effects of mate tea (*Ilex paraguariensis*) on H2O2-induced DNA damage and DNA repair in mice. Mutagenesis 23, 261-265. DOI:10.1093/mutage/gen011.

Monteiro M., et al. (2007) Chlorogenic acid compounds from coffee are differentially absorbed and metabolized in humans. J. Nutr. 137, 2196-2201. DOI:10.1093/jn/137.10.2196.

Moura de Oliveira D., et al. (2017) Bioavailability of chlorogenic acids in rats after acute ingestion of maté tea (*Ilex paraguariensis*) or 5-caffeoylquinic acid. Eur. J Nutr. 56, 2541-2556. DOI:10.1007/s00394-016-1290-1.

Nakamura S., et al. (2006) [Pharmacokinetics of chlorogenic acids absorbed in human plasma and their metabolites following oral ingestion of coffee drink]. Yakuri To Chiryo [Jpn. Pharmacol. Ther.] 34, 1239-1246.

Naylor L. H., et al. (2021) Acute dose-response effect of coffee-derived chlorogenic acids on the human vasculature in healthy volunteers: a randomized controlled trial. Am. J. Clin. Nutr. 113, 370-379. DOI:10.1093/ajcn/nqaa312.

Nowacki L. C., et al. (2021) Ilex paraguariensis extract as an alternative to pain medications. Acta Pharm. 71, 383-398 DOI:10.2478/acph-2021-0029.

Ochiai R., et al. (2019) Effect of chlorogenic acids on cognitive function in mild cognitive impairment: a randomized controlled crossover trial. J. Alzheimers Dis. 72, 1209-1216 [plus supplementary tables]. DOI:10.3233/jad-190757.

Olthof M. R., et al. (2001a) Consumption of high doses of chlorogenic acid, present in coffee, or of black tea increases plasma total homocysteine concentrations in humans. Am. J. Clin. Nutr. 73, 532-538. DOI:10.1093/ajcn/73.3.532.

Olthof M. R., et al. (2001b) Chlorogenic acid and caffeic acid are absorbed in humans. J. Nutr. 131, 66-71. DOI:10.1093/jn/131.1.66.

Olthof M. R., et al. (2003) Chlorogenic acid, quercetin-3-rutinoside and black tea phenols are extensively metabolized in humans. J. Nutr. 133, 1806-1814 [erratum, 133, 2692]. DOI:10.1093/jn/133.6.1806.

Onakpoya I. J., et al. (2015) The effect of chlorogenic acid on blood pressure: a systematic review and meta-analysis of randomized clinical trials. J. Hum. Hypertens. 29, 77-81 [plus supplementary data], DOI:10.1038/jhh.2014.46.

Park I., et al. (2017) Effects of subacute ingestion of chlorogenic acids on sleep architecture and energy metabolism through activity of the autonomic nervous system: a randomised, placebo-controlled, double-blinded cross-over trial. Br. J. Nutr. 117, 979-984. DOI:10.1017/S0007114517000587.

Pereira Panza V., et al. (2019) Effect of mate tea (*Ilex paraguariensis*) on the expression of the leukocyte NADPH oxidase subunit p47phox and on circulating inflammatory cytokines in healthy men: a pilot study. Int. J. Food Sci. Nutr. 70, 212-221DOI:10.1080/09637486.2018.1486393.

Plumb G. W., et al. (1999) Metabolism of chlorogenic acid by human plasma, liver, intestine and gut microflora. J. Sci. Food Agric. 79, 390-392. DOI:10.1002/(SICI)1097-0010(19990301)79:3<390::AID-JSFA258>3.0.CO;2-0.

Renouf M., et al. (2014) Dose-response plasma appearance of coffee chlorogenic and phenolic acids in adults. Mol. Nutr. Food Res. 58, 301-309. DOI:10.1002/mnfr.201300349.

Richling E., et al. (2012) Dose-response relationship of chlorogenic acids in humans. Naunyn Schmiedebergs ArchPharmacol. 385, S75 [abstract 327]. DOI:10.1007/S00210-012-0736-0.

Rocha D. S., et al. (2018) Effect of yerba mate (*Ilex paraguariensis*) extract on the metabolism of diabetic rats. Biomed Pharmacother. 105, 370-376 [plus supplementary figure]. DOI:10.1016/j.biopha.2018.05.132.

Rogerio De Sousa W., et al. (2019) Evaluation of reproductive toxicology of aqueous extract of yerba mate (*Ilex paraguariensis* A. St.-Hil.), a traditional South American beverage. J. Med. Food 22, 97-101. DOI:10.1089/jmf.2018.0060.

Sanchez Boado L., et al (2018) Effects of Ilex paraguariensis polyphenols on magnesium absortion and iron bioavailability: preliminary study. J. Food Res. 7, 114-126. DOI:10.5539/jfr.v7n2p114.

Sarria B., et al. (2020a) Yerba mate may prevent diabetes according to a crossover, randomized, controlled study in humans. Proc. Nutr. Soc. 79, OCE2, E245 DOI:10.1017/S0029665120001937.

Sarria B., et al. (2020b) Yerba mate improves cardiovascular health in normocholesterolemic and hypercholesterolemic subjects. Proc. Nutr. Soc. 79, OCE2, E635. DOI: 10.1017/S0029665120005844.

Shinomiya K., et al. (2004) Effects of chlorogenic acid and its metabolites on the sleep-wakefulness cycle in rats. Eur. J. Pharmacol. 504, 185-189. DOI:10.1016/j.ejphar.2004.09.054.

Simao Do Carmo L., et al. (2013) The effects of yerba maté (*Ilex paraguariensis*) consumption on IL-1, IL-6, TNF-α and IL-10 production by bone marrow cells in Wistar rats fed a high-fat diet. Int J Vitam Nutr Res 83, 26-35. DOI:10.1024/0300-9831/a000142.

Song Z., et al. (2014) [Effect of chlorogenic acid at high dose on expression of hepatic inflammatory cytokines mRNA induced by lipopolysaccharides]. Ying Yang Xue Bao [Acta Nutr. Sin.] 36, 481-485.

Souza S. J., et al. (2017) Effect of chocolate and mate tea on the lipid profile of individuals with HIV/AIDS on antiretroviral therapy: A clinical trial. Nutrition 43-44, 61-68. DOI:10.1016/j.nut.2017.06.017.

Stalmach A., et al. (2009) Metabolite profiling of hydroxycinnamate derivatives in plasma and urine after the ingestion of coffee by humans: identification of biomarkers of coffee consumption. Drug Metab. Dispos. 37, 1749-1758. DOI:10.1124/dmd.109.028019.

Stalmach A., et al. (2010) Bioavailability of chlorogenic acids following acute ingestion of coffee by humans with an ileostomy. Arch. Biochem. Biophys. 501, 98-105. DOI:10.1016/j.abb.2010.03.005.

Stich H. F., et al. (1981) A comparative genotoxicity study of chlorogenic acid (3-O-caffeoylquinic acid). Mutat. Res. 90, 201-212. DOI:10.1016/0165-1218(81)90001-X.

Suzuki A., et al. (2006) Chlorogenic acid attenuates hypertension and improves endothelial function in spontaneously hypertensive rats. J. Hypertens. 24, 1065-1073. DOI:10.1097/01.hjh.0000226196.67052.c0.

U.S. FDA (1993) Appendix I. Table 14. Conversion table for test chemical treatment doses used in PAFA. In Priority Based Assessment of Food Additives (PAFA) Database. U.S. Food and Drug Administration (U.S. FDA), Center for Food Safety & Applied Nutrition (CFSAN), Washington, DC, p. 58.

U.S. FDA (2018) Part 182—Substances generally recognized as safe. Section §182.20—Essential oils, oleoresins (solvent-free), and natural extractives (including distillates). In: U.S. Code of Federal

(56) References Cited

OTHER PUBLICATIONS

Regulations (CFR). Title 21: Food and Drugs. (U.S. Food and Drug Administration). U.S. Government Printing Office (GPO), Washington, DC.

Vargas Alves R. J., et al. (2008) The evaluation of maté (Ilex paraguariensis) genetic toxicity in human lymphocytes by the cytokinesis-block in the micronucleus assay. Toxicol. In Vitro 22, 695-698. DOI:10.1016/j.tiv.2007.11.005.

Wang Y., et al. (2018) [Effects of chlorogenic acid on growth performance, serum immunoglobulins, intestinal mucosa morphology, digestive and absorptive capacity of piglets]. Chin. J. Anim. Nutr. 30, 1136-1145 [DOI:10.7506/spkx1002-6630-201709026.

Wantanabe T., et al. (2019) Coffee abundant in chlorogenic acids reduces abdominal fat in overweight adults: a randomized, double-blind, controlled trial. Nutrients 11, 1617 [13pp]. DOI:10.3390/nu11071617.

Wei Z.-M., et al. (2010) [Clinical tolerability of 1,5-dicaffeoylquinic acid tablets]. Zhongguo Xin Yao Za Zhi [Chin. J. New Drugs] 19, 106-108.

Wnuk M., et al. (2009) Evaluation of the cyto- and genotoxic activity of yerba mate (Ilex paraguariensis) in human lymphocytes in vitro. Mutat. Res. 679, 18-23. DOI:10.1016/j.mrgentox.2009.07.017.

Yang B., et al. (2005) Metabolic profile of 1,5-dicaffeoylquinic acid in rats, an in vivo and in vitro study. Drug Metab. Dispos. 33, 930-936. DOI:10.1124/dmd.104.002154.

Yu S., et al. (2015) Yerba mate (Ilex paraguariensis) improves microcirculation of volunteers with high blood viscosity: a randomized, double-blind, placebo-controlled trial. Exp. Gerontol. 62, 14-22 [plus supplementary tables]. DOI:10.1016/j.exger.2014.12.016.

Zhu Y., et al. (2017) [Effect of caffeine and chlorogenic acid on body weight, lipid accumulation and the expression of lipid metabolism-related genes in high-fat diet-fed mice]. Shipin Kexue [Food Sci.] 38, 162-167 DOI:10.7506/spkx1002-6630-201709026.

Zuniga L. Y., et al. (2018) Effect of chlorogenic acid administration on glycemic control, insulin secretion, and insulin sensitivity in patients with impaired glucose tolerance. J. Med. Food 21, 469-473. DOI:10.1089/jmf.2017.0110.

Baeza Gema et al: "Dihydrocaffeic acid, a major microbial metabolite of chlorogenic acids, shows similar protective effect than a yerba mate phenolic extract against oxidative stress in HepG2 cells", Food Research International, Elsevier, Amsterdam, NL, vol. 87, Jun. 17, 2016 (Jun. 17, 2016), pp. 25-33, XP029671195, ISSN: 0963-9969, DOI:10.1016/J.FOODRES.2016.06.011.

Lorena Deladino et al: "Major Phenolics in Yerba Mate Extracts (Ilex paraguariensis) and Their Contribution to the Total Antioxidant Capacity", Food and Nutrition Sciences, vol. 04, Aug. 1, 2013 (Aug. 1, 2013), pp. 154-162, XP055588480, ISSN: 2157-944X, DOI: 10.4236/fns.2013.48A019.

Prakash et al., "Catalytic Hydrogenation of the Sweet Principles of Stevia rebaudiana, Rebaudioside B, Rebaudioside C, and Rebaudioside D and Sensory Evaluation of Their Reduced Derivatives", Int. J. Mol. Sci. 2012, 13, 15126-15136; doi:10.3390/ijms131115126.

Sirima Puangpraphant et al: "Dicaffeoylquinic acids in Yerba mate (Ilex paraguariensis St. Hilaire) inhibit NF-&kgr;B nucleus translocation in macrophages and induce apoptosis by activating caspases-8 and -3 in human colon cancer cells", Molecular Nutrition & Food Research, vol. 55, No. 10, Oct. 8, 2011 (Oct. 8, 2011), pp. 1509-1522, XP055175515, ISSN: 1613-4125, DOI: 10.1002/mnfr.201100128.

Yara Queiroz et al: The Chlorogenic Acid and Caffeine Content of Yerba Mate (Ilex paraguariensis) Beverages11, Jan. 1, 2005 (Jan. 1, 2005), pp. 91-95, XP055715126, Retrieved from the Internet: URL:https://media.enfasis.com/adjuntos/146 /documentos/000/134/0000134821.pdf [retrieved on Jul. 15, 2020].

Moeenfard, et al., "Quantification of Caffeoylquinic Acids in Coffee Brews by HPLC-DAD," Journal of Analytical Methods in Chemistry, Dec. 21, 2014.

Phenolaeis.com Accessed Aug. 24, 2022 Palm Fruit Extract compositions and applications.

Phenolaeis.com Accessed Sep. 9, 2020 Palm Fruit Bioactives Complex.

Song, "Lenalidomide-Gallic Acid Cocrystals with Constant High Solubility", Crystal Growth & Design, 2015, 15, pp. 4869-4875.

Liu Na, et al., "Review on Stevia rebaudiana research abroad in 2015", Sugar Crops of China. 2017, 39(1): 57-64.

Wang Shaojia, et al., "Progress of functional components in Stevia rebaudiand Bertoni", Science and Technology of Food Industry 2017, vol. 38, No. 20.

Journal of the Brewing Society of Japan, 1959, vol. 54, No. 4, pp. 239-242.

Pimpley et al. "The chemistry of chlorogenic acid from green coffee and its role in attenuation of obesity and diabetes" at https://pubmed.ncbi.nlm.nih.gov/32633686 (Year: 2020).

\* cited by examiner

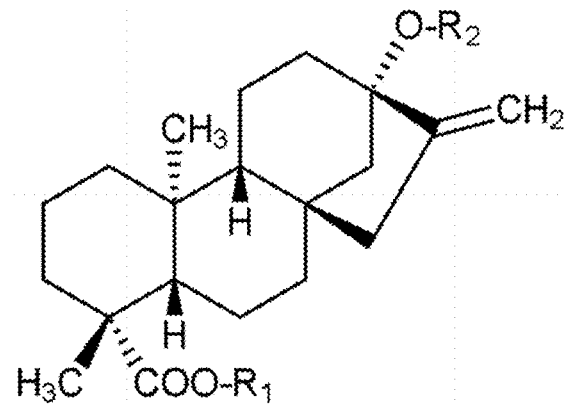

| Compound Name | $R_1$ (C-19) | $R_2$ (C-13) |
|---|---|---|
| 1. Steviol | H | H |
| 2. Steviolmonoside | H | β-Glc |
| 3. Rubusoside | β-Glc | β-Glc |
| 4. Steviolbioside | H | β-Glc-β-Glc(2→1) |
| 5. Stevioside | β-Glc | β-Glc-β-Glc(2→1) |
| 6. Rebaudioside A | β-Glc | β-Glc-β-Glc(2→1) <br> \| <br> β-Glc(3→1) |
| 7. Rebaudioside B | H | β-Glc-β-Glc(2→1) <br> \| <br> β-Glc(3→1) |
| 8. Rebaudioside C (Dulcoside B) | β-Glc | β-Glc-α-Rha(2→1) <br> \| <br> β-Glc(3→1) |
| 9. Rebaudioside D | β-Glc-β-Glc(2→1) | β-Glc-β-Glc(2→1) <br> \| <br> β-Glc(3→1) |
| 10. Rebaudioside E | β-Glc-β-Glc(2→1) | β-Glc-β-Glc(2→1) |
| 11. Rebaudioside F | β-Glc | β-Glc-β-Xyl(2→1) <br> \| <br> β-Glc(3→1) |
| 12. Dulcoside A | β-Glc | β-Glc-α-Rha(2→1) |

FIG. 1

STEVIOL GLYCOSIDE SOLUBILITY ENHANCERS

CROSS-REFERENCE TO RELATED APPLICATIONS

This application is a Continuation of International Application No. PCT/US2018/054691, filed Oct. 5, 2018, entitled "Steviol Glycoside Solubility Enhancers", which claims the benefit of U.S. Provisional Application No. 62/569,279, filed Oct. 6, 2017, and entitled "Steviol Glycoside Solubility Enhancers", each of which is hereby incorporated by reference in its entirety. This application claims the benefit of U.S. Provisional Application No. 62/676,722, filed May 25, 2018, and entitled "Methods for Making Yerba Mate Extract Composition", which application is hereby incorporated by reference in its entirety.

FIELD

The present disclosure relates to solubilized steviol glycoside solutions having one or more steviol glycosides and one or more steviol glycoside solubility enhancers and methods of making and using those solutions. The present disclosure also relates to sweetener compositions and throw syrups to prepare sweetened compositions including food, beverages, dental products, pharmaceuticals, nutraceuticals, and the like.

BACKGROUND

Sugars, such as sucrose, fructose and glucose, are utilized to provide a pleasant taste to beverages, foods, pharmaceuticals, and oral hygienic/cosmetic products. Sucrose, in particular, imparts a taste preferred by consumers. Although sucrose provides superior sweetness characteristics, it is caloric. Non-caloric or lower caloric sweeteners have been introduced to satisfy consumer demand, and there is desire for these types of sweeteners that have favorable taste characteristics.

*Stevia* is a genus of about 240 species of herbs and shrubs in the sunflower family (Asteraceae), native to subtropical and tropical regions from western North America to South America. The species *Stevia rebaudiana*, commonly known as sweetleaf, sweet leaf, sugarleaf, or simply *stevia*, is widely grown for its sweet leaves. *Stevia*-based sweeteners may be obtained by extracting one or more sweet compounds from the leaves. Many of these compounds are steviol glycosides, which are glycosides of steviol, a diterpene compound. These diterpene glycosides are about 150 to 450 times sweeter than sugar.

Examples of steviol glycosides are described in WO 2013/096420 (see, e.g., listing in FIG. 1); and in Ohta et. al., "Characterization of Novel Steviol Glycosides from Leaves of *Stevia rebaudiana* Morita," J. Appl. Glycosi., 57, 199-209 (2010) (See, e.g., Table 4 at p. 204). Structurally, the diterpene glycosides are characterized by a single base, steviol, and differ by the presence of carbohydrate residues at positions C13 and C19, as presented in FIGS. 2*a*-2*k*. See also PCT Patent Publication WO 20013/096420.

Typically, on a dry weight basis, the four major steviol glycosides found in the leaves of *Stevia* are dulcoside A (0.3%), rebaudioside C (0.6-1.0%), rebaudioside A (3.8%) and stevioside (9.1%). Other glycosides identified in *Stevia* extract include one or more of rebaudioside B, D, E, F, G, H, I, J, K, L, M, N, O, steviolbioside and rubusoside.

While the major steviol glycoside Reb A is commonly used as sweetener in beverage applications, it has off-taste issues. More recently, there has been focus on certain minor steviol glycosides which have better taste properties. For example, rebaudioside M has higher sweetness intensity and is more potent than other steviol glycosides (e.g., see Prakash, I., et al. (2013) Nat. Prod. Commun., 8: 1523-1526, and WO 2013/096420). Rebaudioside D tastes about 200-220 times sweeter than sucrose and in a sensory evaluation it had a slow onset of sweetness and was very clean (e.g., see Prakash, I., et al. (2012) Int. J. Mol. Sci., 13:15126-15136).

Rebaudiosides can be challenging to use because they have less than desirable water solubility properties. For example, it has been reported that Reb D is difficult to use in food products because of its low solubility in water at room temperature. For instance, Reb D needs to be heated to near boiling water temperature for 2 hours in order to achieve complete dissolution at 0.8% concentration. At most only 300 to 450 ppm can be solubilized in water at 23° C. (e.g., see US 2013/0251881). As another example, rebaudioside M obtained from *Stevia rebaudiana* has poor aqueous solubility and dissolution qualities in beverage formulations (e.g., see US 2014/0171519).

Certain methods to improve rebaudioside solubility are less than desirable because they are labor intensive, requiring high processing temperatures. For example, see WO 2013148177.

SUMMARY

The present disclosure generally relates to solubilized steviol glycoside compositions, e.g., aqueous solutions, having one or more steviol glycosides and one or more steviol glycoside solubility enhancers. The disclosure also relates to uses of the solubilized steviol glycoside compositions as sweetener compositions, which may be used to prepare sweetened compositions including food, beverages, dental products, pharmaceuticals, nutraceuticals, and the like. In one embodiment, the present disclosure relates to a solid composition such as a powder or an aqueous liquid composition having one or more steviol glycosides, including one or more rebaudiosides (Rebs), and one or more steviol glycoside solubility enhancers, that are present in specific amounts or concentrations, and uses thereof. In one embodiment, the steviol glycoside solubility enhancer is employed in an amount that allows steviol glycosides in aqueous solution to remain in solution at high concentrations, e.g., greater than 0.2% (wt), 1% (wt), 5% (wt), 10% (wt) or more of steviol glycosides. In one embodiment, the steviol glycoside solubility enhancer has a hydroxycinnamic acid moiety, a phenolic moiety, a carboxylic acid moiety with a pKa low enough to be partially charged when the pH of a solution is between 1 and 3.5, or combinations thereof. In one embodiment, the present disclosure relates to a spray dried or freeze dried powder formed from a solubilized steviol glycoside solution (e.g., an aqueous liquid composition) having one or more steviol glycosides, including one or more rebaudiosides (Rebs), and one or more steviol glycoside solubility enhancers, that are present in specific amounts or concentrations, and uses thereof. The combinations of steviol glycosides may include one or more of dulcoside A, Reb C, Reb A, stevioside, Reb B, Reb D, Reb E, Reb F, Reb G, Reb H, Reb I, Reb J, Reb K, Reb L, Reb M, Reb N, Reb O, Reb Q, steviolbioside, and/or rubusoside.

In one embodiment, the steviol glycoside solubility enhancer is a compound of formula (I) or a pharmaceutically acceptable salt or ester thereof:

Formula I

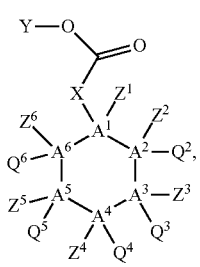

wherein either each of $A^1$-$A^6$ is a carbon atom and $A^1/A^2$, $A^3/A^4$, and $A^5/A^6$ are bonded through carbon-carbon double bonds, each of $A^1$-$A^6$ is a carbon atom and at least one of $A^1/A^2$, $A^3/A^4$, and $A^5/A^6$ are bonded through a carbon-carbon double bond, each of $A^1$-$A^5$ is an aliphatic carbon atom and $A^6$ is O, or each $A^1$-$A^6$ is an aliphatic carbon atom;

each of $Z^1$-$Z^6$ is independently hydrogen, OH, $OR^1$, or absent;

each of $Q^2$-$Q^6$ is independently hydrogen, alkyl, alkenyl, cycloalkyl, aryl, aralkyl, carboxylic acid, OH, $OR^2$,

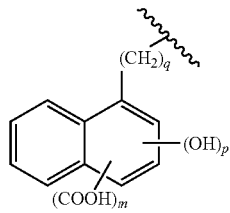

or combinations thereof, or $Q^4$ and $Q^5$ can join to form a fused $C_4$-$C_7$ carbocyclic ring, wherein the $C_4$-$C_7$ carboxylic ring can be substituted by zero to four of OH, $OR^1$, or a combination thereof;

X is

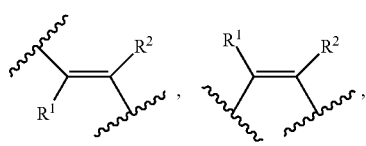

$C_1$-$C_3$ alkyl, or a bond;

$R^1$ and $R^2$ are independently hydrogen, carboxylic acid, OH, alkyl, alkenyl, cycloalkyl, aryl, aralkyl,

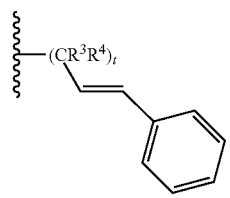

optionally substituted on the phenyl ring with from one to five hydroxyl or methoxy groups or combinations thereof, or

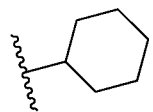 [SMILES: *C1CCCCC1]

optionally substituted on the cyclohexyl ring with from one to six hydroxyl or carboxylic acid groups or combinations thereof,

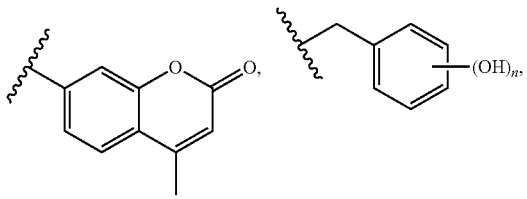

substituted analogs thereof, or combinations thereof;

$R^3$ and $R^4$ are independently hydrogen, OH, carboxylic acid, alkyl, alkenyl, cycloalkyl, aryl, aralkyl, or combinations thereof;

and Y is hydrogen, OH, carboxylic acid, alkyl, alkenyl, cycloalkyl, aryl, aralkyl,

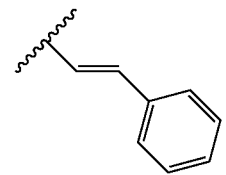 [SMILES: */C=C/c1ccccc1]

optionally substituted on the phenyl ring with from one to five hydroxyl or methoxy groups or combinations thereof, or

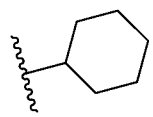 [SMILES: *C1CCCCC1]

optionally substituted on the cyclohexyl ring with from one to six hydroxyl or carboxylic acid groups or combinations thereof, or combinations thereof; and each m, n, p, q, and t is independently an integer from 0 to 5.

In one embodiment, the steviol glycoside solubility enhancer is an analog of hydroxycinnamic acid, hydroxybenzoic acid, quinic acid, caffeic acid, coumaric acid, ferulic acid, sinapic acid, chlorogenic acid, cynarin, a cynarin isomer or quercitrin.

The steviol glycoside solubility enhancer may also function as a sensory modifier. A sensory modifier is a compound or composition that changes the sensory characteristics of a sweetened consumable, e.g., a sweetener composition, a beverage, a food product, and the like. Non-limiting examples of sensory characteristics that a sensory modifier can change include bitterness, sourness, numbness, astringency, metallicness, cloyingness, dryness, sweetness, temporal aspects of sweetness, as well as flavor notes such as licorice, vanilla, prune, cotton candy, and molasses flavor notes. The sensory modifier may enhance a sensory characteristic, such as enhancing sweetness; may suppress a sensory characteristic, such as reducing bitterness; or may change the temporal aspects of a sensory characteristic, e.g., by reducing sweetness lingering.

Steviol glycoside solubility enhancers may be obtained, individually, in isolated and purified form. The isolated steviol glycoside solubility enhancer(s) may then be combined with compounds including steviol glycosides. Steviol glycoside solubility enhancers may also be produced in a mixture with each other and then combined with steviol glycosides or other components.

Thus, in some embodiments, a mixture of one or more steviol glycoside solubility enhancers may be purified from other components, e.g., steviol glycosides or *stevia* leaf extract.

Accordingly, other embodiments are directed to sweetener compositions comprising one or more steviol glycoside solubility enhancers and one or more steviol glycosides, e.g., rebaudioside M, rebaudioside D, rebaudioside A and/or rebaudioside B, and other sweeteners, e.g., non-nutritive sweeteners or nutritive sweeteners such as erythritol, maltose, honey, sucrose, and the like.

In one embodiment, at least one steviol glycoside solubility enhancer and one or more steviol glycosides, including but not limited to rebaudioside M, rebaudioside D, rebaudioside A and/or rebaudioside B, are in a sweetener composition. In one embodiment, two or more steviol glycoside solubility enhancers and one or more other component(s), such as one or more steviol glycosides, e.g., rebaudioside M, rebaudioside D, rebaudioside A and/or rebaudioside B, are in a sweetener composition. In one embodiment, two or more steviol glycoside solubility enhancers and two or more steviol glycosides, including but not limited to rebaudioside M, rebaudioside D, rebaudioside A and/or rebaudioside B, are in a sweetener composition.

In one embodiment, at least one steviol glycoside solubility enhancer and one or more other component(s), such as steviol glycosides or sweeteners other than steviol glycosides, e.g., non-nutritive sweeteners or nutritive sweeteners such as erythritol, maltose, sucrose, honey and the like, can be used in a beverage composition. In one embodiment, two or more steviol glycoside solubility enhancers and one or more other component(s), such as steviol glycosides or sweeteners other than steviol glycosides, e.g., non-nutritive sweeteners or nutritive sweeteners such as erythritol, maltose, sucrose, honey and the like, can be used in a beverage composition. In one embodiment, one or more steviol glycoside solubility enhancers and two or more other component(s), such as steviol glycosides and sweeteners other than steviol glycosides, e.g., erythritol, maltose, honey, sucrose, and the like, can be used in a beverage composition.

Sweetness may be determined by measuring sucrose equivalent values (SEV) using methods and processes well known to those skilled in the art. For example, SEV may be determined by measuring sweetness equivalence to a reference sucrose solution. Typically, taste panelists are trained to detect and scale sweetness of reference sucrose solutions containing between 10 g to 150 g/kg sucrose. A sweetener composition containing one or more glycosides are then tasted at a series of dilutions to determine the concentration of the sweetener composition that is as sweet as a given sucrose reference. For example, if a sweetener composition is as sweet as 50 g/kg of sucrose solution in a citric acid buffer, pH 3.1, then the sweetener composition is assigned a SEV of 5. In one embodiment, a sweetener composition has one or more steviol glycosides present in an amount with a sucrose equivalent value (SEV) of <1.5, <1.0 or <0.5. In one embodiment, a sweetener composition has one or more steviol glycosides present in an amount with a sucrose equivalent value of >1.5, >3, >5 or more.

In some embodiments, one or more steviol glycosdies are used at a concentration resulting in a SEV greater than 1.5 in a beverage or other sweetened composition. In some embodiments, a composition including one or more steviol glycosdies has a SEV of greater than about 5, 6, 7, 8, 9, or 10 when used at a concentration of 1,500 ppm or less, 1,000 or less, 800 or less, 600 or less, 500 or less or 400 or less.

Yet another embodiment is directed to fermentation media comprising one or more steviol glycosides and one or more steviol glycoside solubility enhancers. The fermentation media having the one or more steviol glycoside solubility enhancers can be enriched in steviol glycoside content.

In one embodiment, an aqueous or solid composition is provided having one or more of rebaudioside A, rebaudioside B, rebaudioside M, rebaudioside D, rebaudioside I, rebaudioside Q, rebaudioside N, or stevioside, and one or more steviol glycoside solubility enhancers. In one embodiment the composition is a sweetener composition. In one embodiment, the composition is a beverage. In one embodiment, the pH of the beverage that includes one or more of steviol glycoside solubility enhancers may be in the range of 1.8 to 10, 2 to 5, or 2.5 to 4.2.

In one embodiment, an aqueous or solid composition is provided having one or more of rebaudioside A, rebaudioside B, rebaudioside M, rebaudioside D, and one or more steviol glycoside solubility enhancers. In one embodiment, an aqueous or solid composition is provided having rebaudioside B, rebaudioside M, rebaudioside D, or combinations thereof, and one or more steviol glycoside solubility enhancers. In one embodiment the composition is a sweetener composition. In one embodiment, the composition is a beverage. In one embodiment, the pH of the beverage that includes one or more steviol glycoside solubility enhancers may be in the range of 1.8 to 10, 2 to 5, or 2.5 to 4.2.

In one embodiment, the composition is a beverage and the total glycoside content in the beverage is about 50 to 1500 ppm, 100 to 1200 ppm, 200 to 1000 ppm, 300 to 900 ppm, 350 to 800 ppm, 400 to 600 ppm, 350 to 550 ppm, or 450 to 550 ppm. In one embodiment, one or more steviol glycosides are present in a beverage in a range of about 1 ppm to about 600 ppm, e.g., about 50 ppm to about 500 ppm, 10 to 400 ppm, 50 to 200 ppm, 75 to 150 ppm, 5 to 200 ppm, 10 to 100 ppm, 1 to 100 ppm, 20 to 90 ppm, 30 to 80 ppm, 40 to 70 ppm, 45 to 55 ppm, 1 to 50 ppm, 1 to 40 ppm, 1 to 30 ppm, 1 to 20 ppm, or 1 to 10 ppm.

In one embodiment, one or more steviol glycosides are present in a sweetener composition at about 0.1 to 20% (wt), e.g., about 0.2 to 10% (wt), 0.5 to 10% (wt), 1 to 5% (wt), 1 to 10% (wt), 2 to 15% (wt), 2 to 20% (wt), 2 to 10% (wt), 0.1 to 1.5% (wt), 0.5 to 10% (wt), or 1.5 to 5% (wt). In one embodiment, one or more steviol glycosides are present in a sweetener composition at about 0.3, 0.75, 1.5, 3, 5, 6, 7, 8, 9, 10, 15, 20, 25, 30, 35, or 40% (wt). In one embodiment, steviol glycosides and steviol glycoside solubility enhancers are at a weight ratio of 10:1, 9:1, 8:1, 7:1, 6:1, 5:1, 4:1, 3:1, 2:1, 1:1, 1:0.9, 1:0.8, 1:0.7, 1:0.6, 1:0.5, 1:0.4, 1:0.3, 1:0.2, 1:0.1, 1:0.09, 1:0.05, or 1:0.01.

Steviol glycosides and steviol glycoside solubility enhancers can also be included in a concentrated syrup that can be used to make a beverage, also referred to as a "throw syrup." In some embodiments, the steviol glycoside content is 2 to 10, 3 to 7, 4 to 6, or about 5 times greater in the syrup concentrate than the desired concentration of the finished beverage. Accordingly, the total steviol glycoside content in a syrup concentrate can be in the range of about 100 to 15,000 ppm, 500 to 12,500 ppm, 1,000 to 10,000 ppm, 1,500 to 7,500 ppm, 2,000 to 6,000 ppm, 2,000 to 4,200 ppm, or 2,400 to 3,600 ppm. In some embodiments, the content of any single component in the syrup concentrate is at least 5 ppm, 25 ppm, 50 ppm, 100 ppm, 150 ppm, 200 ppm, 250 ppm, 500 ppm, 750 ppm, or 1,000 ppm.

In another embodiment, the disclosure provides a method for enhancing the solubility of a steviol glycoside in an aqueous composition (solution). The method comprises a step of providing an aqueous composition comprising one or more steviol glycosides and one or more steviol glycoside solubility enhancers. Compounds of formula (I) exemplify steviol glycoside solubility enhancers. As an example, the solubility of steviol glycosides, e.g., in fermentation media, can be enhanced by adding the steviol glycoside solubility enhancers to the steviol glycoside containing solution.

In another embodiment, the disclosure provides another method for enhancing the solubility of a steviol glycoside in an aqueous solution. The method includes a step of combining an aqueous composition having a steviol glycoside composition and a steviol glycoside solubility enhancer composition, or combining an aqueous composition, a steviol glycoside composition and a steviol glycoside solubility enhancer composition.

DESCRIPTION OF THE FIGURES

FIG. 1 shows structures of steviol glycosides.

DETAILED DESCRIPTION

Figure 2:
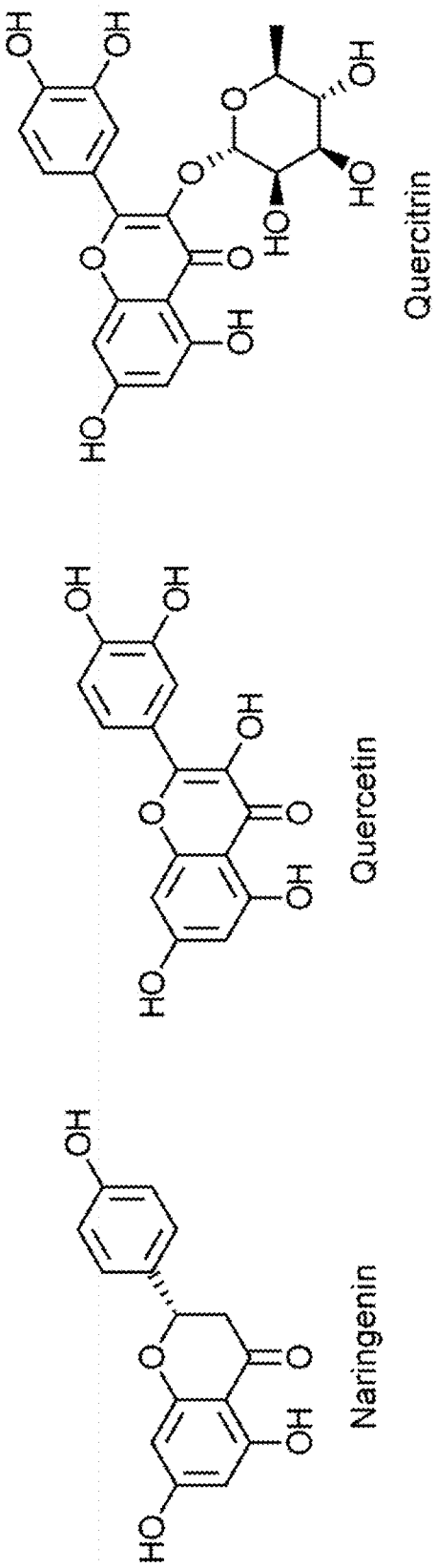
FIG. 2 shows the structure of naringenin, quercetin, and quercitrin.
Figure 3:
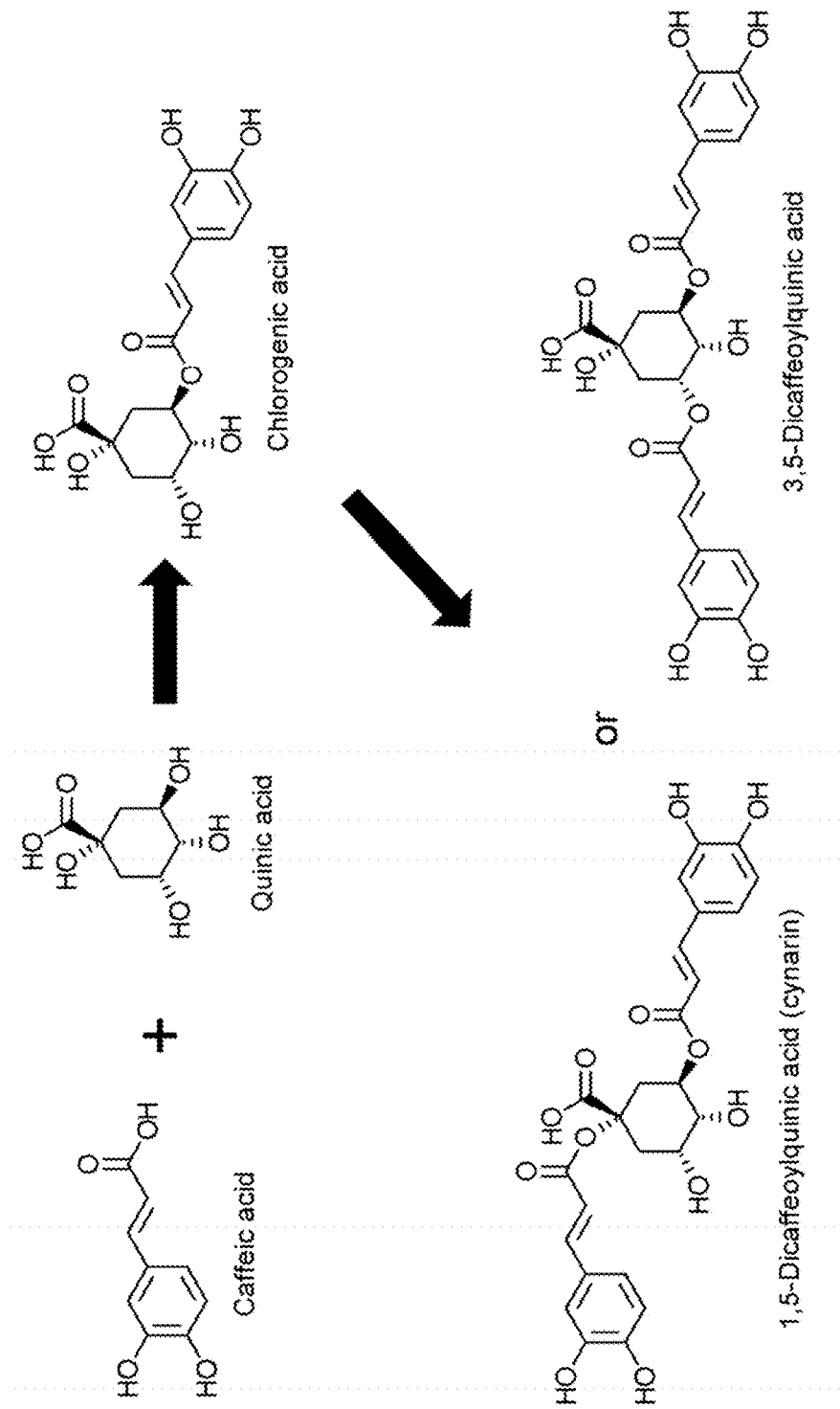
FIG. 3. Structure of compounds in *stevia* leaf that improve SG water solubility. Both chlorogenic acid and cynarin have theoretical pKas of about 2.5. Two additional isomers of chlorogenic acid (neochlorogenic acid and cryptochlorogenic acid) and four additional isomers of cynarin were also detected.

Embodiments of the disclosure described herein are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

For example, some embodiments of the disclosure are directed to compositions having an amount of one or more of steviol glycoside solubility enhancers. In one embodiment, one or more of steviol glycoside solubility enhancers, when present in a sweetener composition, beverage, food product, etc., provide for enhanced solubility.

In one embodiment, the steviol glycoside solubility enhancer may be present in an amount that modifies the temporal aspects of a sensory characteristic. The temporal aspects of a sensory characteristic refers to the perception of the characteristic over time. This includes the onset time of the characteristic, i.e., the time it takes to reach peak of the characteristic. It also includes the linger time of the characteristic, i.e., the time from a peak of the sensory characteristic to a level where it is no longer perceived. The temporal aspects may also include a time-intensity profile showing the perceived sweetness as a function of time. These characteristics can all contribute to a temporal profile for the sensory characteristic.

Thus, in some embodiments, one or more steviol glycoside solubility enhancers can be used as a sensory modifier. A sensory modifier is a compound or composition that in certain amounts changes the sensory characteristics of a sweetened consumable, e.g., a sweetener composition, a beverage, a food product, etc. Non-limiting examples of sensory characteristics that a sensory modifier can change include bitterness, sourness, numbness, astringency, metallic-ness, cloyingness, dryness, sweetness, temporal aspects of sweetness, as well as flavor notes, such as licorice, vanilla, prune, cotton candy, and molasses flavor notes. The sensory modifier may enhance a sensory characteristic, such as enhancing sweetness; may suppress a sensory characteristic, such as reducing bitterness; or may change the temporal aspects of a sensory characteristic, e.g., by reducing sweetness lingering. In some embodiments, the amount employed in a composition having a plurality of steviol glycosides and one or more steviol glycoside solubility enhancers alters at least one sensory characteristic, e.g., the combination may have reduced bitterness or sweetness compared to one or more of the steviol glycosides in the composition, which resulting sensory characteristic in the composition is better than expected. In one embodiment, one or more steviol glycoside solubility enhancers described herein, when present in a sweetener composition, beverage, food product, etc., provide for sensory modification when present at a level below a sweetening threshold.

The sweetness temporal profile of sucrose is deemed highly desirable. The sweetness of some non-nutritive sweeteners, including rebaudioside A, is deemed "sharper" than sucrose in that it has a faster sweetness onset, i.e., it reaches the peak sweetness more swiftly and has a shorter onset time. Such fast-onset sweeteners may also be referred to as "spiky". Some non-nutritive sweeteners may have a sweetness that lingers longer than sucrose, i.e., the flavor takes longer to dissipate from peak sweetness to a level where sweetness is no longer perceived. A sweetener composition that has a sweetness temporal profile closer to that of sucrose is deemed more desirable.

If it is desired to provide steviol glycosides and steviol glycoside solubility enhancers in enriched or purified form, or where one or more steviol glycoside solubility enhancers are separated from steviol glycosides, or separated from one another, further purification can be carried out. Such enrichment or purification of steviol glycoside components and steviol glycoside solubility enhancers can be carried out on liquid fermentation media, or the fermentation media can then be dried down prior to purification. For example, fermentation media can be dried down using lyophilization to form a dry composition (e.g., powder or flakes) including steviol glycosides and one or more of steviol glycoside solubility enhancers that can be subsequently processed.

The amounts of steviol glycosides and one or more steviol glycoside solubility enhancers in the composition can be expressed in relation to one another, or to the total amount of steviol glycosides, such as by a weight percentage of the total amount of steviol glycosides, or a ratio, or range of ratios, expressed as weight percent, or molar percent Total steviol glycosides (TSG) is calculated as the sum of the content of all steviol glycosides in a composition on a dry (anhydrous) basis. Unless expressed herein otherwise, an "amount" of steviol glycoside will refer to the percentage by weight (% wt) of the steviol glycoside, or combination thereof.

As discussed herein, the composition can include one or more steviol glycosides and one or more steviol glycoside solubility enhancers, as well as other compounds. Exemplary steviol glycosides include those such as rebaudioside M, rebaudioside D, rebaudioside A, rebaudioside B, rebaudioside N, and/or stevioside. In some embodiments, the steviol glycosides rebaudioside M and rebaudioside D can be produced by an engineered organism as the predominant steviol glycosides, and therefore can represent the major portion of the steviol glycosides in the composition. Rebaudioside M or rebaudioside D can, in some embodiments, be present in the composition an amount greater than other steviol glycosides.

A steviol glycoside composition that includes one or more steviol glycoside solubility enhancers can optionally be expressed in terms of amounts of rebaudioside M and rebaudioside D. For example, rebaudioside M and rebaudioside D can be present in the composition in a total amount of about 90% (wt) or greater, about 92.5% (wt) or greater, or 95% (wt) or greater, of a total amount steviol glycosides in the composition. Rebaudioside M can be the predominant steviol glycoside in the composition, and can be present, for example, in an amount in the range of about 45% to about 70%, about 50% to about 65%, or about 52.5% to about 62.5% of the total amount steviol glycosides in the composition. Rebaudioside D can be in an amount less than Rebaudioside M, such as in an amount in the range of about 25% to about 50%, about 30% to about 45%, or about 32.5% to about 42.5% of the total amount steviol glycosides in the composition.

The composition can optionally be expressed in terms of amounts of other known steviol glycosides that are present in lower amounts. For example, the composition can include one or more of rebaudioside A, rebaudioside B, or stevioside in an amount of about 1% (wt) or less, about 0.5% (wt) or less, or about 0.25% (wt) or less, of a total amount steviol glycosides in the composition.

The composition can optionally be expressed in terms of the concentration of one or more steviol glycoside(s). Beneficially, it has been found that certain compound(s) can improve solubility of steviol glycosides in an aqueous solution, and therefore compositions can be prepared having a greater concentration of steviol glycosides in solution. As used herein "instantaneous solubility" refers to the solubility of a steviol glycoside, or mixture of steviol glycosides, that are vigorously mixed with water at room temperature (25° C.). As used herein "equilibrium solubility" refers to the solubility of a steviol glycoside, or mixture of steviol glycosides, that are vigorously mixed with deionized water at 80° C. for 15 minutes, cooled to room temperature (25° C.), and then observed at least four days. Clear solutions without precipitates are considered soluble. Unless indicated otherwise herein, the term "solubility" refers to "equilibrium solubility."

In the absence of compounds that enhance solubility, rebaudioside D has a very low instantaneous solubility (less than 0.08% at room temperature) in water. Upon heating to 80° C. for 15 minutes, rebaudioside D has an equilibrium solubility of 0.08% for at least four days at room temperature. Rebaudioside M has a higher solubility than rebaudioside D. The instantaneous solubility of rebaudioside M is about 0.13%, and its equilibrium solubility is about 0.2% at room temperature.

Therefore, the presence of one or more steviol glycoside solubility enhancers can improve the solubility of one or more steviol glycosides by 1, 2, 3, 4, 5, 10, 15, 20, 50 or 100 times.

In some modes of practice, one or more steviol glycoside solubility enhancers can be enriched in a composition. The term "enriched" refers to an increase in the amount of one or more steviol glycoside solubility enhancers relative to one or more other compounds that are present in a composition. A composition that is enriched for one or more steviol glycoside solubility enhancers can be combined with a steviol glycoside composition to improve solubility of those steviol glycosides.

In yet other modes of practice, one or more steviol glycoside solubility enhancers are purified from *stevia* extract to provide a composition comprising one one or more steviol glycoside solubility enhancers essentially free of other components found in, e.g., *stevia* leaves (see Tables 2-6). Such a purified composition can be useful as an additive to steviol glycoside composition(s), to increase the aqueous solubility of the steviol glycosides to form a composition with higher steviol glycoside concentration.

Accordingly, other embodiments of the disclosure provides a method of enhancing the solubility of a steviol glycoside in an aqueous composition comprising a step of providing an aqueous composition comprising a steviol glycoside, e.g., rebaudioside A, rebaudioside B, rebaudioside M, rebaudioside D, rebaudioside I, rebaudioside Q, rebaudioside N, or stevioside, or any combination thereof, and one or more steviol glycoside solubility enhancers. For example, the steviol glycoside can be added to a composition that has the one or more steviol glycoside solubility enhancers, the steviol glycoside and the one or more steviol glycoside solubility enhancers may be mixed, or the one or more steviol glycoside solubility enhancers can be added to a composition having the steviol glycoside.

Sweetener compositions (also referred to as sweetening compositions), as used herein, refers to compositions that include one or more steviol glycosides and one or more steviol glycoside solubility enhancers. Thus, one or more steviol glycoside(s) such as Reb B, Reb M and/or Reb D can be present in a greater amount in the composition, such as greater than about 75%, greater than about 80%, greater than about 85%, greater than about 90%, greater than about 95%, or greater than about 99% of the total amount of steviol glycosides in the composition.

In one embodiment, one or more steviol glycoside solubility enhancers are present in a sweetener composition at a molar ratio of steviol glycoside to steviol glycoside solubility enhancer of about 1:1, 1:0.9, 1:0.8, 1:0.7, 1:0.6, 1:0.5, 1:0.4, 1:0.3, 1:0.2, or 1:0.1. In one embodiment, one or more steviol glycoside solubility enhancers are present in a sweetener composition at a molar ratio of steviol glycoside to steviol glycoside solubility enhancer of about 1:1, 1:2, 1:3, 1:4, 1:5, 1:6, 1:7, 1:8, 1:9, or 1:10.

The sweetener composition can optionally include another sweetener, an additive, a liquid carrier, or combinations thereof. Sweetener compositions are used to sweeten other compositions (sweetenable compositions) such as foods, beverages, medicines, oral hygiene compositions, nutraceuticals, and the like.

Sweetenable compositions, as used herein, mean substances which are contacted with the mouth of man or animal, including substances which are taken into but subsequently ejected from the mouth (such as a mouthwash rinse) and substances which are drunk, eaten, swallowed or otherwise ingested, and are suitable for human or animal consumption when used in a generally acceptable range. Sweetenable compositions are precursor compositions to sweetened compositions and are converted to sweetened compositions by combining the sweetenable compositions with at least one sweetening composition and optionally one or more other sweetenable compositions and/or other ingredients.

Sweetened compositions, as used herein, mean substances that are derived from constituents including at least one sweetenable composition and at least one sweetener composition. In some modes of practice, a sweetened composition may be used itself as a sweetening composition to sweeten still yet further sweetenable compositions. In some modes of practice, a sweetened composition may be used as a sweetenable composition that is further sweetened with one or more additional sweetening compositions. For example, a beverage with no sweetener component is a type of sweetenable composition. A sweetener composition can be added to the un-sweetened beverage, thereby providing a sweetened beverage. The sweetened beverage is a type of sweetened composition.

In some preparations, steviol glycoside provides the sole sweetener component in a sweetening composition.

In some embodiments, a sweetening composition comprises steviol glycosides in an amount effective to provide a sweetness strength equivalent to a specified amount of sucrose. The amount of sucrose in a reference solution may be described in degrees Brix (° Bx). One degree Brix is 1 gram of sucrose in 100 grams of solution and represents the strength of the solution as percentage by weight (% w/w). For example, a sweetener composition contains one or more steviol glycosides in an amount effective to provide a sweetness equivalent from about 0.50 to 14 degrees Brix of sugar when present in a sweetened composition, such as, for example, from about 5 to about 11 degrees Brix, from about 4 to about 7 degrees Brix, or about 5 degrees Brix.

The amount of steviol glycosides in the sweetener composition may vary. Steviol glycosides can be present in a sweetener composition in any amount to impart the desired sweetness when the sweetener composition is incorporated into a sweetened composition. For example, Reb M and/or Reb D are present in the sweetener composition in an amount effective to provide total steviol glycoside concentration from about 1 ppm to about 10,000 ppm when present in a sweetened composition, In another embodiment, the steviol glycosides are present in the sweetener composition in an amount effective to provide a steviol glycoside concentration in the range of about 10 ppm to about 1,000 ppm, more specifically about 10 ppm to about 800 ppm, about 50 ppm to about 800 ppm, about 50 ppm to about 600 ppm, or about 200 ppm to about 500 ppm.

In one embodiment, steviol glycosides other than Reb D, Reb M, Reb G, Reb O, Reb N, and/or Reb E, or other than Reb D, Reb M, Reb B and/or Reb A, or other than Reb D and/or Reb M, are present in a sweetened composition at about 0.05 to 70 wt % of the total content of the sweetener composition; e.g., about 0.1 to 50, 0.5 to 70, 1 to 50, 1 to 35, 2 to 25, 3 to 20, 5 to 15, 0.1 to 15, 0.5 to 10, 1 to 5%, etc. In one embodiment, steviol glycosides other than Reb D, Reb M, Reb G, Reb O, Reb N, and/or Reb E, or other than Reb D, Reb M, Reb B and/or Reb A or other than Reb D and/or Reb M, are at a weight ratio of the total of all other glycosides of 1:1 to 1:20, 1:1.5 to 1:15, 1:2 to 1:10, 1:2.5 to 1:7.5, or 1:3 to 1:5, in a sweetened composition.

Unless otherwise expressly stated, ppm is on a weight basis.

In some embodiments, a sweetener composition having the steviol glycosides and one or more steviol glycoside solubility enhancers, also contain one or more additional non-steviol glycoside sweetener compound(s). The non-steviol glycoside sweetener compounds can be any type of sweetener, for example, a sweetener obtained from a plant or plant product, or a physically or chemically modified sweetener obtained from a plant, or a synthetic sweetener.

For example, exemplary non-steviol glycoside sweeteners include sucrose, fructose, glucose, erythritol, maltitol, lactitol, sorbitol, mannitol, xylitol, tagatose, trehalose, galactose, rhamnose, cyclodextrin (e.g., α-cyclodextrin, β-cyclodextrin, and γ-cyclodextrin), ribulose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, glucosamine, mannosamine, fucose, fuculose, glucuronic acid, gluconic acid, glucono-lactone, abequose, galactosamine, xylo-oligosaccharides (xylotriose, xylobiose and the like), gentio-oligoscaccharides (gentiobiose, gentiotriose, gentiotetraose and the like), galacto-oligosaccharides, sorbose, ketotriose (dehydroxyacetone), aldotriose (glyceraldehyde), nigero-oligosaccharides, fructooligosaccharides (kestose, nystose and the like), maltotetraose, maltotriol, tetrasaccharides, mannan-oligosaccharides, malto-oligosaccharides (maltotriose, maltotetraose, maltopentaose, maltohexaose, maltoheptaose and the like), dextrins, lactulose, melibiose, raffinose, rhamnose, ribose, isomerized liquid sugars such as high fructose corn/starch syrup (HFCS/HFSS) (e.g., HFCS55, HFCS42, or HFCS90), coupling sugars, soybean oligosaccharides, glucose syrup and combinations thereof. D- or L-configurations can be used when applicable.

The steviol glycosides and carbohydrate sweetener may be present in any weight ratio, such as, for example, from about 1:14,000 to about 100:1, such as, for example, about 1:100. Carbohydrates are present in the sweetener composition in an amount effective to provide a concentration from about 100 ppm to about 140,000 ppm when present in a sweetened composition, such as, for example, a beverage.

In other embodiments, the sweetener composition including the steviol glycosides and one or more steviol glycoside solubility enhancers, additionally include one or more synthetic sweeteners. In one embodiment, a synthetic has a sweetness potency greater than sucrose, fructose, and/or glucose, yet has less calories than sucrose, fructose, and/or glucose. Exemplary synthetic non-steviol glycoside sweeteners include include sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof. In embodiments where the sweetener composition includes the steviol glycosides and synthetic sweetener, the synthetic sweetener can be present in an amount effective to provide a concentration from about 0.3 ppm to about 3,500 ppm when present in a sweetened composition, such as, for example, a beverage.

The sweetener compositions can be customized to provide a desired calorie content. For example, sweetener compositions can be "full-calorie", such that they impart the desired sweetness when added to a sweetenable composition (such as, for example, a beverage) and have about 120 calories per 8 oz serving. Alternatively, sweetener compositions can be "mid-calorie", such that they impart the desired sweetness when added to a sweetenable composition (such as, for example, as beverage) and have less than about 60 calories per 8 oz serving. In other embodiments, sweetener compositions can be "low-calorie", such that they impart the desired sweetness when added to a sweetenable composition (such as, for example, as beverage) and have less than 40 calories per 8 oz serving. In still other embodiments, the sweetener compositions can be "zero-calorie," such that they impart the desired sweetness when added to a sweetenable composition (such as, for example, a beverage) and have less than 5 calories per 8 oz. serving. Non-calorie compositions are "non-nutritive." In some embodiments, low calorie compositions can also be referred to as "non-nutritive."

The weight ratio of the total amount of sweetener compositions used to sweeten a sweetened composition can vary over a wide range. In many embodiments, this weight ratio is in the range from 1:10,000 to 10:1.

In addition to the steviol glycosides and one or more steviol glycoside solubility enhancers, the sweetener compositions can optionally include a liquid carrier, binder matrix, additional additives, and/or the like. In some embodiments, the sweetener composition contains additives including, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, flavorants and flavoring ingredients, astringent compounds, proteins or protein hydrolysates, surfactants, emulsifiers, weighing agents, gums, antioxidants, colorants, flavonoids, alcohols, polymers and combinations thereof. In some embodiments, the additives act to improve the temporal and flavor profile of the sweetener to provide a sweetener composition with a favorable taste, such as a taste similar to sucrose.

In one embodiment, the sweetener compositions with steviol glycosides and one or more steviol glycoside solubility enhancers contain one or more polyols. The term "polyol", as used herein, refers to a molecule that contains more than one hydroxyl group. In some embodiments, a polyol may be a diol, triol, or a tetraol which contains 2, 3, and 4 hydroxyl groups respectively. A polyol also may contain more than 4 hydroxyl groups, such as a pentaol, hexaol, heptaol, or the like, which contain 5, 6, 7, or even more hydroxyl groups, respectively. Additionally, a polyol also may be a sugar alcohol, polyhydric alcohol, polymer comprising OH functionality, or polyalcohol which is a reduced form of a carbohydrate, wherein a carbonyl group (aldehyde or ketone, reducing sugar) has been reduced to a primary or secondary hydroxyl group.

Exemplary polyols include erythritol, maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, and sugar alcohols or any other carbohydrates capable of being reduced which do not adversely affect the taste of the sweetener composition.

Exemplary amounts of polyol provide a concentration in the range of about 100 ppm to about 250,000 ppm when present in a sweetened composition, more specifically about 400 ppm to about 80,000 ppm, or about 5,000 ppm to about 40,000 ppm, based on the total weight of the sweetened composition.

Exemplary amino acid additives include any compound comprising at least one amino functionality and at least one acid functionality. Examples include, but are not limited to, aspartic acid, arginine, glycine, glutamic acid, proline, threonine, theanine, cysteine, cystine, alanine, valine, tyrosine, leucine, arabinose, trans-4-hydroxyproline, isoleucine, asparagine, serine, lysine, histidine, ornithine, methionine, carnitine, aminobutyric acid (α-, β-, and/or δ-isomers), glutamine, hydroxyproline, taurine, norvaline, sarcosine, and their salt forms such as sodium or potassium salts or acid salts.

Exemplary amounts of amino acid provide a concentration in the range of about 10 ppm to about 50,000 ppm, or more specifically about 1,000 ppm to about 10,000 ppm, about 2,500 ppm to about 5,000 ppm, or about 250 ppm to about 7,500 ppm, based on the total weight of the sweetened composition.

Exemplary sugar acid additives include, but are not limited to, aldonic, uronic, aldaric, alginic, gluconic, glucuronic, glucaric, galactaric, galacturonic, and salts thereof (e.g., sodium, potassium, calcium, magnesium salts or other physiologically acceptable salts), and combinations thereof.

Exemplary nucleotide additives include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, alkali or alkaline earth metal salts thereof, and combinations thereof. The nucleotides described herein also may comprise nucleotide-related additives, such as nucleosides or nucleic acid bases (e.g., guanine, cytosine, adenine, thymine, uracil). In some embodiments, a nucleotide can be present in the sweetener composition to provide a concentration in the range of about 5 ppm to about 1,000 ppm based on the total weight of the sweetened composition.

Exemplary inorganic acid additives include, but are not limited to, phosphoric acid, phosphorous acid, polyphosphoric acid, hydrochloric acid, sulfuric acid, carbonic acid, sodium dihydrogen phosphate, and alkali or alkaline earth metal salts thereof (e.g., inositol hexaphosphate Mg/Ca).

Exemplary bitter compound additives include, but are not limited to, caffeine, quinine, urea, bitter orange oil, naringin, quassia, and salts thereof.

Exemplary flavorant and flavoring ingredient additives, but are not limited to, vanillin, vanilla extract, mango extract, cinnamon, citrus, coconut, ginger, viridiflorol, almond, menthol (including menthol without mint), grape skin extract, and grape seed extract. In some embodiments, a flavorant is present in the sweetener composition in an amount effective to provide a concentration from about 0.1 ppm to about 4,000 ppm when present in a sweetened composition, such as, for example, a beverage, based on the total weight of the sweetened composition.

Exemplary polymer additives include, chitosan, pectin, pectic, pectinic, polyuronic, polygalacturonic acid, starch, food hydrocolloid or crude extracts thereof (e.g., gum acacia Senegal (Fibergum™), gum acacia seyal, carageenan), poly-L-lysine (e.g., poly-L-a-lysine or poly-L-e-lysine), poly-L-ornithine (e.g., poly-L-a-ornithine or poly-L-e-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, and sodium polyethyleneglycolalginate, sodium hexametaphosphate and its salts, and other cationic polymers and anionic polymers. In some embodiments, a polymer additive is present in the sweetener composition in an amount effective to provide a concentration from about 30 ppm to about 2,000 ppm when present in a sweetened composition, such as, for example, a beverage, based on the total weight of the sweetened composition.

Exemplary protein or protein hydrolysate additives include, but are not limited to, bovine serum albumin (BSA), whey protein, soluble rice protein, soy protein, protein isolates, protein hydrolysates, reaction products of protein hydrolysates, glycoproteins, and/or proteoglycans containing amino acids, collagen (e.g., gelatin), partially hydrolyzed collagen (e.g., hydrolyzed fish collagen), and collagen hydrolysates (e.g., porcine collagen hydrolysate). In some embodiments, a protein hydrosylate is present in the sweetener composition in an amount effective to provide a concentration from about 200 ppm to about 50,000 ppm when present in a sweetened composition, such as, for example, a beverage, based on the total weight of the sweetened composition.

Exemplary surfactant additives include, but are not limited to, polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride (hexadecylpyridinium chloride), hexadecyltrimethylammonium bromide, sodium cholate, carbamoyl, choline chloride, sodium glycocholate, sodium taurodeoxycholate, lauric arginate, sodium stearoyl lactylate, sodium taurocholate, lecithins, sucrose oleate esters, sucrose stearate esters, sucrose palmitate esters, sucrose laurate esters, and other emulsifiers, and the like. In some embodiments, a surfactant additive is present in the sweetener composition in an amount effective to provide a concentration from about 30 ppm to about 2,000 ppm when present in a sweetened composition, such as, for example, a beverage, based on the total weight of the sweetened composition.

Exemplary flavonoid additives are classified as flavonols, flavones, flavanones, flavan-3-ols, isoflavones, or anthocyanidins. Non-limiting examples of flavonoid additives include, but are not limited to, catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-fi Gen F.F.I., Inc., Osaka, Japan)), neohesperidin, naringin, neohesperidin dihydrochalcone, and the like. In some embodiments, a flavonoid additive is present in the sweetener composition in an amount effective to provide a concentration from about 0.1 ppm to about 1,000 ppm when present in sweetened composition, such as, for example, a beverage, based on the total weight of the sweetened composition.

Exemplary alcohol additives include, but are not limited to, ethanol. In some embodiments, an alcohol additive is present in the sweetener composition in an amount effective to provide a concentration from about 625 ppm to about 10,000 ppm when present in a sweetened composition, such as, for example, a beverage, based on the total weight of the sweetened composition.

The sweetener composition can also contain one or more functional ingredients, which provide a real or perceived heath benefit to the composition. Functional ingredients include, but are not limited to, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

Saponins are glycosidic plant products comprising an aglycone ring structure and one or more sugar moieties. The combination of the nonpolar aglycone and the water soluble sugar moiety gives saponins surfactant properties, which allow them to form a foam when shaken in an aqueous solution.

As used herein "antioxidant" refers to any substance which inhibits, suppresses, or reduces oxidative damage to cells and biomolecules. Without being bound by theory, it is believed that antioxidants inhibit, suppress, or reduce oxidative damage to cells or biomolecules by stabilizing free radicals before they can cause harmful reactions. As such, antioxidants may prevent or postpone the onset of some degenerative diseases.

Examples of suitable antioxidants include, but are not limited to, vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, and combinations thereof. In some embodiments, the antioxidant is vitamin A, vitamin C, vitamin E, ubiquinone, mineral selenium, manganese, melatonin, α-carotene, β-carotene, lycopene, lutein, zeanthin, crypoxanthin, reservatol, eugenol, quercetin, catechin, gossypol, hesperetin, curcumin, ferulic acid, thymol, hydroxytyrosol, tumeric, thyme, olive oil, lipoic acid, glutathinone, gutamine, oxalic acid, tocopherol-derived compounds, butylated hydroxyanisole (BHA), butylated hydroxytoluene (BHT), ethylenediaminetetraacetic acid (EDTA), tert-butylhydroquinone, acetic acid, pectin, tocotrienol, tocopherol, coenzyme Q10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms (ECGC) theaflavin and its gallate forms, thearubigins, isoflavone phytoestrogens, genistein, daidzein, glycitein, anythocyanins, cyaniding, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, monocaffeoylquinic acids, cynarin, dicaffeoylquinic acids, chicoric acid, gallotannins, ellagitannins, anthoxanthins, betacyanins and other plant pigments, silymarin, citric acid, lignan, antinutrients, bilirubin, uric acid, R-a-lipoic acid, N-acetylcysteine, emblicanin, apple extract, apple skin extract (applephenon), rooibos extract red, rooibos extract, green, hawthorn berry extract, red raspberry extract, green coffee antioxidant (GCA), aronia extract 20%, grape seed extract (VinOseed), cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon bark extract, grape skin extract, bilberry extract, pine bark extract, pycnogenol, elderberry extract, mulberry root extract, wolf erry (gogi) extract, blackberry extract, blueberry extract, blueberry leaf extract, raspberry extract, turmeric extract, citrus bioflavonoids, black currant, ginger, acai powder, green coffee bean extract, green tea extract, and phytic acid, or combinations thereof. In alternate embodiments, the antioxidant is a synthetic antioxidant such as butylated hydroxytolune or butylated hydroxyanisole, for example. Other sources of suitable antioxidants include, but are not limited to, fruits, vegetables, tea, cocoa, chocolate, spices, herbs, rice, organ meats from livestock, yeast, whole grains, or cereal grains.

Particular antioxidants belong to the class of phytonutrients called polyphenols (also known as "polyphenolics"), which are a group of chemical substances found in plants, characterized by the presence of more than one phenol group per molecule. A variety of health benefits may be derived from polyphenols, including prevention of cancer, heart disease, and chronic inflammatory disease and improved mental strength and physical strength, for example. Suitable polyphenols include but are not limited to catechins, proanthocyanidins, procyanidins, anthocyanins, quercerin, rutin, reservatrol, isoflavones, curcumin, punicalagin, ellagitannin, hesperidin, naringin, citrus flavonoids, chlorogenic acid, other similar materials, and combinations thereof.

Numerous polymeric carbohydrates having significantly different structures in both composition and linkages fall within the definition of dietary fiber. Such compounds are well known to those skilled in the art, non-limiting examples of which include non-starch polysaccharides, lignin, cellulose, methylcellulose, the hemicelluloses, β-glucans, pectins, gums, mucilage, waxes, inulins, oligosaccharides, fructooligosaccharides, cyclodextrins, chitins, and combinations thereof.

As used herein, "fatty acid" refers to any straight chain monocarboxylic acid and includes saturated fatty acids, unsaturated fatty acids, long chain fatty acids, medium chain fatty acids, short chain fatty acids, fatty acid precursors (including omega-9 fatty acid precursors), and esterified fatty acids. As used herein, "long chain polyunsaturated fatty acid" refers to any polyunsaturated carboxylic acid or organic acid with a long aliphatic tail. As used herein, "omega-3 fatty acid" refers to any polyunsaturated fatty acid having a first double bond as the third carbon-carbon bond from the terminal methyl end of its carbon chain. In particular embodiments, the omega-3 fatty acid may comprise a long chain omega-3 fatty acid. As used herein, "omega-6 fatty acid" any polyunsaturated fatty acid having a first double bond as the sixth carbon-carbon bond from the terminal methyl end of its carbon chain.

As used herein, the at least one vitamin may be single vitamin or a plurality of vitamins as a functional ingredient for the sweetener and sweetened compositions provided herein. Generally, according to particular embodiments, the at least one vitamin is present in the sweetener composition or sweetened composition in an amount sufficient to promote health and wellness.

Vitamins are organic compounds that the human body needs in small quantities for normal functioning. The body uses vitamins without breaking them down, unlike other nutrients such as carbohydrates and proteins. To date, thirteen vitamins have been recognized, and one or more can be used in the functional sweetener and sweetened compositions herein. Suitable vitamins include, vitamin A, vitamin D, vitamin E, vitamin K, vitamin B1, vitamin B2, vitamin B3, vitamin B5, vitamin B6, vitamin B7, vitamin B9, vitamin B 12, and vitamin C Many of vitamins also have alternative chemical names, non-limiting examples of which are provided below.

In certain embodiments, the functional ingredient comprises glucosamine or chondroitin sulfate. Glucosamine, also called chitosamine, is an amino sugar that is believed to be an important precursor in the biochemical synthesis of glycosylated proteins and lipids. D-glucosamine occurs in the cartilage in the form of glucosamine-6-phosphate, which is synthesized from fructose-6-phosphate and glutamine. However, glucosamine also is available in other forms, non-limiting examples of which include glucosamine hydrochloride, glucosamine sulfate, N-acetyl-glucosamine, or any other salt forms or combinations thereof.

In certain embodiments, the functional ingredient comprises at least one mineral. Minerals comprise inorganic chemical elements required by living organisms. Minerals are comprised of a broad range of compositions (e.g., elements, simple salts, and complex silicates) and also vary broadly in crystalline structure. They may naturally occur in foods and beverages, may be added as a supplement, or may be consumed or administered separately from foods or beverages. In particular embodiments of this disclosure, the mineral is chosen from bulk minerals, trace minerals or combinations thereof. Non-limiting examples of bulk minerals include calcium, chlorine, magnesium, phosphorous, potassium, sodium, and sulfur. Non-limiting examples of trace minerals include chromium, cobalt, copper, fluorine, iron, manganese, molybdenum, selenium, zinc, and iodine. Although iodine generally is classified as a trace mineral, it is required in larger quantities than other trace minerals and often is categorized as a bulk mineral.

In certain embodiments, the functional ingredient comprises at least one preservative. In particular embodiments of this disclosure, the preservative is chosen from antimicrobials, antioxidants, antienzymatics or combinations thereof. Non-limiting examples of antimicrobials include sulfites, propionates, benzoates, sorbates, nitrates, nitrites, bacteriocins, salts, sugars, acetic acid, dimethyl dicarbonate (DMDC), ethanol, and ozone.

In certain embodiments, the functional ingredient is at least one hydration agent. Hydration products help the body to replace fluids that are lost through excretion. In a particular embodiment, the hydration product is a composition that helps the body replace fluids that are lost during exercise. Accordingly, in a particular embodiment, the hydration product is an electrolyte, non-limiting examples of which include sodium, potassium, calcium, magnesium, chloride, phosphate, bicarbonate, and combinations thereof. In particular embodiments of this disclosure, the hydration product is a carbohydrate to supplement energy stores burned by muscles. In another particular embodiment, the hydration agent is at least one flavanol that provides cellular rehydration. Flavanols are a class of substances present in plants, and generally comprise a 2-phenylbenzopyrone molecular skeleton attached to one or more chemical moieties. In a particular embodiment, the hydration agent comprises a glycerol solution to enhance exercise endurance. The ingestion of a glycerol containing solution has been shown to provide beneficial physiological effects, such as expanded blood volume, lower heart rate, and lower rectal temperature.

In certain embodiments, the functional ingredient comprises at least one probiotic, prebiotic and combination thereof. Probiotics comprise microorganisms that benefit health when consumed in an effective amount. Desirably, probiotics beneficially affect the human body's gastrointestinal microflora and impart health benefits apart from nutrition. Probiotics may include, without limitation, bacteria, yeasts, and fungi. Examples of probiotics include, but are not limited to, bacteria of the genus Lactobacilli, Bifidobacteria, Streptococci, or combinations thereof, that confer beneficial effects to humans. Prebiotics are compositions that promote the growth of beneficial bacteria in the intestines.

In certain embodiments, the functional ingredient is at least one weight management agent. As used herein, "a weight management agent" includes an appetite suppressant and/or a thermogenesis agent. As used herein, the phrases "appetite suppressant", "appetite satiation compositions", "satiety agents", and "satiety ingredients" are synonymous. The phrase "appetite suppressant" describes macronutrients, herbal extracts, exogenous hormones, anorectics, anorexigenics, pharmaceutical drugs, and combinations thereof, that when delivered in an effective amount, suppress, inhibit, reduce, or otherwise curtail a person's appetite. The phrase "thermogenesis agent" describes macronutrients, herbal extracts, exogenous hormones, anorectics, anorexigenics, pharmaceutical drugs, and combinations thereof, that when delivered in an effective amount, activate or otherwise enhance a person's thermogenesis or metabolism.

In certain embodiments, the functional ingredient is at least one osteoporosis management agent. In certain embodiments, the osteoporosis management agent is at least one calcium source. According to a particular embodiment, the calcium source is any compound containing calcium, including salt complexes, solubilized species, and other forms of calcium. According to a particular embodiment, the osteoporosis management agent is a magnesium source. The magnesium source is any compound containing magnesium, including salt complexes, solubilized species, and other forms of magnesium. In other embodiments, the osteoporosis agent is chosen from vitamins D, C, K, their precursors and/or beta-carotene and combinations thereof.

In certain embodiments, the functional ingredient is at least one phytoestrogen. In one embodiment, a sweetener composition comprises at least one phytoestrogen. As used herein, "phytoestrogen" refers to any substance which, when introduced into a body causes an estrogen-like effect of any degree. Examples of suitable phytoestrogens include, but are not limited to, isoflavones, stilbenes, lignans, resorcyclic acid lactones, coumestans, coumestrol, equol, and combinations thereof.

Isoflavones belong to the group of phytonutrients called polyphenols. In general, polyphenols (also known as "polyphenolics"), are a group of chemical substances found in plants, characterized by the presence of more than one phenol group per molecule. Suitable phytoestrogen isoflavones include but are not limited to genistein, daidzein, glycitein, biochanin A, formononetin, their respective glycosides and glycoside conjugates, matairesinol, secoisolariciresinol, enterolactone, enterodiol, textured vegetable protein, and combinations thereof.

In certain embodiments, the functional ingredient is at least one long chain primary aliphatic saturated alcohol. Non-limiting examples of particular long-chain primary aliphatic saturated alcohols for use in particular embodiments include but are not limited to the 8 carbon atom 1-octanol, the 9 carbon 1-nonanol, the 10 carbon atom 1-decanol, the 12 carbon atom 1-dodecanol, the 14 carbon atom 1-tetradecanol, the 16 carbon atom 1-hexadecanol, the 18 carbon atom 1-octadecanol, the 20 carbon atom 1-eicosanol, the 22 carbon 1-docosanol, the 24 carbon 1-tetracosanol, the 26 carbon 1-hexacosanol, the 27 carbon 1-heptacosanol, the 28 carbon 1-octanosol, the 29 carbon 1-nonacosanol, the 30 carbon 1-triacontanol, the 32 carbon 1-dotriacontanol, and the 34 carbon 1-tetracontanol.

In certain embodiments, the functional ingredient is at least one phytosterol, phytostanol or combination thereof. As used herein, the phrases "stanol", "plant stanol" and "phytostanol" are synonymous. Sterols are a subgroup of steroids with a hydroxyl group at C-3. Generally, phytosterols have a double bond within the steroid nucleus, like cholesterol; however, phytosterols also may comprise a substituted sidechain (R) at C-24, such as an ethyl or methyl group, or an additional double bond. The structures of phytosterols are well known to those of skill in the art. Phytosterols well known to those or ordinary skill in the art include 4-desmethylsterols (e.g., β-sitosterol, campesterol, stigmasterol, brassicasterol, 22-dehydrobrassicasterol, and Δ5-avenasterol), 4-monomethyl sterols, and 4,4-dimethyl sterols (triterpene alcohols) (e.g., cycloartenol, 24-methylenecycloartanol, and cyclobranol). Examples of phytostanols include β-sitostanol, campestanol, cycloartanol, and saturated forms of other triterpene alcohols.

Generally, the amount of functional ingredient in the sweetener composition or sweetened composition varies widely depending on the particular sweetener composition or sweetened composition and the desired functional ingredient. Those of ordinary skill in the art will readily acertain the appropriate amount of functional ingredient for each sweetener composition or sweetened composition.

Steviol glycosides having one or more steviol glycoside solubility enhancers can be incorporated in any known edible material (referred to herein as a "sweetenable composition") or other composition intended to be ingested and/or contacted with the mouth of a human or animal, such as, for example, pharmaceutical compositions, edible gel mixes and compositions, dental and oral hygiene compositions, foodstuffs (confections, condiments, chewing gum, cereal compositions, baked goods, baking goods, cooking adjuvants, dairy products, and tabletop sweetener compositions), beverages, and other beverage products (e.g., beverage mixes, beverage concentrates, etc.).

In one embodiment, a sweetened composition is derived from ingredients comprising a sweetenable composition and a composition having steviol glycosides and one or more steviol glycoside solubility enhancers. In another embodiment, the sweetened composition is derived from ingredients comprising a sweetener composition comprising steviol glycosides and one or more steviol glycoside solubility enhancers. The sweetened compositions can optionally include one or more additives, liquid carriers, binders, sweeteners, functional ingredients, other adjuvants, and combinations thereof.

In one embodiment, a pharmaceutical composition contains a pharmaceutically active substance (including prodrug forms thereof) and steviol glycosides and one or more steviol glycoside solubility enhancers. In another embodiment, a pharmaceutical composition contains a pharmaceutically active substance and a sweetener composition comprising steviol glycosides, including one or more steviol glycoside solubility enhancers. The steviol glycoside sweetener composition can be present as an excipient material in the pharmaceutical composition, which can mask a bitter or otherwise undesirable taste of a pharmaceutically active substance or another excipient material. The pharmaceutical composition may be in the form of a tablet, a capsule, a liquid, an aerosol, a powder, an effervescent tablet or powder, a syrup, an emulsion, a suspension, a solution, or any other form for providing the pharmaceutical composition to a patient. In particular embodiments, the pharmaceutical composition may be in a form for oral administration, buccal administration, sublingual administration, or any other route of administration as known in the art.

As referred to herein, "pharmaceutically active substance" means any drug, drug formulation, medication, prophylactic agent, therapeutic agent, or other substance having biological activity. Pharmaceutically active substances also include prodrug forms of these. As referred to herein, "excipient material" refers to any other ingredient used in a pharmaceutically active composition used in combination with pharmaceutically active substance(s) that are present (including prodrugs thereof. Excipients included but are not limited to inactive substances used as a vehicle for an active ingredient, such as any material to facilitate handling, stability, dispersibility, wettability, and/or release kinetics of a pharmaceutically active substance.

Suitable pharmaceutically active substances include, but are not limited to, medications for the gastrointestinal tract or digestive system, for the cardiovascular system, for the central nervous system, for pain or consciousness, for musculo-skeletal disorders, for the eye, for the ear, nose and oropharynx, for the respiratory system, for endocrine problems, for the reproductive system or urinary system, for contraception, for obstetrics and gynecology, for the skin, for infections and infestations, for immunology, for allergic disorders, for nutrition, for neoplastic disorders, for diagnostics, for euthanasia, or other biological functions or disorders.

Examples of suitable pharmaceutically active substances include, but are not limited to, antacids, reflux suppressants, antiflatulents, antidopaminergics, proton pump inhibitors, cytoprotectants, prostaglandin analogues, laxatives, antispasmodics, antidiarrhoeals, bile acid sequestrants, opioids, beta-receptor blockers, calcium channel blockers, diuretics, cardiac glycosides, antiarrhythmics, nitrates, antianginals, vasoconstrictors, vasodilators, peripheral activators, ACE inhibitors, angiotensin receptor blockers, alpha blockers, anticoagulants, heparin, antiplatelet drugs, fibrinolytics, anti-hemophilic factors, haemostatic drugs, hypolipidaemic agents, statins, hynoptics, anaesthetics, antipsychotics, antidepressants, anti-emetics, anticonvulsants, antiepileptics, anxiolytics, barbiturates, movement disorder drugs, stimulants, benzodiazepines, cyclopyrrolones, dopamine antagonists, antihistamines, cholinergics, anticholinergics, emetics, cannabinoids, analgesics, muscle relaxants, antibiotics, aminoglycosides, anti-virals, anti-fungals, anti-inflammatories, anti-gluacoma drugs, sympathomimetics, steroids, ceruminolytics, bronchodilators, NSAIDS, antitussive, mucolytics, decongestants, corticosteroids, androgens, antiandrogens, gonadotropins, growth hormones, insulin, antidiabetics, thyroid hormones, calcitonin, diphosponates, vasopressin analogues, alkalizing agents, quinolones, anticholinesterase, sildenafil, oral contraceptives, Hormone Replacement Therapies, bone regulators, follicle stimulating hormones, luteinizings hormones, gamolenic acid, progestogen, dopamine agonist, oestrogen, prostaglandin, gonadorelin, clomiphene, tamoxifen, diethylstilbestrol, antileprotics, antituberculous drugs, antimalarials, anthelmintics, antiprotozoal, antiserums, vaccines, interferons, tonics, vitamins, cytotoxic drugs, sex hormones, aromatase inhibitors, somatostatin inhibitors, or similar type substances, or combinations thereof. Such components generally are recognized as safe (GRAS) and/or are U.S. Food and Drug Administration (FDA)-approved.

The pharmaceutical composition also may comprise other pharmaceutically acceptable excipient materials in addition to a sweetener composition comprising steviol glycosides and one or more steviol glycoside solubility enhancers. Examples of other suitable excipient materials include, but are not limited to, other sweetening compounds, antiadherents, binders (e.g., microcrystalline cellulose, gum tragacanth, or gelatin), liquid carriers, coatings, disintegrants, fillers, diluents, softeners, emulsifiers, flavoring agents, coloring agents, adjuvants, lubricants, functional agents (e.g., nutrients), viscosity modifiers, bulking agents, glidiants (e.g., colloidal silicon dioxide) surface active agents, osmotic agents, diluents, or any other non-active ingredient, or combinations thereof. For example, the pharmaceutical compositions of the present disclosure may include excipient materials selected from the group consisting of calcium carbonate, coloring agents, whiteners, preservatives, and flavors, triacetin, magnesium stearate, sterotes, natural or artificial flavors, essential oils, plant extracts, fruit essences, gelatins, or combinations thereof.

In one embodiment, an edible gel or edible gel mix comprises a sweetener composition comprising steviol glycosides and one or more steviol glycoside solubility enhancers. The edible gel or edible gel mixes can optionally include additives, functional ingredients or combinations thereof. One or more one or more steviol glycoside solubility enhancers, e.g., a mixture of steviol glycoside solubility enhancers, may be combined with one or more steviol glycosides, such as Reb D or Reb M, so as to constitute a sweetener composition of the present disclosure. However, in many embodiments, a sweetener composition comprises one or more steviol glycoside solubility enhancers, or a mixture thereof, with one or more steviol glycosides, such as Reb D or Reb M and one or more other ingredient(s) that is not a steviol glycoside.

Edible gels are gels that can be eaten by a human or animal. Gels often appear to be solid, jelly-like materials. Non-limiting examples of edible gel compositions for use in particular embodiments include gel desserts, puddings, jellies, pastes, trifles, aspics, marshmallows, gummy candies, or the like. Edible gel mixes generally are powdered or granular solids to which a fluid may be added to form an edible gel composition. Because edible gel products found in the marketplace typically are sweetened with sucrose, it is desirable to sweeten edible gels with an alternative sweetener in order provide a low-calorie or non-calorie alternative.

Non-limiting examples of gelling ingredients for use in particular embodiments include gelatin, alginate, carageenan, gum, pectin, konjac, agar, food acid, rennet, starch, starch derivatives, and combinations thereof. It is well known to those having ordinary skill in the art that the amount of gelling ingredient used in an edible gel mix or an edible gel composition varies considerably depending on a number of factors, such as the particular gelling ingredient used, the particular fluid base used, and the desired properties of the gel.

Edible gel mixes and edible gels may be prepared using other ingredients in addition to the sweetener composition comprising steviol glycosides and one or more steviol glycoside solubility enhancers, and the gelling agent. Non-limiting examples of other ingredients for use in particular embodiments include a food acid, a salt of a food acid, a buffering system, a bulking agent, a sequestrant, a cross-linking agent, one or more flavors, one or more colors, and combinations thereof.

In one embodiment, a dental composition comprises a sweetener composition comprising comprising steviol glycosides and one or more steviol glycoside solubility enhancers. Dental compositions generally comprise an active dental substance and a base material. A sweetener composition comprising steviol glycosides and oneor more steviol glycoside solubility enhancers can be used as the base material to sweeten the dental composition. The dental composition may be in the form of any oral composition used in the oral cavity such as mouth freshening agents, gargling agents, mouth rinsing agents, toothpaste, tooth polish, dentifrices, mouth sprays, teeth-whitening agent, dental floss, compositions to treat one or more oral indications (e.g., gingivitis), and the like, for example.

As referred to herein, "active dental substance" means any composition which can be used to improve the aesthetic appearance and/or health of teeth or gums or prevent dental caries. As referred to herein, "base material" refers to any inactive substance used as a vehicle for an active dental substance, such as any material to facilitate handling, stability, dispersibility, wettability, foaming, and/or release kinetics of an active dental substance.

Suitable active dental substances include, but are not limited to, substances which remove dental plaque, remove food from teeth, aid in the elimination and/or masking of halitosis, prevent tooth decay, and prevent gum disease (i.e., Gingiva). Examples of suitable active dental substances include, but are not limited to, anticaries drugs, fluoride, sodium fluoride, sodium monofluorophosphate, stannos fluoride, hydrogen peroxide, carbamide peroxide (i.e., urea peroxide), antibacterial agents, plaque removing agents, stain removers, anticalculus agents, abrasives, baking soda, percarbonates, perborates of alkali and alkaline earth metals, or similar type substances, or combinations thereof. Such components generally are recognized as safe (GRAS) and/or are U.S. Food and Drug Administration (FDA)-approved.

In a particular embodiment, a dental composition comprises a sweetener composition comprising steviol glycosides and one or more steviol glycoside solubility enhancers, and an active dental substance. Generally, the amount of the sweetener varies widely depending on the nature of the particular dental composition and the desired degree of sweetness. Those skilled in the art will be able to discern a suitable amount of sweetener for such dental composition. In a particular embodiment, steviol glycosides are present in the dental composition in a total amount in the range of about 1 to about 5,000 ppm of the dental composition and the at least one additive is present in the dental composition in an amount in the range of about 0.1 to about 100,000 ppm of the dental composition.

Foodstuffs include, but are not limited to, confections, condiments, chewing gum, cereal, baked goods, and dairy products.

In one embodiment, a confection comprises a sweetener composition comprising steviol glycosides and one or more steviol glycoside solubility enhancers. As referred to herein, "confection" can mean a sweet, a lollie, a confectionery, or similar term. The confection generally contains a base composition component and a sweetener component. A sweetener composition comprising steviol glycosides and one or more steviol glycoside solubility enhancers can serve as the sweetener component. The confection may be in the form of any food that is typically perceived to be rich in sugar or is typically sweet. According to particular embodiments, the confections may be bakery products such as pastries; desserts such as yogurt, jellies, drinkable jellies, puddings, Bavarian cream, blancmange, cakes, brownies, mousse and the like, sweetened food products eaten at tea time or following meals; frozen foods; cold confections, e. g. types of ice cream such as ice cream, ice milk, lacto-ice and the like (food products in which sweeteners and various other types of raw materials are added to milk products, and the resulting mixture is agitated and frozen), and ice confections such as sherbets, dessert ices and the like (food products in which various other types of raw materials are added to a sugary liquid, and the resulting mixture is agitated and frozen); general confections, e. g., baked confections or steamed confections such as crackers, biscuits, buns with bean-jam filling, halvah, alfajor, and the like; rice cakes and snacks; table top products; general sugar confections such as chewing gum (e.g. including compositions which comprise a substantially water-insoluble, chewable gum base, such as chicle or substitutes thereof, including jetulong, guttakay rubber or certain comestible plant derived or synthetic resins or waxes), hard candy, soft candy, mints, nougat candy, jelly beans, fudge, toffee, taffy, Swiss milk tablet, licorice candy, chocolates, gelatin candies, marshmallow, marzipan, divinity, cotton candy, and the like; sauces including fruit flavored sauces, chocolate sauces and the like; edible gels; cremes including butter cremes, flour pastes, whipped cream and the like; jams including strawberry jam, marmalade and the like; and breads including sweet breads and the like or other starch products, and combinations thereof. As referred to herein, "base composition" means any composition which can be a food item and provides a matrix for carrying the wsweetener component.

In a particular embodiment, steviol glycosides are present in the confection in an amount in the range of about 30 ppm to about 6000 ppm, about 1 ppm to about 10,000 ppm, or about 10 ppm to about 5000 ppm, about 500 ppm to about 5000 ppm, about 100 ppm to about 5000 ppm, about 100 ppm to about 7000 ppm, about 200 ppm to about 4000 ppm, about 500 ppm to about 7500 ppm, about 1000 ppm to about 8000 ppm, about 2000 ppm to about 5000 ppm, about 3000 ppm to about 7000 ppm or about 4000 ppm to about 6000 ppm of the confection.

In another embodiment, a condiment comprises steviol glycosides and one or more steviol glycoside solubility enhancers. In another embodiment a condiment comprises a sweetener composition comprising steviol glycosides and one or more steviol glycoside solubility enhancers. Condiments, as used herein, are compositions used to enhance or improve the flavor of a food or beverage. Non-limiting examples of condiments include ketchup (catsup); mustard; barbecue sauce; butter; chili sauce; chutney; cocktail sauce; curry; dips; fish sauce; horseradish; hot sauce; jellies, jams, marmalades, or preserves; mayonnaise; peanut butter; relish; remoulade; salad dressings (e.g., oil and vinegar, Caesar, French, ranch, bleu cheese, Russian, Thousand Island, Italian, and balsamic vinaigrette), salsa; sauerkraut; soy sauce; steak sauce; syrups; tartar sauce; and Worcestershire sauce.

In one embodiment, a chewing gum composition comprises a sweetener composition comprising steviol glycosides and one or more steviol glycoside solubility enhancers. Chewing gum compositions generally comprise a water-soluble portion and a water-insoluble chewable gum base portion. The water soluble portion, which typically includes the sweetener or sweetener composition, dissipates with a portion of the flavoring agent over a period of time during chewing while the insoluble gum base portion is retained in the mouth. The insoluble gum base generally determines whether a gum is considered chewing gum, bubble gum, or a functional gum.

In a particular embodiment, a chewing gum composition comprises a sweetener composition comprising steviol glycosides and one or more steviol glycoside solubility enhancer, and a gum base. In a particular embodiment, steviol glycosides are present in the chewing gum composition in a total amount in the range of about 1 ppm to about 10,000 ppm of the chewing gum composition.

In one embodiment, a cereal composition comprises a sweetener composition comprising steviol glycosides and one or more steviol glycoside solubility enhancers. Cereal compositions typically are eaten either as staple foods or as snacks. Non-limiting examples of cereal compositions for use in particular embodiments include ready-to-eat cereals as well as hot cereals. Ready-to-eat cereals are cereals which may be eaten without further processing (i.e. cooking) by the consumer. Examples of ready-to-eat cereals include breakfast cereals and snack bars. Breakfast cereals typically are processed to produce a shredded, flaky, puffy, or extruded form. Breakfast cereals generally are eaten cold and are often mixed with milk and/or fruit. Snack bars include, for example, energy bars, rice cakes, granola bars, and nutritional bars. Hot cereals generally are cooked, usually in either milk or water, before being eaten. Non-limiting examples of hot cereals include grits, porridge, polenta, rice, and rolled oats.

A sweetener composition comprising steviol glycosides and one or more steviol glycoside solubility enhancers can be is added to the cereal composition as a coating, such as, for example, by combining a sweetener comprising the steviol glycosides with a food grade oil and applying the mixture onto the cereal. In a different embodiment, a sweetener composition comprising the steviol glycosides and the food grade oil may be applied to the cereal separately, by applying either the oil or the sweetener first. A sweetener composition comprising steviol glycosides can also be added to the cereal composition as a glaze. Steviol glycosides can be added as a glaze by combining with a glazing agent and a food grade oil or fat and applying the mixture to the cereal. In yet another embodiment, a gum system, such as, for example, gum acacia, carboxymethyl cellulose, or algin, may be added to the glaze to provide structural support. In addition, the glaze also may include a coloring agent, and also may include a flavor. A sweetener composition comprising steviol glycosides can also be added to the cereal composition as a frosting. In one such embodiment, a sweetener composition comprising steviol glycosides is combined with water and a frosting agent and then applied to the cereal.

In a particular embodiment, steviol glycosides are present in the cereal composition in an amount in the range of about 0.02 to about 1.5 weight percent of the cereal composition.

In another embodiment, a baked good comprises a sweetener composition comprising steviol glycosides one or more steviol glycoside solubility enhancers. Baked goods, as used herein, include ready to eat and all ready to bake products, flours, and mixes requiring preparation before serving. Non-limiting examples of baked goods include cakes, crackers, cookies, brownies, muffins, rolls, bagels, donuts, strudels, pastries, croissants, biscuits, bread, bread products, and buns.

Exemplary baked goods can be classified into three groups: bread-type doughs (e.g., white breads, variety breads, soft buns, hard rolls, bagels, pizza dough, and flour tortillas), sweet doughs (e.g., danishes, croissants, crackers, puff pastry, pie crust, biscuits, and cookies), and batters (e.g., cakes such as sponge, pound, devil's food, cheesecake, and layer cake, donuts or other yeast raised cakes, brownies, and muffins). Doughs generally are characterized as being flour-based, whereas batters are more water-based.

Baked goods in accordance with particular embodiments generally comprise a combination of sweetener, water, and fat. Baked goods made in accordance with many embodiments of this disclosure also contain flour in order to make a dough or a batter. The term "dough" as used herein is a mixture of flour and other ingredients stiff enough to knead or roll. The term "batter" as used herein consists of flour, liquids such as milk or water, and other ingredients, and is thin enough to pour or drop from a spoon.

In one embodiment, a dairy product comprises a sweetener composition comprising comprising steviol glycosides and one or more steviol glycoside solubility enhancers. Dairy products and processes for making dairy products are well known to those of ordinary skill in the art. Dairy products, as used herein, comprise milk or foodstuffs produced from milk. Non-limiting examples of dairy products suitable for use in embodiments include milk, milk cream, sour cream, creme fraiche, buttermilk, cultured buttermilk, milk powder, condensed milk, evaporated milk, butter, cheese, cottage cheese, cream cheese, yogurt, ice cream, frozen custard, frozen yogurt, gelato, via, piima, filmjOlk, kajmak, kephir, viili, kumiss, airag, ice milk, casein, ayran, lassi, khoa, or combinations thereof. Milk is a fluid secreted by the mammary glands of female mammals for the nourishment of their young. The female ability to produce milk is one of the defining characteristics of mammals and provides the primary source of nutrition for newborns before they are able to digest more diverse foods. In particular embodiments, the dairy products are derived from the raw milk of cows, goats, sheep, horses, donkeys, camels, water buffalo, yaks, reindeer, moose, or humans.

In a particularly desirable embodiment, the dairy composition comprises a sweetener composition comprising steviol glycosides and one or more steviol glycoside solubility enhancers, in combination with a dairy product. In a particular embodiment, steviol glycosides are present in the dairy composition in a total amount in the range of about 200 to about 20,000 ppm of the dairy composition.

Tabletop sweetener compositions containing steviol glycosides and including compounds one or more steviol glycoside solubility enhancers, are also contemplated herein. The tabletop composition can further include a variety of other ingredients, including but not limited to at least one bulking agent, additive, anti-caking agent, functional ingredient or combination thereof.

Suitable "bulking agents" include, but are not limited to, maltodextrin (10 DE, 18 DE, or 5 DE), corn syrup solids (20 or 36 DE), sucrose, fructose, glucose, invert sugar, sorbitol, xylose, ribulose, mannose, xylitol, mannitol, galactitol, erythritol, maltitol, lactitol, isomalt, maltose, tagatose, lactose, inulin, glycerol, propylene glycol, polyols, polydextrose, fructooligosaccharides, cellulose and cellulose derivatives, and the like, and mixtures thereof. Additionally, in accordance with still other embodiments, granulated sugar (sucrose) or other caloric sweeteners such as crystalline fructose, other carbohydrates, or sugar alcohol can be used as a bulking agent due to their provision of good content uniformity without the addition of significant calories.

The tabletop sweetener compositions can be packaged in any form known in the art. Non-limiting forms include, but are not limited to, powder form, granular form, packets, tablets, sachets, pellets, cubes, solids, and liquids. The amount of steviol glycosides in a dry-blend tabletop sweetener formulation can vary. In a particular embodiment, a dry-blend tabletop sweetener formulation may contain steviol glycosides in an amount from about 1 (w/w) to about 10% (w/w) of the tabletop sweetener composition.

A tabletop sweetener composition also may be embodied in the form of a liquid, wherein a sweetener composition comprising steviol glycoside and including one or more steviol glycoside solubility enhancers, is combined with a liquid carrier. Suitable non-limiting examples of carrier agents for liquid tabletop functional sweeteners include water, alcohol, polyol, glycerin base or citric acid base dissolved in water, and mixtures thereof.

In one embodiment, the sweetened composition is a beverage product comprising steviol glycosides and including one or more steviol glycoside solubility enhancers. As used herein a "beverage product" is a ready-to-drink beverage, a beverage concentrate, a beverage syrup, frozen beverage, or a powdered beverage. Suitable ready-to-drink beverages include carbonated and non-carbonated beverages. Carbonated beverages include, but are not limited to, enhanced sparkling beverages, cola, lemon-lime flavored sparkling beverage, orange flavored sparkling beverage, grape flavored sparkling beverage, strawberry flavored sparkling beverage, pineapple flavored sparkling beverage, ginger-ale, soft drinks and root beer. Non-carbonated beverages include, but are not limited to fruit juice, fruit-flavored juice, juice drinks, nectars, vegetable juice, vegetable-flavored juice, sports drinks, energy drinks, enhanced water drinks, enhanced water with vitamins, near water drinks (e.g., water with natural or synthetic flavorants), coconut water, tea type drinks (e.g. black tea, green tea, red tea, oolong tea), coffee, cocoa drink, beverage containing milk components (e.g. milk beverages, coffee containing milk components, cafe au lait, milk tea, fruit milk beverages), beverages containing cereal extracts, smoothies and combinations thereof.

Examples of frozen beverages, include, but are not limited to, icees, frozen cocktails, daiquiris, pina coladas, margaritas, milk shakes, frozen coffees, frozen lemonades, granitas, and slushees.

Beverage concentrates and beverage syrups can be prepared with an initial volume of liquid matrix (e.g. water) and the desired beverage ingredients. Full strength beverages are then prepared by adding further volumes of water. Powdered beverages are prepared by dry-mixing all of the beverage ingredients in the absence of a liquid matrix. Full strength beverages are then prepared by adding the full volume of water.

In one embodiment, a beverage contains a sweetener composition comprising steviol glycosides and including one or more steviol glycoside solubility enhancers. Any sweetener composition comprising steviol glycosides and one or more steviol glycoside solubility enhancers detailed herein can be used in the beverages. In another embodiment, a method of preparing a beverage comprises combining a liquid matrix, steviol glycosides and one or more steviol glycoside solubility enhancers. The method can further comprise addition of one or more sweeteners, additives and/or functional ingredients. In still another embodiment, a method of preparing a beverage comprises combining a liquid matrix and a sweetener composition comprising steviol glycosides and one or more steviol glycoside solubility enhancers.

In another embodiment, a beverage contains a sweetener composition containing steviol glycosides, wherein the steviol glycosides are present in the beverage in an amount ranging from about 1 ppm to about 10,000 ppm, such as, for example, from about 25 ppm to about 800 ppm. In another embodiment, steviol glycosides are present in the beverage in an amount ranging from about 100 ppm to about 600 ppm. In yet other embodiments, steviol glycosides are present in the beverage in an amount ranging from about 100 to about 200 ppm, from about 100 ppm to about 300 ppm, from about 100 ppm to about 400 ppm, or from about 100 ppm to about 500 ppm. In still another embodiment, steviol glycosides are present in the beverage in an amount ranging from about 300 to about 700 ppm, such as, for example, from about 400 ppm to about 600 ppm. In a particular embodiment, steviol glycosides are present in the beverage in an amount of about 500 ppm.

In one embodiment, the composition is a beverage and the total glycoside content in the beverage is about 50 to 1500 ppm, or 100 to 1200 ppm, 200 to 1000 ppm, 300 to 900 ppm, 350 to 800 ppm, 400 to 600 ppm, or 450 to 550 ppm. In one embodiment, steviol glycosides other than Reb D, Reb M, Reb B and/or Reb A, or other than Reb D and/or Reb B, and optionally other than Reb G, Reb O, Reb N, and/or Reb E, e.g., one or more steviol glycoside solubility enhancers, are present in a beverage at about at least 1 ppm to about 600 ppm, e.g., about 50 ppm to about 500 ppm, including at least 1, 5, 10, 20, 30, 40, 50, 125, 150, 150, 175, or 200 ppm. In one embodiment, steviol glycosides other than Reb D, Reb M, Reb B and/or Reb A, or other than Reb D and/or Reb B, and optionally other than Reb G, Reb O, Reb N, and/or Reb E, are present in a beverage at about 1 to 600 ppm 10 to 400, 50 to 200, 75 to 150, 5 to 200, 10 to 100, 20 to 90, 30 to 80 ppm, and the like. In one embodiment, steviol glycosides other than Reb D, Reb M, Reb B and/or Reb A, are present in a beverage at about 1 to 600 ppm 10 to 400, 50 to 200, 75 to 150, 5 to 200, 10 to 100, 20 to 90, 30 to 80 ppm, and the like.

In certain embodiments, an agglomerate of steviol glycosides and one or more steviol glycoside solubility enhancers as a sweetener composition is provided. As used herein, "sweetener agglomerate" means a plurality of sweetener particles clustered and held together. Examples of sweetener agglomerates include, but are not limited to, binder held agglomerates, extrudates, and granules. Methods for making agglomerates are known to those of ordinary skill in the art, and are disclosed in more detail in U.S. Pat. No. 6,180,157. Generally described, the process for preparing an agglomerate in accordance with a certain embodiment comprises the steps of preparing a premix solution comprising steviol glycosides including one or more steviol glycoside solubility enhancers, sweetener composition and a binding agent in a solvent, heating the premix to a temperature sufficient to effectively form a mixture of the premix, applying the premix onto a fluidized carrier by a fluid bed agglomerator, and drying the resulting agglomerate. The sweetness level of the resulting agglomerate may be modified by varying the amount of the sweetener composition in the premix solution.

In some embodiments provided are substantially dustless and substantially free-flowing extrudates or extruded agglomerates of steviol glycosides including one or more steviol glycoside solubility enhancers, for a sweetener composition. Such particles may be formed with or without the use of binders using extrusion and spheronization processes.

"Extrudates" or "extruded sweetener composition", as used herein, refers to cylindrical, free-flowing, relatively non-dusty, mechanically strong granules of steviol glycosides including one or more steviol glycoside solubility enhancers. The terms "spheres" or "spheronized sweetener composition", as used herein, refer to relatively spherical, smooth, free-flowing, relatively non-dusty, mechanically strong granules. A process for making extrudates are described in U.S. Pat. No. 6,365,216.

In another embodiment, granulated forms of steviol glycosides, including one or more steviol glycoside solubility enhancers are provided. As used herein, the terms "granules," "granulated forms," and "granular forms" are synonymous and refer to free-flowing, substantially non-dusty, mechanically strong agglomerates of the steviol glycoside sweetener composition. Methods of granulation are known to those of ordinary skill in the art and are described in more detail in the PCT Publication WO 01/60842.

Exemplary Natural Sources of Steviol Glycoside Solubility Enhancers

Steviol glycoside solubility enhancers may be prepared synthetically or isolated from organisms including but not limited to plants, e.g., plant leaves and stems. The following Table provides genera of plants that are examples of plants likely to contain compounds within the scope of the disclosed steviol glycoside solubility enhancers, e.g., formula (I), including for instance caffeic acid, chlorogenic acid, cynarin, and/or structurally-related compounds which likely aid in the solubility of steviol glycosides.

TABLE 1

| Genus | Exemplary species and synonymous species (Syn.) | Exemplary common names |
| --- | --- | --- |
| Stevia | rebaudiana | Stevia |
| Siraitia | grosvenorii | Monkfruit |
| Coffea | Coffea arabica, | Coffee |
|  | Coffea canephora, | Coffee beans |
|  | Coffea ambongensis, | Green coffee beans |
|  | Coffea boinensis, |  |
|  | Coffea labatii, |  |
|  | Coffea pterocarpa, |  |
|  | Coffea bissetiae, |  |
|  | Coffea namorokensis |  |
|  | Coffea charrieriana, |  |
|  | Coffea anthonyi |  |
| Camellia | Camellia sinensis, | Tea |
|  | Camellia japonica, | White tea |
|  | Camellia sasanqua, | Yellow tea |
|  | Camellia oleifera, | Green tea |
|  | Camellia crapnelliana, | Oolong tea |
|  | Camellia reticulata, | Black tea |
|  | Camellia cuspidata, | Red tea |
|  | Camellia saluenensis, | Post-fermented tea |
|  | Camellia × williamsii, |  |
|  | Camellia taliensis, |  |
|  | Camellia rusticana |  |
| Phyllostachys | Phyllostachys edulis, | Bamboo, |
|  | Syn. Bambos moosoo, | moso bamboo, |
|  | Syn. Bambusa heterocycle, | tortoise-shell bamboo, |
|  | Syn. Bambusa mitis, | mao zhu |
|  | Syn. Bambusa pubescens, |  |
|  | Phyllostachys bicolor, |  |
|  | Phyllostachys heterocycla, |  |
|  | Phyllostachys pubescens |  |
| Calluna | Calluna vulgaris | common heather, ling, heather |
| Helianthus | Helianthus annuus, | Sunflower |
|  | Helianthus tuberosus, | Sunflower seeds |
|  | Helianthus verticillatus, |  |
|  | Helianthus giganteus, |  |
|  | Helianthus petiolaris, |  |
| Vaccinium | Vaccinium corymbosum, | Blueberries, |
|  | Vaccinium alaskaense, | cranberries, |
|  | Vaccinium angustifolium, | bilberries, |
|  | Vaccinium crassifolium, | grouseberries, |
|  | Vaccinium boreale, | whortleberry, |
|  | Vaccinium darrowii, | lingonberry, |
|  | Vaccinium koreanum | cowberry, |
|  | Vaccinium myrtillus, | huckleberry |
|  | Vaccinium uliginosum, |  |
|  | Vaccinium macrocarpon, |  |
|  | Vaccinium oxycoccos, |  |
|  | Vaccinium ovatum, |  |
|  | Vaccinium uliginosum, |  |
|  | Vaccinium vitis-idaea |  |
| Vitis | Vitis vinifera | Grapes Wine Raisins |
| Cichorium | Cichorium intybus | Chicory |
| Echinacea | Echinacea purpurea, Echinacea angustifolia | Eastern purple coneflower Echinacea |
| Parietaria | Parietaria officinalis | Eastern pellitory-of-the-wall, Upright pellitory, Lichwort |

TABLE 1-continued

| Genus | Exemplary species and synonymous species (Syn.) | Exemplary common names |
|---|---|---|
| Chelidonium | Chelidonium majus | Greater celandine, Tetterwort, Nipplewort, Swallowwort |
| Sanguinaria | Sanguinaria canadensis | Bloodroot |
| Urtica | Urtica dioica | Common nettle, Stinging nettle |
| Solanum | Solanum tuberosum, Solanum stenotomum, Solanum phureja, Solanum goniocalyx, Solanum ajanhuiri, Solanum chaucha, Solanum juzepczukii, Solanum melongena, Solanum lycopersicum, Solanum incanum Syn. Lycopersicon esculentum | Potato, Potato leaves, Eggplant, Aubergine, Tomato, Cherry tomato, Bitter apple, Thorn apple |
| Ipomoea | Ipomoea batatas | Sweet potato |
| Malus | Malus pumila, Malus domestica | Apple, Apple juice |
| Prunus | Prunus persica, Prunus dulcis, Prunus amygdalus, Prunus avium, Prunus cerasus, Prunus domestica, Prunus salicina | Peach, Nectarine, Cherry, Sour cherry, Wild cherry, Apricot, Almond, Plum, Prune |
| Ilex | Ilex paraguariensis, Ilex guayusa, Ilex kudingcha, Ilex vomitoria, Ilex aquifolium, Ilex latifolia, Ilex opaca | Holly, Yerba mate, Mate, Guayusa, Yaupon Holly, Kuding |
| Paullinia | Paullinia cupana | Guarana |
| Theobroma | Theobroma cacao | Cocoa, Cocoa bean, Cacao, Cacao bean |
| Cola | Cola acuminata, Cola nitida, Cola elegans, Cola reticulate, Cola nigerica, Cola umbratilis | Kola nut, Kola tree, Cola nut, Cola tree |
| Matteuccia | Matteuccia struthiopteris, Matteuccia orientalis, Matteuccia intermedia, | Ostrich fern, Oriental ostrich fern, Fiddlehead fern, Shuttlecock fern |
| Pentarhizidium | Pentarhizidium orientalis | Oriental ostrich fern |
| Osmunda | Osmunda japonica, Osmunda regalis | Asian royal fern, Royal fern |
| Pteridium | Pteridium aquilinum | Bracken, Brake, Common bracken, Eagle fern, Eastern brakenfern |
| Syzygium | Syzygium aromaticum | Clove |
| Cinnamomum | Cinnamomum verum, Cinnamomum cassia, Cinnamomum tamala | Cinnamon, Indian bay leaf |
| Myristica | Myristica fragrans, Myristica argentea, Myristica malabarica | Nutmeg |
| Laurus | Laurus nobilis | Bay laurel, Bay leaf |
| Ocimum | Ocimum basilicum | Basil, Great basil, Saint-Joseph's-wort |
| Thymus | Thymus vulgaris | Thyme |
| Salvia | Salvia officinalis | Sage, Garden sage, Common sage, Culinary sage |
| Rosmarinus | Rosmarinus officinalis | Rosemary |
| Origanum | Origanum vulgare, Origanum majorana, Syn. Majorana hortensis, Syn. Majorana majorana, Origanum onites, Origanum pulchellum | Oregano, Wild marjoram, Marjoram, Sweet marjoram, Knotted marjoram, Pot marjoram |
| Anethum | Anethum graveolens | Dill |
| Pimpinella | Pimpinella anisum | Anise |
| Illicium | Illicium verum | Star anise |
| Foeniculum | Foeniculum vulgare | Fennel, Florence fennel |
| Artemisia | Artemisia dracunculus, Artemisia vulgaris | Tarragon, Estragon, Mugwort |
| Glycyrrhiza | Glycyrrhiza glabra | Licorice, Liquorice |
| Glycine | Glycine max | Soy, Soybean, Soyabean, Soya bean |
| Triticum | Triticum aestivum, | Wheat, Common wheat |
| Oryza | Oryza sativa, Oryza glaberrima | Rice |
| Brassica | Brassica napus, Brassica rapa, Brassica campestres, Brassica juncea, Brassica oleracea | Canola, Broccoli, Cauliflower, Cabbage, Bok choy, Kale, Collard greens, Brussels sprouts, Kohlrabi |
| Drimys | Drimys winteri | Winter's bark |
| Sambucus | Sambucus nigra | Elderflower |
| Boehmeria | Boehmeria caudata | Assa-Peixe |
| Cynara | Cynara scolymus | Artichoke |
| Arctium | Arctium lappa | Greater burdock |
| Valeriana | Valeriana officinalis | Valerian |
| Matricaria | Matricaria chamomilla | Chamomile |
| Strychnos | Strychnos nux-vomica | strychnine tree, nux vomica, poison nut, semen strychnos, quaker buttons |

Exemplary Steviol Glycoside Solubility Enhancers and Formulations

In one embodiment, a steviol glycoside solubility enhancer comprises a compound of formula (I) or a pharmaceutically acceptable salt or ester thereof:

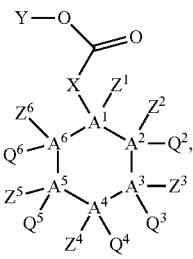

Formula I wherein
either each of $A^1$-$A^6$ is a carbon atom and $A^1/A^2$, $A^3/A^4$, and $A^5/A^6$ are bonded through carbon-carbon double bonds, each of $A^1$-$A^6$ is a carbon atom and at least one of $A^1/A^2$, $A^3/A^4$, and $A^5/A^6$ are bonded through a carbon-carbon double bond, each of $A^1$-$A^5$ is an aliphatic carbon atom and $A^6$ is O, or each $A^1$-$A^6$ is an aliphatic carbon atom;

each of $Z^1$-$Z^6$ is independently hydrogen, OH, $OR^1$, or absent;

each of $Q^2$-$Q^6$ is independently hydrogen, alkyl, alkenyl, cycloalkyl, aryl, aralkyl, carboxylic acid, OH, $OR^2$,

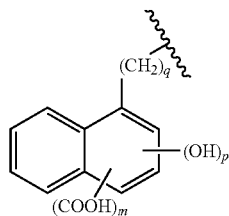

or combinations thereof, or $Q^4$ and $Q^5$ can join to form a fused $C_4$-$C_7$ carbocyclic ring, wherein the $C_4$-$C_7$ carboxylic ring can be substituted by zero to four of OH, $OR^1$, or a combination thereof;

X is

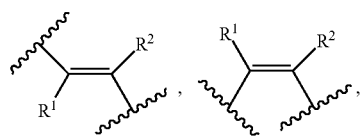

$C_1$-$C_3$ alkyl, or a bond;

$R^1$ and $R^2$ are independently hydrogen, carboxylic acid, OH, alkyl, alkenyl, cycloalkyl, aryl, aralkyl,

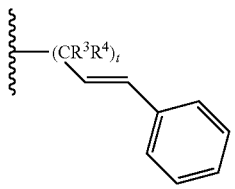

optionally substituted on the phenyl ring with from one to five hydroxyl or methoxy groups or combinations thereof,

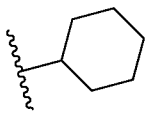 [SMILES: *C1CCCCC1]

or optionally substituted on the cyclohexyl ring with from one to six hydroxyl or carboxylic acid groups or combinations thereof,

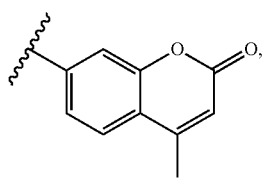

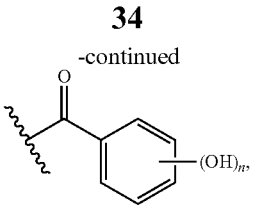

substituted analogs thereof, or combinations thereof;

$R^3$ and $R^4$ are independently hydrogen, OH, carboxylic acid, alkyl, alkenyl, cycloalkyl, aryl, aralkyl, or combinations thereof;

and Y is hydrogen, OH, carboxylic acid, alkyl, alkenyl, cycloalkyl, aryl, aralkyl,

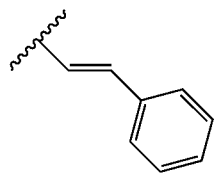 [SMILES: */C=C/c1ccccc1]

optionally substituted on the phenyl ring with from one to five hydroxyl or methoxy groups or combinations thereof, or

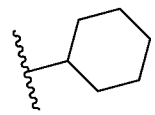 [SMILES: *C1CCCCC1]

optionally substituted on the cyclohexyl ring with from one to six hydroxyl or carboxylic acid groups or combinations thereof, or combinations thereof; and each m, n, p, q, and t is independently an integer from 0 to 5.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O) CH$_2$C(O)R, C(S)R, C(O)OR, OC(O)R, C(O)N(R)$_2$, OC(O) N(R)$_2$, C(S)N(R)$_2$, (CH$_2$)$_{0-2}$N(R)C(O)R, (CH$_2$)$_{0-2}$N(R) N(R)$_2$, N(R)N(R)C(O)R, N(R)N(R)C(O)OR, N(R)N(R) CON(R)$_2$, N(R)SO$_2$R, N(R)SO$_2$N(R)$_2$, N(R)C(O)OR, N(R) C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms, from 1 to 6 carbon atoms, or from 1 to 4 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group. The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "heterocyclyl" as used herein refers to aromatic and non-aromatic ring compounds containing three or more ring members, of which one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein. The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

The term "amine" as used herein refers to primary, secondary, and tertiary amines having, e.g., the formula N(group)$_3$ wherein each group can independently be H or non-H, such as alkyl, aryl, and the like Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

When the term "combinations thereof" is used with a list of possible substituents, it refers to an arrangement of those groups in any combination. For example, if Y is defined as hydrogen, OH, carboxylic acid, alkyl, or alkenyl, it means any fragment using those groups is encompassed by Y. Thus, without limitation, Y can be an alkyl moiety bonded to an alkene moiety bonded to a carboxylic acid moiety, etc.

In one embodiment, each $A^1$-$A^6$ is an aliphatic carbon atom. In one embodiment, Y is hydrogen, X is a bond, and $Z^1$ is OH. In one embodiment, $Q^3$ and $Q^4$ are OH and $Z^3$ and $Z^4$ are hydrogen.

In one embodiment, the compound has the structure:

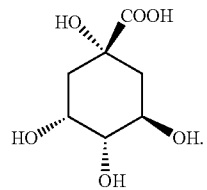 [SMILES: O=C(O)[C@]1(O)C[C@@H](O)[C@@H](O)[C@H](O)C1]

In one embodiment, the compound has the structure:

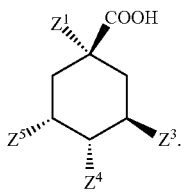

In one embodiment, the compound has the structure:

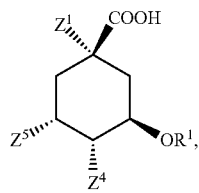

wherein $R^1$ has the structure:

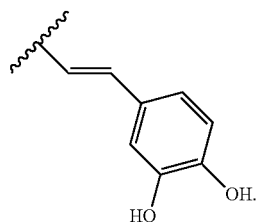 [SMILES: */C=C/c1ccc(O)c(O)c1]

In one embodiment, the compound has the structure:

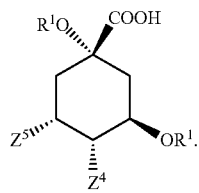

In one embodiment, the compound has the structure:

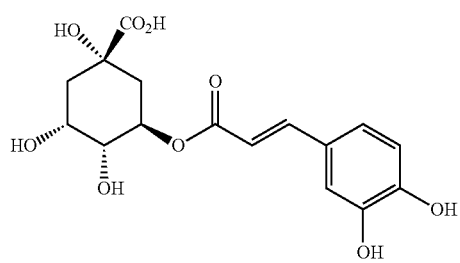 or

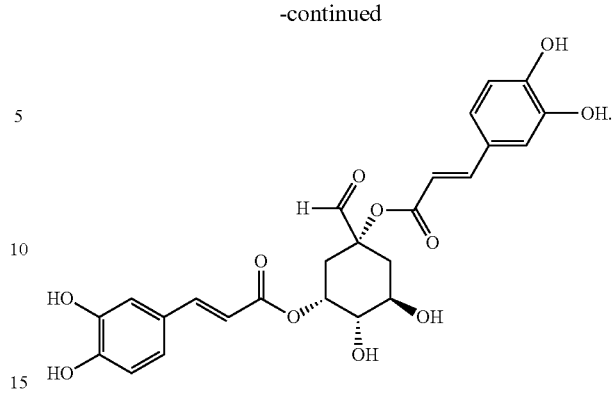

In one embodiment, the compound has the structure:

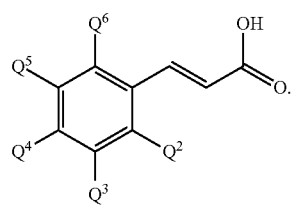

In one embodiment, the compound has the structure:

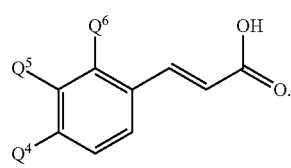

In one embodiment, the compound has a structure selected from:

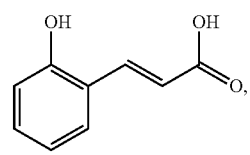

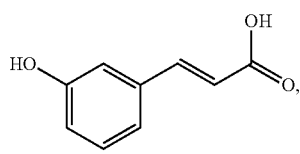

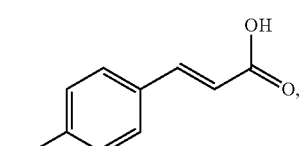

and combinations thereof.

In one embodiment, the compound has the structure:

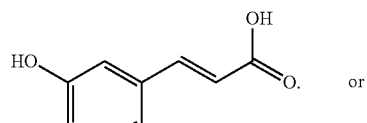 or

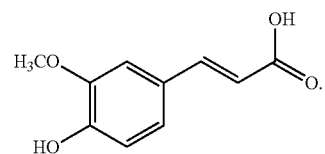

In one embodiment, the compound has the structure:

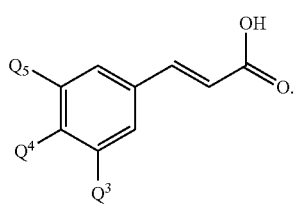

In one embodiment, the compound has the structure:

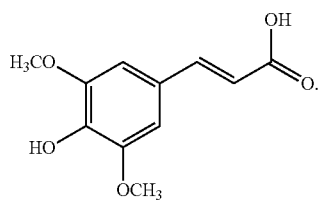 [SMILES: COc1cc(/C=C/C(=O)O)cc(OC)c1O]

In one embodiment, the compound has the structure:

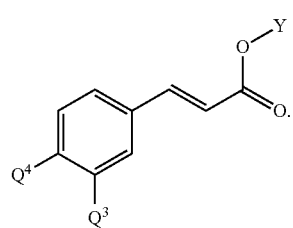

In one embodiment, the compound has the structure:

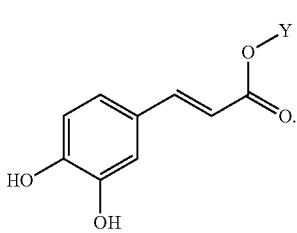

In one embodiment, the compound has the structure:

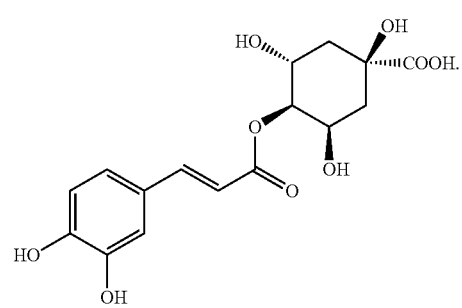 [SMILES: O=C(/C=C/c1ccc(O)c(O)c1)O[C@H]1[C@H](O)C[C@](O)(C(=O)O)C[C@H]1O]

In one embodiment, the compound has the structure:

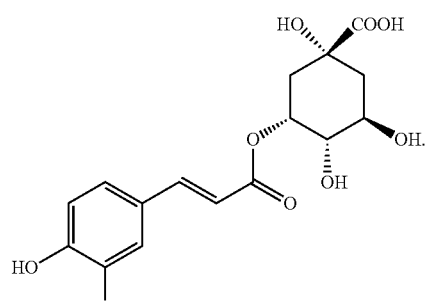

In one embodiment, the compound has the structure:

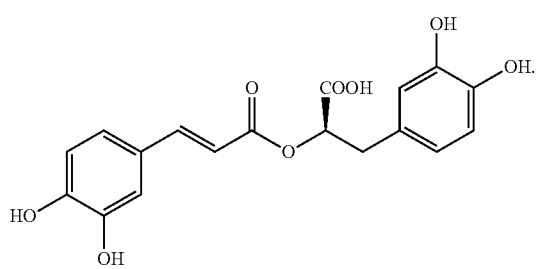 [SMILES: O=C(/C=C/c1ccc(O)c(O)c1)O[C@H](Cc1ccc(O)c(O)c1)C(=O)O]

In one embodiment, the compound has the structure:

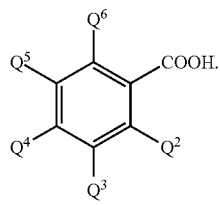

In one embodiment, the compound has the structure:

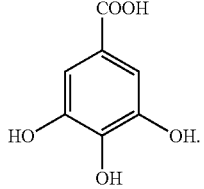

In one embodiment, the compound has the structure:

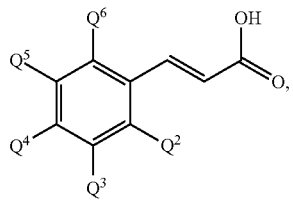

and at least two of $Q^2$-$Q^6$ are OH, e.g., $Q^2$ and $Q^4$ are OH.

In one embodiment, a solid (dry) composition, such as a powder, e.g., a spray dried powder or a freeze-dried powder, having one or more steviol glycoside solubility enhancers, e.g., a powder prepared from a plant extract which powder is not supplemented with isolated steviol glycosides, does not include one or more of the following compounds, or any combination thereof, at the disclosed cutoff wt %.

TABLE 2

| Class of compounds | Cutoff Level (% wt) | % wt of compounds in steviol glycoside solubility enhancer solid (dry) compositions |
|---|---|---|
| Organic acids | <3% | Malonate/malonic acid |
|  | <3% | Oxalate/oxalic acid |
|  | <3% | Lactate/lactic acid |
|  | <0.5% | Tartrate/tartaric acid |
|  | <0.5% | Pyruvate/pyruvic acid |
|  | <0.5% | Fumarate/fumaric acid |
|  | <3% | Succinate/succinic acid |
|  | <0.5% | Ascorbic acid |
|  | <0.5% | Sorbate/sorbic acid |
|  | <0.5% | Acetate/acetic acid |
|  | <3% | Malate/malic acid |
|  | <3% | Citrate/citric acid |
| Inorganic acids | <1% | Sulfate/sulfuric acid |
|  | <1% | Phosphate/phosphoric acid |
|  | <1% | Nitrate/nitric acid |
|  | <1% | Nitrite/nitrous acid |
|  | <1% | Chloride/hydrochloric acid |
|  | <1% | Ammonia/ammonium |
| Flavanoids, isoflavanoids, and neoflavanoids | <5% | Quercetin, Kaempferol, Myricetin, Fisetin, Galangin, Isorhamnetin, Pachypodol, Rhamnazin, Pyranoflavonols, Furanoflavonols, Luteolin, Apigenin, Tangeritin, Taxifolin (or Dihydroquercetin), Dihydrokaempferol, Hesperetin, Naringenin, Eriodictyol, Homoeriodictyol, Genistein, Daidzein, Glycitein |
| Flavanoid glycosides | <5% | Hesperidin, Naringin, Rutin, Quercitrin, luteolin-glucoside, quercetin-xyloside |
| Anthocyanidins | <5% | Cyanidin, Delphinidin, Malvidin, Pelargonidin, Peonidin, Petunidin |
| Tannins | <1% | Tannic acid |
| Amino acids + total protein | <0.1% | Alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine |
| Total Fat | <1% | Monoglycerides, diglycerides, triglycerides |
| Monosaccharides, disaccharides, and polysaccharides | <1% | Glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, and maltotriose, panose |
| Sugar alcohols | <1% | Glycerol, Sorbitol, mannitol, xylitol, maltitol, lactitol, erythritol, isomalt, inositol |

TABLE 2-continued

| Class of compounds | Cutoff Level (% wt) | % wt of compounds in steviol glycoside solubility enhancer solid (dry) compositions |
|---|---|---|
| Dietary fiber | <0.1% | Acacia (arabic) gum, Agar-agar, Algin-alginate, Arabynoxylan, Beta-glucan, Beta mannan, Carageenan gum, Carob or locust bean gum, Fenugreek gum, Galactomannans, Gellan gum, Glucomannan or konjac gum, Guar gum, Hemicellulose, Inulin, Karaya gum, Pectin, Polydextrose, Psyllium husk mucilage, Resistant starches, Tara gum, Tragacanth gum, Xanthan gum, Cellulose, Chitin, and Chitosan |
| Steviol glycosides | <55% | Stevioside; steviolbioside; rubusoside; 13- and 19-SMG; Dulcosides A, B, C, D; and rebaudiosides A, B, C, D, E, F, I, M, N, O, T |
| Other compounds | <0.5% | Chlorophyll |

In one embodiment, a solid (dry) composition such as a powder composition having one or more steviol glycosides and one or more solubility enhancers does not include one or more of the following compounds, or any combination thereof, at the cutoff % wt.

TABLE 3

| Class of compounds | Cutoff Level (% wt) | % wt of compounds in solud (dry) mixtures of steviol glycosides and steviol glycoside solubility enhancers |
|---|---|---|
| Organic acids | <3% | Malonate/malonic acid |
| | <3% | Oxalate/oxalic acid |
| | <3% | Lactate/lactic acid |
| | <0.5% | Tartrate/tartaric acid |
| | <0.5% | Pyruvate/pyruvic acid |
| | <0.5% | Fumarate/fumaric acid |
| | <3% | Succinate/succinic acid |
| | <0.5% | Ascorbic acid |
| | <0.5% | Sorbate/sorbic acid |
| | <0.5% | Acetate/acetic acid |
| | <3% | Malate/malic acid |
| | <3% | Citrate/citric acid |
| Inorganic acids | <1% | Sulfate/sulfuric acid |
| | <1% | Phosphate/phosphoric acid |
| | <1% | Nitrate/nitric acid |
| | <1% | Nitrite/nitrous acid |
| | <1% | Chloride/hydrochloric acid |
| | <1% | Ammonia/ammonium |
| Flavanoids, isoflavanoids, and neoflavanoids | <5% | Quercetin, Kaempferol, Myricetin, Fisetin, Galangin, Isorhamnetin, Pachypodol, Rhamnazin, Pyranoflavonols, Furanoflavonols, Luteolin, Apigenin, Tangeritin, Taxifolin (or Dihydroquercetin), Dihydrokaempferol, Hesperetin, Naringenin, Eriodictyol, Homoeriodictyol, Genistein, Daidzein, Glycitein |
| Flavanoid glycosides | <5% | Hesperidin, Naringin, Rutin, Quercitrin, luteolin-glucoside, quercetin-xyloside |
| Anthocyanidins | <5% | Cyanidin, Delphinidin, Malvidin, Pelargonidin, Peonidin, Petunidin |
| Tannins | <1% | Tannic acid |
| Amino acids + total protein | <0.1% | Alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine |
| Total Fat | <1% | Monoglycerides, diglycerides, triglycerides |
| Monosaccharides, disaccharides, and polysaccharides | <1% | Glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, and maltotriose, panose |
| Sugar alcohols | <1% | Glycerol, Sorbitol, mannitol, xylitol, maltitol, lactitol, erythritol, isomalt, inositol |

TABLE 3-continued

| Class of compounds | Cutoff Level (% wt) | % wt of compounds in solud (dry) mixtures of steviol glycosides and steviol glycoside solubility enhancers |
|---|---|---|
| Dietary fiber | <0.1% | Acacia (arabic) gum, Agar-agar, Algin-alginate, Arabynoxylan, Beta-glucan, Beta mannan, Carageenan gum, Carob or locust bean gum, Fenugreek gum, Galactomannans, Gellan gum, Glucomannan or konjac gum, Guar gum, Hemicellulose, Inulin, Karaya gum, Pectin, Polydextrose, Psyllium husk mucilage, Resistant starches, Tara gum, Tragacanth gum, Xanthan gum, Cellulose, Chitin, and Chitosan |
| Steviol glycosides | <75% | Stevioside; steviolbioside; rubusoside; 13- and 19-SMG; Dulcosides A, B, C, D; and rebaudiosides A, B, C, D, E, F, I, M, N, O, T |
| Other compounds | <0.5% | Chlorophyll |

In one embodiment, a liquid concentrate having one or more steviol glycosides and one or more steviol glycoside solubility enhancers may be formed from a steviol glycoside solubility enhancer composition that does not include one or more of the following compounds, or any combination thereof, at the disclosed wt % cutoff.

TABLE 4

| Class of compounds | Cutoff Level (% wt) | % (wt) of compounds in liquid mixtures of steviol glycoside(s) and steviol glycoside solubility enhancer(s) |
|---|---|---|
| Organic acids | <0.3% | Malonate/malonic acid |
| | <0.3% | Oxalate/oxalic acid |
| | <0.3% | Lactate/lactic acid |
| | <0.05% | Tartrate/tartaric acid |
| | <0.05% | Pyruvate/pyruvic acid |
| | <0.05% | Fumarate/fumaric acid |
| | <0.3% | Succinate/succinic acid |
| | <0.05% | Ascorbic acid |
| | <0.05% | Sorbate/sorbic acid |
| | <0.05% | Acetate/acetic acid |
| | <0.3% | Malate/malic acid |
| Inorganic acids | <1% | Sulfate/sulfuric acid |
| | <1% | Nitrate/nitric acid |
| | <1% | Nitrite/nitrous acid |
| | <1% | Chloride/hydrochloric acid |
| | <1% | Ammonia/ammonium |
| Flavanoids, isoflavanoids, and neoflavanoids | <0.5% | Quercetin, Kaempferol, Myricetin, Fisetin, Galangin, Isorhamnetin, Pachypodol, Rhamnazin, Pyranoflavonols, Furanoflavonols, Luteolin, Apigenin, Tangeritin, Taxifolin (or Dihydroquercetin), Dihydrokaempferol, Hesperetin, Naringenin, Eriodictyol, Homoeriodictyol, Genistein, Daidzein, Glycitein |
| Flavanoid glycosides | <0.5% | Hesperidin, Naringin, Rutin, Quercitrin, luteolin-glucoside, quercetin-xyloside |
| Anthocyanidins | <0.5% | Cyanidin, Delphinidin, Malvidin, Pelargonidin, Peonidin, Petunidin |
| Tannins | <0.1% | Tannic acid |
| Amino acids + total protein | <0.01% | Alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine |
| Total Fat | <0.1% | Monoglycerides, diglycerides, triglycerides |
| Monosaccharides, disaccharides, and polysaccharides | <0.1% | Glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, and maltotriose, panose |
| Sugar alcohols | <0.1% | Glycerol, Sorbitol, mannitol, xylitol, maltitol, lactitol, erythritol, isomalt, inositol |
| Dietary fiber | <0.01% | Acacia (arabic) gum, Agar-agar, Algin-alginate, Arabynoxylan, Beta-glucan, Beta mannan, Carageenan gum, Carob or locust bean gum, Fenugreek gum, Galactomannans, Gellan gum, Glucomannan or konjac gum, Guar gum, Hemicellulose, Inulin, Karaya gum, Pectin, Polydextrose, Psyllium husk mucilage, Resistant starches, Tara gum, Tragacanth gum, Xanthan gum, Cellulose, Chitin, and Chitosan |
| Other compounds | <0.05% | Chlorophyll |

In one embodiment, a beverage having one or more steviol glycosides and one or more steviol glycoside solubility enhancers does not include one or more of the following compounds, or any combination thereof, at the disclosed wt % cutoffs.

TABLE 5

| Class of compounds | Cutoff Level (% wt) | % (wt) of compounds in beverages having steviol glycoside(s) and steviol glycoside solubility enhancer(s) |
|---|---|---|
| Organic acids | <0.1% | Malonate/malonic acid |
| | <0.1% | Oxalate/oxalic acid |
| | <0.1% | Pyruvate/pyruvic acid |
| | <0.1% | Fumarate/fumaric acid |
| Inorganic acids | <1% | Sulfate/sulfuric acid |
| | <1% | Nitrate/nitric acid |
| | <1% | Nitrite/nitrous acid |
| | <1% | Ammonia/ammonium |
| Flavanoids, isoflavanoids, and neoflavanoids | <0.5% | Quercetin, Kaempferol, Myricetin, Fisetin, Galangin, Isorhamnetin, Pachypodol, Rhamnazin, Pyranoflavonols, Furanoflavonols, Luteolin, Apigenin, Tangeritin, Taxifolin (or Dihydroquercetin), Dihydrokaempferol, Hesperetin, Naringenin, Eriodictyol, Homoeriodictyol, Genistein, Daidzein, Glycitein |

TABLE 5-continued

| Class of compounds | Cutoff Level (% wt) | % (wt) of compounds in beverages having steviol glycoside(s) and steviol glycoside solubility enhancer(s) |
|---|---|---|
| Flavanoid glycosides | <0.5% | Hesperidin, Naringin, Rutin, Quercitrin, luteolin-glucoside, quercetin-xyloside |
| Anthocyanidins | <0.5% | Cyanidin, Delphinidin, Malvidin, Pelargonidin, Peonidin, Petunidin |
| Tannins | <0.1% | Tannic acid |
| Amino acids + total protein | <5% | Alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine |
| Total Fat | <0.5% | Monoglycerides, diglycerides, triglycerides |
| Dietary fiber | <5% | Acacia (arabic) gum, Agar-agar, Algin-alginate, Arabynoxylan, Beta-glucan, Beta mannan, Carageenan gum, Carob or locust bean gum, Fenugreek gum, Galactomannans, Gellan gum, Glucomannan or konjac gum, Guar gum, Hemicellulose, Inulin, Karaya gum, Pectin, Polydextrose, Psyllium husk mucilage, Resistant starches, Tara gum, Tragacanth gum, Xanthan gum, Cellulose, Chitin, and Chitosan |
| Other compounds | <0.05% | Chlorophyll |

In one embodiment, compounds with phenolic and/or carboxylic acid groups that may increase the solubility of steviol glycosides include but are not limited to those in Table 6.

TABLE 6

| molecular formula | substance name | temperature (° C.) | solubility (ppm) |
|---|---|---|---|
| C8H6O3 | alpha-oxobenzeneacetic acid | 0 | 4.79E+05 |
| C18H25I3N3O9 | 3,5-diacetylamino-2,4,6-triiodobenzoic acid methyl-glucamide | 20 | 4.71E+05 |
| C11H17N3O3 | orotic acid triethylamide | 25 | 3.51E+05 |
| C9H6O5 | phthalonic acid | 15 | 3.49E+05 |
| C11H9I3N2O4 | diatrizoic acid | 25 | 3.33E+05 |
| C14H8O8S2 | 1,6-anthraquinone disulfonic acid | 18 | 3.33E+05 |
| C7H8O3S | p-toluenesulfonic acid | 36.5 | 3.33E+05 |
| C7H8O3S·H2O | o-toluenesulfonic acid (monohydrate) | 32.5 | 3.28E+05 |
| C8H8O4 | 2,5-hydroxybenzeneacetic acid | 25 | 3.15E+05 |
| C7H8O3S·H2O | p-toluenesulfonic acid (monohydrate) | 20.1 | 2.92E+05 |
| C14H8O8S2 | 1,5-anthraquinone disulfonic acid | 18 | 2.86E+05 |
| C14H8O8S2 | 1,8-anthraquinonedisulfinic acid | 18 | 2.86E+05 |
| C7H8O3S·2H2O | o-toluenesulfonic acid (dihydrate) | 16.8 | 2.83E+05 |
| C14H7ClO5S | 1,5-chloroanthraquinone sulfonic acid | 18 | 2.50E+05 |
| C7H12O6 | quinic acid (coffee beans) | 9 | 2.25E+05 |
| C14H7ClO5S | 1,7-chloroanthraquinone sulfonic acid | 18 | 1.67E+05 |
| C14H7ClO5S | 1,6-chloroanthraquinone sulfonic acid | 18 | 1.67E+05 |
| C10H9NO9S3 | 1-naphthylamine-2,4,7-trisulfonic acid | 20 | 1.55E+05 |
| C8H8O3 | mandelic acid (almonds) | 25 | 1.53E+05 |
| C7H10O5 | shikimic acid (star anise) | 21 | 1.30E+05 |
| C8H8O3 | alpha-hydroxybenzeneacetic acid, (±) | 20 | 1.21E+05 |
| C9H14O6 | L-camphoronic acid | 16 | 9.99E+04 |
| C23H16O6 | pamoic acid (used in drugs to increase solubility) |  | 9.80E+04 |
| C8H8O3 | alpha-hydroxybenzeneacetic acid, (S) | 25 | 9.26E+04 |

TABLE 6-continued

| molecular formula | substance name | temperature (° C.) | solubility (ppm) |
|---|---|---|---|
| C8H8O3 | 3-hydroxy-4-methylbenzoic acid | 100 | 4.17E+04 |
| C8H9NO4 | biliverdic acid | 20 | 3.75E+04 |
| C7H9NO3S | 6-amino-m-toluenesulfonic acid | 19 | 3.10E+04 |
| C9H6O6 | 1,2,3-benzenetricarboxylic acid | 19 | 2.97E+04 |
| C8H6O5 | 2-hydroxyisophthalic acid | 100 | 2.57E+04 |
| C26H20N2O8S2 | 1,8-anthraquinone disulfonic acid anilide | 18 | 2.27E+04 |
| C7H6O4 | 2,5-dihydroxybenzoic acid | 25 | 2.15E+04 |
| C8H8O3 | 2-hydroxy-5-methylbenzoic acid | 100 | 2.14E+04 |
| C8H5ClO4 | 3-chlorophthalic acid | 14 | 2.08E+04 |
| C7H3N3O8 | 2,4,6-trinitrobenzoic acid | 23 | 1.97E+04 |
| C8H5NO6 | 3-nitrophthalic acid | 25 | 1.97E+04 |
| C15H18I3NO5 | iopronic acid | 37 | 1.97E+04 |
| C9H10O3 | alpha-(hydroxymethyl)benzeneacetic acid | 20 | 1.91E+04 |
| C7H4N2O6 | 2,4-dinitrobenzoic acid | 25 | 1.79E+04 |
| C7H6O4 | 3,4-dihydroxybenzoic acid | 14 | 1.79E+04 |
| C8H8O2 | benzeneacetic acid | 25 | 1.70E+04 |
| C7H4N2O6 | 2,6-dinitrobenzoic acid |  | 1.59E+04 |
| C7H4O6 | 4-oxo-4H-pyran-2,6-dicarboxylic acid | 25 | 1.41E+04 |
| C10H6O8 | pyromellitic acid | 16 | 1.40E+04 |
| C7H4Cl2O2 | 2,6-dichlorobenzoic acid |  | 1.39E+04 |
| C8H5NO6 | 2,3,4-pyridinetricarboxylic acid | 15 | 1.19E+04 |
| C7H6O5 | 3,4,5-trihydroxybenzoic acid | 20 | 1.18E+04 |
| C8H8O3 | 2-hydroxy-3-methylbenzoic acid | 100 | 1.15E+04 |
| C10H10O4 | acetyl-r-mandelic acid | 25 | 1.11E+04 |
| C7H5NO4 | 2,3-pyridinedicarboxylic acid | 25 | 1.09E+04 |
| C9H8O2 | cis-cinnamic acid | 25 | 1.09E+04 |
| C8H8O3 | 2-hydroxy-4-methylbenzoic acid | 100 | 1.00E+04 |
| C7H14O2 | 2-ethyl-2-methylbutanoic acid | 25 | 9.69E+03 |
| C7H4ClNO4 | 5-chloro-2-nitrobenzoic acid | 25 | 9.58E+03 |
| C7H6O4 | 2,6-dihydroxybenzoic acid |  | 9.47E+03 |
| C10H12O2 | (±)-3-phenylbutyric acid | 30 | 9.17E+03 |
| C10H9N4O5 | picrolonic acid | 17 | 8.92E+03 |
| C10H7NO3 | 4-hydroxy-2-quinolinecarboxylic acid | 100 | 8.84E+03 |
| C7H6O3 | m-hydroxybenzoic acid | 20 | 8.45E+03 |
| C7H3Cl3O2 | 2,3,6-trichlorobenzoic acid | 20 | 8.33E+03 |
| C7H4O7 | 3-hydroxy-4-oxo-4H-pyran-2,6-dicarboxylic acid | 25 | 8.33E+03 |
| C8H7NO3 | oxanilic acid | 25 | 8.17E+03 |
| C15H12O4 | benzoyl-r-mandelic acid | 25 | 7.78E+03 |
| C16H21NO5 | benzoic acid, 2-(acetyloxy)-, 2-(diethylamino)-1-methyl-2-oxoethyl ester | 21 | 7.62E+03 |
| C11H20O4 | a,a,a'-tetramethylheptanedioic acid | 25 | 7.55E+03 |
| C10H16O4 | cis-1,2,2-trimethyl-1,3-cyclopentanedicarboxylic acid, (1R) | 25 | 7.54E+03 |
| C13H15NO5 | benzoic acid, 2-(acetyloxy)-, 2-(dimethylamino)-2-oxoethyl ester | 21 | 7.44E+03 |
| C7H5NO4 | o-nitrobenzoic acid | 25 | 7.44E+03 |
| C7H4BrNO4 | 3-bromo-2-nitrobenzoic acid | 25 | 7.36E+03 |
| C7H5FO2 | 2-fluorobenzoic acid | 25 | 7.15E+03 |
| C7H12O2 | 5-heptenoic acid | 25 | 6.79E+03 |
| C7H4N2O6 | 3,4-dinitrobenzoic acid | 25 | 6.66E+03 |
| C12H13NO5 | acid succinyl acetaminophen | 37 | 6.46E+03 |
| C7H6O3 | p-hydroxybenzoic acid | 25 | 6.36E+03 |
| C12H15NO5 | benzoic acid, 2-hydroxy-, 2-[(2-hydroxyethyl)methylamino]-2-oxoethyl ester | 21 | 6.26E+03 |
| C10H18O4 | 3-tert-butyl adipic acid | 25 | 6.14E+03 |
| C7H14O2 | 2-methylhexanoic acid, (±) | 25 | 6.07E+03 |
| C7H14O2 | 2-methylhexanoic acid | 25 | 6.07E+03 |
| C8H14O2 | 5-ethyl-2-hexenoic acid | 25 | 6.06E+03 |
| C8H14O2 | 4-ethyl-2-hexenoic acid | 25 | 6.06E+03 |

TABLE 6-continued

| molecular formula | substance name | temperature (° C.) | solubility (ppm) |
|---|---|---|---|
| C8H14O2 | 3-ethyl-2-hexenoic acid | 25 | 6.06E+03 |
| C8H14O2 | 2-ethyl-2-hexenoic acid | 25 | 6.06E+03 |
| C7H6O4 | 2,4-dihydroxybenzoic acid | 25 | 5.96E+03 |
| C9H6O6 | hydrastic acid | 15 | 5.96E+03 |
| C7H10N2O3 | isopropylbarbituric acid | 20 | 5.89E+03 |
| C7H7NO2 | aniline-3-carboxylic acid | 14.9 | 5.87E+03 |
| C9H10O2 | benzenepropanoic acid | 20 | 5.87E+03 |
| C8H2Cl4O4 | tetrachlorophthalic acid | 14 | 5.67E+03 |
| C9H14N2O3 | 5-ethyl-5-n-propylbarbituric acid | 25 | 5.66E+03 |
| C11H16N2O2 | 4-aminobenzoic aciD-2-(ethyl-amino)ethyl ester | | 5.59E+03 |
| C7H12O2 | 6-heptenoic acid | 25 | 5.55E+03 |
| C10H18O4 | 3-methylnonanedioic acid | 25 | 5.53E+03 |
| C11H20O4 | octylpropanedioic acid | 25 | 5.53E+03 |
| C13H15NO5 | benzoic acid, 2-(acetyloxy)-, 2-(ethylamino)-2-oxoethyl ester | 21 | 5.49E+03 |
| C7H12O2 | 5-methyl-2-hexenoic acid | 25 | 5.37E+03 |
| C7H12O2 | 4-heptenoic acid | 25 | 5.37E+03 |
| C7H12O2 | trans-2-heptenoic acid | 25 | 5.37E+03 |
| C7H12O2 | 3-heptenoic acid | 25 | 5.37E+03 |
| C12H13I3N2O3 | iocetamic acid | 37 | 5.26E+03 |
| C11H12O4 | propionyl-r-mandelic acid | 25 | 5.15E+03 |
| C8H14O5 | propanoic acid, 2-[(propoxycarbonyl)oxy]-, methyl ester | 25 | 5.15E+03 |
| C11H20O4 | undecanedioic acid | 21 | 5.07E+03 |
| C7H14N2O4S2 | djenkolic acid | 100 | 4.98E+03 |
| C7H7NO2 | aniline-4-carboxylic acid | 25 | 4.98E+03 |
| C7H9NO3S | 4-amino-3-methylbenzene sulfonic acid | 20 | 4.98E+03 |
| C7H14O2 | 3-methylhexanoic acid | 25 | 4.80E+03 |
| C8H14O4 | tetramethylbutanedioic acid | 13.5 | 4.78E+03 |
| C8H5F3O2 | 2-(trifluoromethyl)benzoic acid | 25 | 4.78E+03 |
| C9H12N2O3 | 5-allyl-5-ethylbarbituric acid | 25 | 4.75E+03 |
| C8H7NO4 | 6-nitro-3-methylbenzoic acid | 20 | 4.68E+03 |
| C8H14O2 | 6-methyl-4-heptenoic acid | 25 | 4.64E+03 |
| C8H14O2 | 5-methyl-4-heptenoic acid | 25 | 4.64E+03 |
| C8H14O2 | 4-methyl-4-heptenoic acid | 25 | 4.64E+03 |
| C8H14O2 | 3-methyl-4-heptenoic acid | 25 | 4.64E+03 |
| C8H14O2 | 2-methyl-4-heptenoic acid | 25 | 4.64E+03 |
| C8H14O2 | 6-methyl-3-heptenoic acid | 25 | 4.64E+03 |
| C8H14O2 | 5-methyl-3-heptenoic acid | 25 | 4.64E+03 |
| C8H14O2 | 4-methyl-3-heptenoic acid | 25 | 4.64E+03 |
| C8H14O2 | 3-methyl-3-heptenoic acid | 25 | 4.64E+03 |
| C8H14O2 | 2-methyl-3-heptenoic acid | 25 | 4.64E+03 |
| C8H14O2 | 5-methyl-2-heptenoic acid | 25 | 4.64E+03 |
| C8H14O2 | 4-methyl-2-heptenoic acid | 25 | 4.64E+03 |
| C8H14O2 | 3-methyl-2-heptenoic acid | 25 | 4.64E+03 |
| C8H14O2 | 2-methyl-2-heptenoic acid | 25 | 4.64E+03 |
| C9H8O4 | 2-(acetyloxy)benzoic acid | 25 | 4.58E+03 |
| C10H9NO4S | 6-amino-4-hydroxy-2-naphthalenesulfonic acid | | 4.48E+03 |
| C7H9NO3S | 4-amino-o-toluenesulfonic acid | 20 | 4.48E+03 |
| C8H6Cl2O3 | 3,6-dichloro-2-methoxybenzoic acid | 25 | 4.48E+03 |
| C11H12O5S | 2-(acetoxy)-benzoic acid, (methylsulfinyl)methyl ester | 21 | 4.21E+03 |
| C8H8O3 | 2-methoxybenzoic acid | 25 | 4.18E+03 |
| C10H9NO3S | 1-naphthylamine-2-sulfonic acid | 20 | 4.08E+03 |
| C10H9NO3S | 2-amino-1-naphthalenesulfonic acid | 20 | 4.07E+03 |
| C13H20N2O3 | 5-allyl-5-ethylbutylbarbituric acid | 20 | 3.99E+03 |
| C12H15NO6 | ethonyphenyl tartramic acid | 14 | 3.97E+03 |
| C26H20N2O8S2 | 1,5-anthraquinone disulfonic acid anilide | 18 | 3.97E+03 |
| C7H14O2 | 5-methylhexanoic acid | 25 | 3.93E+03 |
| C11H11NO5 | benzoic acid, 2-(acetyloxy)-, 2-amino-2-oxoethyl ester | 21 | 3.83E+03 |
| C9H6O6 | 1,3,5-benzenetricarboxylic acid | 16 | 3.79E+03 |
| C7H8N2O3 | 5,5-trimethylenebarbituric acid | 25 | 3.71E+03 |
| C7H14O2 | 4-methylhexanoic acid, (±) | 25 | 3.56E+03 |
| C7H14O2 | 4-methylhexanoic acid | 25 | 3.56E+03 |
| C7H5NO4 | m-nitrobenzoic acid | 25 | 3.53E+03 |
| C12H16N2O3 | D-(−)-carbanilic acid (1-ethylcarbamoyl)ethyl ester | 20 | 3.49E+03 |
| C7H3Br3O2 | 2,4,6-tribromobenzoic acid | 15 | 3.49E+03 |
| C7H7NO2 | aniline-2-carboxylic acid | 20 | 3.48E+03 |
| C8H16O2 | 2,2-dimethylhexanoic acid | 25 | 3.44E+03 |
| C7H6O2 | benzoic acid | 25.1 | 3.39E+03 |

In one embodiment, the steviol glycoside solubility enhancer may be one or a combination of the compounds in Table 7.

TABLE 7

Compounds that enhance water solubility of steviol glycosides, based on laboratory data collected for this patent application:

| Common Name | IUPAC Name | Structure |
|---|---|---|
| Caffeic acid | 3-(3,4-Dihydroxyphenyl)-2-propenoic acid | 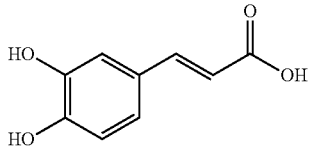 [SMILES: O=C(O)/C=C/c1ccc(O)c(O)c1] |
| Chlorogenic acid And all stereoisomers. | (1S,3R,4R,5R)-3-{[(2E)-3-(3,4-dihydroxyphenyl)prop-2-enoyl]oxy}-1,4,5-trihydroxycyclohexanecarboxylic acid | 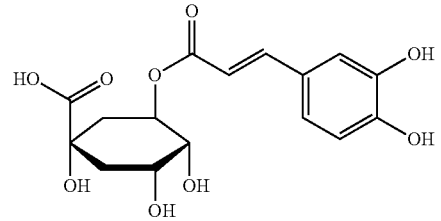 |

TABLE 7-continued

Compounds that enhance water solubility of steviol glycosides, based on laboratory data collected for this patent application:

| Common Name | IUPAC Name | Structure |
| --- | --- | --- |
| Neochlorogenic acid<br>And all stereoisomers. | (1R,3R,4S,5R)-3-{[(2E)-3-(3,4-Dihydroxyphenyl)prop-2-enoyl]oxy}-1,4,5-trihydroxycyclohexanecarboxylic acid | |
| Cryptochlorogenic acid<br>And all stereoisomers. | 4-{[(2E)-3-(3,4-dihydioxyphenyl)prop-2-enoyl]oxy}-1,3,5-trihydroxycyclohexanecarboxylic acid | |
| Cynarin<br>Alternative name:<br>1,5-dicaffeoylquinic acid<br>And its positional isomers:<br>1,4-dicaffeoylquinic acid<br>1,3-dicaffeoylquinic acid<br>3,5-dicaffeoylquinic acid<br>4,5-dicaffeoylquinic acid<br>3,4-dicaffeoylquinic acid<br>And all stereoisomers. | (1S,3R,4S,5R)-1,3-bis[[(E)-3-(3,4-dihydroxyphenyl)prop-2-enoyl]oxy]-4,5-dihydroxycyclohexane-1-carboxylic acid | |

TABLE 7-continued

Compounds that enhance water solubility of steviol glycosides, based on laboratory data collected for this patent application:

| Common Name | IUPAC Name | Structure |
|---|---|---|
| Ferulic acid And its positional isomers | (E)-3-(4-hydroxy-3-methoxy-phenyl)prop-2-enoic acid | 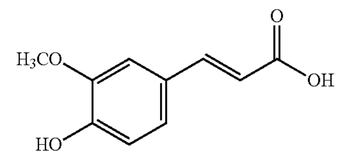 [SMILES: COc1cc(/C=C/C(=O)O)ccc1O] |
| Umbellic acid | (E)-3-(2,4-dihydroxyphenyl)prop-2-acid | 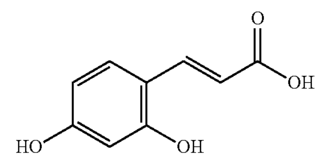 [SMILES: O=C(O)/C=C/c1ccc(O)cc1O] |
| Sinapic acid, or Sinapinic acid And its positional isomers | 3-(4-hydroxy-3,5-dimethoxyphenyl)prop-2-enoic acid | 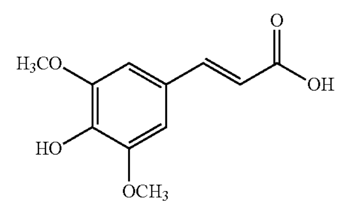 [SMILES: COc1cc(/C=C/C(=O)O)cc(OC)c1O] |
| p-coumaric acid And its positional isomers | (E)-3-(4-hydroxyphenyl)-2-propenoic acid | 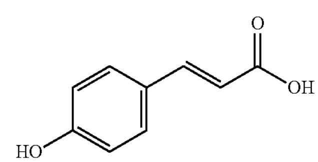 [SMILES: O=C(O)/C=C/c1ccc(O)cc1] |
| Rosmarinic acid | (2R)-2-[[(2"E")-3-(3,4-Dihydroxyphenyl)-1-oxo-2-propenyl]]oxy]-3-(3,4-dihydroxyphenyl)propanoic acid | 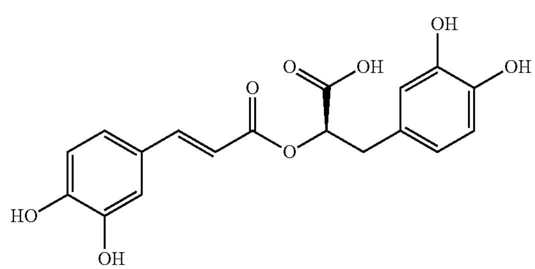 [SMILES: O=C(/C=C/c1ccc(O)c(O)c1)O[C@H](Cc1ccc(O)c(O)c1)C(=O)O] |

Based on structural similarity to caffeic acid, chlorogenic acid, cynarin, and the other solubility enhancers listed above, the following compounds (Table 8) will likely also enhance steviol glycoside solubility, compounds including dimerization products of ferulic and caffeic acids, which can spontaneously form under high temperatures when ferulic or caffeic acid reacts with itself.

TABLE 8

Compounds likely to enhance water solubility of steviol glycosides

| Common Name | IUPAC Name | Structure |
|---|---|---|
| 8,8'-Diferulic acid | 3-[(E)-2-(4-Hydroxy-3-methoxyphenyl)ethenyl](E)2-[(4-hydroxy-3-methoxyphenyl)methylidene] succinic acid | 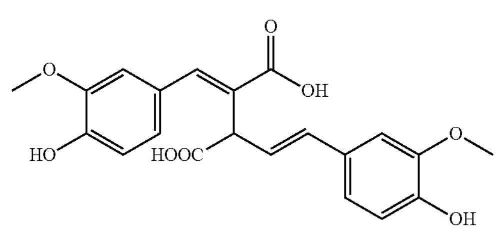 |

TABLE 8-continued

Compounds likely to enhance water solubility of steviol glycosides

| Common Name | IUPAC Name | Structure |
| --- | --- | --- |
| 8,5'-diferulic acid | (E)-2-[(Z)-7-Carboxy-6,14-dihydroxy-5,10-dimethoxy-3-stilbenyl]acrylic acid | 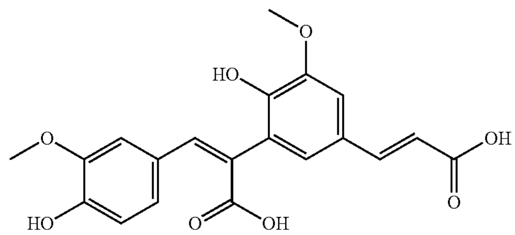 [SMILES: COc1cc(/C=C(\C(=O)O)c2cc(/C=C/C(=O)O)cc(OC)c2O)ccc1O] |
| 5,5'-diferulic acid | (E)-3-{5'-[(E)-2-Carboxyethenyl]-2',6-dihydroxy-3',5-dimethoxy-3-biphenylyl}acrylic acid | 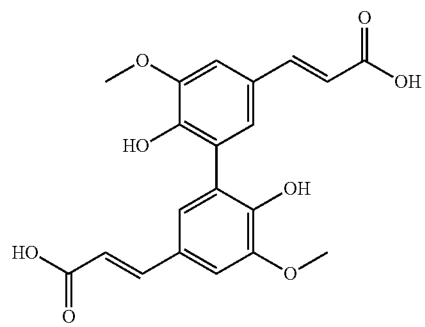 [SMILES: COc1cc(/C=C/C(=O)O)cc(-c2cc(/C=C/C(=O)O)cc(OC)c2O)c1O] |
| 4-O-5'-diferulic acid | (E)-3-(3-{4-[(E)-2-Carboxyethenyl]-2-methoxyphenoxy}-4-hydroxy-5-methoxyphenyl)acrylic acid | 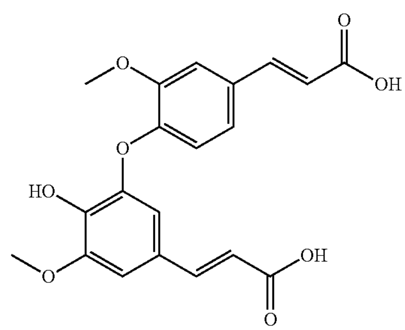 [SMILES: COc1cc(/C=C/C(=O)O)ccc1Oc1cc(/C=C/C(=O)O)cc(OC)c1O] |
| 8,5'-diferulic acid, decarboxylated | (E)-3-[(E)-6,14-Dihydroxy-5,10-dimethoxy-3-stilbenyl]acrylic acid | 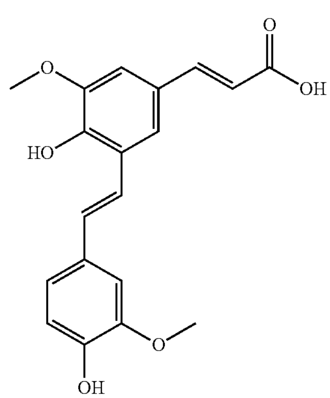 [SMILES: COc1cc(/C=C/c2cc(/C=C/C(=O)O)cc(OC)c2O)ccc1O] |

TABLE 8-continued

Compounds likely to enhance water solubility of steviol glycosides

| Common Name | IUPAC Name | Structure |
| --- | --- | --- |
| 8,8'-diferulic acid, cyclized | 7-Hydroxy-1-(4-hydroxy-3-methoxyphenyl)-6-methoxy-1,2-dihydronaphthalene-2,3-dicarhoxylic acid | 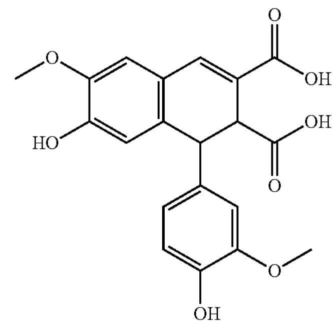 |
| 5,5'-Dicaffeic acid And its positional isomers And other dimeric caffeic acids, analogous to molecules above | (E)-3-{5'-[(E)-2-Carboxyethenyl]-2',3',5,6-tetrahydroxy-3-biphenylyl}aciylic acid | 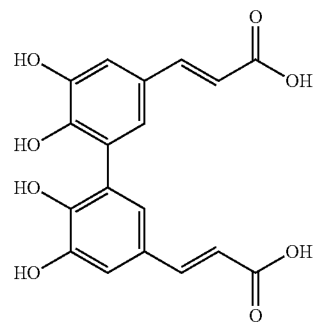 [SMILES: O=C(O)/C=C/c1cc(O)c(O)c(-c2cc(/C=C/C(=O)O)cc(O)c2O)c1] |
| Dihydroxyphenyl acetic acids And its positional isomers | (3,4-Dihydroxyphenyl)acetic acid | 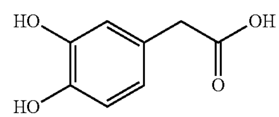 [SMILES: O=C(O)Cc1ccc(O)c(O)c1] |
| Lunularic acid And its positional isomers | 2-hydroxy-6-[2-(4-hydroxyphenyl)ethyl] benzoic acid | 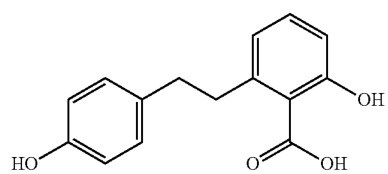 [SMILES: O=C(O)c1c(O)cccc1CCc1ccc(O)cc1] |
| Theogallin And its positional isomers | (1S,3R,4R,5R)-1,3,4-trihydroxy-5-(3,4,5-trihydroxybenzoyl)oxycyclohexane-1-carboxylic acid | 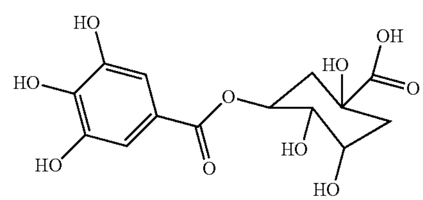 [SMILES: O=C(OC1CC(O)(C(=O)O)CC(O)C1O)c1cc(O)c(O)c(O)c1] |
| Trigalloylquinic acid And its positional isomers | (1S,3R,4S,5R)-1-Hydroxy-3,4,5-tris((3,4,5-trihydroxybenzoyl)oxy) cyclohexanecarboxylic acid | 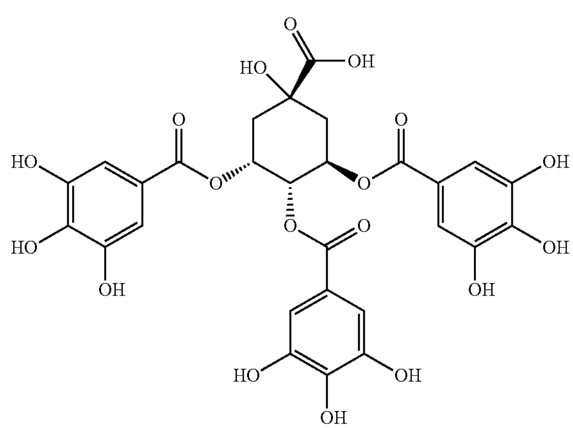 [SMILES: O=C(O[C@@H]1C[C@](O)(C(=O)O)C[C@@H](OC(=O)c2cc(O)c(O)c(O)c2)[C@H]1OC(=O)c1cc(O)c(O)c(O)c1)c1cc(O)c(O)c(O)c1] |

TABLE 8-continued

Compounds likely to enhance water solubility of steviol glycosides

| Common Name | IUPAC Name | Structure |
| --- | --- | --- |
| Resveratrol glucuronide And its positional isomers | (2S,3S,4S,5R,6S)-3,4,5-trihydroxy-6-[3-hydroxy-5-[(E)-2-(4-hydroxyphenyl)ethenyl]phenoxy]oxane-2-carboxylic acid | 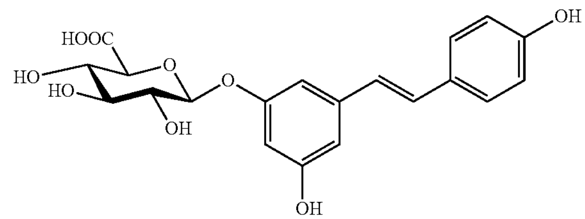 |
| Dactylifric acid And its positional isomers | 5-{[(2Z)-3-(3,4-dihydroxyphenyl)prop-2-enoyl]oxy}-3,4-dihydroxycyclohex-1-ene-1-carboxylic acid | 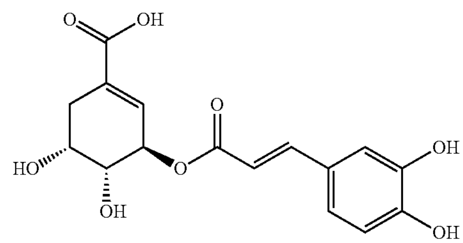 [SMILES: O=C(/C=C/c1ccc(O)c(O)c1)O[C@@H]1C=C(C(=O)O)C[C@@H](O)[C@H]1O] |
| Cichoric acid And its positional isomers | (2S,3R)-2,3-bis{[(E)-3-(3,4-dihydroxyphenyl)prop-2-enoyl]oxy}butanedioic acid | 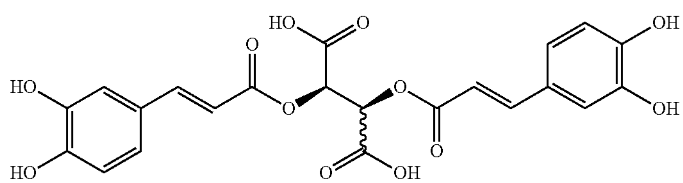 |
| Trilepisiumic acid. And its positional isomers | 4-[(E)-2-(3,4-Dihydroxyphenyl)ethenyl carbonyloxy]-3-hydroxybenzoic acid | 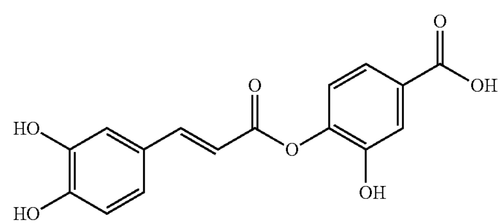 [SMILES: O=C(/C=C/c1ccc(O)c(O)c1)Oc1ccc(C(=O)O)cc1O] |
| 4-Methylumbelliferyl-beta-D-glucuronide And its positional isomers | (2S,3S,4S,5R,6S)-3,4,5-Trihydroxy-6-(4-methyl-7-coumarinyloxy)tetrahydro-2H-pyran-2-carboxylic acid | 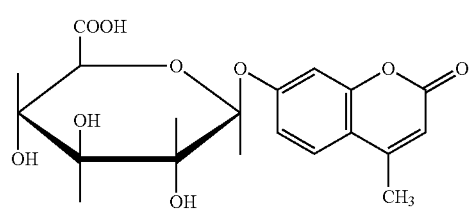 |
| Allenolic acid And its positional isomers | 3-(6-Hydroxy-2-naphthyl)propionic acid | 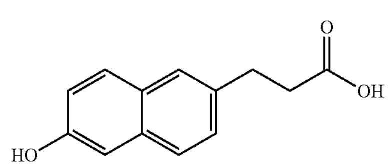 [SMILES: O=C(O)CCc1ccc2cc(O)ccc2c1] |

TABLE 8-continued

Compounds likely to enhance water solubility of steviol glycosides

| Common Name | IUPAC Name | Structure |
| --- | --- | --- |
| Globoidnan A And its positional isomers | (2R)-(3,4-dihydroxyphenyl)-2-{[4-(3,4-dihydroxyphenyl)-6,7-dihydroxy-2-naphthoyl]oxy}propanoic acid | 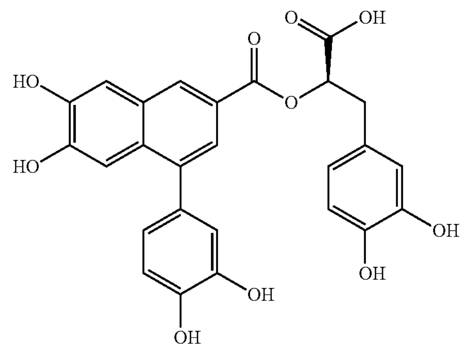 [SMILES: O=C(O[C@H](Cc1ccc(O)c(O)c1)C(=O)O)c1cc(-c2ccc(O)c(O)c2)c2cc(O)c(O)cc2c1] |
| Pamoic acid And its positional isomers | 4,4'-Methylenebis(3-hydroxynaphthalene-2-carboxylic acid) | 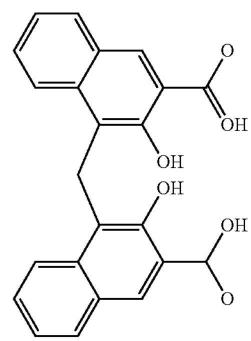 [SMILES: O=C(O)c1cc2ccccc2c(Cc2c(O)c(C(O)O)cc3ccccc23)c1O] |
| Caftaric acid And related isomers | (2R,3R)-2-[(E)-3-(3,4-Dihydroxyphenyl)prop-2-enoyl]oxy-3-hydroxybutanedioic acid | 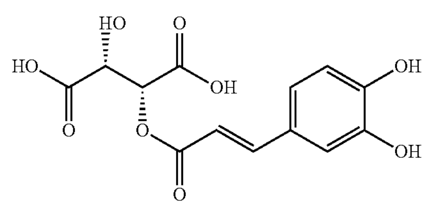 [SMILES: O=C(/C=C/c1ccc(O)c(O)c1)O[C@@H](C(=O)O)[C@@H](O)C(=O)O] |
| Coutaric acid And related isomers | (2R,3R)-2-Hydroxy-3-(((E)-3-(4-hydroxyphenyl)acryloyl)oxy)succinic acid | 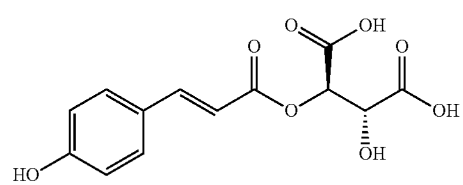 [SMILES: O=C(/C=C/c1ccc(O)cc1)O[C@@H](C(=O)O)[C@@H](O)C(=O)O] |
| Caffeoylmalic acid And related isomers | 2-[(E)-3-(3,4-dihydroxyphenyl)prop-2-enoyl]oxybutanedioic acid | 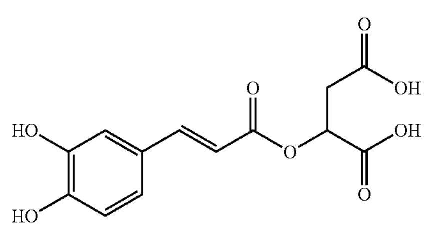 [SMILES: O=C(O)CC(OC(=O)/C=C/c1ccc(O)c(O)c1)C(=O)O] |
| Shikimic acid And substitutions of shikimic acid | (3R,4S,5R)-3,4,5-trihydroxycyclohex-1-ene-1-carboxylic acid | 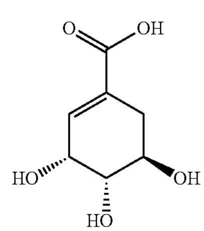 [SMILES: O=C(O)C1=C[C@@H](O)[C@@H](O)[C@H](O)C1] |

TABLE 8-continued

Compounds likely to enhance water solubility of steviol glycosides

| Common Name | IUPAC Name | Structure |
| --- | --- | --- |
| Coumaric acid 5-O-shikimate And related isomers | 5-[(E-2-(p-Hydroxyphenyl) ethenylcarbonyloxy]-3,4-dihydroxy-1-cyclohexene-1-carboxylic acid | 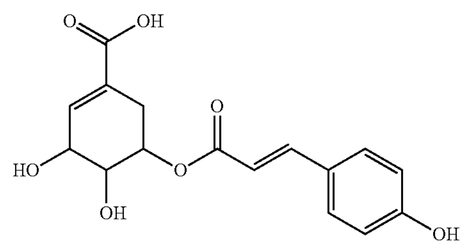 [SMILES: O=C(/C=C/c1ccc(O)cc1)OC1CC(C(=O)O)=CC(O)C1O] |
| | 3,5-Bis[(E)-2-(p-hydroxyphenyl) ethenylcarbonyloxy]-4-hydroxy-1-cyclohexene-1-carboxylic acid | |
| 3,4,5-Tricaffeoylquinic acid And its positional isomers 1,3,4-Tricaffeoylquinic acid 1,3,5-Tricaffeoylquinic acid 1,4,5-Tricaffeoylquinic acid | 3,4,5-Tris[(E)-2-(3,4-dihydroxyphenyl) ethenylcarbonyloxy]-1-hydroxycyclohexanecarboxylic acid | 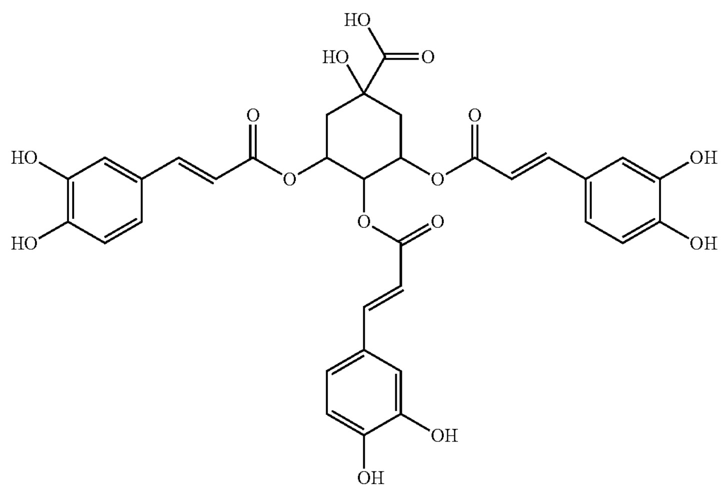 [SMILES: O=C(/C=C/c1ccc(O)c(O)c1)OC1CC(O)(C(=O)O)CC(OC(=O)/C=C/c2ccc(O)c(O)c2)C1OC(=O)/C=C/c1ccc(O)c(O)c1] |
| 1,3,4,5-Tetracaffeoylquinic acid | 1,3,4,5-Tetrakis[(E)-2-(3,4-dihydroxyphenyl) ethenylcarbonyloxy] cyclohexanecarboxylic acid | 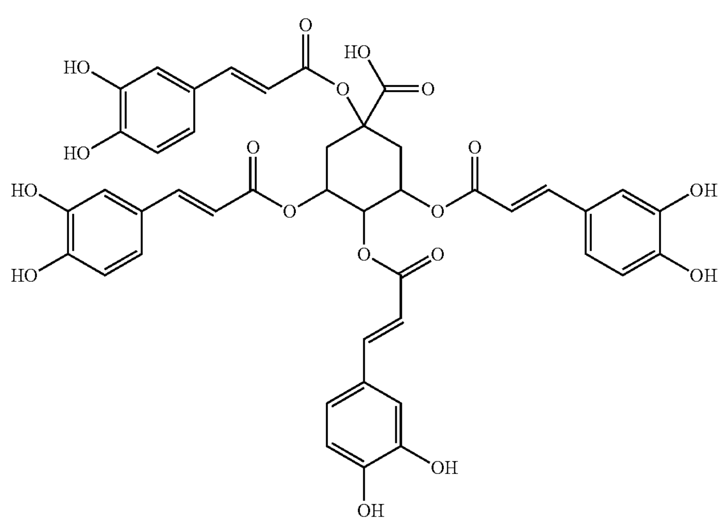 [SMILES: O=C(/C=C/c1ccc(O)c(O)c1)OC1CC(OC(=O)/C=C/c2ccc(O)c(O)c2)(C(=O)O)CC(OC(=O)/C=C/c2ccc(O)c(O)c2)C1OC(=O)/C=C/c1ccc(O)c(O)c1] |

Examples of solubility enhancer include: caffeic acid, an ester of caffeic acid, an ester of caffeic acid and quinic acid, an ester of caffeic acid and quinic acid comprising a single caffeic acid moiety (e.g., chlorogenic, cryptochlorogenic, and neochlorogenic acid; structures of each are provided herein), an ester of caffeic acid and quinic acid comprising more than one caffeic acid moiety (e.g., 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, and 4,5-dicaffeoylquinic acid; structures of each are provided herein); ferulic acid, an ester of ferulic acid, an ester of ferulic acid and quinic acid, an ester of ferulic acid and quinic acid comprising a single ferulic acid moiety, an ester of ferulic acid and quinic acid comprising more than one ferulic acid moiety; quinic acid, an ester of quinic acid; tartaric acid, a tartaric acid derivative, an ester of tartaric acid, an ester of a tartaric acid derivative, 3-(3,4-dihydroxyphenyl)lactic acid, a 3-(3,4-dihydroxyphenyl)lactic acid derivative, an ester of 3-(3,4-dihydroxyphenyl)lactic acid, an ester of a 3-(3,4-dihydroxyphenyl)lactic acid derivative, p-coumaric acid, an ester of p-coumaric acid, an ester of p-coumaric acid and quinic acid, an ester of p-coumaric acid and quinic acid comprising a single p-coumaric acid moiety, an ester of p-coumaric acid and quinic acid comprising more than one p-coumaric acid moiety; sinapic acid, an ester of sinapic acid, an ester of sinapic acid and quinic acid, an ester of sinapic acid and quinic acid comprising a single sinapic acid moiety, an ester of sinapic acid and quinic acid comprising more than one sinapic acid moiety; and 3-O-feruloylquinic acid, 4-O-feruloylquinic acid, 5-O-feruloylquinic acid, 3,4-diferuloylquinic acid, 3,5-diferuloylquinic acid, and 4,5-diferuloylquinic acid.

In some aspects, the solubility enhancer compound comprises one or more compounds selected from the group consisting of 3-O-coumaroylquinic acid, 4-O-coumaroylquinic acid, 5-O-coumaroylquinic acid, 3,4-dicoumaroylquinic acid, 3,5-dicoumaroylquinic acid, 4,5-dicoumaroylquinic acid.

Caffeic acid has the structure:

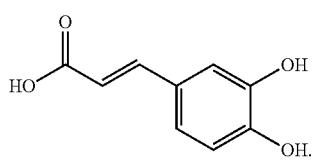

Ferulic acid has the structure:

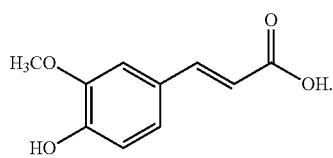 [SMILES: COc1cc(/C=C/C(=O)O)ccc1O]

p-Coumaric acid has the structure:

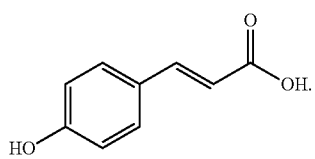

Sinapic acid has the structure:

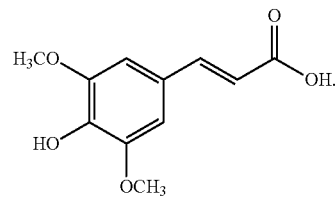 [SMILES: COc1cc(/C=C/C(=O)O)cc(OC)c1O]

Quinic acid has the structure:

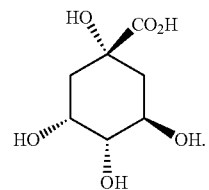

3-(3,4-dihydroxyphenyl)lactic acid has the structure:

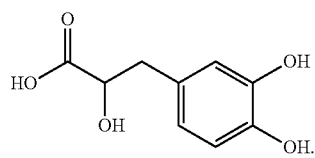 [SMILES: O=C(O)C(O)Cc1ccc(O)c(O)c1]

Tartaric acid has the structure:

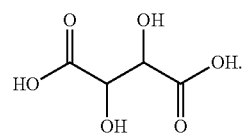

and can be in the D and L forms.

Examples of the esters of the various acids contemplated herein include the ester of caffeic acid and quinic acid, which includes monocaffeoylquinic acids (e.g., chlorogenic acid, neochlorogenic acid, and cryptochlorogenic acid), and dicaffeoylquinic acids (e.g., 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, and 4,5-dicaffeoylquinic acid), and salts thereof:

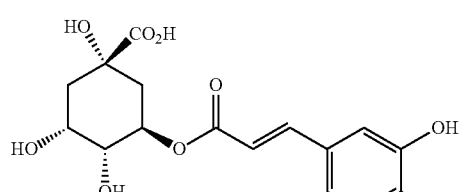

Chlorogenic acid

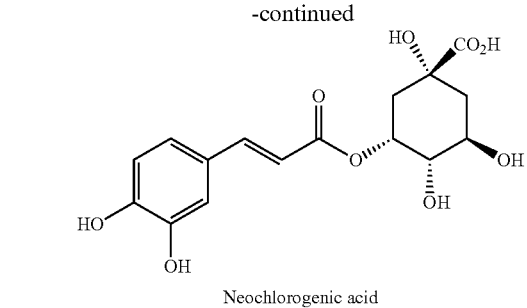
Neochlorogenic acid
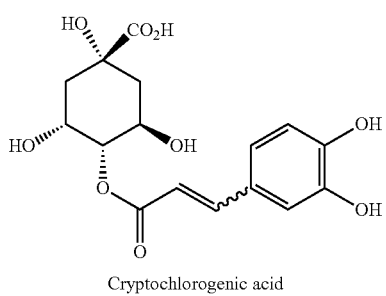
Cryptochlorogenic acid
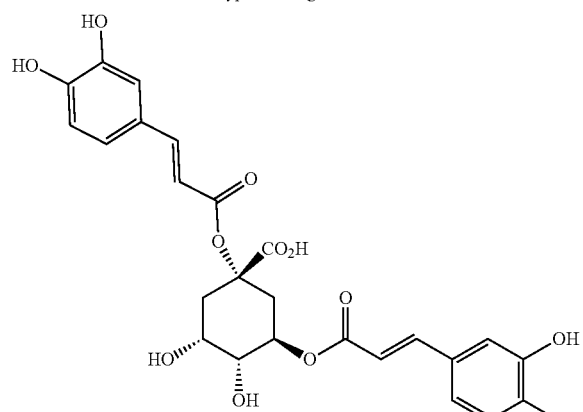
1,5-Dicaffeoylquinic acid
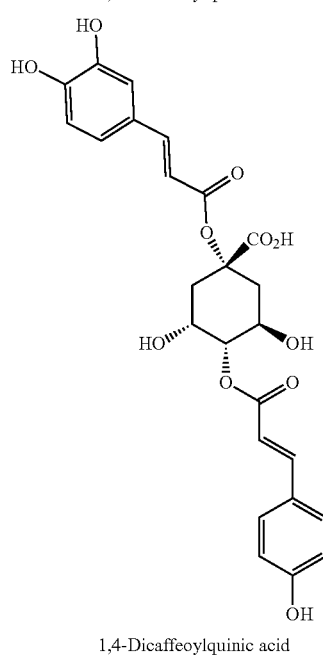
1,4-Dicaffeoylquinic acid
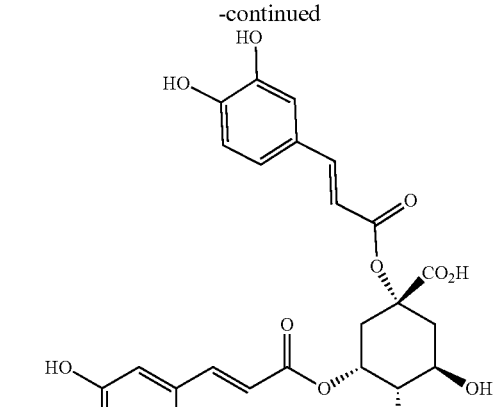
1,3-Dicaffeoylquinic acid
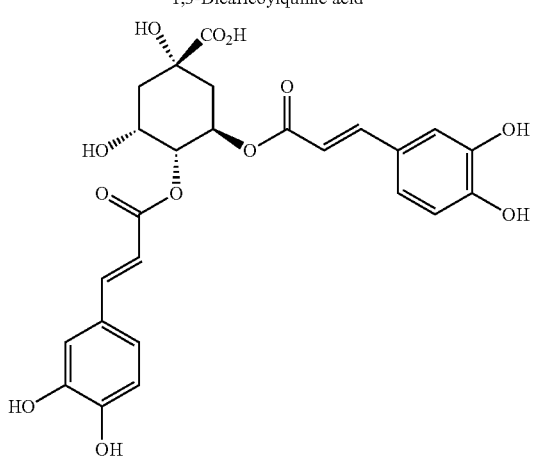
4,5-Dicaffeoylquinic acid
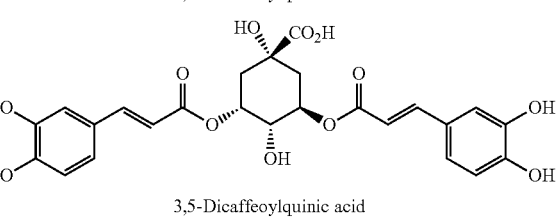
3,5-Dicaffeoylquinic acid
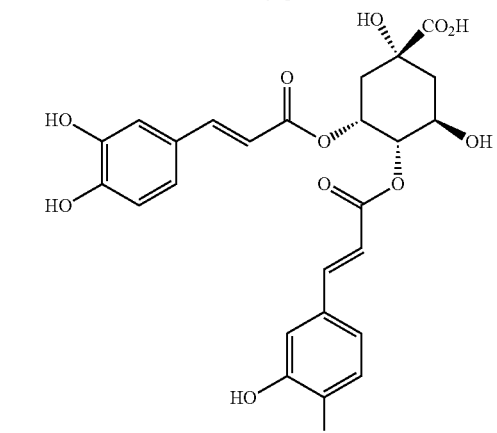
3,4-Dicaffeoylquinic acid
with 4,5-dicaffeoylquinic acid, 3,5-dicaffeoylquinic acid, and 3,4-dicaffeoylquinic acid being most prevalent in the compositions contemplated herein and most prevalent in abundant in *stevia*, yerba mate, globe artichoke, and green coffee.

Examples of the esters of the various acids contemplated herein include the ester of caffeic acid and tartaric acid, which includes cichoric acid having the structure:

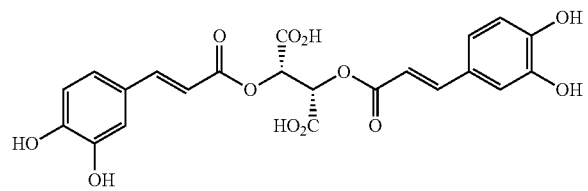 [SMILES: O=C(/C=C/c1ccc(O)c(O)c1)O[C@H](C(=O)O)[C@H](OC(=O)/C=C/c1ccc(O)c(O)c1)C(=O)O]

which has two caffeic acid molecules linked to a tartaric acid core; and caftaric acid having the structure:

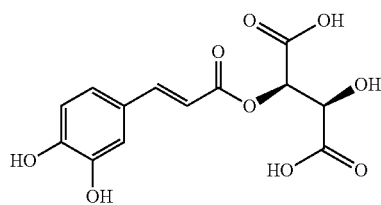 [SMILES: O=C(/C=C/c1ccc(O)c(O)c1)O[C@@H](C(=O)O)[C@@H](O)C(=O)O]

which has one caffeic acid molecule linked to a tartaric acid core.

Examples of the esters of the various acids contemplated herein include the ester of caffeic acid and 3-(3,4-dihydroxyphenyl)lactic acid including, for example, rosmarinic acid, which has the structure:

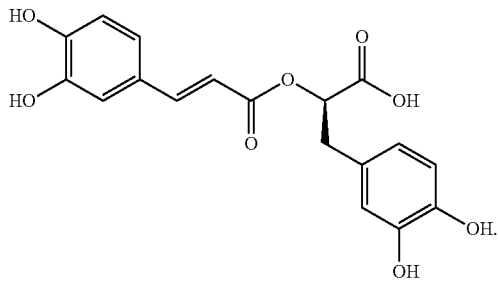 [SMILES: O=C(/C=C/c1ccc(O)c(O)c1)O[C@H](Cc1ccc(O)c(O)c1)C(=O)O]

Each of the caffeic acid, monocaffeoylquinic acids, dicaffeoylquinic acids and other solubility enhancer compounds can be considered weak acids and can each exist in at least one of their conjugate acid form, conjugate base form (e.g., in their salt form), and mixed conjugate acid-conjugate base form, wherein a fraction (e.g., mole fraction) of the compounds exist in the conjugate acid form and another fraction exist in the conjugate base form. The fraction of conjugate acid form to conjugate base form for the caffeic acid, monocaffeoylquinic acids, dicaffeoylquinic acids, and other solubility enhancer compounds will depend on various factors, including the pKa of each compound and the pH of the composition.

Examples of salts of caffeic acid, monocaffeoylquinic acids, dicaffeoylquinic acids, and other solubility enhancer compounds include, but are not limited to, quaternary ammonium, sodium, potassium, lithium, magnesium, and calcium salts of caffeic acid, monocaffeoylquinic acids, dicaffeoylquinic acids, and other solubility enhancer compounds and the like.

In some aspects, the solubility enhancer compound can be enriched for one or more of caffeic acid, monocaffeoylquinic acids, and dicaffeoylquinic acids. The term "enriched" refers to an increase in an amount of one of caffeic acid, monocaffeoylquinic acids, and dicaffeoylquinic acids relative to one or more other compounds that are present in the solubility enhancer compound. An solubility enhancer compound that is enriched for one or more of caffeic acid, monocaffeoylquinic acids, and dicaffeoylquinic acids can increase solubility of the steviol glycoside composition.

In some aspects, a solubility enhancer compound enriched for one or more dicaffeoylquinic acids can increase solubility of the steviol glycoside composition. An solubility enhancer compound that is enriched for dicaffeoylquinic acids can comprise 10% or more, 15% or more, 20% or more, 25% or more, 30% or more, 35% or more, 40% or more, 45% or more, or 50% or more, 60% or more, 70% or more, or 80% or more, or 90% or more dicaffeoylquinic acids. In other aspects, a solubility enhancer compound that is enriched for dicaffeoylquinic acids can comprise 10% or more, 15% or more, 20% or more, 25% or more, 30% or more, 35% or more, 40% or more, 45% or more, or 50% or more, 60% or more, 70% or more, or 80% or more, or 90% or more of a combination of one or more of 1,3-dicaffeoylquinic acid, 1,4-dicaffeoylquinic acid, 1,5-dicaffeoylquinic acid, 3,4-dicaffeoylquinic, 3,5-dicaffeoylquinic acid, and 4,5-dicaffeoylquinic acid, and salts thereof.

In some aspects, an amount of solubility enhancer compound effective to increase solubility of the steviol glycoside for one or more dicaffeoylquinic acids and comprising 10% or more, 15% or more, 20% or more, 25% or more, 30% or more, 35% or more, 40% or more, 45% or more, or 50% or more, 60% or more, 70% or more, or 80% or more, or 90% or more dicaffeoylquinic acids. In other aspects, a solubility enhancer compound that is enriched for dicaffeoylquinic acids can comprise 10% or more, 15% or more, 20% or more, 25% or more, 30% or more, 35% or more, 40% or more, 45% or more, or 50% or more, 60% or more, 70% or more, or 80% or more, or 90% or more of a combination of one or more of 1,3-dicaffeoylquinic acid, 1,4-dicaffeoylquinic acid, 1,5-dicaffeoylquinic acid, 3,4-dicaffeoylquinic, 3,5-dicaffeoylquinic acid, and 4,5-dicaffeoylquinic acid, and salts thereof.

In some aspects, an amount of solubility enhancer compound effective to increase solubility of the steviol glycoside is an amount such that the solubility enhancer compound comprises a 1:0.3 to 1:3 ratio by weight of steviol glycoside to solubility enhancer compound. In other aspects, an amount of solubility enhancer compound effective to increase solubility of the steviol glycoside is an amount such that the solubility enhancer compound comprises a 1:1 to 1:3 ratio by weight of steviol glycoside to solubility enhancer compound. An amount of solubility enhancer compound effective to increase solubility of the steviol glycoside can be an amount such that the solubility enhancer compound comprises a ratio by weight of steviol glycoside to solubility enhancer compound of 1:0.1 to 1:10. In some aspects an amount of solubility enhancer compound effective to increase solubility of the steviol glycoside can be an amount such that the solubility enhancer compound comprises a ratio by weight of steviol glycoside to solubility enhancer compound of about 1:0.1 to 1:5, about 1:0.5 to 1:4, about 1:0.3 to 1:3, or about 1:1 to 1:3. In other aspects an amount of solubility enhancer compound effective to increase solubility of the steviol glycoside can be an amount such that the solubility enhancer compound comprises a ratio by weight of steviol glycoside to solubility enhancer compound of about 1:0.1, 1:0.5, 1:1, 1:2, 1:3, 1:4, 1:5, 1:6, 1:7, 1:8, 1:9, or 1:10 by weight. In some aspects, an amount of solubility enhancer compound effective to increase solubility of the steviol glycoside can be an amount such that the solubility enhancer compound comprises a ratio by weight of steviol glycoside to solubility enhancer compound of about 1:0.3 to 1:3.

In some aspects, an amount of solubility enhancer compound effective to increase solubility of the steviol glycoside is a final concentration of solubility enhancer compound of greater than 100 ppm, 200 ppm, 300 ppm, 400 ppm, 700 ppm, 800 ppm, 900 ppm, or 1000 ppm. The final concentration of solubility enhancer compound can be greater than 1100 ppm, 1200 ppm, 1300 ppm, 1400 ppm, 1500 ppm, 1600 ppm, 1700 ppm, 1800 ppm, or 1900 ppm. The final concentration of solubility enhancer compound can be greater than 2100 ppm, 2200 ppm, 2300 ppm, 2400 ppm, 2500 ppm, 2600 ppm, 2700 ppm, 2800 ppm, or 2900 ppm. The final concentration of solubility enhancer compound can be greater than 3100 ppm, 3200 ppm, 3300 ppm, 3400 ppm, 3500 ppm, 3600 ppm, 3700 ppm, 3800 ppm, or 3900 ppm. The final concentration of solubility enhancer compound can be greater than 3000 ppm, 4000 ppm, 5000 ppm, 6000 ppm, 7000 ppm, 8000 ppm, or 9000 ppm. The final concentration of solubility enhancer compound can be greater than 1%, 2%, 3%, 4%, 5%, 6%, 7%, 8%, 9%, 10%, or higher.

The invention will be further described by the following non-limiting examples.

Example 1

Steviol glycosides (SGs), such as EverSweet, have limited water solubility, especially at acidic pH. It is desirable to create concentrates, e.g., acidic liquid concentrates, of steviol glycosides for ease of use, e.g., at bottler's locations.

Compounds in a charged state, such as Reb B, can create solutions of SG at very high concentrations (about 10% SG). However, Reb B has a carboxylic acid group with a relatively high pKa, resulting in solubility problems under acidic pH. A compound that would be in a charged state at lower pH, e.g., has a pKa of 3.0 or lower, and having a flavonoid-like phenolic functionality is likely useful to solubilize SGs at low pH.

As many natural plants contain flavonoids, stevia leaf extract was investigated to determine what similar compounds may exist in that extract that could improve water solubility of SGs. 70% ethanol stevia leaf extract was also dried and re-solubilized at high concentration in water in an attempt to crystallize. The solution never crystallized, showing that compounds are present in the leaf extract that naturally keep SGs in solution at high concentrations in water. Several exemplary compounds in the stevia leaf that improve SG water solubility are described below.

Solubility Characteristics
Chlorogenic Acid (CGA):

Chlorogenic acid and its two isomers are some of the highest concentration polyphenols in stevia leaves. The ratio of chlorogenic acid to its isomers is approximately 3:1:1 (chlorogenic:neochlorogenic:cryptochlorogenic). Solutions of EverSweet and chlorogenic acid remain fully solubilized, even under extreme acidity (pH<1). At these pH extremes, some degradation or dimerization occurs, which can be observed by the discoloration in FIG. 4, which may be mitigated by adjusting the pH higher. To obtain high levels of SG solubility, methods including heating the solution may be employed.

Cynarin:

Cynarin and its isomers are some of the highest concentration polyphenols in the stevia leaf. The distribution of isomers is mainly two compounds, 3,5- and 3,4-dicaffeoylquinic acid. Purified cynarin isomers are superior to chlorogenic acid for solubilizing properties, likely due to the additional caffeic ester moiety. Cynarin isomers are also able to solubilize EverSweet at a lower molar ratio than chlorogenic acid (less than 1 mole of cynarin isomer per mole of glycosides).

Figure 10:
FIG. 10. Image of stable solution of 1% EverSweet in solution with 1% purified cynarin isomers adjusted to pH 4 with sodium hydroxide (left). Dilution of this solution to 300 ppm results in an application-level product that has no visible color.

Purified 3,5-dicaffeoylquinic acid material has a slight yellow-brown color. To investigate whether a final solution can appear clear and colorless, a cynarin containing solution having 300 ppm EverSweet and 300 ppm cynarin was prepared (FIG. 10). The yellow-brown color was too dilute to be visible. As noted above, cynarin isomers are effective at solubilizing EverSweet at a lower ratio than this, thus the color could be diluted further. Decoloring processing, such as ultrafiltration, can be employed to further reduce colored bodies from the material.

Figure 11:
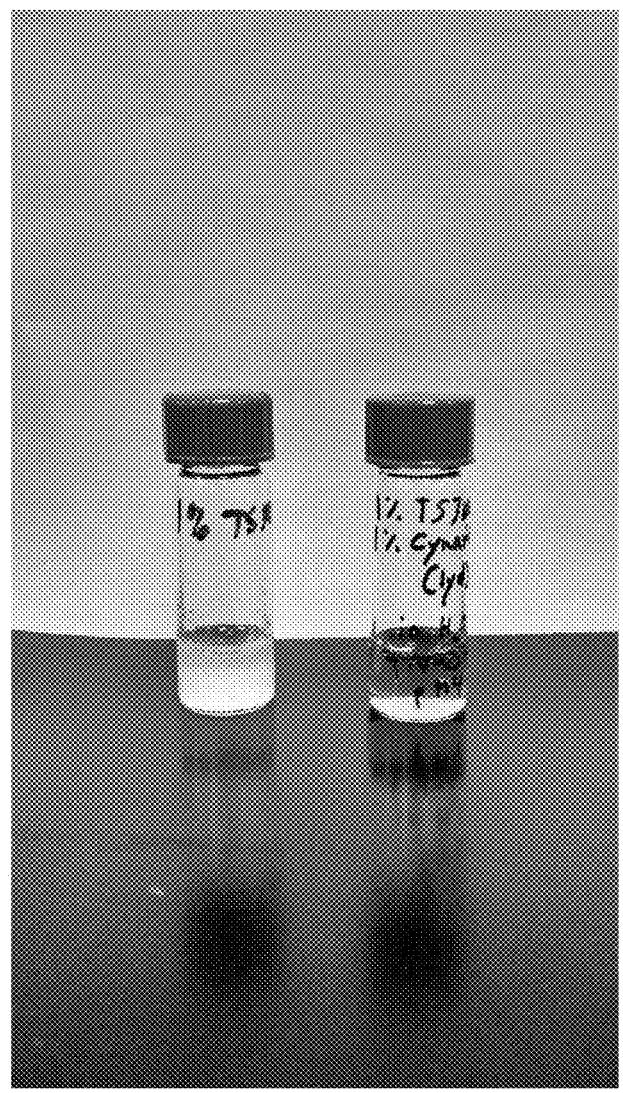
FIG. 11. Image of stable solution of 1% (wt) TS300 (leaf-based SGs, containing 30% Reb B in its acid form) in solution for two days with 1% purified cynarin isomers adjusted to pH 4 with sodium hydroxide. For comparison, the solution on the left is 1% (wt) TS300 in water without solubility enhancers.
Figure 12:
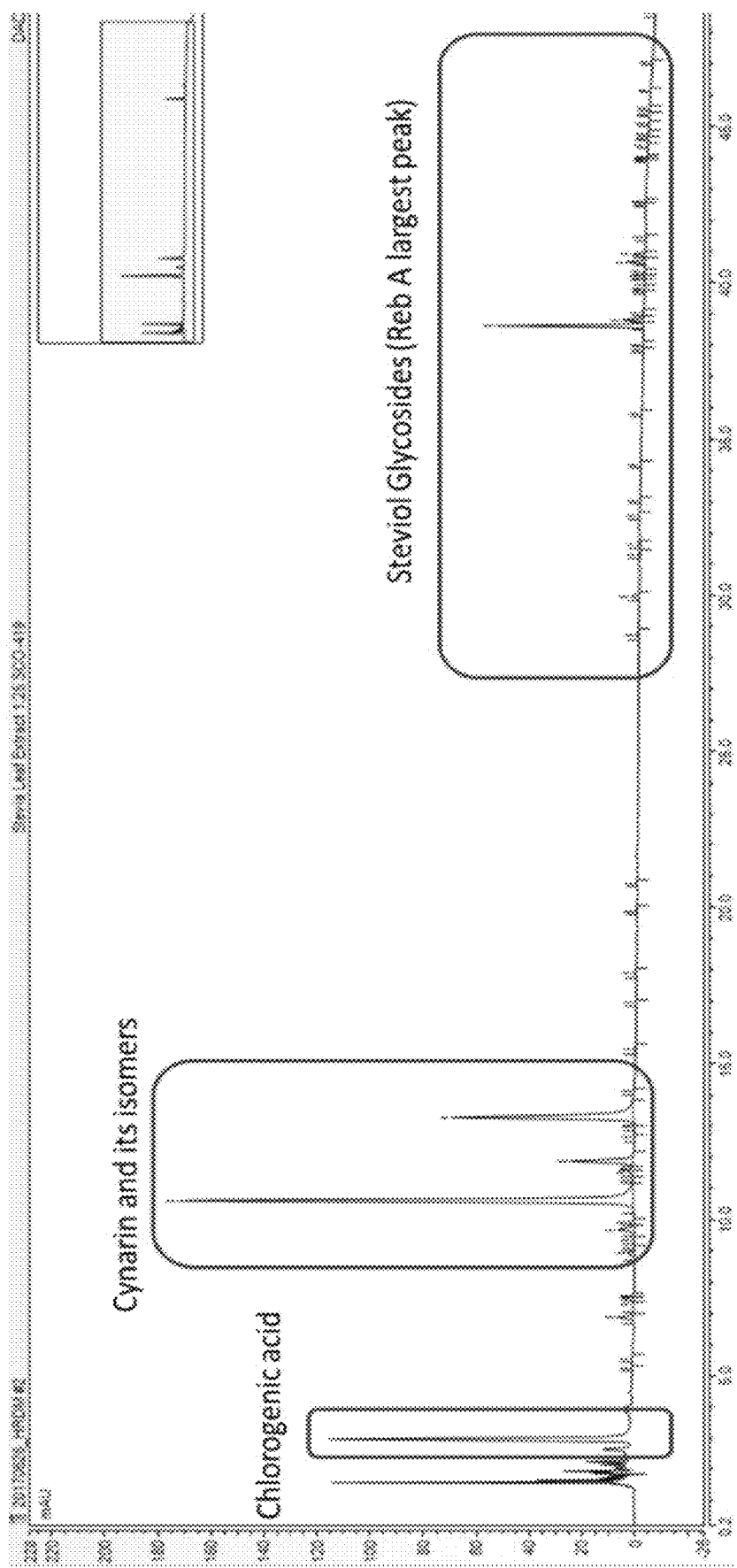
FIG. 12. A *stevia* leaf extract chromatogram at 210 nm, showing the solubility enhancers and steviolg glycosides (SGs).
Figure 13:
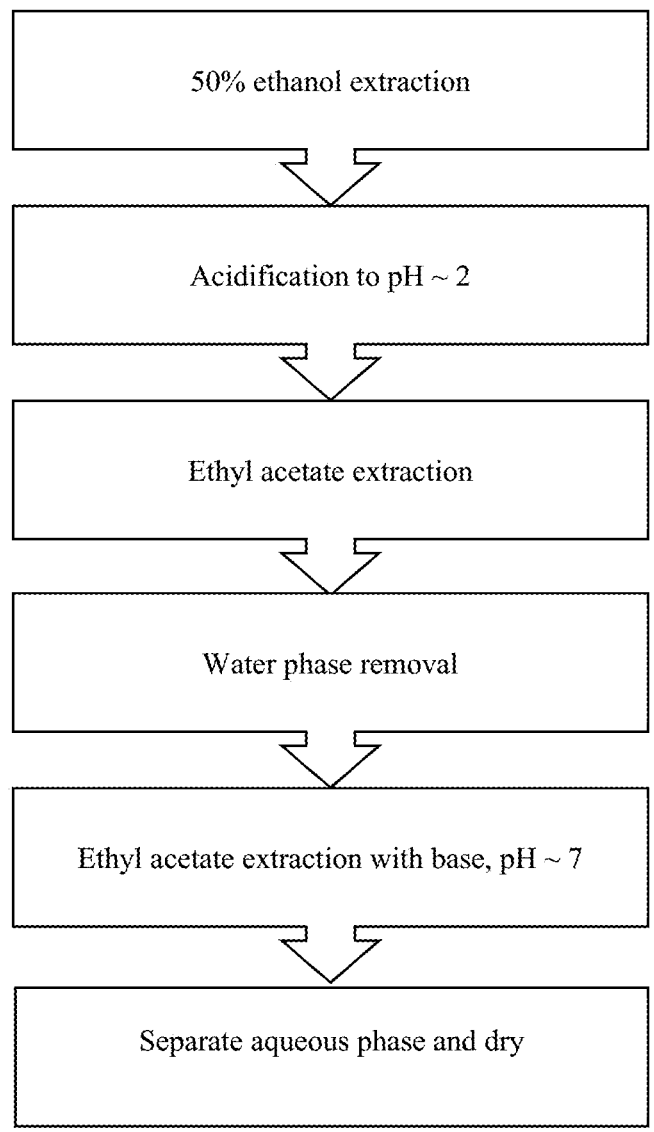
FIG. 13. Overall process for purification of SE from *stevia* leaf, resulting in mixed salt form material (mixture of salt form and acid form). Steviol glycoside solubility enhancers (SE) yield estimates are >90%.
Figure 14:
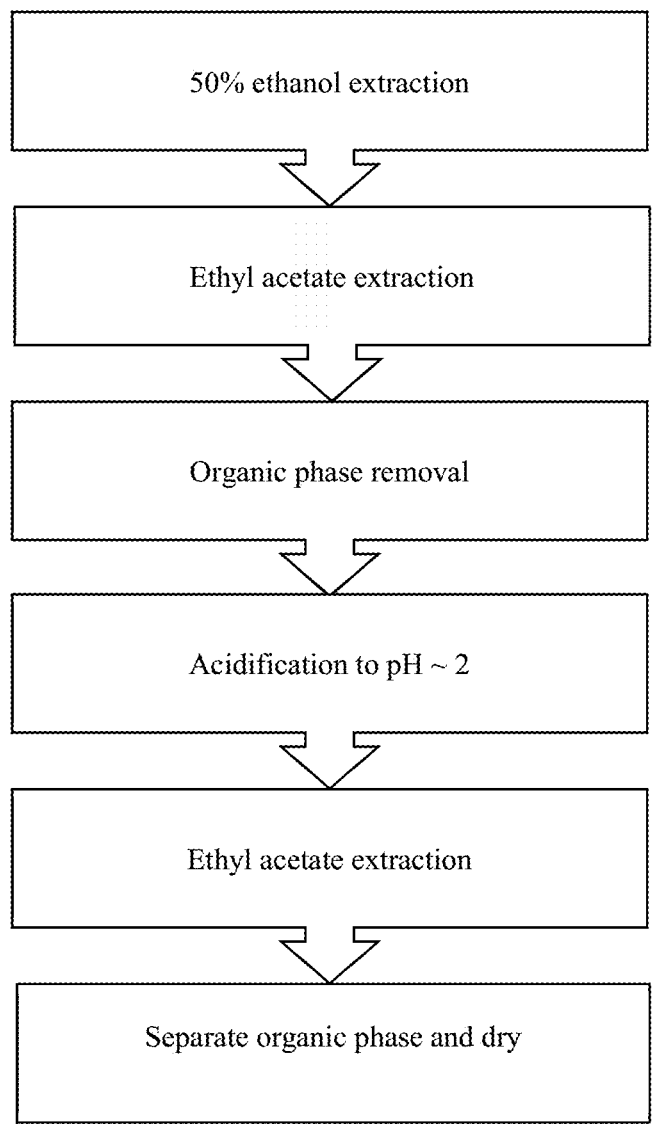
FIG. 14. Overall process for purification of SE from *stevia* leaf, resulting in acid form material. SE yield estimates are >90%.

One of the least soluble products that has been isolated from stevia leaves is Viatech TS300, which has a solubility limit in water of only <0.1 (wt) %. TS300 at 1% (wt) was solubilized using 1% (wt) of purified 3,5-dicaffeoylquinic acid material for two days. 1% (wt) TS300 in water alone crystallized in less than two hours under the same conditions (FIG. 11, left).

A mixture of chlorogenic acids and cynarin isomers also works very well to solubilize steviol glycosides. Thus, in general, mono-, di- or tri hydoxycinnamic acids or esters thereof, e.g., esters of quinic acid, may be useful to enhance the solubility of steviol glycosides.

Other Steviol Glycoside Solubility Enhancers:

Caffeic acid is also present in the stevia leaf. Although caffeic acid is not as water soluble as are chlorogenic acid and cynarin isomers, other hydroxycinnamic acids (coumaric, ferulic, and sinapic) may be used in a mixture with caffeic acid in order to increase the solubility of SGs.

Rosmarinic acid (1.6% (wt)) was pH adjusted to 4 with NaOH and then used to solubilize 1.6% (wt) EverSweet. That composition remained in solution for at least 3 weeks.

Stevia Leaf

Due to the relatively high concentration of cynarin, chlorogenic acid, and their isomers in stevia leaves, current waste streams of the leaf-based SGs being produced can be used to create a SG solubilization product, which can be added to leaf-based and/or fermentation-based SG solutions to improve water solubility.

Example 2

A variety of steviol glycoside solubility enhancers are found in stevia leaves and other plant parts, e.g., in the stems of artichokes, and may be in other leaves (tea leaves, etc.) or plant parts. In one embodiment, the solubility enhancers are mono-, di- or tri-hydroxycinnamic acid esters of quinic acid, such as chlorogenic acid, cynarin, neochlorogenic acid, cryptochlorogenic acid, 3-5-dicaffeoylquinic acid, etc. Exemplary methods to purify those solubility enhancers is described below.

Purification from *Stevia* Leaf:

Chlorogenic acid, neochlorogenic acid, cryptochlorogenic acid, cynarin, and other cynarin isomers account for approximately 7% of the material in the *stevia* leaf on a dry weight basis.

Ethyl Acetate Purification (Resulting in Mixed Salt Form Material):

*Stevia* leaf can be first extracted with 50% (vol/vol) ethanol to liberate all the SGs and SEs from the solids. Once extracted and the solids removed (e.g., via filtration and/or centrifugation), the resulting extract may be acidified to a pH 2-2.5 with a common inorganic acid, such as hydrochloric acid or phosphoric acid. The acidified extract may then be extracted via a liquid-liquid extraction with ethyl acetate to yield purified fractions, and the SGs (aqueous layer) separated from the SEs (organic layer). Each phase can then be further purified separately to obtain the desired final product.

The SE ethyl acetate layer may be further purified by adding basic solutions in water (for example, 0.05% calcium hydroxide, 0.1% sodium bicarbonate, etc.) and performing another liquid-liquid extraction. The colored species stay in the ethyl acetate phase and can be discarded, while the aqueous phase contains the SE product and can be dried directly.

Ethyl Acetate Purification (Resulting in Acid Form Material):

*Stevia* leaf may be first extracted with 50% (vol/vol) ethanol to liberate all the SGs and SEs from the solids. Once extracted and the solids removed (e.g., via filtration and/or centrifugation), the resulting extract may be extracted via a liquid-liquid extraction with ethyl acetate to remove colored species. The organic phase can be discarded and the aqueous layer may be acidified to a pH 2-2.5 with a common inorganic acid, such as hydrochloric acid or phosphoric acid. Fresh ethyl acetate may be added and another liquid-liquid extraction may be performed to yield purified fractions, separating the SGs (aqueous layer) from the SEs (organic layer). The aqueous phase, containing SGs, may be further purified for the desired SG product, while the organic phase may be dried directly to make the desired SE product in an acid form.

Resin Purification:

Resins, such as polystyrene divinylbenzene and polymethacrylate, may be used to purify these compounds. When using these resins, pH control allows for chlorogenic acid and cynarin isomer purification.

For polymethacrylate resin under acidic conditions, chlorogenic acid elutes before SGs, while cynarin isomers elute after SGs using ethanol/water elution. Under neutral conditions, both cynarin isomers and chlorogenic acid elute before SGs.

For polystyrene divinylbenzene under acidic conditions, chlorogenic acid elutes before SGs, while cynarin isomers elute with SGs using ethanol/water elution. Under neutral conditions, both cynarin isomers and chlorogenic acid elute before SGs.

Other hydrophobic resins and stationary phases can be used to purify these compounds.

Cynarin (and its Isomers) Only Purification:

To purify only cynarin and its isomers (removing chlorogenic acid and its isomers), an aqueous solution of SE material can be made at a high concentration to start the purification. Higher concentrations of cynarin include some base, such as NaOH, usually at ½ molar concentration, resulting in a solution of pH about 4. This material may be loaded on a polymethacrylate resin and washed with water (to remove excess acids). The chlorogenic acid (and its isomers) can be eluted with 15% (vol/vol) ethanol and dried separately to create one product. The column may then be treated with 60% (vol/vol) ethanol to elute cynarin and its isomers. This material can then be dried, e.g., in the absence of strong acids or high heat, to create a cynarin only SE material.

Purification from Artichoke:

Artichokes also contain high concentrations of chlorogenic acid and cynarin isomers. Unlike *stevia*, the highest concentration of the SEs resides in the artichoke stem. Processing artichoke is no different than *stevia* leaf, other than the extraction, due to the fibrous nature of the artichoke stem. The extraction may be done with 50% ethanol as well, but grinding or processing the artichoke stems may require a different grinding/mixing apparatus, e.g. cryogrinding, etc.

Once the SE material is extracted from the artichoke stem, the rest of the purification process may proceed similarly as described above.

Initial sensory evaluations from artichoke stem extract made with the process described above suggest that the sweetness from EverSweet is more sucrose like than without the SE added.

Other Natural Sources:

Other potential sources of solubility enhancers of SGs include but are not limited to tea, cocoa, coffee, and plants such as soy, canola, or plant parts such as leave or stems, and the like.

Example 3

Solubility Experiment

Steviol glycosides (SG) were weighed into a gas tight glass vial. Steviol glycoside solubility enhancers (SE) were added to the same vial. Purified water was added to the vial to make the final concentrations range from 0.3% to 10% ((wt)). The solution was heated at 80° C. until dissolved (0.1 to 5 minutes). The solutions were allowed to cool to RT (20-25° C.) and stored at either RT or 4° C. to monitor solubility. See Table 9.

TABLE 9

Summary of solubility experiments.

| SG Type | SE Type | SE Source | SG (mg) | SE (mg) | Total Volume (mL) | SG % | SE % | pH | pH Adjusted Using | Storage (deg C.) | Time to precipitate (days) | Storage Time (days) |
|---|---|---|---|---|---|---|---|---|---|---|---|---|
| EverSweet | chlorogenic acid (CGA) | Sigma | 15 | 5 | 5 | 0.3 | 0.1 | 6 | N/A | RT | N/A | 90* |
| EverSweet | CGA | Sigma | 50 | 50 | 1 | 5 | 5 | <1 | N/A | RT | N/A | 85* |
| Reb B | CGA** | Sigma | 50 | 50 | 1 | 5 | 5 | <1 | N/A | N/A | N/A | 85* |
| EverSweet (5%) & Reb B (1.75%) | CGA** | Sigma | 67.5 | 50 | 1 | 6.75 | 5 | <1 | N/A | RT | N/A | 85* |

TABLE 9-continued

Summary of solubility experiments.

| SG Type | SE Type | SE Source | SG (mg) | SE (mg) | Total Volume (mL) | SG % | SE % | pH | pH Adjusted Using | Storage (deg C.) | Time to precipitate (days) | Storage Time (days) |
|---|---|---|---|---|---|---|---|---|---|---|---|---|
| TS300 (35% Reb B) | CGA | Sigma | 10 | 10 | 1 | 1 | 1 | <1 | N/A | RT | 7 | 14 |
| Reb A | CGA | Sigma | 100 | 50 | 1 | 10 | 5 | <1 | N/A/ | RT | N/A | 65* |
| EverSweet | 3,5-dicaffeoylquinic acid | Stevia Leaf | 10 | 10 | 1 | 1 | 1 | 2 | NaOH | RT | N/A | 65* |
| EverSweet | 3,5-dicaffeoylquinic acid | Stevia Leaf | 14 | 10 | 1 | 1.4 | 1 | 4 | Formate | RT | N/A | 65* |
| EverSweet | 3,5-dicaffeoylquinic acid | Stevia Leaf | 7 | 5 | 1 | 0.7 | 0.5 | 2.5 | Citrate/PO4 | RT | N/A | 65* |
| EverSweet | 3,5- and 3,4-dicaffeoylquinic acid | Stevia Leaf | 10 | 7.5 | 1 | 1 | 0.75 | 4 | Ca(OH)2 | RT | N/A | 35* |
| EverSweet | 3,5- and 3,4-dicaffeoylquinic acid | Stevia Leaf | 10 | 7.5 | 1 | 1 | 0.75 | 4 | NaOH | RT | N/A | 35* |
| EverSweet | 3,5- and 3,4-dicaffeoylquinic acid | Stevia Leaf | 10 | 7.5 | 1 | 1 | 0.75 | 3 | Citrate/PO4 | RT | N/A | 35* |
| EverSweet | 3,5- and 3,4-dicaffeoylquinic acid | Stevia Leaf | 100 | 100 | 1 | 10 | 10 | 4 | Ca(OH)2 | RT | 28 | 60 |
| EverSweet | Saturated ferulic, caffeic, and coumaric acids | Sigma | 10 | ? | 1 | 1 | ? | 4 | N/A | RT | 10 | 21 |
| EverSweet | Saturated ferulic, caffeic, and coumaric acids | Sigma | 5 | ? | 1 | 0.5 | ? | 4 | N/A | RT | N/A | 60* |
| EverSweet | Saturated ferulic, caffeic, and coumaric acids | Sigma | 6 | ? | 2 | 0.3 | ? | 4 | N/A | RT | N/A | 60* |
| EverSweet | CGA isomers and cynarin isomers | Stevia Leaf | 10 | 10 | 1 | 1 | 1 | 2 | NaOH | RT | N/A | 30* |
| T5300 (35% Reb B) | CGA isomers and cynarin isomers | Stevia Leaf | 11 | 14 | 1 | 1.1 | 1.4 | 4 | NaOH | RT | 4 | 14 |
| EverSweet | Crude Aqueous Extract | Stevia Leaf | 10 | 30 | 1 | 1 | 3 | 4 | N/A | RT | N/A | 30* |
| EverSweet | Rosemarinic acid | Sigma | 16 | 16 | 1 | 1.6 | 1.6 | 4 | NaOH | RT | N/A | 30* |
| EverSweet | CGA isomers and cynarin isomers | Stevia Leaf | 10 | 10 | 1 | 1 | 1 | 4 | NaOH | 4 C. | N/A | 40* |
| EverSweet | 3,5- and 3,4-dicaffeoylquinic acid | Stevia Leaf | 10 | 10 | 1 | 1 | 1 | 4 | NaOH | 4 C. | N/A | 40* |
| EverSweet | 3,5- and 3,4-dicaffeoylquinic acid | Stevia Leaf | 10 | 10 | 1 | 1 | 1 | 4 | Ca(OH)2 | 4 C. | N/A | 40* |
| TS300 (35% Reb B) | 3,5- and 3,4-dicaffeoylquinic acid | Stevia Leaf | 10 | 10 | 1 | 1 | 1 | 4 | Ca(OH)2 | 4 C. | 14 | 21 |

*on-going experiment
**CGA material isomerized to neochlorogenic acid and cryptochlorogenic acid during heating Co-Drying Experiment SGs and SEs were added to the same vial, diluted with purified water, and heated to get into solution. Once in solution, the pH was adjusted using varying bases (see Table 2 below). The solution was then transferred to a lyophilizer flask and frozen in a dry ice IPA bath for 5-15 minutes. Once frozen, the flask was dried via lyophilization (LabConco FreeZone 6L).

TABLE 10

Summary of co-drying experiments.

| SG Type | SE Type | SE Source | SG:SE Ratio | pH in Solution | pH Adjusted Using |
|---|---|---|---|---|---|
| EverSweet | 3,5- and 3,4-dicaffeoylquinic acid | Stevia Leaf | 1:1 | 4 | NaOH |
| TS300 | 3,5- and 3,4-dicaffeoylquinic acid | Stevia Leaf | 1:1 | 3.5 | NaOH |

Freeze-Thaw Experiment: 1% EverSweet, 1% CGA Isomers and Cynarin Isomers Blend, pH 2

After solubilization, a solution was repeated frozen and thawed (four times) to determine impact on chemical and solubility stability. No precipitation was generated during the repeated freeze-thaw cycles and chemical stability showed no signs of degradation for either the SGs or the SEs.

Stevia Leaf Extraction

Dried *stevia* leaf was cryoground using liquid nitrogen and mortar and pestle to a powder. *Stevia* leaf powder was extracted using 50% aqueous ethanol and stirring for greater than four hours. Leaf solids were removed through filtration. The resulting *stevia* leaf extract was further purified as below to generate the various SE materials.

Purification of 3,5-Dicaffeoylquinic Acid

*Stevia* leaf extract was further diluted in purified water to 10% ethanol content. This extract was filtered through a 0.2 μm PTFE filter and purified via prep LC. The material was separated on a C18 prep column, using a purified water and ethanol gradient (10-25% ethanol). The 3,5-dicaffeoylquinic acid peak was collected, over repeated injections and pooled. The pooled collections were dried under nitrogen and RT and resulted in a product>95% pure.

Purification of 3,5- and 3,4-Dicaffeoylquinic Acid Mixture

*Stevia* leaf extract was dried under nitrogen at RT until mostly dry. The solids were dissolved in purified water and acidified to pH<2 with hydrochloric acid. This solution was loaded onto a polymethacrylate resin at 5 bed volumes/hr flow rate. The column was washed with 35% acidified aqueous ethanol to remove all SGs and unwanted material. The desired material was eluted with 65% aqueous ethanol. The eluted fraction was dried under nitrogen at RT and resulted in a product of mainly 3,5- and 3,4-dicaffeoylquinic acids, >95% pure.

Purification of CGA Isomers and Cynarin Isomers

*Stevia* leaf extract was pH adjusted to 8 with sodium bicarbonate. To the solution, an equal volume of ethyl acetate was added and a liquid-liquid extract was performed. The ethyl acetate layer was removed and discarded. Two additional ethyl acetate extractions were performed, each time discarding the ethyl acetate. The resulting aqueous solution was then pH adjusted with hydrochloric acid to pH<2. Ethyl acetate was again added at equal volume and another liquid-liquid extraction was performed. The ethyl acetate layer was removed and collected. Another ethyl acetate extraction was performed and the ethyl acetate was pooled. The combined ethyl acetate was dried under nitrogen at RT to yield a mixture of CGA and its isomers and cynarin and its isomers, >95% pure.

Purification of Crude *Stevia* Aqueous Extract

Chloroform was added to an equal volume of *stevia* leaf extract and liquid-liquid extraction was performed. The aqueous layer was removed and dried to near dryness under nitrogen at RT. This crude mixture contained the SE material and SGs from the leaf.

Example 4

Example A. HPLC Analytical Methods

Solubility of various combinations of steviol glycosides and solubility enhancers were assayed by HPLC (high performance liquid chromatography). In general, solutions of steviol glycosides and solubility enhancers were prepared and then assayed by HPLC after varying shelf times. The HPLC assays indicated the amount of particular steviol glycosides present in a soluble fraction of the respective solutions at the end of the respective shelf times. The HPLC was equipped with two Agilent ED-C18 columns (4.6 mm×150 mm, 2.7 μm) connected in series. Chromatography runs were performed on the two Agilent ED-C18 columns at a flow rate of 0.6 ml/min with a Mobile Phase A (0.01% trifluoroacetic acid in water) and a Mobile Phase B (acetonitrile) using a gradient as indicated below in Table 11. The total run time was 35 minutes, the column temperature was 50° C., the sample temperature was 20° C., and the sample injection volume was 10 μL. Standard samples of the respective steviol glycosides and the respective solubility enhancers were first assayed and then the various solutions were assayed and compared to the standard samples.

TABLE 11

| Time (min.) | Mobile Phase A | Mobile Phase B |
|---|---|---|
| 0 | 68 | 32 |
| 15 | 68 | 32 |
| 22 | 50 | 50 |
| 26.5 | 50 | 50 |
| 27 | 10 | 90 |
| 30 | 10 | 90 |
| 30.5 | 68 | 32 |
| 35 | 68 | 32 |

Example B. Soluble Solution of Gallic Acid, Corn Starch Fiber, and Steviol Glycoside Gallic acid was obtained (Sigma Aldrich, about 97.5% purity). Gallic acid, 0.035 g, and corn starch fiber, 0.5 ml, were mixed with 100 mL of Millipore water until dissolved. A spray dried steviol glycoside mix, 0.4 g, (about 95% total steviol glycosides with about 75% Reb M and about 5% Reb D), was added and mixed for 10 min. The spray dried steviol glycoside was completely dissolved within 10 min. and produced a clear solution. The solution of gallic acid, corn starch fiber, and steviol glycoside mix remained clear for more than 3 days. This experiment showed that a solution of gallic acid, corn starch fiber, and spray dried steviol glycoside mix was soluble in water for at least 3 days.

Example C. Soluble Solution of Gallic Acid, Gellan Gum, and Steviol Glycoside Gallic acid was obtained (Sigma Aldrich, about 97.5% purity). Gallic acid, 0.035 g, was mixed with 50 mL of Millipore water until dissolved. Gellan gum, 0.01 g, and a spray dried steviol glycoside mix, 0.2 g, (about 95% total steviol glycosides with about 75% Reb M and about 5% Reb D) was added and mixed for 10 min. The gellan gum and spray dried steviol glycoside was completely dissolved within 10 min. and produced a clear solution. The solution of gallic acid, gellan gum, and steviol glycoside mix remained clear for more than 3 days. The solution of gallic acid, gellan gum, and steviol glycoside mix was assayed 24 h after mixing by HPLC as described above. The assay indicated Rebaudoside M at a 0.27% by weight concentration and Rebaudoside D at a 0.056% by weight concentration for a total of 0.326% by weight steviol glycoside concentration. This experiment showed that a solution of gallic acid, gellan gum, and spray dried steviol glycoside mix was soluble in water for at least 3 days.

Example D. Soluble Solution of Gallic Acid and Steviol Glycoside

Gallic acid was obtained (Sigma Aldrich, about 97.5% purity). Gallic acid, 0.035 g, was mixed with 50 mL of Millipore water until dissolved. A spray dried steviol glycoside mix, 0.2 g (about 95% total steviol glycosides with about 75% Reb M and about 5% Reb D), F was added and mixed for 10 minutes. The solution of gallic acid and steviol glycoside mix remained clear for more than 3 days. The solution of gallic acid and steviol glycoside mix was assayed 24 hours after mixing by HPLC as described above. The assay indicated Rebaudoside M at a 0.297% by weight concentration and Rebaudoside D at a 0.06% by weight concentration for a total of 0.357% by weight steviol glycoside concentration. This experiment showed that a solution of gallic acid and spray dried steviol glycoside mix was soluble in water for at least 3 days.

Example E. Soluble Solution of Gallic Acid, Corn Starch Fiber, and Steviol Glycoside Gallic acid was obtained (Sigma Aldrich, about 97.5% purity). Gallic acid, 0.035 g, was mixed with 50 mL of Millipore water until dissolved. Corn starch fiber, 0.2 ml, and a spray dried steviol glycoside mix, 0.2 g (about 95% total steviol glycosides with about 75% Reb M and about 5% Reb D), was added and mixed for 10 minutes. The solution of gallic acid and steviol glycoside mix remained clear for more than 7 days. The solution of gallic acid, corn starch fibers and steviol glycoside mix was assayed 24 hours after mixing by HPLC as described above. The assay indicated Rebaudoside M at a 0.278% by weight concentration and Rebaudoside D at a 0.057% by weight concentration for a total of 0.335% by weight steviol glycoside concentration. This experiment showed that a solution of gallic acid, corn starch fibers, and spray dried steviol glycoside mix was soluble in water for at least 7 days.

Example F. Soluble Solution of Gallic Acid, Corn Starch Fibers, and Steviol Glycoside Gallic acid was obtained (Sigma Aldrich, about 97.5% purity). Gallic acid, 0.11 g, was mixed with 100 mL of Millipore water until dissolved. Corn starch fiber, 0.05 ml, and a spray dried steviol glycoside mix, 0.43 g (about 95% total steviol glycosides with about 75% Reb M and about 5% Reb D), was added and mixed for 10 min. The solution of gallic acid and steviol glycoside mix remained clear for more than 10 days. The solution of gallic acid, corn starch fibers and steviol glycoside mix was assayed 24 hours after mixing by HPLC as described above. The assay indicated Rebaudoside M at a 0.289% by weight concentration and Rebaudoside D at a 0.052% by weight concentration for a total of 0.341% by weight steviol glycoside concentration. This experiment showed that a solution of gallic acid, corn starch fibers, and spray dried steviol glycoside mix was soluble in water for at least 10 days.

Example G. Soluble Solution of Gallic Acid and Steviol Glycoside

Gallic acid was obtained (Sigma Aldrich, about 97.5% purity). Gallic acid, 0.11 g, was mixed with 100 mL of Millipore water until dissolved. A spray dried steviol glycoside mix, 0.43 g (about 95% total steviol glycosides with about 75% Reb M and about 5% Reb D), was added and mixed for 10 min. The solution of gallic acid and steviol glycoside mix remained clear for more than 3 days. The solution of gallic acid and steviol glycoside mix was assayed 24 hours after mixing by HPLC as described above. The assay indicated Rebaudoside M at a 0.279% by weight concentration and Rebaudoside D at a 0.051% by weight concentration for a total of 0.33% by weight steviol glycoside concentration. This experiment showed that a solution of gallic acid and spray dried steviol glycoside mix was soluble in water for at least 3 days.

Example H. Solubility of Rebaudoside B with Gallic Acid

Gallic acid was obtained (Sigma Aldrich, about 97.5% purity). Gallic acid, 0.4 g, and 2 g of Rebaudoside B were mixed with 50 mL of a 50%/50% ethanol-water solution for 24 hours, filtered, and dried under a vacuum. Crystals of Rebaudoside B and gallic acid resulted. A kinetic/instant solubility was measured for the resulting crystals by HPLC. At less than 48 h the crystals possessed a kinetic/instant solubility of 550 ppm, at 55 hours the crystals possessed a kinetic/instant solubility of 500 ppm, and at 72 hours the crystals possessed a kinetic/instant solubility of 140 ppm. A comparison with only Rebaudoside B and without gallic acid was also performed. 2 g of Rebaudoside B was mixed with 50 mL of a 50%/50% ethanol-water solution for 24 hours, filtered, and dried under a vacuum. Crystals of Rebaudoside B resulted. A kinetic/instant solubility was measured for the resulting crystals by HPLC. At less than 48 hours the crystals possessed a kinetic/instant solubility of 500 ppm, at 55 hours the crystals possessed a kinetic/instant solubility of 220 ppm, and at 72 hours the crystals possessed a kinetic/instant solubility of 130 ppm. This experiment showed that crystals comprising a combination of gallic acid and Rebaudoside B possessed a higher kinetic/instant solubility than crystals comprising Rebaudoside B alone.

Example I. Solubility of Steviol Glycoside with Mandelic Acid, Pyromellitic Acid, Quinic Acid, and Gallic Acid The solubilities of various steviol glycosides mixtures in combination with mandelic acid (Sigma Aldrich, 99%), pyromellitic acid (Sigma Aldrich, 96%), quinic acid (Sigma Aldrich, 98%), and gallic acid (Sigma Aldrich, 97.5%) were tested. For each of mandelic acid, pyromellitic acid, quinic acid, and gallic acid, solutions were prepared by adding steviol glycoside (about 95% total steviol glycosides with about 75% Reb M and about 5% Reb D) to a solution of the respective acid. The samples were prepared with a total concentration of the steviol glycoside mixture of 0.3% by weight and a molar ratio of acid to steviol glycoside of 5:1, 2:1, 1:1, 0.5:1, 0.25:1, 0.1:1. Similar samples were also prepared of individual steviol glycosides with each of the respective organic acids. Each sample was stirred on a magnetic stir plate for 30-60 minutes, heated to 75° C., and then cooled to room temperature. A pH of each sample was measured and the samples were observed for precipitation. Mandelic acid, pyromellitic acid, quinic acid, and gallic acid were shown to promote a soluble solution of a 0.3% steviol glycoside mixture over 3 days at a 5:1 molar ratio of acid to steviol glycoside. Gallic acid was shown to promote a soluble solution of a 0.3% steviol glycoside mixture over 3 days at a 7:1 molar ratio of acid to steviol glycoside.

Mandelic Acid

Samples of mandelic acid and steviol glycoside (about 95% total steviol glycosides with about 75% Reb M and about 5% Reb D) were prepared as described above. Mandelic acid was obtained (Sigma Aldrich, 99% purity). Mandelic acid was dissolved in Millipore water and then a steviol glycoside mix was added and the sample stirred for approximately 30 minutes. The sample was then heated to 75° C. and allowed to cool to room temperature. Samples were prepared with a final steviol glycoside concentration of 0.3% by weight (2.35 mM) and at a 5:1 and 2:1 molar ratio of acid to steviol glycoside. A pH of each sample was measured. A turbidity of each sample was measured in NTU (Nephelometric Turbidity Units)(measured with Turbiscan LA10 Expert, Formulaction S.A.). The results are shown in Table 12. These experiments show that a sample of mandelic acid and 0.3% steviol glycoside was soluble for at least 3 days.

Pyromellitic Acid

Samples of pyromellitic acid and a steviol glycoside mix were prepared as described above. Pyromellitic acid was obtained (Sigma Aldrich, about 96% purity). Pyromellitic acid was dissolved in Millipore water and then a steviol glycoside mix (about 95% total steviol glycosides with about 75% Reb M and about 5% Reb D) was added and the sample stirred for approximately 30 minutes. The sample was then heated to 75° C. and allowed to cool to room temperature. Samples were prepared with a final steviol glycoside concentration of 0.3% by weight (2.35 mM) and at a 5:1 and 2:1 molar ratio of acid to steviol glycoside. A pH of each sample was measured. A turbidity of each sample was measured in NTU (Nephelometric Turbidity Units) (measured with Turbiscan LA10 Expert, Formulaction S.A.). Each sample was observed for solubility. The results are shown in Table 13. These experiments show that a sample of pyromellitic acid and 0.3% steviol glycoside was soluble for at least 3 days.

TABLE 13

| Sample | pH on Day 0 | Day 0 | Day 2 | Day 3 | Day 4 |
|---|---|---|---|---|---|
| Pyromellitic acid (5:1 molar ratio acid to steviol glycoside), 0.3% steviol glycoside | 2.50 | 0.804 NTU | Clear 0.790 NTU | Clear | Clear 0.910 NTU |
| Pyromellitic acid (2:1 molar ratio acid to steviol glycoside), 0.3% steviol glycoside | 2.76 | 0.762 NTU | Clear 0.780 NTU | Clear (some floating dust) | Clear 1.47 NTU |

Pamoic Acid

Samples of pamoic acid and a steviol glycoside mix (about 95% total steviol glycosides with about 75% Reb M and about 5% Reb D) were prepared as described above. Pamoic acid was obtained (Sigma Aldrich, 97%). Pamoic acid was dissolved in Millipore water and then a steviol glycoside mix was added and the sample stirred for approximately 30 minutes. The pH of the solution was not adjusted at any point within the experiment. The sample was then heated to 75° C. and allowed to cool to room temperature. Samples were prepared with a final steviol glycoside concentration of 0.3% by weight (2.35 mM) and at a 5:1 and 2:1 molar ratio of pamoic acid to steviol glycoside. The sample with a final steviol glycoside concentration of 0.3% by weight (2.35 mM) and at a 5:1 molar ratio of pamoic acid to steviol glycoside comprised 11.8 mM pamoic acid (or 0.46% by weight percent). The sample with a final steviol glycoside concentration of 0.3% by weight (2.35 mM) and at a 2:1 molar ratio of pamoic acid to steviol glycoside comprised 4.7 mM pamoic acid (or 0.18% by weight percent). Each sample was observed for solubility. The results are shown in Table 14. These experiments show that a sample of pamoic acid and 0.3% steviol glycoside was not initially soluble and remained insoluble at least after 1 day under the conditions tested.

TABLE 12

| Sample | pH on Day 0 | Day 0 | Day 2 | Day 3 | Day 4 |
|---|---|---|---|---|---|
| Mandelic acid (5:1 molar ratio acid to steviol glycoside), 0.3% steviol glycoside | 3.20 | 1.07 NTU | Clear (some floating dust) 0.944 NTU | Clear | Clear 1.42 NTU |
| Mandelic acid (2:1 molar ratio acid to steviol glycoside), 0.3% steviol glycoside | 3.36 | 0.620 NTU | Clear 0.672 NTU | Clear (some floating dust) | Clear 1.58 NTU |

TABLE 14

| Sample | Day 0 | Day 1 |
|---|---|---|
| Pamoic acid (5:1 molar ratio acid to steviol glycoside), 0.3% steviol glycoside | Bright yellow, opaque, undissolved crystals | Bright yellow, particles settled/gradient of ppt, heavy ppt at bottom |
| Pamoic acid (2:1 molar ratio acid to steviol glycoside), 0.3% steviol glycoside | Bright yellow, opaque, undissolved crystals | Bright yellow, particles settled/gradient of ppt, heavy ppt at bottom |

Quinic Acid

Samples of quinic acid and a steviol glycoside mix were prepared as described above. Quinic acid was obtained (Sigma Aldrich, 98%). Quinic acid was dissolved in Millipore water and then steviol glycoside (about 95% total steviol glycosides with about 75% Reb M and about 5% Reb D) was added and the sample stirred for approximately 30 minutes. The sample was then heated to 75° C. and allowed to cool to room temperature. Samples were prepared with a final steviol glycoside concentration of 0.3% by weight (2.35 mM) and at a 5:1 and 2:1 molar ratio of quinic acid to steviol glycoside. Samples were also prepared with a final steviol glycoside concentration of 0.6% by weight (4.7 mM) and at a 5:1 and 2:1 molar ratio of quinic acid to steviol glycoside. The sample with a final steviol glycoside concentration of 0.3% by weight (2.35 mM) and at a 5:1 molar ratio of acid to steviol glycoside comprised 11.8 mM quinic acid (or 0.23% by weight percent). The sample with a final steviol glycoside concentration of 0.3% by weight (2.35 mM) and at a 2:1 molar ratio of acid to steviol glycoside comprised 4.7 mM quinic acid (or 0.09% by weight percent).

The sample with a final steviol glycoside concentration of 0.6% by weight (4.7 mM) and at a 5:1 molar ratio of acid to steviol glycoside comprised 11.8 mM quinic acid (or 0.45% by weight percent). The sample with a final steviol glycoside concentration of 0.6% by weight (4.7 mM) and at a 2:1 molar ratio of acid to steviol glycoside comprised 4.7 mM quinic acid (or 0.18% by weight percent). A pH of each sample was measured. A turbidity of each sample was measured in NTU (Nephelometric Turbidity Units) (measured with Turbiscan LA10 Expert, Formulaction S.A.). Each sample was observed for solubility. The results are shown in Table 15. These experiments show that a sample of quinic acid and either 0.3% or 0.6% steviol glycoside was soluble for at least a day.

TABLE 15

| Sample | pH | Day 0 | Day 1 |
|---|---|---|---|
| Quinic acid (5:1 molar ratio acid to steviol glycoside), 0.3% steviol glycoside | 3.63 | Clear 0.906 NTU | Clear 0.791 NTU |
| Quinic acid (2:1 molar ratio acid to steviol glycoside), 0.3% steviol glycoside | 3.68 | Clear 0.915 NTU | Clear 1.08 NTU |
| Quinic acid (5:1 molar ratio acid to steviol glycoside), 0.6% steviol glycoside | 3.47 | Clear 2.07 NTU | Ppt at bottom 15.4 NTU |
| Quinic acid (2:1 molar ratio acid to steviol glycoside), 0.6% steviol glycoside | 3.67 | Clear 1.44 NTU | Ppt at bottom 13.2 NTU |

Ppt = precipitate

Comparison of Mandelic Acid, Pyromellitic Acid, and Quinic Acid at 1:1 or a 1:0.5 Molar Ratio of Acid to Steviol Glycoside Samples of each of mandelic acid (Sigma Aldrich, 99%), pyromellitic acid (Sigma Aldrich, 96%), and quinic acid (Sigma Aldrich, 98%) were prepared with steviol glycoside (about 95% total steviol glycosides with about 75% Reb M and about 5% Reb D). Each acid was dissolved in Millipore water and then a steviol glycoside mix was added and each sample stirred for approximately 30 minutes. Each sample was then heated to 75° C. and allowed to cool to room temperature. Samples were prepared with a final steviol glycoside concentration of 0.3% by weight (2.35 mM) and at a 1:1 or a 0.5:1 molar ratio of acid to steviol glycoside as shown in Table 16. A pH of each sample was measured. A turbidity of each sample was measured in NTU (Nephelometric Turbidity Units)(measured with Turbiscan LA10 Expert, Formulaction S.A.). Each sample was observed for solubility. The solubility results for each sample are shown in Table 17. These experiments showed that 0.3% steviol glycoside was soluble for at least 3 days with samples of each of mandelic acid, pyromellitic acid, and quinic acid at a 1:1 or a 0.5:1 molar ratio of acid to steviol glycoside.

TABLE 16

| Acid | MW of acid | Ratio of acid to steviol glycoside | % acid | mM of acid | % steviol glycoside | mM of steviol glycoside |
|---|---|---|---|---|---|---|
| Mandelic acid | 152.15 g/mol | 1:1 | 0.035% | 2.35 mM | 0.3% | 2.35 mM |
| Mandelic acid | 152.15 g/mol | 0.5:1 | 0.018% | 1.18 mM | 0.3% | 2.35 mM |
| Pyromellitic acid | 254.15 g/mol | 1:1 | 0.060% | 2.35 mM | 0.3% | 2.35 mM |

TABLE 16-continued

| Acid | MW of acid | Ratio of acid to steviol glycoside | % acid | mM of acid | % steviol glycoside | mM of steviol glycoside |
|---|---|---|---|---|---|---|
| Pyromellitic acid | 254.15 g/mol | 0.5:1 | 0.030% | 1.18 mM | 0.3% | 2.35 mM |
| Quinic acid | 192.17 g/mol | 1:1 | 0.045% | 2.35 mM | 0.3% | 2.35 mM |
| Quinic acid | 192.17 g/mol | 0.5:1 | 0.023% | 1.18 mM | 0.3% | 2.35 mM |

TABLE 17

| Sample | pH | Day 0 | Day 1 | Day 2 | Day 3 |
|---|---|---|---|---|---|
| Mandelic acid 1:1 ratio | 3.64 | Clear 1.18 NTU | Clear 1.52 NTU | Clear 2.56 NTU | Clear 3.21 NTU |
| Mandelic acid 0.5:1 ratio | 3.86 | Clear 0.857 NTU | Clear 1.16 NTU | Clear (some floating dust) 2.56 NTU | Clear 4.05 NTU |
| Pyromellitic acid 1:1 ratio | 2.99 | Clear 1.18 NTU | Clear 1.13 NTU | Clear 1.51 NTU | Clear 1.91 NTU |
| Pyromellitic acid 0.5:1 ratio | 3.21 | Clear 1.06 NTU | Clear 0.992 NTU | Clear (some floating dust, could be ppt?) 1.85 NTU | Clear 3.65 NTU |
| Quinic acid 1:1 ratio | 3.51 | Clear 0.909 NTU | Clear 1.07 NTU | Clear 2.22 NTU | Clear 3.24 NTU |
| Quinic acid 0.5:1 ratio | 3.72 | Clear 0.813 NTU | Clear 0.948 NTU | Clear (some floating dust, could be ppt?) 1.85 NTU | Clear 3.74 NTU |

Ppt = precipitate

Comparison of Mandelic Acid, Pyromellitic Acid, and Quinic Acid at a 0.25:1 or a 0.1:1 Molar Ratio of Acid to Steviol Glycoside Samples of each of mandelic acid, pyromellitic acid, and quinic acid were prepared with steviol glycoside. Each acid was dissolved in Millipore water and then steviol glycoside (about 95% total steviol glycosides with about 75% Reb M and about 5% Reb D) was added and each sample stirred for approximately 30 min. Each sample was then heated to 75° C. and allowed to cool to room temperature. Samples were prepared with a final steviol glycoside concentration of 0.3% by weight (2.35 mM) and at a 0.25:1 or a 0.1:1 molar ratio of acid to steviol glycoside as shown in Table 18. A pH of each sample was measured. A turbidity of each sample was measured in NTU (Nephelometric Turbidity Units)(measured with Turbiscan LA10 Expert, Formulaction S.A.). Each sample was observed for solubility. The solubility results for each sample are shown in Table 19. These experiments showed that 0.3% steviol glycoside was soluble for at least several days with samples of each of mandelic acid, pyromellitic acid, and quinic acid at a 0.25:1 or a 0.1:1 molar ratio of acid to steviol glycoside. These experiments also showed that 0.3% steviol glycoside was soluble for at least 5 days with samples of pyromellitic acid at a 0.25:1 or a 0.1:1 molar ratio of pyromellitic acid to steviol glycoside.

TABLE 18

| Sample Acid | MW of acid | Ratio of acid to steviol glycoside | % acid | mM of acid | % steviol glycoside | mM of steviol glycoside |
|---|---|---|---|---|---|---|
| Mandelic acid | 152.15 g/mol | 0.25:1 | 0.009% | 0.588 mM | 0.3% | 2.35 mM |
| Mandelic acid | 152.15 g/mol | 0.1:1 | 0.004% | 0.235 mM | 0.3% | 2.35 mM |
| Pyromellitic acid | 254.15 g/mol | 0.25:1 | 0.015% | 0.588 mM | 0.3% | 2.35 mM |
| Pyromellitic acid | 254.15 g/mol | 0.1:1 | 0.006% | 0.235 mM | 0.3% | 2.35 mM |
| Quinic acid | 192.17 g/mol | 0.25:1 | 0.011% | 0.588 mM | 0.3% | 2.35 mM |
| Quinic acid | 192.17 g/mol | 0.1:1 | 0.005% | 0.235 mM | 0.3% | 2.35 mM |

TABLE 19

| Sample | pH | Day 0 | Day 1 | Day 2 | Day 5 |
|---|---|---|---|---|---|
| Mandelic acid 0.25:1 ratio | 3.75 | Clear 0.899 NTU | Clear 1.05 NTU | Clear 1.37 NTU | Slight ppt 3.03 NTU |
| Mandelic acid 0.1:1 ratio | 3.93 | Clear 1.29 NTU | Clear 2.57 NTU | Clear 3.88 NTU | Ppt 6.53 NTU |
| Pyromellitic acid 0.25:1 ratio | 3.43 | Clear 1.14 NTU | Clear 1.21 NTU | Clear 2.45 NTU | Clear 5.17 NTU |

TABLE 19-continued

| Sample | pH | Day 0 | Day 1 | Day 2 | Day 5 |
|---|---|---|---|---|---|
| Pyromellitic acid 0.1:1 ratio | 3.64 | Clear 1.19 NTU | Clear 1.28 NTU | Clear 1.81 NTU | Clear 2.62 NTU |
| Quinic acid 0.25:1 ratio | 3.92 | Clear 1.36 NTU | Clear 1.89 NTU | Clear 2.77 NTU | Ppt 5.67 NTU |
| Quinic acid 0.1:1 ratio | 4.03 | Clear 0.966 NTU | Clear 1.54 NTU | Clear 2.27 NTU | Ppt 4.11 NTU |

Ppt = precipitate

Comparison of Mandelic Acid, Pyromellitic Acid, and Quinic Acid at a 5:1 or a 2:1 Molar Ratio of Acid to Steviol Glycoside for Each of Rebaudoside B, Rebaudoside D, and Rebaudoside M Samples of each of mandelic acid (Sigma Aldrich, 99%), pyromellitic acid (Sigma Aldrich, 96%), and quinic acid (Sigma Aldrich, 98%) were prepared with each of Rebaudoside B, Rebaudoside D, and Rebaudoside M to assay for solubility. Stock solutions of mandelic acid, pyromellitic acid, and quinic acid were prepared in volumetric flasks. Mandelic acid and quinic acid were prepared at a 5% by weight concentration and pyromellitic acid was prepared at a 0.75% by weight concentration. The Rebaudoside B samples were prepared with a final concentration of 0.06% by weight concentration of Rebaudoside B. The Rebaudoside D samples were prepared with a final concentration of 0.12% by weight concentration of Rebaudoside D. The Rebaudoside M samples were prepared with a final concentration of 0.5% by weight concentration of Rebaudoside M. For each of the Rebaudoside B, Rebaudoside D, and Rebaudoside M samples at each of the 5:1 and 2:1 molar acid to steviol glycoside ratios, the respective acid concentration is shown in Table 20.

TABLE 20

| Molar ratio (acid:steviol glycoside) | Rebaudoside B (at 0.06% final concentration) | Rebaudoside D (at 0.12% final concentration) | Rebaudoside M (at 0.5% final concentration) |
|---|---|---|---|
| 5:1 | 3.727 mM acid | 5.314 mM acid | 19.360 mM acid |
| 2:1 | 1.491 mM acid | 2.125 mM acid | 7.744 mM acid |

Sample solutions of mandelic acid, pyromellitic acid, and quinic acid were prepared by adding stock acid solutions and water to a final volume of 40 mL as shown in Table 21 for a 5:1 molar ratio of acid to steviol glycoside and in Table 22 for a 2:1 molar ratio of acid to steviol glycoside.

TABLE 21

| Acid 5:1 molar ratio of acid to steviol glycoside | Rebaudoside B (at 0.06% final concentration) | Rebaudoside D (at 0.12% final concentration) | Rebaudoside M (at 0.5% final concentration) |
|---|---|---|---|
| Mandelic acid | 0.454 mL of acid | 0.647 mL of acid | 2.357 mL of acid |
| Pyromellitic acid | 5.052 mL of acid | 7.203 mL of acid | 26.242 mL of acid |
| Quinic acid | 0.573 mL of acid | 0.817 mL of acid | 2.976 mL of acid |

TABLE 22

| Acid 2:1 molar ratio of acid to steviol glycoside | Rebaudoside B (at 0.06% final concentration) | Rebaudoside D (at 0.12% final concentration) | Rebaudoside M (at 0.5% final concentration) |
|---|---|---|---|
| Mandelic acid | 0.181 mL of acid | 0.259 mL of acid | 0.943 mL of acid |
| Pyromellitic acid | 2.021 mL of acid | 2.881 mL of acid | 10.497 mL of acid |
| Quinic acid | 0.229 mL of acid | 0.327 mL of acid | 1.191 mL of acid |

After the sample acid solutions were prepared, the respective steviol glycosides (Rebaudoside B, Rebaudoside D, and Rebaudoside M) were added as solid powder to the corresponding sample acid solutions at the corresponding steviol glycoside concentrations (0.06% by weight concentration of Rebaudoside B, 0.12% by weight concentration of Rebaudoside D, 0.5% by weight concentration of Rebaudoside M). The sample solutions with the respective steviol glycoside were stirred for 1 h, heated to 75° C., and promptly removed to cool to room temperature. A pH of each sample acid solution with steviol glycoside was measured. A turbidity of each sample acid solution with steviol glycoside was measured in NTU (Nephelometric Turbidity Units) (measured with Turbiscan LA10 Expert, Formulaction S.A.). Each sample acid solution with steviol glycoside was observed for solubility. The solubility results for each sample acid solution with steviol glycoside are shown in Table 23. These experiments showed that some samples of each of mandelic acid, pyromellitic acid, and quinic acid and individual steviol glycosides (Rebaudoside B, Rebaudoside D, and Rebaudoside M) were soluble for one or more days with samples of each of mandelic acid, pyromellitic acid, and quinic acid at a 5:1 or a 2:1 molar ratio of acid to steviol glycoside.

TABLE 23

| Sample | pH | Day 0 | Day 1 | Day 4 |
|---|---|---|---|---|
| Mandelic acid:Reb B 5:1 molar ratio acid 0.06% Reb B | 3.56 | Ppt upon cooling 46.2 NTU | Heavy ppt 814 NTU | Heavy ppt 1045 NTU |
| Mandelic:Reb B 2:1 molar ratio acid 0.06% Reb B | 3.78 | Slight ppt upon cooling 11.5 NTU | Heavy ppt 821 NTU | Heavy ppt 983 NTU |
| Mandelic:Reb D 5:1 molar ratio acid 0.12% Reb D | 3.45 | Clear 1.38 NTU | Slight ppt 1.31 NTU | Ppt 1.45 NTU |
| Mandelic:Reb D 2:1 molar ratio acid 0.12% Reb D | 3.7 | Clear 0.463 NTU | Clear 0.982 | Slight ppt 1.99 NTU |
| Mandelic:Reb M 5:1 molar ratio acid 0.5% Reb M | 3.15 | Clear 1.54 NTU | Ppt 6.48 | Ppt 154 NTU |

TABLE 23-continued

| Sample | pH | Day 0 | Day 1 | Day 4 |
|---|---|---|---|---|
| Mandelic:Reb M 2:1 molar ratio acid 0.5% Reb M | 3.53 | Clear 1.29 NTU | Ppt 3.42 NTU | Ppt 60.4 NTU |
| Pyromellitic:Reb B 5:1 molar ratio acid 0.06% Reb B | 2.77 | Very slight ppt 0.627 NTU | Heavy ppt 917 NTU | Heavy ppt 1011 NTU |
| Pyromellitic:Reb B 2:1 molar ratio acid 0.06% Reb B | 3.07 | Very slight ppt/particles 0.607 NTU | Heavy ppt 778 NTU | Heavy ppt 817 NTU |
| Pyromellitic:Reb D 5:1 molar ratio acid 0.12% Reb D | 2.73 | Clear 0.732 NTU | Clear 1.51 NTU | Clear 2.15 NTU |
| Pyromellitic:Reb D 2:1 molar ratio acid 0.12% Reb D | 3.00 | Clear 0.425 NTU | Clear 0.619 NTU | Clear 0.972 NTU |
| Pyromellitic:Reb M 5:1 molar ratio acid 0.5% Reb M | 2.31 | Clear 0.694 NTU | Ppt 13.0 NTU | Ppt 84.3 NTU |
| Pyromellitic:Reb M 2:1 molar ratio acid 0.5% Reb M | 2.55 | Clear 0.845 NTU | Very slight ppt 3.63 NTU | Ppt 261 NTU |
| Quinic:Reb B 5:1 molar ratio acid 0.06% Reb B | 3.68 | Very slight suspended ppt 2.01 NTU | Heavy ppt 843 NTU | Heavy ppt 842 NTU |
| Quinic:Reb B 2:1 molar ratio acid 0.06% Reb B | 3.94 | Very slight suspended ppt 0.395 NTU | Heavy ppt 838 NTU | Heavy ppt 1033 NTU |
| Quinic:Reb D 5:1 molar ratio acid 0.12% Reb D | 3.70 | Clear 0.528 NTU | Clear 0.782 NTU | Very slight ppt 1.43 NTU |
| Quinic:Reb D 2:1 molar ratio acid 0.12% Reb D | 3.98 | Clear 0.384 NTU | Clear 0.383 NTU | Very slight ppt 0.991 NTU |
| Quinic:Reb M 5:1 molar ratio acid 0.5% Reb M | 3.45 | Clear 1.16 NTU | Ppt 8.79 NTU | Ppt 247 NTU |
| Quinic:Reb M 2:1 molar ratio acid 0.5% Reb M | 3.68 | Clear 1.44 NTU | Ppt 22.4 NTU | Ppt 204 NTU |

Ppt = precipitate

Comparison of Gallic Acid at a 5:1 or a 2:1 Molar Ratio of Gallic Acid to Steviol Glycoside for Each of Rebaudoside B, Rebaudoside D, and Rebaudoside M Samples of gallic acid were prepared with each of Rebaudoside B, Rebaudoside D, and Rebaudoside M to assay for solubility. A stock solution of gallic acid (Sigma Aldrich, 97.5%) was prepared in volumetric flasks at a 0.5% by weight concentration. The Rebaudoside B samples were prepared with a final concentration of 0.06% by weight concentration of Rebaudoside B. The Rebaudoside D samples were prepared with a final concentration of 0.12% by weight concentration of Rebaudoside D. The Rebaudoside M samples were prepared with a final concentration of 0.5% by weight concentration of Rebaudoside M. For each of the Rebaudoside B, Rebaudoside D, and Rebaudoside M samples at each of the 5:1 and 2:1 molar acid to steviol glycoside ratios, the respective gallic acid concentrations are shown in Table 24.

TABLE 24

| Molar ratio (gallic acid:steviol glycoside) | Rebaudoside B (at 0.06% final concentration) | Rebaudoside D (at 0.12% final concentration) | Rebaudoside M (at 0.5% final concentration) |
|---|---|---|---|
| 5:1 | 5.073 mM gallic acid | 7.232 mM gallic acid | 26.349 mM gallic acid |
| 2:1 | 2.029 mM gallic acid | 2.893 mM gallic acid | 10.540 mM gallic acid |

Sample solutions of gallic acid were prepared by adding the stock gallic acid solutions and water to a final volume of 40 mL for 5:1 molar ratios of gallic acid to steviol glycoside and for 2:1 molar ratios of gallic acid to individual steviol glycosides (Rebaudoside B, Rebaudoside D, and Rebaudoside M). After the sample gallic acid solutions were prepared, the respective steviol glycosides (Rebaudoside B, Rebaudoside D, and Rebaudoside M) were added as solid powder to the corresponding sample gallic acid solutions at the corresponding steviol glycoside concentrations (0.06% by weight concentration of Rebaudoside B, 0.12% by weight concentration of Rebaudoside D, 0.5% by weight concentration of Rebaudoside M). The sample solutions with the respective steviol glycoside were stirred for 1 hour, heated to 75° C., and promptly removed to cool to room temperature. A pH of each sample gallic acid solution with steviol glycoside was measured. A turbidity of each sample gallic acid solution with steviol glycoside was measured in NTU (Nephelometric Turbidity Units)(measured with Turbiscan LA10 Expert, Formulaction S.A.). Each sample gallic acid solution with steviol glycoside was observed for solubility. The solubility results for each sample gallic acid solution with steviol glycoside are shown in Table 25. These experiments showed that some samples of gallic acid and individual steviol glycosides (Rebaudoside B, Rebaudoside D, and Rebaudoside M) were soluble for one or more days with gallic acid at a 5:1 or a 2:1 molar ratio of gallic acid to steviol glycoside. These experiments also showed that some samples of gallic acid and Rebaudoside D were soluble for 3 or more days with gallic acid at a 5:1 or a 2:1 molar ratio of gallic acid to steviol glycoside.

TABLE 25

| Sample | pH | Day 0 | Day 1 | Day 2 | Day 3 |
|---|---|---|---|---|---|
| Gallic acid:Reb B 5:1 molar ratio acid 0.06% Reb B | 3.74 | Ppt (fine dust), 1.37 NTU | Heavy ppt, 574 NTU | Heavy ppt, 820 NTU | Heavy ppt, 752 NTU |
| Gallic acid:Reb B 2:1 molar ratio acid 0.06% Reb B | 4.07 | Ppt (fine dust), 1.54 NTU | Heavy ppt, 675 NTU | Heavy ppt, 863 NTU | Heavy ppt, 984 NTU |
| Gallic acid:Reb D 5:1 molar ratio acid 0.12% Reb D | 3.78 | Clear (with a few floaties), 0.584 NTU | Clear, 0.545 NTU | Clear, 0.526 NTU | Clear, 0.654 NTU |
| Gallic acid:Reb D 2:1 molar ratio acid 0.12% Reb D | 4.00 | Clear (with a few floaties), 0.500 NTU | Clear, 0.681 NTU | Clear, 0.824 NTU | Very slight ppt, 1.18 NTU |
| Gallic acid:Reb M 5:1 molar ratio acid 0.5% Reb M | 3.55 | Clear, 1.04 NTU | Clear, 1.13 NTU | Very slight ppt, 2.34 NTU | Ppt, 5.31 NTU |
| Gallic acid:Reb M 2:1 molar ratio acid 0.5% Reb M | 3.85 | Clear, 2.79 NTU | Ppt, 14.0 NTU | Ppt, 30.0 NTU | Ppt, 107 NTU |

Comparison of Gallic Acid at Various Molar Ratios of Gallic Acid to Steviol Glycoside for a Solution of Steviol Glycoside s (about 95% Total Steviol Glycosides with about 75% Reb M and about 5% Reb D)

Samples of gallic acid (Sigma Aldrich, 97.5%) were prepared with steviol glycoside (about 95% total steviol glycosides with about 75% Reb M and about 5% Reb D) to assay for solubility. A stock solution of gallic acid was prepared by volumetric flask at a 0.5% by weight concentration. The steviol glycoside samples were prepared with a final concentration of 0.3% or 0.6% by weight concentrations of a combination of steviol glycoside at molar ratios of 0.5:1 to 7:1 gallic acid to steviol glycoside ratios, the respective gallic acid concentrations are shown in Table 26.

TABLE 26

| Molar ratio (gallic acid:steviol glycoside) | Steviol glycosides (at 0.3% final concentration) | Steviol glycosides (at 0.6% final concentration) |
|---|---|---|
| 7:1 | — | 0.56% gallic acid |
| 5:1 | 0.20% gallic acid | 0.40% gallic acid |
| 2:1 | 0.08% gallic acid | 0.16% gallic acid |
| 1:1 | 0.04% gallic acid | 0.08% gallic acid |
| 0.5:1 | 0.02% gallic acid | 0.04% gallic acid |

Sample solutions of gallic acid were prepared by adding the stock gallic acid solutions and water to a final volume of 40 mL for 7:1, 5:1, 2:1, 1:1, and 0.5:1 molar ratios of gallic acid to steviol glycoside. After the sample gallic acid solutions were prepared, the steviol glycoside was added as solid powder to the corresponding sample gallic acid solutions at 0.3% or 0.6% by weight concentrations of steviol glycoside. The sample solutions were stirred for 1 hour, heated to 75° C., and promptly removed to cool to room temperature. A pH of each sample gallic acid solution with steviol glycoside was measured. A turbidity of each sample gallic acid solution with steviol glycoside was measured in NTU (Nephelometric Turbidity Units)(measured with Turbiscan LA10 Expert, Formulaction S.A.). Each sample gallic acid solution with steviol glycoside was observed for solubility. The solubility results for each sample gallic acid solution with steviol glycoside are shown in Tables 27 and 28.

These experiments showed that samples of gallic acid and steviol glycosides were soluble for 3 or more days with 5:1 or 2:1 molar ratios of gallic acid to steviol glycoside and at 0.3% by weight total concentration of steviol glycoside.

These experiments also showed that samples of gallic acid and steviol glycosides were soluble for 3 or more days with 1:1 or 0.5:1 molar ratios of gallic acid to steviol glycoside and at 0.3% by weight total concentration of steviol glycoside. These experiments also showed that samples of gallic acid and steviol glycosides were soluble for 5 or more days with a 7:1 molar ratio of gallic acid to steviol glycoside at a 0.6% by weight total concentration of steviol glycoside. It was also noted that gallic acid imparted a brownish tinge to the sample solutions that was more apparent at higher concentrations. This brownish tinge was observed after about 3 days.

TABLE 27

| Sample | pH | Day 0 | Day 1 | Day 2 | Day 3 |
|---|---|---|---|---|---|
| Gallic acid:SG 5:1 molar ratio acid 0.3% SG | 3.53 | Clear 1.16 NTU | Clear 1.24 NTU | Clear 1.26 NTU | Clear 1.56 NTU |
| Gallic acid:SG 2:1 molar ratio acid 0.3% SG | 3.88 | Clear 0.796 NTU | Clear 1.19 NTU | Clear 1.49 NTU | Very slight ppt 3.38 NTU |
| Gallic acid:SG 5:1 molar ratio acid 0.6% SG | 3.61 | Clear 2.85 NTU | Very slight ppt 3.46 NTU | Clear 3.50 NTU | Ppt 6.36 NTU |
| Gallic acid:SG 2:1 molar ratio acid 0.6% SG | 3.83 | Clear 2.37 NTU | Slight ppt 3.07 NTU | Slight ppt 6.00 NTU | Ppt 58.9 NTU |

SG = steviol glycoside
Ppt = precipitate

TABLE 28

| Sample | Day 0 | Day 3 | Day 4 | Day 5 |
|---|---|---|---|---|
| Gallic acid:SG 1:1 molar ratio acid 0.3% SG | Clear 0.846 NTU | Clear | Clear | Clear 0.882 NTU |
| Gallic acid:SG 0.5:1 molar ratio acid 0.3% SG | Clear 1.16 NTU | Clear | Clear | Clear 1.28 NTU |
| Gallic acid:SG 7:1 molar ratio acid 0.6% SG | Clear 2.33 NTU | Clear | Clear | Clear 1.60 NTU |

SG = steviol glycoside
Ppt = precipitate

Comparison of Solubilities of Samples Comprising Mandelic Acid, Pyromellitic Acid, Quinic Acid, and Gallic Acid and Steviol Glycoside (about 95% Total Steviol Glycosides with about 75% Reb M and about 5% Reb D) in Citrate Buffer Samples of mandelic acid, pyromellitic acid, quinic acid, and gallic acid were prepared with steviol glycoside (about 95% total steviol glycosides with about 75% Reb M and about 5% Reb D) to assay for solubility. The samples were prepared in a citrate buffer (50 mM, pH 3, with 0.009% sodium benzoate) and comprised either 0.3% steviol glycoside, 0.6% steviol glycoside, 0.06% Rebaudoside B, 0.12% Rebaudoside D, and 0.5% Rebaudoside M and either mandelic acid, pyromellitic acid, quinic acid, gallic acid, or no acid. The sample solutions were stirred for 1 h, heated to 75° C., and promptly removed to cool to room temperature. A turbidity of each sample solution with steviol glycoside was measured in NTU (Nephelometric Turbidity Units)(measured with Turbiscan LA10 Expert, Formulaction S.A.). Each sample solution with steviol glycoside was observed for solubility. The solubility results for each sample solution with steviol glycoside is shown in Table 29.

TABLE 29

| Sample | Day 0 | Day 1 | Day 2 | Day 3 |
| --- | --- | --- | --- | --- |
| 0.3% SG and No acid | Clear | Clear | Clear | Very slight ppt |
| 0.3% SG and mandelic acid | Clear | Clear | Clear | Ppt |
| 0.3% SG and pyromellitic acid | Clear | Clear | Clear | Very slight ppt |
| 0.3% SG and quinic acid | Clear | Clear | Very slight ppt | Ppt |
| 0.3% SG and gallic acid | Clear | Clear | Very slight ppt | Ppt |
| 0.6% SG and No acid | Clear | Clear | Ppt | Ppt |
| 0.6% SG and Mandelic acid | Clear | Ppt | Ppt | Ppt |
| 0.6% SG and Pyromellitic acid | Clear | Very slight ppt | Ppt | Ppt |
| 0.6% SG and quinic acid | Clear | Ppt | Ppt | Ppt |
| 0.6% SG and gallic acid | Clear | Ppt | Ppt | Ppt |
| 0.06% Reb B and no acid | Ppt | Ppt | Ppt | Ppt |
| 0.06% Reb B and Mandelic acid | Ppt | Ppt | Ppt | Ppt |
| 0.06% Reb B and Pyromellitic acid | Ppt | Ppt | Ppt | Ppt |
| 0.06% Reb B and Quinic acid | Ppt | Ppt | Ppt | Ppt |
| 0.06% Reb B and Gallic acid | Ppt | Ppt | Ppt | Ppt |
| 0.12% Reb D and no acid | Clear | Clear | Ppt | Ppt |
| 0.12% Reb D and Mandelic acid | Clear | Clear | Very slight ppt | Ppt |
| 0.12% Reb D and Pyromellitic acid | Clear | Clear | Very slight ppt | Ppt |
| 0.12% Reb D and Quinic acid | Clear | Clear | Slight ppt | Ppt |
| 0.12% Reb D and Gallic acid | Clear | Clear | Ppt | Ppt |
| 0.5% Reb M and no acid | Clear | Clear | Ppt | Ppt |
| 0.5% Reb M and Mandelic acid | Clear | Ppt | Ppt | Ppt |
| 0.5% Reb M and Pyromellitic acid | Clear | Clear | Ppt | Ppt |
| 0.5% Reb M and Quinic acid | Clear | Clear | Ppt | Ppt |
| 0.5% Reb M and Gallic acid | Clear | Clear | Ppt | Ppt |
| 0.3% SG and No Acid No Heating Stirred Overnight | Cloudy | Cloudy | — | — |
| 0.3% SG and Mandelic acid No Heating Stirred Overnight | Cloudy | Cloudy | — | — |
| 0.3% SG and Pyromellitic acid No Heating Stirred Overnight | Cloudy | Cloudy | — | — |
| 0.3% SG and Quinic acid No Heating Stirred Overnight | Cloudy | Cloudy | — | — |
| 0.3% SG and Gallic acid No Heating Stirred Overnight | Cloudy | Cloudy | — | — |

SG = steviol glycoside
Ppt = precipitate

Example J. Sensory Evaluation of Several Solubility Enhancers with Steviol Glycoside A sensory evaluation of solutions of several steviol solubility enhancers with steviol glycoside was carried out. Test solutions were prepared of steviol glycoside (>80% Reb M, >10% Reb D, <1% Reb A, <1% Reb B) and various steviol solubility enhancers at various ratios of steviol solubility enhancers to steviol glycoside. The test solutions comprised a total steviol glycoside concentration of either about 300 ppm or about 120 ppm and a steviol solubility enhancer to steviol glycoside ratio of about 0.4:1 or about 1:1 by weight. A panel of three tasters then tasted the solutions to determine a sensory profile which included attributes such as sweetness, sweetness linger, astringency, metallic taste, rough mouth feeling, and bitterness. The panel also tasted control solutions of only steviol solubility enhancers. The panel also tasted control solutions of only steviol glycoside. The panel then reported a sensory profile for each test solution as compared to the control solutions. The sensory profile results are shown in Table 30. These experiments showed that solutions of solubility enhancers and steviol glycoside had similar sensory profiles compared to solutions of steviol glycoside alone. These experiments also showed that solutions of solubility enhancers and steviol glycoside may have improved sensory profiles compared to solutions of steviol glycoside alone.

TABLE 30

| Solubility Enhancer | Ratio of Solubility Enhancer:Steviol glycoside by weight | Concentration of Solubility Enhancer | Concentration of Steviol glycoside | Sensory profile |
|---|---|---|---|---|
| Cynarin* | 0.4:1 | about 120 ppm | about 300 ppm | Not tasted, mixture did not go into solution |
| Cynarin* | 1:1 | about 300 ppm | about 300 ppm | Similar sweetness as steviol glycoside control, similar to melon flavor in Life Saver flavor in the tropical pack, less sweetness linger than steviol glycoside control |
| Cynarin isomers* control | — | about 300 ppm | — | Not tasted, mixture did not go into solution |
| Chlorogenic acid and cynarin isomers** | 0.4:1 | about 120 ppm | about 300 ppm | Similar sweetness to steviol glycoside control, very similar sensory profile to steviol glycoside control |
| Chlorogenic acid and cynarin isomers** | 1:1 | about 300 ppm | about 300 ppm | Sweetness lingers less than steviol glycoside control, did not get the astringency, metallic taste, or rough feeling as in the chlorogenic acid and cynarin** control |
| Chlorogenic acid and cynarin isomers control** | — | about 300 ppm | — | Faint metallic taste, astringent taste, rough feeling in mouth |
| Chlorogenic acid and cynarin isomers*** | 0.4:1 | about 120 ppm | about 300 ppm | Similar sweetness as steviol glycoside control, Not nearly as sugar like as the 1:1 ratio |

TABLE 30-continued

| Solubility Enhancer | Ratio of Solubility Enhancer:Steviol glycoside by weight | Concentration of Solubility Enhancer | Concentration of Steviol glycoside | Sensory profile |
|---|---|---|---|---|
| Chlorogenic acid and cynarin isomers*** | 1:1 | about 300 ppm | about 300 ppm | Similar sweetness as steviol glycoside control, Tastes very similar to sugar character, slight reduction in sweetness linger |
| Chlorogenic acid and cynarin isomers control*** | — | about 300 ppm | — | Slightly bitter taste or metallic taste, depended on panelist |
| Steviol glycoside control | — | — | about 300 ppm | typical steviol glycoside sensory profile |

*Derived from *stevia* leaf and isolated in acid form. The acid form was not very water soluble.
**Derived from *stevia* leaf and isolated in calcium salt form.
***Derived from artichoke stem and isolated in sodium salt form.

Example K. Solubility Tests of Solubility Enhancers with Steviol Glycoside

Figure 4:
FIG. 4. Image of stable solutions of EverSweet and Reb B in chlorogenic acid. The three solutions on the left are at equal concentration of SG and CGA (about 4 weeks old). The four solutions on the right are at equal molar concentration (about 3:1 concentration ratio, about 1 week old, except the 0.3% (wt) OPS (internal naming for EverSweet) that is about 5 weeks old). In this scenario (equal molar concentration), the higher concentration solutions start to crystallize after a few days (>1% (wt) OPS). CGA isomers are needed to solubilize Reb B completely and for a long duration.

Stable solutions of EverSweet and Reb B in chlorogenic acid were prepared. Three solutions of equal concentration of SG (5% Reb B, 5% Eversweet, and 5% Eversweet with 1.75% Reb B) and CGA by weight were prepared and remained solubilized over about 4 weeks old. Four solutions (3% Eversweet, 1.5% Eversweet, 0.75% Eversweet, and 0.3% Eversweet) were prepared at equal molar concentration (about 3:1 by weight concentration ratio) and remained solubilized over about 1 week old (except the 0.3% (wt) OPS (internal naming for EverSweet) that is about 5 weeks old). In this scenario (equal molar concentration), the higher concentration solutions start to crystallize after a few days (>1% (wt) OPS). CGA isomers are needed to solubilize Reb B completely and for a long duration. The solutions are shown in FIG. 4.

Figure 5:
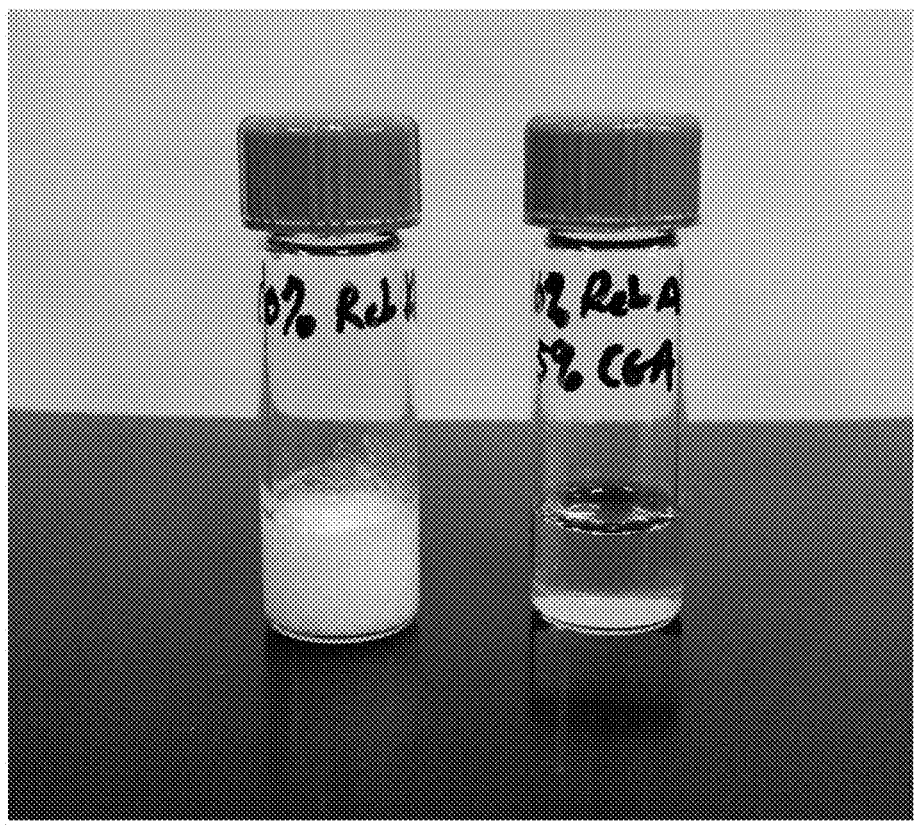
FIG. 5. Image of stable solution of leaf-based 10% (wt) Reb A in chlorogenic acid compared to 10% (wt) Reb A in water only solution. The Reb A alone clearly precipitates quickly out of solution, while the CGA containing solution is stable for greater than two months.

Solutions of leaf-based 10% (wt) Reb A in chlorogenic acid and 10% (wt) Reb A in water only solution were prepared and compared. The Reb A alone solution clearly precipitates quickly out of solution, while the CGA containing solution is stable for greater than two months. FIG. 5 shows the solutions. After 78 days at room temperature, the RebA with CGA solution remained solubilized.

Figure 6:
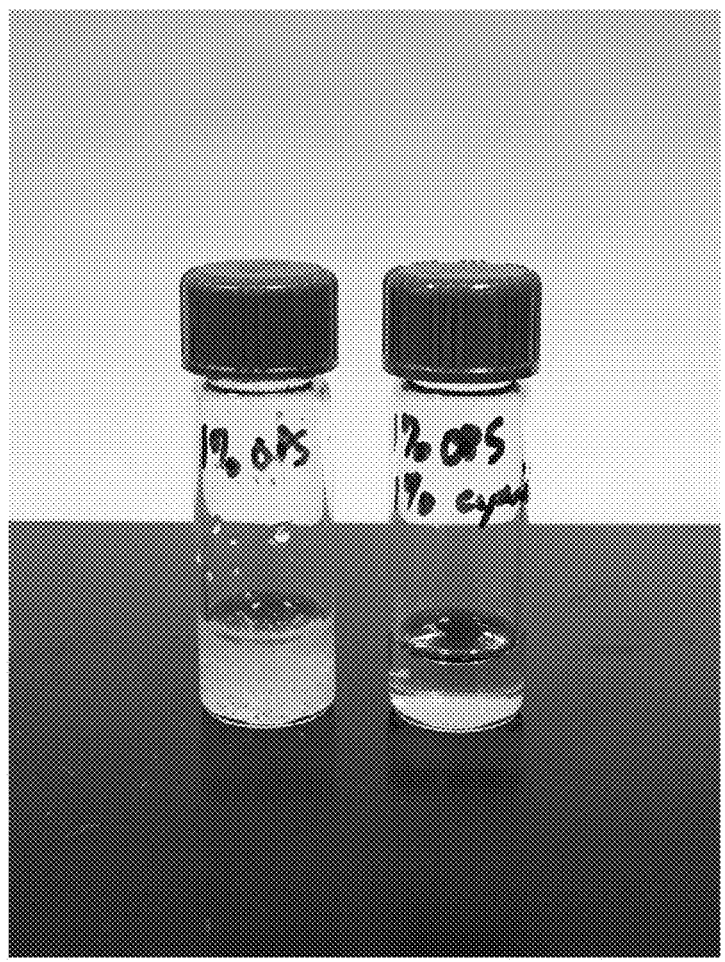
FIG. 6. Image of stable solution of EverSweet in 3,5-dicaffeoylquinic acid (cynarin isomer) compared to an EverSweet in water only solution. The EverSweet clearly precipitates quickly out of solution, while the cynarin isomer solution is stable.

Solutions of EverSweet in 3,5-dicaffeoylquinic acid (cynarin isomer) were prepared and compared to an EverSweet in water only solution. The EverSweet alone solution clearly precipitates quickly out of solution, while the EverSweet with cynarin isomer solution is stable. FIG. 6 shows the solutions.

Figure 7:
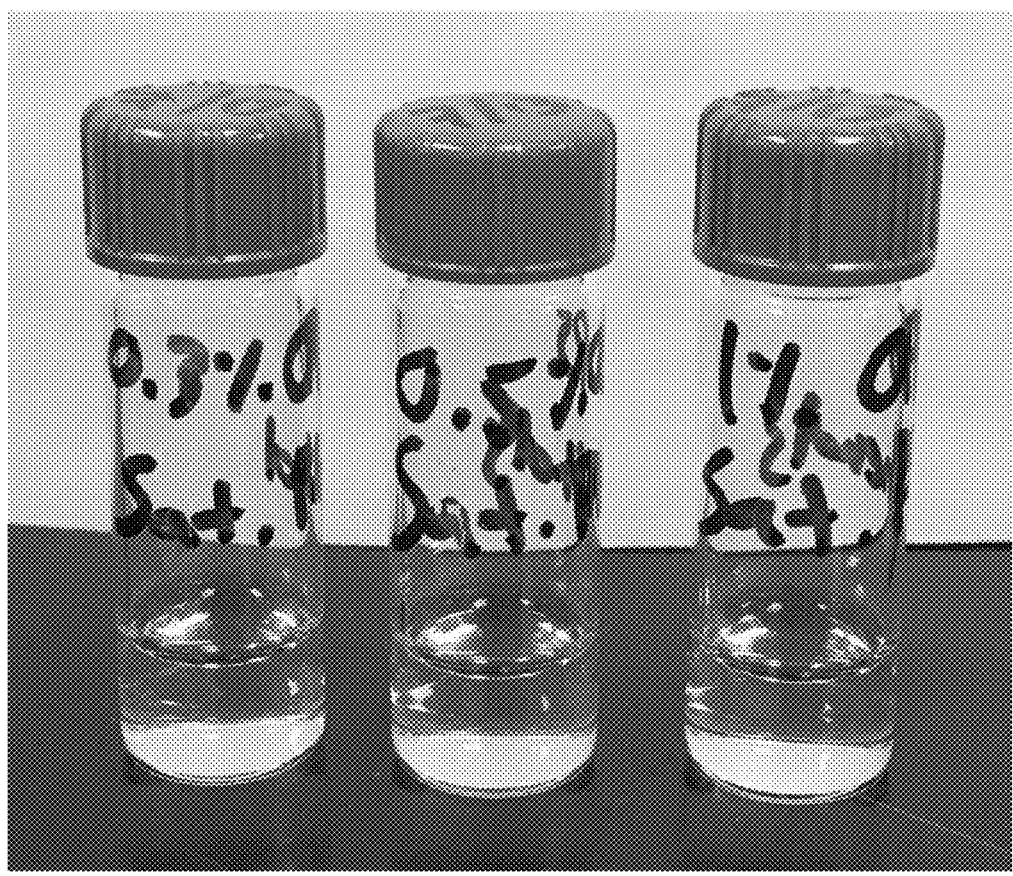
FIG. 7. Image of stable solution of EverSweet in hydroxycinnamic acid mixture (caffeic, coumaric, and ferulic acids near their respective saturation points in water at room temperature). Solutions of 0.3% (wt), 0.5% (wt), and 1% (wt) are stable for >1 week.

Solution of EverSweet (0.3% (wt), 0.5% (wt), and 1% (wt)) in hydroxycinnamic acid mixture (caffeic, coumaric, and ferulic acids at concentrations near their respective saturation points in water at room temperature) were prepared and compared. The solutions of 0.3% (wt), 0.5% (wt), and 1% (wt) EverSweet with hydroxycynamic acid mixture are stable for >1 week. FIG. 7 shows the solutions.

Figure 8:
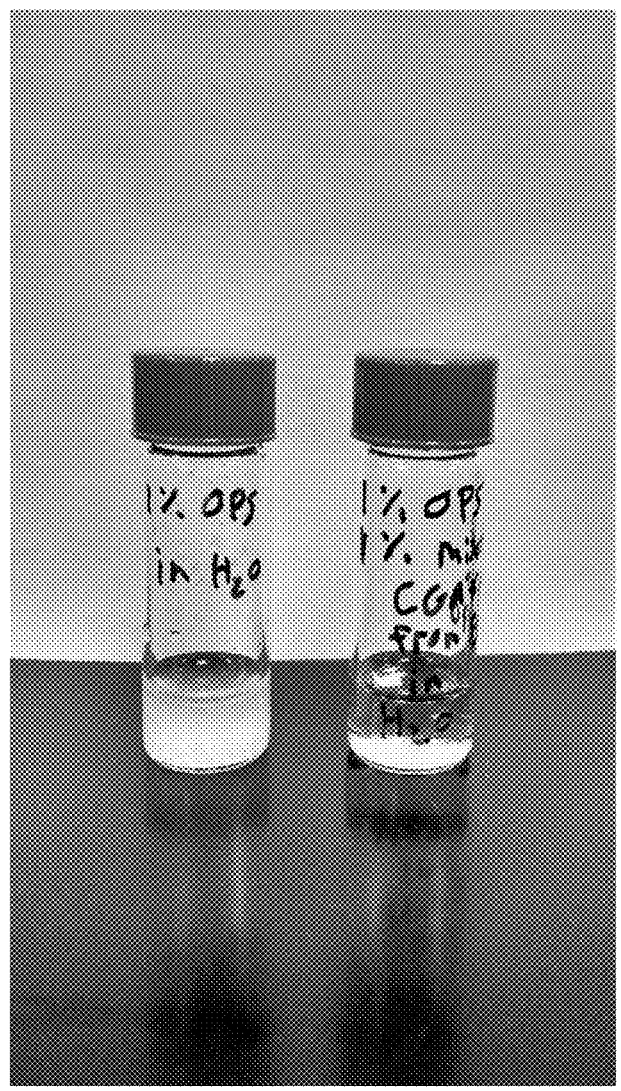
FIG. 8. Image of stable solution of 1% DS ((wt)) EverSweet in a mixture of chlorogenic acids and cynarin isomers with other minor components extracted from *stevia* leaf (right). The solution on the left is the same concentration (1% DS) of EverSweet in water without solubility enhancers.

Solutions of 1% (wt) EverSweet in a mixture of chlorogenic acids and cynarin isomers with other minor components extracted from *stevia* leaf was prepared and remained solubilized. A solution of 1% DS of EverSweet in water without solubility enhancers was prepared and did not solubilize. FIG. 8 shows the solutions.

Figure 9:
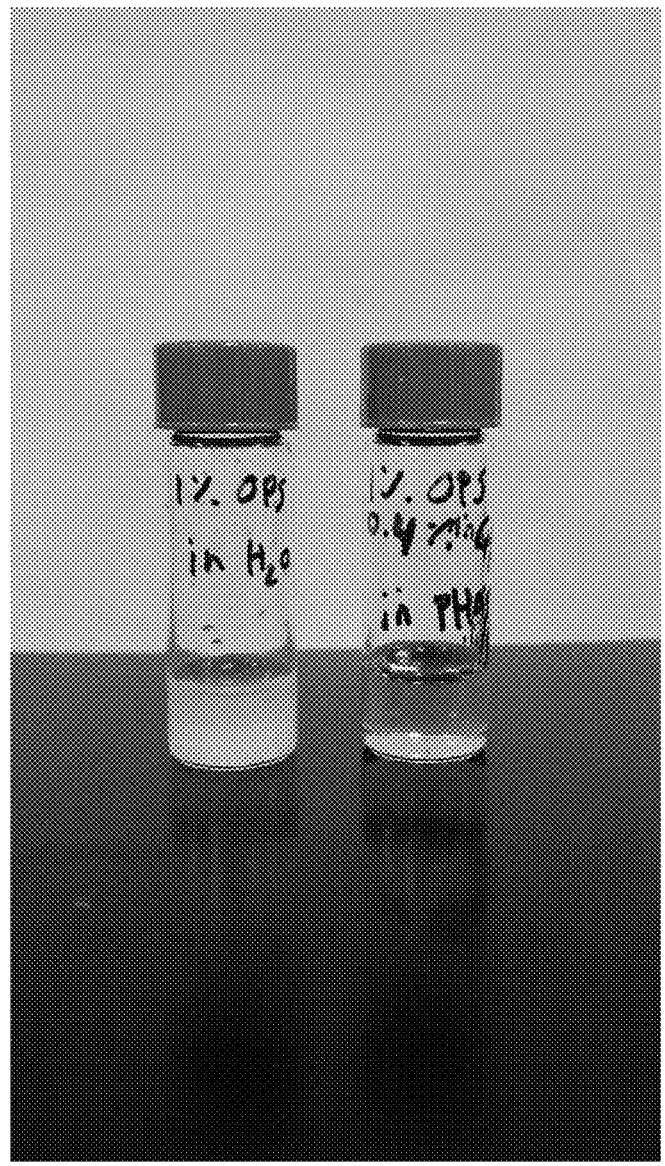
FIG. 9. Image of stable solution of EverSweet in solution with purified cynarin and its isomers (right) compared to an EverSweet in water only solution (left). A mixture of 1% (wt) OPS and 0.4% cynarin isomers yields a molar ratio of 1:0.91 glycosides:cynarin isomers. This solution was prepared in a phosphate-citrate buffer at pH 2.5-3 to more closely replicate applications in the soft drink industry.

Solutions of EverSweet in solution with purified cynarin and its isomers was prepared and compared to an EverSweet in water only solution. The EverSweet in solution with purified cynarin and its isomers remained solubilized. The EverSweet in water only solution did not solubilize. A mixture of 1% (wt) OPS and 0.4% cynarin isomers yields a molar ratio of 1:0.91 glycosides:cynarin isomers. This solution was prepared in a phosphate-citrate buffer at pH 2.5-3 to more closely replicate applications in the soft drink industry. FIG. 9 shows the solutions.

Solution of 1% EverSweet in solution with 1% purified cynarin isomers adjusted to pH 4 with sodium hydroxide was prepared and observed. The solutions remained solubilized but demonstrated a yellow-brownish color. Dilution of this solution to 300 ppm results in an application-level product that has no visible color. FIG. 10 shows the solutions.

Solution of 1% (wt) TS300 (leaf-based SGs, containing 30% Reb B in its acid form) was prepared and remained solubilized in solution for two days with 1% purified cynarin isomers adjusted to pH 4 with sodium hydroxide. A solution of 1% (wt) TS300 in water without solubility enhancers was prepared and did not go into solution. FIG. 11 shows the solutions.

Figure 15:
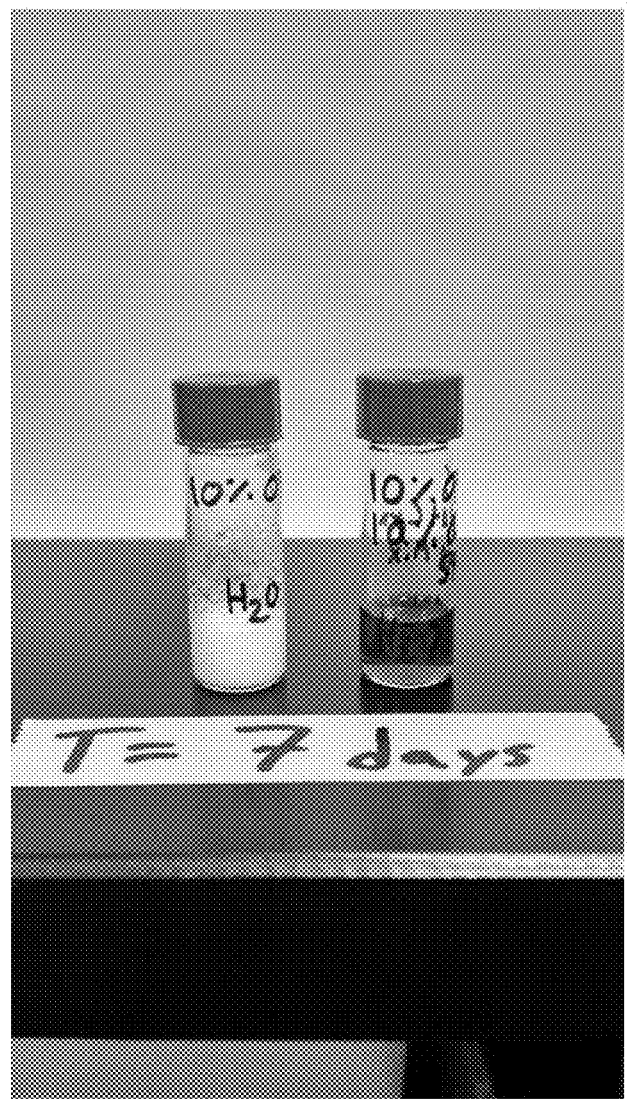
FIG. 15. Image of stable solution of 10% EverSweet in solution with 10% purified cynarin isomers (3,4- and 3,5-dicaffeoylquinic acids) and chlorogenic acid isomers in solution for 7 days (right). 10% EverSweet in water alone will solidify in less than 2 hours (left).

A solution of 10% EverSweet in solution with 10% purified cynarin isomers (3,4- and 3,5-dicaffeoylquinic acids) and chlorogenic acid isomers was prepared and remained solubilized in solution for 7 days. A 10% Ever- Sweet in water alone was prepared and solidified in less than 2 hours. FIG. 15 shows the solutions.

Figure 16:
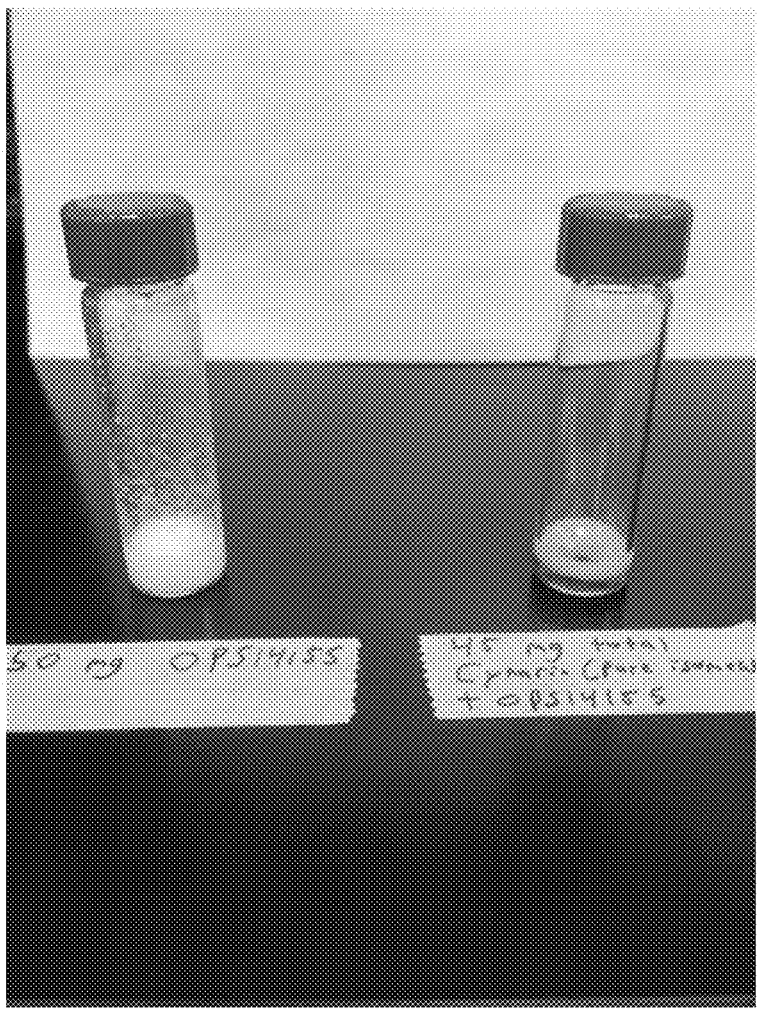
FIG. 16. Image demonstrating instantaneous solubility of 5% EverSweet (OPS1415S) co-dried with 5% purified cynarin isomers (3,4- and 3,5-dicaffeoylquinic acid) versus EverSweet alone (left). Room temperature water was added to each of the solid powders, and the vials were capped and shaken by hand for approximately 10 seconds. Image was taken immediately after shaking, and the solution (right) remained clear for >2 weeks (ongoing experiment).

A solution was prepared to show instantaneous solubility of 5% EverSweet (OPS1415S) co-dried with 5% purified cynarin isomers (3,4- and 3,5-dicaffeoylquinic acid) versus a similar solution of EverSweet alone. Room temperature water was added to each of the solid powders, and the vials were capped and shaken by hand for approximately 10 seconds. The first solution remained solubilized for >2 weeks. The second solution did not go into solution. FIG. 16 shows the solutions.

Figure 17A:
FIGS. 17A and 17B. Images demonstrating solubility of 30% (wt) EverSweet in 30% steviol glycoside solubility enhancers. The solution was adjusted to pH 2. After five days of room temperature storage the solution appeared free of turbidity and was free-flowing.
Figure 17B:
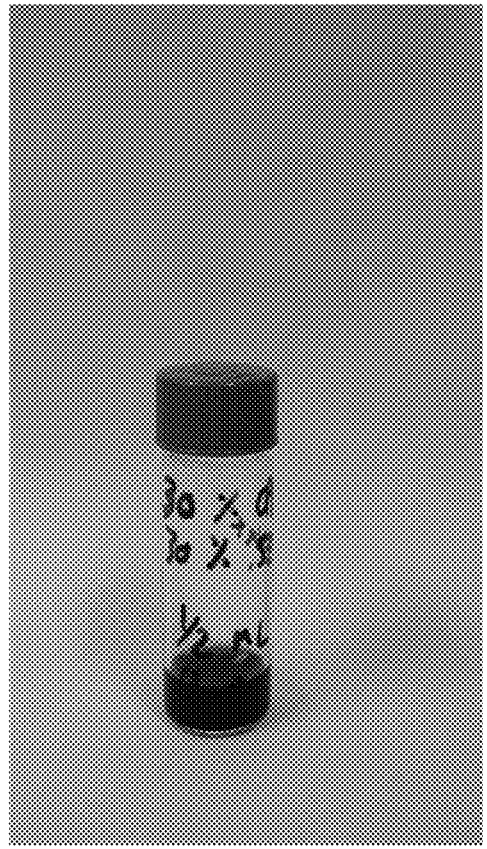

A solution was prepared to show solubility of 30% (wt) EverSweet in 30% steviol glycoside solubility enhancers. The solution was adjusted to pH 2. After five days of room temperature storage the solution appeared free of turbidity and was free-flowing. FIG. 17 shows the solution.

Example K. Long Term Solubility Tests of Solubility Enhancers with Steviol Glycoside Samples were prepared via the design shown in Table 31, in weight to volume percentage. An appropriate amount of steviol glycoside (SG) was weighed into a 10 mL glass vial and diluted with an appropriate volume of pH 4 citrate buffer, e.g., for 0.6% level, 27 mg was diluted into 4.5 mL of buffer. This was repeated for all conditions in Table 1. Samples that were designed for pH 2.5 were then adjusted via phosphoric acid and pH meter to pH 2.5, dropwise. For these samples, the same lot of SE was used, which was purified from *stevia* leaves. Two different SG sources were used, RM80 (>80% Reb M on a dry weight basis) and RA95 (>95% Reb A on a dry weight basis).

At each time point, the solutions were centrifuged at 10,000 rpm for two minutes to remove any insoluble material from the analysis (even though none was visible). An aliquot of the supernatant was diluted into 55% methanol for analysis by UHPLC-UV. The chromatographic analysis was performed on a C18-based reversed-phase chromatography column at elevated temperature under gradient conditions, utilizing trifluoroacetic acid in water and acetonitrile. SGs were detected utilizing a UV detector set to 210 nm. A linear calibration curve was applied using a high-purity (>99%) Reb A standard as a reference solution.

TABLE 31

| SG % | SG Type | SE % | Storage Cond | pH | Times (weeks) | # of Pulls | # of Replicates |
|---|---|---|---|---|---|---|---|
| 0.6% | RM80 | 0.6% | RT | 2.5 | 0, 14, 26, 52 | 4 | 3 |
| 1.5% | RM80 | 1.5% | RT | 2.5 | 0, 4, 14, 26, 39, 52 | 6 | 1 |
| 3.0% | RM80 | 3.0% | RT | 2.5 | 0, 4, 14, 26, 39, 52 | 6 | 3 |
| 3.0% | RM80 | 4.5% | RT | 2.5 | 0, 4, 14, 26, 39, 52 | 6 | 3 |
| 6.0% | RM80 | 6.0% | RT | 2.5 | 0, 4, 14, 26, 39, 52 | 6 | 1 |
| 6.0% | RA95 | 6.0% | RT | 2.5 | 0, 4, 14, 26, 39, 52 | 6 | 3 |
| 0.6% | RM80 | 0.6% | 4 C. | 2.5 | 14, 26, 52 | 3 | 1 |
| 1.5% | RM80 | 1.5% | 4 C. | 2.5 | 4, 14, 26, 39, 52 | 5 | 3 |
| 3.0% | RM80 | 3.0% | 4 C. | 2.5 | 4, 14, 26, 39, 52 | 5 | 1 |
| 3.0% | RM80 | 4.5% | 4 C. | 2.5 | 4, 14, 26, 39, 52 | 5 | 1 |
| 6.0% | RM80 | 6.0% | 4 C. | 2.5 | 4, 14, 26, 39, 52 | 5 | 3 |
| 6.0% | RA95 | 6.0% | 4 C. | 2.5 | 4, 14, 26, 39, 52 | 5 | 1 |
| 0.6% | RM80 | 0.6% | RT | 4.0 | 0, 14, 26, 52 | 4 | 3 |
| 1.5% | RM80 | 1.5% | RT | 4.0 | 0, 4, 14, 26, 39, 52 | 6 | 1 |
| 3.0% | RM80 | 3.0% | RT | 4.0 | 0, 4, 14, 26, 39, 52 | 6 | 3 |
| 3.0% | RM80 | 4.5% | RT | 4.0 | 0, 4, 14, 26, 39, 52 | 6 | 3 |
| 6.0% | RM80 | 6.0% | RT | 4.0 | 0, 4, 14, 26, 39, 52 | 6 | 1 |
| 35.0% | RM80 | 35.0% | RT | 4.0 | 0, 26, 40, 52 | 4 | 1 |
| 6.0% | RA95 | 6.0% | RT | 4.0 | 0, 4, 14, 26, 39, 52 | 6 | 3 |
| 0.6% | RM80 | 0.6% | 4 C. | 4.0 | 14, 26, 52 | 3 | 1 |
| 1.5% | RM80 | 1.5% | 4 C. | 4.0 | 4, 14, 26, 39, 52 | 5 | 3 |
| 3.0% | RM80 | 3.0% | 4 C. | 4.0 | 4, 14, 26, 39, 52 | 5 | 1 |
| 3.0% | RM80 | 4.5% | 4 C. | 4.0 | 4, 14, 26, 39, 52 | 5 | 1 |
| 6.0% | RM80 | 6.0% | 4 C. | 4.0 | 4, 14, 26, 39, 52 | 5 | 3 |
| 6.0% | RA95 | 6.0% | 4 C. | 4.0 | 4, 14, 26, 39, 52 | 5 | 1 |

Briefly, this long term storage solubility study showed that SG solutions with SE that were stored at 4° C.; room temperature (~22° C.); at pH 4; and at pH 2.5 demonstrated >94% recovery of the SG after 48+ weeks of storage. The long term solubility data is given in Table 32. A value of NM denotes that no measurement was taken at that time.

TABLE 32a

| Experiment | | Time (weeks) | | | | | |
|---|---|---|---|---|---|---|---|
| | | 0 | 4 | 14 | 26 | 39 | 40 | 48 |
| 6% RA95 with 6% SE at 4 C. and pH 2.5 | Reb A % Recovery | 100.0 | 99.5 | 98.3 | 98.3 | 98.6 | NM | 98.5 |
| 6% RA95 with 6% SE at 4 C. and pH 4 | Reb A % Recovery | 100.0 | 98.8 | 99.1 | 98.0 | 98.7 | NM | 98.6 |

TABLE 32a-continued

| Experiment | | Time (weeks) | | | | | | |
|---|---|---|---|---|---|---|---|---|
| | | 0 | 4 | 14 | 26 | 39 | 40 | 48 |
| 6% RA95 with 6% SE at RT and pH 2.5 | Reb A % Recovery | 100.0 | 99.5 | 98.6 | 98.2 | 98.0 | NM | 97.8 |
| 6% RA95 with 6% SE at RT and pH 4 | Reb A % Recovery | 100.0 | 99.4 | 98.4 | 98.4 | 98.3 | NM | 98.3 |
| 0.6% RM80 with 0.6% SE at 4 C. and pH 2.5 | Reb M % Recovery | 100.0 | NM | 102.4 | 102.4 | NM | NM | 98.0 |
| 0.6% RM80 with 0.6% SE at 4 C. and pH 4 | Reb M % Recovery | 100.0 | NM | 102.8 | 102.6 | NM | NM | 99.0 |
| 0.6% RM80 with 0.6% SE at RT and pH 2.5 | Reb M % Recovery | 100.0 | NM | 101.1 | 100.2 | NM | NM | 96.0 |
| 0.6% RM80 with 0.6% SE at RT and pH 4 | Reb M % Recovery | 100.0 | NM | 101.7 | 101.5 | NM | NM | 99.2 |
| 1.5% RM80 with 1.5% SE at 4 C. and pH 2.5 | Reb M % Recovery | 100.0 | 102.6 | 102.6 | 102.5 | 98.5 | NM | 97.9 |
| 1.5% RM80 with 1.5% SE at 4 C. and pH 4 | Reb M % Recovery | 100.0 | 102.7 | 102.5 | 102.9 | 98.8 | NM | 98.7 |
| 1.5% RM80 with 1.5% SE at RT and pH 2.5 | Reb M % Recovery | 100.0 | 101.8 | 100.8 | 98.6 | 97.3 | NM | 95.3 |
| 1.5% RM80 with 1.5% SE at RT and pH 4 | Reb M % Recovery | 100.0 | 102.1 | 101.5 | 101.8 | 99.2 | NM | 98.3 |
| 3% RM80 with 3% SE at 4 C. and pH 2.5 | Reb M % Recovery | 100.0 | 102.5 | 102.2 | 102.1 | 98.5 | NM | 97.9 |
| 3% RM80 with 3% SE at 4 C. and pH 4 | Reb M % Recovery | 100.0 | 102.6 | 102.1 | 102.5 | 98.9 | NM | 98.5 |
| 3% RM80 with 3% SE at RT and pH 2.5 | Reb M % Recovery | 100.0 | 101.8 | 101.0 | 99.8 | 95.9 | NM | 95.0 |
| 3% RM80 with 3% SE at RT and pH 4 | Reb M % Recovery | 100.0 | 102.0 | 101.6 | 101.2 | 98.2 | NM | 97.7 |
| 3% RM80 with 4.5% SE at 4 C. and pH 2.5 | Reb M % Recovery | 100.0 | 103.5 | 103.4 | 103.3 | 98.3 | NM | 96.7 |
| 3% RM80 with 4.5% SE at 4 C. and pH 4 | Reb M % Recovery | 100.0 | 103.4 | 102.8 | 103.6 | 97.4 | NM | 97.7 |
| 3% RM80 with 4.5% SE at RT and pH 2.5 | Reb M % Recovery | 100.0 | 102.7 | 101.5 | 100.6 | 96.2 | NM | 94.0 |

TABLE 32a-continued

| Experiment | | 0 | 4 | 14 | 26 | 39 | 40 | 48 |
|---|---|---|---|---|---|---|---|---|
| 3% RM80 with 4.5% SE at RT and pH 4 | Reb M % Recovery | 100.0 | 103.4 | 102.3 | 102.2 | 98.0 | NM | 97.7 |
| 6% RM80 with 6% SE at 4 C. and pH 2.5 | Reb M % Recovery | 100.0 | 102.0 | 102.0 | 101.8 | 97.9 | NM | 97.4 |
| 6% RM80 with 6% SE at 4 C. and pH 4 | Reb M % Recovery | 100.0 | 102.0 | 101.6 | 102.2 | 98.3 | NM | 97.7 |
| 6% RM80 with 6% SE at RT and pH 2.5 | Reb M % Recovery | 100.0 | 101.6 | 100.7 | 99.5 | 95.0 | NM | 94.1 |
| 6% RM80 with 6% SE at RT and pH 4 | Reb M % Recovery | 100.0 | 101.6 | 101.2 | 100.8 | 97.2 | NM | 96.7 |
| 35% RM80 with 35% SE at RT and pH 4 | Reb M % Recovery | 100.0 | NM | NM | 99.5 | NM | 95.9 | 96.2 |

The long term storage chemical stability data is given in Table 32b. The same samples were also assessed for absolute concentration of the dissolved steviol glycosides. The data presented in Table 32b shows the concentration of steviol glycosides at each time point. In some of the vials, there was some evaporation of the solvent during the year-long experiment. Thus the concentration increased in most samples over time, but no crystals were observed at any time in any sample. A value of NM denotes that no measurement was taken at that time.

TABLE 32b

| Experiment | | 0 | 4 | 14 | 26 | 39 | 40 | 48 |
|---|---|---|---|---|---|---|---|---|
| 6% RA95 with 6% SEs at 4 C. and pH 2.5 | Reb A (g/L) | 5.69 | 8.57 | 5.37 | 6.18 | 7.76 | NM | 8.44 |
| 6% RA95 with 6% SEs at 4 C. and pH 4 | Reb A (g/L) | 5.21 | 5.39 | 5.13 | 5.63 | 6.45 | NM | 7.06 |
| 6% RA95 with 6% SEs at RT and pH 2.5 | Reb A (g/L) | 5.69 | 5.35 | 5.63 | 6.99 | 8.44 | NM | 7.87 |
| 6% RA95 with 6% SEs at RT and pH 4 | Reb A (g/L) | 5.21 | 5.15 | 5.78 | 6.06 | 7.21 | NM | 7.41 |
| 0.6% RM80 with 0.6% SEs at 4 C. and pH 2.5 | Reb M (g/L) | 0.45 | NM | 0.44 | 0.44 | NM | NM | 0.55 |
| 0.6% RM80 with 0.6% SEs at 4 C. and pH 4 | Reb M (g/L) | 0.45 | NM | 0.48 | 0.55 | NM | NM | 0.53 |
| 0.6% RM80 with 0.6% SEs at RT and pH 2.5 | Reb M (g/L) | 0.45 | NM | 0.45 | 0.47 | NM | NM | 0.57 |
| 0.6% RM80 with 0.6% SEs at RT and pH 4 | Reb M (g/L) | 0.45 | NM | 0.49 | 0.54 | NM | NM | 0.77 |
| 1.5% RM80 with 1.5% SEs at 4 C. and pH 2.5 | Reb M (g/L) | 1.09 | 0.99 | 1.07 | 1.06 | 1.26 | NM | 1.19 |
| 1.5% RM80 with 1.5% SEs at 4 C. and pH 4 | Reb M (g/L) | 1.10 | 1.06 | 1.12 | 1.21 | 1.53 | NM | 1.41 |

TABLE 32b-continued

| Experiment | | 0 | 4 | 14 | 26 | 39 | 40 | 48 |
|---|---|---|---|---|---|---|---|---|
| 1.5% RM80 with 1.5% SEs at RT and pH 2.5 | Reb M (g/L) | 1.09 | 1.01 | 1.05 | NM | 1.28 | NM | 1.33 |
| 1.5% RM80 with 1.5% SEs at RT and pH 4 | Reb M (g/L) | 1.10 | 1.08 | 1.17 | 1.43 | 1.69 | NM | 1.81 |
| 3% RM80 with 3% SEs at 4 C. and pH 2.5 | Reb M (g/L) | 2.11 | 1.99 | 2.08 | NM | 2.71 | NM | 2.45 |
| 3% RM80 with 3% SEs at 4 C. and pH 4 | Reb M (g/L) | 2.06 | 1.99 | 2.09 | 2.18 | 2.64 | NM | 2.44 |
| 3% RM80 with 3% SEs at RT and pH 2.5 | Reb M (g/L) | 2.11 | 1.97 | 1.90 | 2.17 | 2.59 | NM | 2.67 |
| 3% RM80 with 3% SEs at RT and pH 4 | Reb M (g/L) | 2.06 | 1.98 | 2.18 | 2.50 | 2.86 | NM | 2.96 |
| 3% RM80 with 4.5% SEs at 4 C. and pH 2.5 | Reb M (g/L) | 2.05 | 2.74 | 2.01 | 2.11 | 2.71 | NM | 2.47 |
| 3% RM80 with 4.5% SEs at 4 C. and pH 4 | Reb M (g/L) | 1.98 | 1.95 | 2.09 | 2.14 | 2.53 | NM | 2.30 |
| 3% RM80 with 4.5% SEs at RT and pH 2.5 | Reb M (g/L) | 2.05 | 1.99 | 2.08 | 2.28 | 2.72 | NM | 2.84 |
| 3% RM80 with 4.5% SEs at RT and pH 4 | Reb M (g/L) | 1.98 | 1.98 | 2.08 | 2.40 | 2.79 | NM | 2.90 |
| 6% RM80 with 6% SEs at 4 C. and pH 2.5 | Reb M (g/L) | 4.54 | 3.98 | 4.25 | 4.67 | 5.62 | NM | 5.25 |
| 6% RM80 with 6% SEs at 4 C. and pH 4 | Reb M (g/L) | 3.83 | 3.86 | 3.99 | 4.30 | 5.02 | NM | 4.72 |
| 6% RM80 with 6% SEs at RT and pH 2.5 | Reb M (g/L) | 4.54 | 3.85 | 4.35 | 5.05 | 5.46 | NM | 7.29 |
| 6% RM80 with 6% SEs at RT and pH 4 | Reb M (g/L) | 3.83 | 3.72 | 3.71 | 4.34 | 5.32 | NM | 5.41 |
| 35% RM80 with 35% SEs at RT and pH 4 | Reb M (g/L) | 20.3 | NM | NM | 24.4 | 24.4 | NM | 27.8 |

This example shows that the SE are effective to solubilize steviol glycoside over time. SE are effective to solubilize steviol glycoside solutions over 48 weeks at 4° C., at room temperature, at pH 4, and/or at pH 2.5 with greater than 94% recovery of the steviol glycoside.

Example L—NMR Studies

It has been hypothesized that steviol glycosides (SGs) and SE will form a tight-binding complex in solution. If this is true, the magnetic environment of the complex would be substantially different than of the individual compounds dissolved in water. This would result in substantial shifting ($\Delta \delta > 0.02$ ppm) in their respective 1H NMR spectra.

A total of four samples were prepared for this study, and they are listed below. Each sample was dissolved fully in water, with or without heat as noted below, flash frozen at −80° C., and then placed on a lyophilizer until dry. The dry powders were subsequently dissolved in D2O at room temperature and analyzed by 1H and 13C NMR. The concentration of Sample 1 is substantially lower than Samples 2-4, as Reb M solubility in D2O is much lower when SEs are not present, and this resulted in relatively poor quality spectra.

Sample 1: 10 mg Reb M in 1 mL water—heated in H$_2$O
Sample 2: 10 mg SE in 1 mL water—heated in H$_2$O
Sample 3: 10 mg Reb M+10 mg SE in 1 mL water—heated in H$_2$O
Sample 4: 10 mg Reb M+10 mg SE in 3 mL water—not heated in H$_2$O Using the following numbering convention for SE molecules:

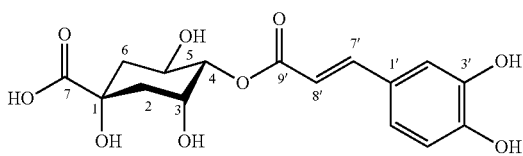

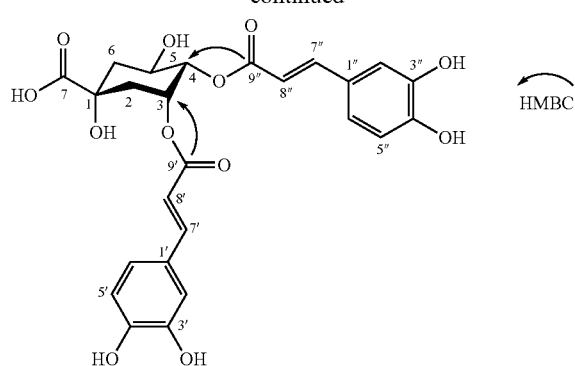

in this case, monocaffeoylquinic acid and dicaffeoylquinic acid. The observed signals are the sum of the mixture of isomers. The 1H NMR data are shown in Tables 33 (showing 1H NMR data with significant shifting in the caffeic acid moieties of the SEs) and 34 (Showing 1H NMR data with significant shifting in the steviol core of the SG).

TABLE 33

| Protons | δ ppm range | Average Shifting Sample 3 vs. 2 | Average Shifting Sample 4 vs. 2 |
| --- | --- | --- | --- |
| C7' and C7" | 7.5-7.7 | +0.034 and +0.053 | +0.029 and +0.045 |
| C2' and C2" | 7.15-7.2 | +0.039 | +0.034 |
| C6' and C6" | 7.05-7.15 | +0.030 | +0.024 |
| C5' and C5" | 6.9-7.0 | +0.022 | +0.018 |
| C8' and C8" | 6.3-6.5 | +0.033 and +0.055 | +0.028 and +0.047 |

TABLE 34

| Protons | δ ppm range | Average Shifting Sample 3 vs 1 | Average Shifting Sample 4 vs 1 |
| --- | --- | --- | --- |
| C20 Methyl | 0.90 | −0.13 | −0.15 |
| C18 Methyl | 1.27 | −0.09 | −0.10 |

There is a substantial amount of shifting in both the SE signals and the SG signals when the mixture of molecules is present. This shifting is similar when the compounds are heated in water together versus when they are mixed at room temperature, but slightly greater when heated. The moieties which show the strongest shifting are the caffeic acid moieties of the SEs and the steviol backbone of the SGs, suggesting a strong interaction between the most hydrophobic regions of each molecule, leaving the glucose and quinic acid moieties free to interact with water, thus possibly increasing the solubility of SGs and SEs.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

Embodiments

The present application provides for the following embodiments, the numbering of which is not to be construed as designating levels of importance:

A1. An aqueous steviol glycoside solution comprising:
a) greater than 0.2% (wt) of a total steviol glycoside composition comprising one or more steviol glycosides, wherein if the steviol glycoside composition includes rebaudioside A, rebaudioside D, or rebaudioside M, the rebaudioside A individual concentration is at least 1% (wt), the rebaudioside D individual concentration is at least 0.2% (wt), or the rebaudioside M individual concentration is at least 0.3% (wt);
b) less than 0.3% (wt) of malonate, malonic acid, oxalate, oxalic acid, lactate, lactic acid, succinate, succinic acid, malate, or malic acid; or less than 0.05% (wt) of pyruvate, pyruvic acid, fumarate, fumaric acid, tartrate, tartaric acid, sorbate, sorbic acid, acetate, or acetic acid; or less than about 0.05% (wt) of chlorophyll; and
c) a steviol glycoside solubility enhancer composition comprising at least one compound having one or more C6 carbocycles, at least one of the carbocycles having at least one carboxylic acid group linked to the carbocycle by a C1-C3 alkyl or alkenyl moiety, or salts or esters thereof, in an amount that enhances the solubility of at least one of the steviol glycosides.

A2. The aqueous steviol glycoside solution of embodiment A1 wherein the steviol glycoside remains in solution for at least three days, at least 4 days, at least 5 days, at least 7 days, at least 10 days, at least 20 days, at least 30 days, at least 45 days, at least 60 days, or at least 90 days, when stored at a temperature of about 20° C. to about 30° C., or about 23° C. to about 28° C.

A3. The aqueous steviol glycoside solution of embodiment A1 wherein the steviol glycoside composition comprises rebaudioside A.

A4. The aqueous steviol glycoside solution of embodiment A1, A2 or A3 wherein the steviol glycoside composition comprises rebaudioside D or rebaudioside M.

A5. The aqueous steviol glycoside solution of any one of embodiments A1 to A4 comprising less than 50% (wt), 40% (wt), 30% (wt), 20% (wt), 10% (wt), or 5% (wt) of a C1-C4 alcohol.

A6. The aqueous steviol glycoside solution of embodiment A5 which is free of the C1-C4 alcohol.

A7. The aqueous steviol glycoside solution of any one of embodiments A1 to A6 being substantially free of one or more of malonate, malonic acid, oxalate, oxalic acid, succinate, succinic acid, malate, malic acid, pyruvate, pyruvic acid, fumarate, fumaric acid, tartrate, tartaric acid, sorbate, sorbic acid, acetate, acetic acid, ammonia, ammonium, kaempferol, myricetin, fisetin, galangin, isorhamnetin, pachypodol, rhamnazin, pyranoflavonols, furanoflavonols, luteolin, apigenin, tangeritin, or chlorophyll.

A8. The aqueous steviol glycoside solution of any one of embodiments A1 to A7 having greater than 0.3% (wt) steviol glycosides, greater than 0.4% (wt), greater than 0.5% (wt), greater than 0.6% (wt), greater than 0.7% (wt), greater than 0.8% (wt), or greater than 0.9% (wt) steviol glycosides, greater than 1.0% (wt), greater than 1.25% (wt), greater than 1.5% (wt), greater than 1.75% (wt), greater than 2.0% (wt), or greater than 2.5% (wt) steviol glycosides.

A9. The aqueous steviol glycoside solution of any one of embodiments A1 to A7 having greater than 3% (wt) steviol glycosides, greater than 5% (wt), greater than 7% (wt), greater than 9% (wt), greater than 10% (wt), greater than 15% (wt), or greater than 20% (wt) steviol glycosides, greater than 25% (wt), greater than 30% (wt), greater than 35% (wt), or greater than 40% (wt) steviol glycosides.

A10. The aqueous steviol glycoside solution of any one of embodiments A1 to A 9 having a pH of 1 to 6, preferably 2 to 4.

A11. The aqueous steviol glycoside solution of any one of embodiments A1 to A10 wherein at least one of the carbocycles has two or more hydroxyls.

A12. The aqueous steviol glycoside solution of any one of embodiments A1 to A11 wherein the compound has two or three carbocycles.

A13. The aqueous steviol glycoside solution of any one of embodiments A1 to A12 wherein the compound comprises a cynarin, a caffeic acid, a quinic acid, a chlorogenic acid, or combinations thereof.

A14. A beverage composition comprising the aqueous steviol glycoside solution of any one of embodiments A1 to A13, which aqueous steviol glycoside solution further comprises one or more of phosphoric acid, citric acid, sodium citrate, and carbonated water.

A15. A sweetener comprising:
   a) a steviol glycoside composition comprising one or more steviol glycosides;
   b) a steviol glycoside solubility enhancer composition comprising at least one compound having one or more C6 carbocycles, at least one of the carbocycles having at least one carboxylic acid group linked to the carbocycle by a C1-3 alkyl or alkenyl moiety, or salts or esters thereof,
wherein the sweetener is soluble in water without alcohol at a temperature of about 20° C. to about 30° C. at a total steviol glycoside concentration of greater than 0.2% (wt).

B1. A solubilized steviol glycoside solution comprising a steviol glycoside and a steviol glycoside solubility enhancer composition in an aqueous solution,
   wherein the total steviol glycoside in the solubilized steviol glycoside solution is greater than 0.2% (wt);
   wherein the steviol glycoside solubility enhancer comprises a compound of formula (I), quercitrin, a pharmaceutically acceptable salt or ester thereof, or combinations thereof; and
   wherein the steviol glycoside solubility enhancer composition has less than about 0.1% (wt)(wt) of malonate, malonic acid, oxalate, oxalic acid, pyruvate, pyruvic acid, fumarate or fumaric acid, or less than about 0.05% (wt)(wt) of chlorophyll, or
   wherein the steviol glycoside solubility enhancer composition has less than about 0.3% (wt) of malonate, malonic acid, oxalate, or oxalic acid, or less than about 0.05% (wt) pyruvate, pyruvic acid, fumarate, or fumaric acid, or less than about 0.05% (wt) of chlorophyll,
   wherein the compound of formula (I) or the pharmaceutically acceptable salt or ester thereof is:

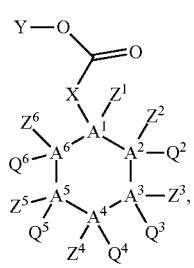

Formula I wherein
either each of $A^1$-$A^6$ is a carbon atom and $A^1/A^2$, $A^3/A^4$, and $A^5/A^6$ are bonded through carbon-carbon double bonds, each of $A^1$-$A^6$ is a carbon atom and at least one of $A^1/A^2$, $A^3/A^4$, and $A^5/A^6$ are bonded through a carbon-carbon double bond, each of $A^1$-$A^5$ is an aliphatic carbon atom and $A^6$ is O, or each $A^1$-$A^6$ is an aliphatic carbon atom;

each of $Z^1$-$Z^6$ is independently hydrogen, OH, $OR^1$, or absent;

each of $Q^2$-$Q^6$ is independently hydrogen, alkyl, alkenyl, cycloalkyl, aryl, aralkyl, carboxylic acid, OH, $OR^2$,

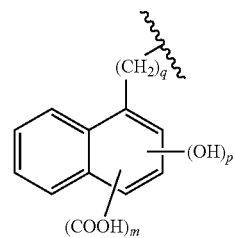

or combinations thereof, or $Q^4$ and $Q^5$ can join to form a fused $C_4$-$C_7$ carbocyclic ring, wherein the $C_4$-$C_7$ carboxylic ring can be substituted by zero to four of OH, $OR^1$, or a combination thereof;

X is

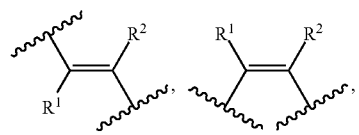

$C_1$-$C_3$ alkyl, or a bond;

$R^1$ and $R^2$ are independently hydrogen, carboxylic acid, OH, alkyl, alkenyl, cycloalkyl, aryl, aralkyl

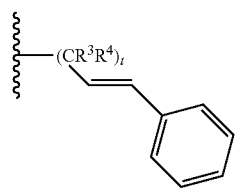

optionally substituted on the phenyl ring with from one to five hydroxyl or methoxy groups or combinations thereof, or

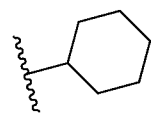 [SMILES: *C1CCCCC1]

optionally substituted on the cyclohexyl ring with from one to six hydroxyl or carboxylic acid groups or combinations thereof,

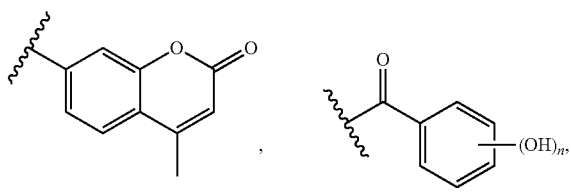

substituted analogs thereof, or combinations thereof;
R³ and R⁴ are independently hydrogen, OH, carboxylic acid, alkyl, alkenyl, cycloalkyl, aryl, aralkyl, or combinations thereof;
and Y is hydrogen, OH, carboxylic acid, alkyl, alkenyl, cycloalkyl, aryl, aralkyl,

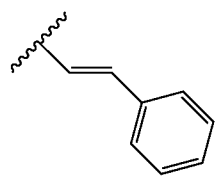 [SMILES: */C=C/c1ccccc1]

optionally substituted on the phenyl ring with from one to five hydroxyl or methoxy groups or combinations thereof, or

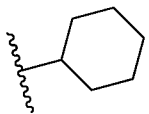 [SMILES: *C1CCCCC1]

optionally substituted on the cyclohexyl ring with from one to six hydroxyl or carboxylic acid groups or combinations thereof, or combinations thereof; and; and each m, n, p, q, and t is independently an integer from 0 to 5.

B2. The solubilized steviol glycoside solution of embodiment B1, wherein the steviol glycoside comprises a stevioside, a Steviol-19-O-glucoside, a Rubusoside, a Dulcoside A, a Steviol-13-O-glucoside, a Steviol-1,2-bioside, a Steviol-1,3-bioside, a Rebaudoside A, a Rebaudoside B, a Rebaudoside C, a Rebaudoside D, a Rebaudoside E, a Rebaudoside F, a Rebaudoside G, a Rebaudoside I, a Rebaudoside M, a Rebaudoside Q, or combinations thereof.

B3. The solubilized steviol glycoside solution of embodiment B1 or B2, wherein the steviol glycoside comprises a Rebaudoside B, a Rebaudoside D, a Rebaudoside M, or combinations thereof.

B4. The solubilized steviol glycoside solution of embodiment B1, B2 or B3, wherein the steviol glycoside solubility enhancer comprises a gallic acid, a rosmarinic acid, a chlorogenic acid, a cynarin isomer, a caffeic acid, a coumaric acid, a ferulic acid, a sinapic acid, or combinations thereof.

B5. The solubilized steviol glycoside solution of any one of embodiments 1 to 4, wherein the steviol glycoside solubility enhancer comprises a 3-O-Caffeoylquinic acid (chlorogenic acid), a 4-O-Caffeoylquinic acid (cryptochlorogenic acid), a 5-O-Caffeoylquinic acid (neochlorogenic acid), or combinations thereof.

B6. The solubilized steviol glycoside solution of any one of embodiments B1 to B5, wherein the steviol glycoside solubility enhancer comprises a mono-, di- or tri-hydroxycinnamic acid.

B7. The solubilized steviol glycoside solution of any one of embodiments B1 to B6, wherein the steviol glycoside solubility enhancer comprises a chlorogenic acid.

B8. The solubilized steviol glycoside solution of any one of embodiments B1 to B7, wherein the steviol glycoside solubility enhancer comprises a cynarin isomer.

B9. The solubilized steviol glycoside solution of any one of embodiments B1 to B8, wherein the steviol glycoside solubility enhancer comprises a mono-, di-, or tri-hydroxybenzoic acid.

B10. The solubilized steviol glycoside solution of any one of embodiments B1 to B9, wherein the steviol glycoside solubility enhancer comprises a gallic acid.

B11. The solubilized steviol glycoside solution of any one of embodiments B1 to B10, wherein the steviol glycoside solubility enhancer comprises a quinic acid or an ester thereof.

B12. The solubilized steviol glycoside solution of any one of embodiments B1 to B11, wherein the steviol glycoside solubility enhancer composition comprises a plant extract.

B13. The solubilized steviol glycoside solution of embodiment B12, wherein the plant extract is is derived from *stevia*, coffee bean, artichoke, yerba mate, or tea.

B14. The solubilized steviol glycoside solution of any one of embodiments B1 to B12, wherein the steviol glycoside solubility enhancer composition comprises a *stevia* leaf extract.

B15. The solubilized steviol glycoside solution of any one of embodiments B1 to B14, wherein the steviol glycoside and the steviol glycoside solubility enhancer are at a molar ratio of about 10:1, 9:1, 8:1, 7:1, 6:1, 5:1, 4:1, 3:1, 2:1, 1:1, 1:0.9, 1:0.8, 1:0.7, 1:0.6, 1:0.5, 1:0.4, 1:0.3, 1:0.2, or 1:0.1.

B16. The solubilized steviol glycoside solution of any one of embodiments B1 to B15, wherein a total concentration of steviol glycoside in the solubilized steviol glycoside solution is about 0.3, 0.75, 1.5, 3, 5, 6, 7, 8, 9, 10, 15, 20, 25, 30, 35, or 40% (wt).

B17. The solubilized steviol glycoside solution of any one of embodiments B1 to B16, wherein the pH of the solubilized steviol glycoside solution is less than about pH 4, 3, 2 or 1.

B18. The solubilized steviol glycoside solution of any one of embodiments B1 to B16, wherein the pH of the solubilized steviol glycoside solution is above pH 7.

B19. The solubilized steviol glycoside solution of any one of embodiments B1 to B16, wherein the pH of the solubilized steviol glycoside solution is pH 4 or less.

B20. The solubilized steviol glycoside solution of any one of embodiments B1 to B16, wherein the pH of the solubilized steviol glycoside solution is less than about pH 7.

B21. The solubilized steviol glycoside solution of any one of embodiments B1 to B16, wherein the pH of the solubilized steviol glycoside solution is about pH 7.

B22. The solubilized steviol glycoside solution of any one of embodiments B1 to B21, wherein the steviol glycoside solubility enhancer is in an amount that allows the steviol glycoside to be solubilized in the solubilized steviol glycoside solution for at least 30 days.

B23. The solubilized steviol glycoside solution of any one of embodiments B1 to B22, wherein in formula (I) each $A^1$-$A^6$ is an aliphatic carbon atom.

B24. The solubilized steviol glycoside solution of any one of embodiments B1 to B22, wherein in formula (I) each of $A^1$-$A^5$ is an aliphatic carbon atom and $A^6$ is O.

B25. The solubilized steviol glycoside solution of any one of embodiments B1 to B22, wherein in formula (I) each of $A^1$-$A^6$ is a carbon atom and $A^1/A^2$, $A^3/A^4$, and $A^5/A^6$ are bonded through carbon-carbon double bonds.

B26. The solubilized steviol glycoside solution of any one of embodiments B1 to B25, wherein in formula (I) at least two of $Z^1$-$Z^6$ are OH.

B27. The solubilized steviol glycoside solution of any one of embodiments B1 to B25, wherein in formula (I) at least one of $Z^1$-$Z^6$ is OH.

B28. The solubilized steviol glycoside solution of any one of embodiments 1 to 27, wherein in formula (I) X is

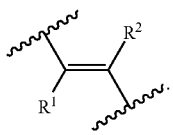

B29. The solubilized steviol glycoside solution of any one of embodiments 1 to 27, wherein in formula (I) X is

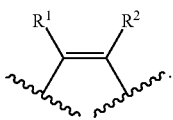

B30. The solubilized steviol glycoside solution of any one of embodiments B1 to B27, wherein in formula (I) X is a bond.

B31. The solubilized steviol glycoside solution of any one of embodiments B1 to B27, wherein in formula (I) X is $C_1$-$C_3$ alkyl.

B32. The solubilized steviol glycoside solution of any one of embodiments B1 to B31, wherein in formula (I) Y is hydrogen or $C_1$-$C_3$ alkyl.

B33. The solubilized steviol glycoside solution of any one of embodiments B1 to B32, wherein in formula (I) Y is hydrogen, X is a bond, and $Z^1$ is OH.

B34. The solubilized steviol glycoside solution of any one of embodiments B1 to B33, wherein in formula (I) $Q^3$ and $Q^4$ are OH and $Z^3$ and $Z^4$ are hydrogen.

B35. A beverage composition or a throw syrup composition having the composition of any one of embodiments B1 to B34.

B36. The beverage composition or throw syrup composition of embodiment B35, wherein the beverage is carbonated.

B37. The beverage composition or throw syrup composition of embodiment 35, which is a throw syrup composition.

B38. A method for solubilizing an aqueous solution of steviol glycoside, comprising: combining a steviol glycoside, a steviol glycoside solubility enhancer composition and an aqueous solution to generate a solubilized steviol glycoside solution, wherein the steviol glycoside concentration in the solubilized steviol glycoside solution is greater than 0.2% (wt), wherein the steviol glycoside solubility enhancer comprises comprises a compound of formula (I), quercitrin, a pharmaceutcially acceptable salt or ester thereof, or combinations thereof, and wherein prior to combining, the steviol glycoside solubility enhancer composition in solution has less than about 0.1% (wt) of malonate, malonic acid, oxalate, oxalic acid, pyruvate, pyruvic acid, fumarate or fumaric acid, or less than about 0.05% (wt) of chlorophyll, or has less than about 0.3% (wt) of malonate, malonic acid, oxalate, or oxalic acid, or less than about 0.05% (wt) pyruvic, pyruvic acid, fumarate or fumaric acid, or less than about 0.05% (wt) of chlorophyll.

B39. The method of embodiment B38, wherein the steviol glycoside comprises a stevioside, a Steviol-19-O-glucoside, a Rubusoside, a Dulcoside A, a Steviol-13-O-glucoside, a Steviol-1,2-bioside, a Steviol-1,3-bioside, a Rebaudoside A, a Rebaudoside B, a Rebaudoside C, a Rebaudoside D, a Rebaudoside E, a Rebaudoside F, a Rebaudoside G, a Rebaudoside I, a Rebaudoside M, a Rebaudoside Q, or combinations thereof.

B40. The method of embodiment B38 or B39, wherein wherein the steviol glycoside comprises a Rebaudoside B, a Rebaudoside M, a Rebaudoside D, or combinations thereof.

B41. The method of embodiment B38, B39 or B40, wherein the steviol glycoside solubility enhancer comprises a gallic acid, a rosmarinic acid, a chlorogenic acid, cynarin, a cynarin isomer, a caffeic acid, a coumaric acid, a ferulic acid, a sinapic acid, or combinations thereof.

B42. The method of any one of embodiments B38 to B41, wherein the steviol glycoside solubility enhancer comprises a 3-O-Caffeoylquinic acid (chlorogenic acid), a 4-O-Caffeoylquinic acid (cryptochlorogenic acid), a 5-O-Caffeoylquinic acid (neochlorogenic acid), or combinations thereof.

B43. The method of any one of embodiments B38 to B42, wherein the steviol glycoside solubility enhancer comprises a mono-, di- or tri-hydroxycinnamic acid.

B44. The method of any one of embodiments B38 to B43, wherein the steviol glycoside solubility enhancer comprises a chlorogenic acid.

B45. The method of any one of embodiments B38 to B44, wherein the steviol glycoside solubility enhancer comprises cynarin or a cynarin isomer.

B46. The method of any one of embodiments B38 to B45, wherein the steviol glycoside solubility enhancer comprises a mono-, di- or tri-hydroxybenzoic acid.

B47. The method of any one of embodiments B38 to B46, wherein the steviol glycoside solubility enhancer comprises a gallic acid.

B48. The method of any one of embodiments B38 to B47, wherein the steviol glycoside solubility enhancer comprises an ester of a quinic acid and one or more caffeic acids.

B49. The method of any one of embodiments B38 to B48, wherein the steviol glycoside solubility enhancer comprises a *stevia* leaf extract.

B50. The method of any one of embodiments B38 to B49, wherein the steviol glycoside solubility enhancer comprises a plant extract.

B51. The method of embodiment B50 wherein the plant extract is derived from *stevia*, coffe bean, artichoke, yerba mate, or tea.

B52. The method of any one of embodiments B38 to B51, wherein the steviol glycoside and the steviol glycoside solubility enhancer are at a molar ratio of about 10:1, 9:1, 8:1, 7:1, 6:1, 5:1, 4:1, 3:1, 2:1, 1:1, 1:0.9, 1:0.8, 1:0.7, 1:0.6, 1:0.5, 1:0.4, 1:0.3, 1:0.2, or 1:0.1.

B53. The method of any one of embodiments B38 to B52, wherein a total concentration of steviol glycoside in the solubilized steviol glycoside solution is about 0.3, 0.75, 1.5, 3, 5, 6, 7, 8, 9, 10, 15, 20, 25, 30, 35, or 40% (wt).

B54. The method of any one of embodiments B38 to B53, wherein the pH of the solubilized steviol glycoside solution is less than about pH 4, 3, 2 or 1.

B55. The method of any one of embodiments B38 to B53, wherein the pH of the solubilized steviol glycoside solution is above pH 7.

B56. The method of any one of embodiments B38 to B53, wherein the pH of the solubilized steviol glycoside solution pH 4 or less.

B57. The method of any one of embodiments B38 to B53, wherein the pH of the solubilized steviol glycoside solution is less than about pH 7.
B58. The method of any one of embodiments B38 to B53, wherein the pH of the solubilized steviol glycoside solution is about pH 7.
B59. The method of any one of embodiments B38 to B58, wherein the amount of the steviol glycoside solubility enhancer allows the steviol glycoside to be solubilized in the solubilized steviol glycoside solution for at least 30 days.
B60. The method of any one of embodiments B38 to B59, wherein the steviol glycoside and the steviol glycoside solubility enhancer in the aqueous solution has been heated to generate the solubilized steviol glycoside solution.
B61. A solubilized steviol glycoside solution having a pH of less than 4 comprising a steviol glycoside and a steviol glycoside solubility enhancer composition in an aqueous solution,
 wherein the steviol glycoside comprises a stevioside, a Steviol-19-O-glucoside, a Rubusoside, a Dulcoside A, a Steviol-13-O-glucoside, a Steviol-1,2-bioside, a Steviol-1,3-bioside, a Rebaudoside A, a Rebaudoside B, a Rebaudoside C, a Rebaudoside D, a Rebaudoside E, a Rebaudoside F, a Rebaudoside G, a Rebaudoside I, a Rebaudoside M, a Rebaudoside Q, or combinations thereof, wherein the total steviol glycoside in the solubilized steviol glycoside solution is greater than 0.2% (wt); and
 wherein the steviol glycoside solubility enhancer comprises a compound of formula (I), quercitrin, a pharmaceutically acceptable salt or ester thereof, or combinations thereof; and
 wherein the steviol glycoside solubility enhancer composition has less than about 0.1% (wt) of malonate, malonic acid, oxalate, oxalic acid, pyruvate, pyruvic acid, fumarate or fumaric acid, or less than about 0.05% (wt) of chlorophyll, or
 wherein the steviol glycoside solubility enhancer composition has less than about 0.3% (wt) of malonate, malonic acid, oxalate, or oxalic acid, or less than about 0.05% (wt) pyruvate, pyruvic acid, fumarate or fumaric acid, or less than about 0.05% (wt) of chlorophyll.
B62. A solubilized steviol glycoside solution comprising a steviol glycoside and a steviol glycoside solubility enhancer composition in an aqueous solution,
 wherein the steviol glycoside comprises a stevioside, a Steviol-19-O-glucoside, a Rubusoside, a Dulcoside A, a Steviol-13-O-glucoside, a Steviol-1,2-bioside, a Steviol-1,3-bioside, a Rebaudoside A, a Rebaudoside B, a Rebaudoside C, a Rebaudoside D, a Rebaudoside E, a Rebaudoside F, a Rebaudoside G, a Rebaudoside I, a Rebaudoside M, a Rebaudoside Q, or combinations thereof, wherein the total steviol glycoside concentration in the solubilized steviol glycoside solution is greater than 1% (wt);
 wherein the steviol glycoside solubility enhancer comprises a compound of formula (I), quercitrin, a pharmaceutically acceptable salt or ester thereof, or combinations thereof; and
 wherein the steviol glycoside solubility enhancer composition has less than about 0.1% (wt) of malonate, malonic acid, oxalate, oxalic acid, pyruvate, pyruvic acid, fumarate or fumaric acid, or less than about 0.05% (wt) of chlorophyll or
 wherein the steviol glycoside solubility enhancer composition has less than about 0.3% (wt) of malonate, malonic acid, oxalate, or oxalic acid, or less than about 0.05% (wt) pyruvate, pyruvic acid, fumarate or fumaric acid, or less than about 0.05% (wt) of chlorophyll.

B63. A solubilized steviol glycoside solution comprising a steviol glycoside and a steviol glycoside solubility enhancer composition in an aqueous solution,
 wherein the steviol glycoside comprises a stevioside, a Steviol-19-O-glucoside, a Rubusoside, a Dulcoside A, a Steviol-13-O-glucoside, a Steviol-1,2-bioside, a Steviol-1,3-bioside, a Rebaudoside A, a Rebaudoside B, a Rebaudoside C, a Rebaudoside D, a Rebaudoside E, a Rebaudoside F, a Rebaudoside G, a Rebaudoside I, a Rebaudoside M, a Rebaudoside Q, or combinations thereof;
 wherein the steviol glycoside solubility enhancer comprising a compound of formula (I), quercitrin, a pharmaceutically acceptable salt or ester thereof, or combinations thereof;
 wherein the steviol glycoside solubility enhancer composition has less than about 0.1% (wt) of malonate, malonic acid, oxalate, oxalic acid, pyruvate, pyruvic acid, fumarate or fumaric acid, or less than about 0.05% (wt) of chlorophyll or
 wherein the steviol glycoside solubility enhancer composition has less than about 0.3% (wt) of malonate, malonic acid, oxalate, or oxalic acid, or less than about 0.05% (wt) pyruvate, pyruvic acid, fumarate or fumaric acid, or less than about 0.05% (wt) of chlorophyll; and
 wherein the molar ratio of the steviol glycoside enhancer and the steviol glycoside in the solubilized solution is about 10:1, 9:1, 8:1, 7:1, 6:1, 5:1, 4:1, 3:1, 2:1, 1:1, 1:0.9, 1:0.8, 1:0.7, 1:0.6, 1:0.5, 1:0.4, 1:0.3, 1:0.2, or 1:0.1.
B64. A powder composition comprising a steviol glycoside and a steviol glycoside solubility enhancer composition,
 wherein the total steviol glycoside in the composition is greater than 0.2% wt;
 wherein the steviol glycoside solubility enhancer comprises a compound of formula (I), quercitrin, a salt or ester thereof, or combinations thereof; and
 wherein the steviol glycoside solubility enhancer composition has less than about 3% wt of malonate, malonic acid, oxalate, or oxalic acid, or less than 0.5% wt of pyruvate, malonic acid, oxalate, or oxalic acid, or less than 0.5% wt of chlorophyll, or less than about 55% wt steviol glycoside, or
 wherein the steviol glycoside solubility enhancer composition has less than about 0.3% wt of malonate, malonic acid, oxalate, or oxalic acid, or oxalate, or less than 0.05% wt of pyruvate, malonic acid, oxalate, or oxalic acid, or or less than 0.05% wt of chlorophyll or less than about 75% wt steviol glycoside.
B65. The powder composition of embodiment B64, which is a spray dried composition.
B66. The powder composition of embodiment B64, which is a freeze dried composition.
B67. The solubilized steviol glycoside solution of any one of embodiments 1 to 66, wherein the steviol glycoside solubility enhancer comprises a 3,4-dicaffeoylquinic acid, a 3,5-dicaffeoylquinic acid, a 4,5-dicaffeoylquinic acid, a 1,3-dicaffeoylquinic acid, a 1,4-dicaffeoylquinic acid, a 1,5-dicaffeoylquinic acid (cynarin), or combinations thereof.
B68. The solubilized steviol glycoside solution of any one of embodiments B1 to B67, wherein the steviol glycoside and the steviol glycoside solubility enhancer are at a molar ratio of about 1:1, 1:2, 1:3, 1:4, 1:5, 1:6, 1:7, 1:8, 1:9, or 1:10.
C1. An aqueous steviol glycoside solution comprising:
 a) greater than 0.2% (wt) of a total steviol glycoside composition comprising one or more steviol glycosides, wherein if the steviol glycoside composition includes rebaudioside A, rebaudioside D, or rebaudioside M, the rebaudioside A individual concentration is at least 1% (wt), the rebaudioside D individual concentration is at least 0.2% (wt), or the rebaudioside M individual concentration is at least 0.3% (wt); and b) a steviol glycoside solubility enhancer composition comprising at least one caffeic ester of tartaric acid or caffeic ester of 3-(3,4-dihydroxyphenyl)lactic acid, in an amount that enhances the solubility of at least one of the steviol glycosides.

C2. The aqueous steviol glycoside solution of embodiment C1 wherein the steviol glycoside remains in solution for at least three days, at least 4 days, at least 5 days, at least 7 days, at least 10 days, at least 20 days, at least 30 days, at least 45 days, at least 60 days, or at least 90 days, when stored at a temperature of about 20° C. to about 30° C., or about 23° C. to about 28° C.

C3. The aqueous steviol glycoside solution of embodiment C1 wherein the steviol glycoside composition comprises rebaudioside A.

C4. The aqueous steviol glycoside solution of embodiment C1, C2 or C3 wherein the steviol glycoside composition comprises rebaudioside D or rebaudioside M.

C5. The aqueous steviol glycoside solution of any one of embodiments C1 to C4 comprising less than 50% (wt), 40% (wt), 30% (wt), 20% (wt), 10% (wt), or 5% (wt) of a C1-C4 alcohol.

C6. The aqueous steviol glycoside solution of embodiment C5 which is free of the C1-C4 alcohol.

C7. The aqueous steviol glycoside solution of any one of embodiments C1 to C6 being substantially free of one or more of malonate, malonic acid, oxalate, oxalic acid, succinate, succinic acid, malate, malic acid, pyruvate, pyruvic acid, fumarate, fumaric acid, tartrate, tartaric acid, sorbate, sorbic acid, acetate, acetic acid, ammonia, ammonium, kaempferol, myricetin, fisetin, galangin, isorhamnetin, pachypodol, rhamnazin, pyranoflavonols, furanoflavonols, luteolin, apigenin, tangeritin, or chlorophyll.

C8. The aqueous steviol glycoside solution of any one of embodiments C1 to C7 having greater than 0.3% (wt) steviol glycosides, greater than 0.4% (wt), greater than 0.5% (wt), greater than 0.6% (wt), greater than 0.7% (wt), greater than 0.8% (wt), or greater than 0.9% (wt) steviol glycosides, greater than 1.0% (wt), greater than 1.25% (wt), greater than 1.5% (wt), greater than 1.75% (wt), greater than 2.0% (wt), or greater than 2.5% (wt) steviol glycosides.

C9. The aqueous steviol glycoside solution of any one of embodiments C1 to C7 having greater than 3% (wt) steviol glycosides, greater than 5% (wt), greater than 7% (wt), greater than 9% (wt), greater than 10% (wt), greater than 15% (wt), or greater than 20% (wt) steviol glycosides, greater than 25% (wt), greater than 30% (wt), greater than 35% (wt), or greater than 40% (wt) steviol glycosides.

C10. The aqueous steviol glycoside solution of any one of embodiments C1 to C9 having a pH of 1 to 6, preferably 2 to 4.

C11. The aqueous steviol glycoside solution of any one of embodiments C1 to C10 wherein the at least one caffeic ester of tartaric acid comprises a cichoric acid.

C12. The aqueous steviol glycoside solution of any one of embodiments C1 to C11 wherein the at least one caffeic ester of 3-(3,4-dihydroxyphenyl)lactic acid comprises a rosmarinic acid.

C13. The aqueous steviol glycoside solution of any one of embodiments C1 to C12 wherein the aqueous solution comprises less than 0.3% (wt) of malonate, malonic acid, oxalate, oxalic acid, lactate, lactic acid, succinate, succinic acid, malate, or malic acid; or less than 0.05% (wt) of pyruvate, pyruvic acid, fumarate, fumaric acid, tartrate, tartaric acid, sorbate, sorbic acid, acetate, or acetic acid; or less than about 0.05% (wt) of chlorophyll.

C14. A beverage composition comprising the aqueous steviol glycoside solution of any one of embodiments C1 to C13, which aqueous steviol glycoside solution further comprises one or more of phosphoric acid, citric acid, sodium citrate, and carbonated water.

C15. A sweetener comprising:
a) a steviol glycoside composition comprising one or more steviol glycosides;
b) a steviol glycoside solubility enhancer composition comprising at least one caffeic ester of tartaric acid or caffeic ester of 3-(3,4-dihydroxyphenyl)lactic acid, in an amount that enhances the solubility of at least one of the steviol glycosides, wherein the sweetener is soluble in water without alcohol at a temperature of about 20° C. to about 30° C. at a total steviol glycoside concentration of greater than 0.2% (wt).

C16. The sweetener of embodiment C15 wherein the at least one caffeic ester of tartaric acid comprises a cichoric acid.

C17. The sweetener of embodiment C15 wherein the at least one caffeic ester of 3-(3,4-dihydroxyphenyl)lactic acid comprises a rosmarinic acid.

D1. An aqueous steviol glycoside solution comprising:
a) greater than 0.2% (wt) of a total steviol glycoside composition comprising one or more steviol glycosides, wherein if the steviol glycoside composition includes rebaudioside A, rebaudioside D, or rebaudioside M, the rebaudioside A individual concentration is at least 1% (wt), the rebaudioside D individual concentration is at least 0.2% (wt), or the rebaudioside M individual concentration is at least 0.3% (wt); and
b) a steviol glycoside solubility enhancer composition comprising at least one caffeic ester of a quinic acid, in an amount that enhances the solubility of at least one of the steviol glycosides.

D2. The aqueous steviol glycoside solution of embodiment D1 wherein the steviol glycoside remains in solution for at least three days, at least 4 days, at least 5 days, at least 7 days, at least 10 days, at least 20 days, at least 30 days, at least 45 days, at least 60 days, or at least 90 days, when stored at a temperature of about 20° C. to about 30° C., or about 23° C. to about 28° C.

D3. The aqueous steviol glycoside solution of embodiment D1 wherein the steviol glycoside composition comprises rebaudioside A.

D4. The aqueous steviol glycoside solution of embodiment D1, D2 or D3 wherein the steviol glycoside composition comprises rebaudioside D or rebaudioside M.

D5. The aqueous steviol glycoside solution of any one of embodiments D1 to D4 comprising less than 50% (wt), 40% (wt), 30% (wt), 20% (wt), 10% (wt), or 5% (wt) of a C1-C4 alcohol.

D6. The aqueous steviol glycoside solution of embodiment D5 which is free of the C1-C4 alcohol.

D7. The aqueous steviol glycoside solution of any one of embodiments D1 to D6 being substantially free of one or more of malonate, malonic acid, oxalate, oxalic acid, succinate, succinic acid, malate, malic acid, pyruvate, pyruvic acid, fumarate, fumaric acid, tartrate, tartaric acid, sorbate, sorbic acid, acetate, acetic acid, ammonia, ammonium, kaempferol, myricetin, fisetin, galangin, isorhamnetin, pachypodol, rhamnazin, pyranoflavonols, furanoflavonols, luteolin, apigenin, tangeritin, or chlorophyll.

D8. The aqueous steviol glycoside solution of any one of embodiments D1 to D7 having greater than 0.3% (wt) steviol glycosides, greater than 0.4% (wt), greater than 0.5%

(wt), greater than 0.6% (wt), greater than 0.7% (wt), greater than 0.8% (wt), or greater than 0.9% (wt) steviol glycosides, greater than 1.0% (wt), greater than 1.25% (wt), greater than 1.5% (wt), greater than 1.75% (wt), greater than 2.0% (wt), or greater than 2.5% (wt) steviol glycosides.

D9. The aqueous steviol glycoside solution of any one of embodiments D1 to D7 having greater than 3% (wt) steviol glycosides, greater than 5% (wt), greater than 7% (wt), greater than 9% (wt), greater than 10% (wt), greater than 15% (wt), or greater than 20% (wt) steviol glycosides, greater than 25% (wt), greater than 30% (wt), greater than 35% (wt), or greater than 40% (wt) steviol glycosides.

D10. The aqueous steviol glycoside solution of any one of embodiments D1 to D9 having a pH of 1 to 6, preferably 2 to 4.

D11. The aqueous steviol glycoside solution of any one of embodiments D1 to D10 wherein the at least one caffeic ester of a quinic acid comprises a monocaffeoylquinic acid.

D12. The aqueous steviol glycoside solution of any one of embodiments D1 to D10 wherein the at least one caffeic ester of a quinic acid comprises a dicaffeoylquinic acid D13. The aqueous steviol glycoside solution of any one of embodiments D1 to D12 wherein the compound comprises a cynarin, a caffeic acid, a quinic acid, a chlorogenic acid, or combinations thereof.

D14. The aqueous steviol glycoside solution of any one of embodiments D1 to D13 wherein the aqueous solution comprises less than 0.3% (wt) of malonate, malonic acid, oxalate, oxalic acid, lactate, lactic acid, succinate, succinic acid, malate, or malic acid; or less than 0.05% (wt) of pyruvate, pyruvic acid, fumarate, fumaric acid, tartrate, tartaric acid, sorbate, sorbic acid, acetate, or acetic acid; or less than about 0.05% (wt) of chlorophyll.

D15. A beverage composition comprising the aqueous steviol glycoside solution of any one of embodiments D1 to D14, which aqueous steviol glycoside solution further comprises one or more of phosphoric acid, citric acid, sodium citrate, and carbonated water.

D16. A sweetener comprising:
a) a steviol glycoside composition comprising one or more steviol glycosides;
b) a steviol glycoside solubility enhancer composition comprising at least one caffeic ester of a quinic acid, in an amount that enhances the solubility of at least one of the steviol glycosides,
wherein the sweetener is soluble in water without alcohol at a temperature of about 20° C. to about 30° C. at a total steviol glycoside concentration of greater than 0.2% (wt).

The invention claimed is:

1. An aqueous steviol glycoside solution comprising:
a) greater than 0.2% by weight of a total steviol glycoside composition comprising one or more steviol glycosides, wherein if the steviol glycoside composition includes rebaudioside A, rebaudioside D, or rebaudioside M, the rebaudioside A individual concentration in the aqueous steviol glycoside solution is at least 1% by weight, the rebaudioside D individual concentration in the aqueous steviol glycoside solution is at least 0.2% by weight, or the rebaudioside M individual concentration in the aqueous steviol glycoside solution is at least 0.3% by weight;
b) less than 0.3% by weight of malonate, malonic acid, oxalate, oxalic acid, lactate, lactic acid, succinate, succinic acid, malate, or malic acid; or less than 0.05% by weight of pyruvate, pyruvic acid, fumarate, fumaric acid, tartrate, tartaric acid, sorbate, sorbic acid, acetate, or acetic acid; or less than about 0.05% by weight of chlorophyll; and
c) at least 1% by weight of a steviol glycoside solubility enhancer composition comprising
i) one or more monocaffeoylquinic acids or salts thereof;
ii) at least 20% by weight of one or more dicaffeoylquinic acids or salts thereof; and
iii) at least one of an ester of ferulic acid and quinic acid, an ester of caffeic acid and tartaric acid, an ester of caffeic acid and 3-(3,4-dihydroxyphenyl)lactic acid, an ester of p-coumaric acid and quinic acid, an ester of sinapic acid and quinic acid, and isomers thereof;
wherein the aqueous steviol glycoside solution comprises a 1:0.3 to 1:3 ratio by weight of total steviol glycoside to steviol glycoside solubility enhancer composition.

2. The solution of claim 1, wherein the aqueous steviol glycoside solution comprises a 1:0.3 to 1:3 ratio by weight of total steviol glycoside to total concentration of esters of caffeic acid and quinic acid, esters of ferulic acid and quinic acid, esters of caffeic acid and tartaric acid, esters of caffeic acid and 3-(3,4-dihydroxyphenyl)lactic acid, esters of p-coumaric acid and quinic acid, esters of sinapic acid and quinic acid, and isomers thereof.

3. The solution of claim 1, wherein the aqueous steviol glycoside solution comprises a 1:1 to 1:3 ratio by weight of total steviol glycoside to total concentration of esters of caffeic acid and quinic acid, esters of ferulic acid and quinic acid, esters of caffeic acid and tartaric acid, esters of caffeic acid and 3-(3,4-dihydroxyphenyl)lactic acid, esters of p-coumaric acid and quinic acid, esters of sinapic acid and quinic acid, and isomers thereof.

4. The solution of claim 1, wherein the solution comprises at least 1000 ppm of the steviol glycoside solubility enhancer composition.

5. The solution of claim 1, wherein the solution comprises less than 10% by weight of a C1-C4 alcohol.

6. The solution of claim 5, wherein the solution is free of a C1-C4 alcohol.

7. The solution of claim 1, wherein the steviol glycoside solubility enhancer composition comprises at least 40% by weight of dicaffeoylquinic acids.

8. The solution of claim 1, wherein the steviol glycoside composition remains in solution for at least 7 days when stored a temperature of about 25° C.

9. The solution of claim 1, wherein the aqueous solution is free of C1-C4 alcohol, has greater than 0.5% by weight of the total steviol glycoside composition, and remains in solution for at least 7 days when stored a temperature of about 25° C.

10. The solution of claim 1, wherein the aqueous solution comprises greater than 1.0% by weight total steviol glycoside composition and the total steviol glycoside composition comprises great than about 90% by weight rebaudioside D and rebaudioside M.

11. An aqueous steviol glycoside solution comprising:
a) greater than 0.2% by weight of a total steviol glycoside composition comprising one or more steviol glycosides, wherein if the steviol glycoside composition includes rebaudioside A, rebaudioside D, or rebaudioside M, the rebaudioside A individual concentration is at least 1% by weight, the rebaudioside D individual concentration is at least 0.2% by weight, or the rebaudioside M individual concentration is at least 0.3% by weight;

b) less than 0.3% by weight of malonate, malonic acid, oxalate, oxalic acid, lactate, lactic acid, succinate, succinic acid, malate, or malic acid; or less than 0.05% by weight of pyruvate, pyruvic acid, fumarate, fumaric acid, tartrate, tartaric acid, sorbate, sorbic acid, acetate, or acetic acid; or less than about 0.05% by weight of chlorophyll; and c) a steviol glycoside solubility enhancer in an amount that enhances the solubility of at least one of the steviol glycosides composition, the steviol glycoside solubility enhancer comprising
  i) one or more monocaffeoylquinic acids or salts thereof;
  ii) at least 10% by weight of one or more dicaffeoylquinic acids or salts thereof;
  iii) at least one of an ester of ferulic acid and quinic acid, an ester of p-coumaric acid and quinic acid, an ester of sinapic acid and quinic acid, an ester of caffeic acid and tartaric acid, an ester of caffeic acid and 3-(3,4-dihydroxyphenyl)lactic acid, and isomers thereof, wherein the aqueous steviol glycoside solution comprises a ratio between 1:0.3 and 1:3 by weight of total steviol glycoside to steviol glycoside solubility enhancer composition, wherein the steviol glycoside composition remains in solution for at least 7 days when stored a temperature of about 25° C.

12. The solution of claim 11, wherein the steviol glycoside composition remains in solution for at least 10 days when stored at a temperature of about 25° C.

13. The solution of claim 11, wherein the steviol glycosides composition remains in solution for at least 20 days when stored at a temperature of about 25° C.

14. The solution of claim 11, wherein the aqueous solution comprises greater than 0.5% by weight total steviol glycoside composition.

15. The solution of claim 11, wherein the aqueous solution comprises greater than 1.0% by weight total steviol glycoside composition.

16. The solution of claim 11, wherein the aqueous solution comprises greater than 1.0% by weight total steviol glycoside composition and the total steviol glycoside composition comprises great than about 90% (wt) rebaudioside D and rebaudioside M.

* * * * *